(12) United States Patent
Cheung

(10) Patent No.: US 9,062,110 B2
(45) Date of Patent: *Jun. 23, 2015

(54) USES OF MONOCLONIAL ANTIBODY 8H9

(71) Applicant: SLOAN-KETTERING INSTITUTE FOR CANCER RESEARCH, New York, NY (US)

(72) Inventor: Nai-Kong V. Cheung, New York, NY (US)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,234

(22) Filed: Apr. 8, 2013

(65) Prior Publication Data
US 2013/0287798 A1   Oct. 31, 2013

Related U.S. Application Data

(60) Continuation of application No. 12/721,798, filed on Mar. 11, 2010, now Pat. No. 8,414,892, which is a division of application No. 10/505,658, filed as application No. PCT/US03/07004 on Mar. 6, 2003, now Pat. No. 7,740,845, which is a continuation-in-part of application No. 10/273,762, filed on Oct. 17, 2002, now Pat. No. 7,666,424, and a continuation-in-part of application No. PCT/US02/33331, filed on Oct. 17, 2002, which is a continuation-in-part of application No. 10/097,558, filed on Mar. 8, 2002, now Pat. No. 7,737,258, which is a continuation-in-part of application No. 10/097,558, filed on Mar. 8, 2002, now Pat. No. 7,737,258, which is a continuation-in-part of application No. PCT/US01/32565, filed on Oct. 18, 2001.

(60) Provisional application No. 60/330,396, filed on Oct. 17, 2001, provisional application No. 60/241,344, filed on Oct. 18, 2000.

(51) Int. Cl.
| C07K 16/28 | (2006.01) |
| A61K 47/48 | (2006.01) |
| A61K 49/00 | (2006.01) |
| C07K 16/00 | (2006.01) |
| C07K 16/18 | (2006.01) |
| C07K 16/30 | (2006.01) |
| C07K 16/42 | (2006.01) |
| A61K 39/00 | (2006.01) |

(52) U.S. Cl.
CPC .............. *C07K 16/28* (2013.01); *A01K 2217/05* (2013.01); *A61K 47/48623* (2013.01); *A61K 47/48653* (2013.01); *A61K 49/0004* (2013.01); *A61K 49/0006* (2013.01); *A61K 2039/505* (2013.01); *C07K 16/00* (2013.01); *C07K 16/18* (2013.01); *C07K 16/30* (2013.01); *C07K 16/3053* (2013.01); *C07K 16/4208* (2013.01); *C07K 16/4266* (2013.01); *C07K 2317/24* (2013.01); *C07K 2317/622* (2013.01); *C07K 2317/732* (2013.01); *C07K 2319/00* (2013.01)

(58) Field of Classification Search
CPC ................................. C07K 16/00; A61K 39/00
See application file for complete search history.

(56) References Cited

U.S. PATENT DOCUMENTS

| 5,270,202 | A  |   | 12/1993 | Raychaudhuri |
| 5,693,762 | A  | * | 12/1997 | Queen et al. ............... 530/387.3 |
| 6,132,718 | A  |   | 10/2000 | Hansen |
| 6,326,471 | B1 |   | 12/2001 | Kokolus et al. |
| 6,632,431 | B2 |   | 10/2003 | Wu |
| 8,148,154 | B2 |   | 4/2012  | Cheung et al. |
| 8,414,892 | B2 |   | 4/2013  | Cheung |
| 8,501,471 | B2 |   | 8/2013  | Cheung |
| 2002/0102264 | A1 |   | 8/2002 | Cheung |
| 2002/0132983 | A1 |   | 9/2002 | Junghans |
| 2003/0103963 | A1 |   | 6/2003 | Cheung |
| 2003/0149998 | A1 |   | 8/2003 | Blatcher et al. |

FOREIGN PATENT DOCUMENTS

| WO | 0118021 | 3/2001 |
| WO | 0210187 | 2/2002 |

(Continued)

OTHER PUBLICATIONS

Modaks et al (Proceedings of the American Association for Cancer Research Annual Meeting, 1999, 40: p. 474, abstract #3133).*
Cheung, N. K. V. et al., Anti-GD2 antibody treatment of minimal residual stage 4 neuroblastoma diagnosed at more than 1 year of age. J. Clin. Oncol., 16:3053-3060, 1998. (Exhibit 1).
Yu, A. et al. et al., Phase I trial of human-mouse chimeric anti-disialoganglioside monoclonal antibody ch14.18 in patients with refractory neuroblastoma and osteosarcoma. J. Clin. Oncol., 16:2169-2180, 1998. (Exhibit 2).
Jurcic, J. G. et al., Sequential targeted therapy for acute promyelocytic leukemia with all-trans retinoic acid and anti-CD33 monoclonal antibody M195. Leuk., 9:244-248, 1995. (Exhibit 3).

(Continued)

*Primary Examiner* — Sean Aeder
(74) *Attorney, Agent, or Firm* — Law Offices of Albert Wai-Kit Chan, PLLC

(57) ABSTRACT

This invention provides an antibody that binds the same antigen as that of monoclonal antibody 8H9, wherein the heavy chain CDR (Complementary Determining Region)1 comprises NYDIN, heavy chain CDR2 comprises WIFPGDGSTQY, heavy chain CDR3 comprises QTTATWFAY, and the light chain CDR1 comprises RASQSISDYLH, light chain CDR2 comprises YASQSIS, and light chain CDR3 comprises QNGHSFPLT. In another embodiment, there is provided a polypeptide that binds the same antigen as that of monoclonal antibody 8H9, wherein the polypeptide comprises NYDIN, WIFPGDGSTQY, QTTATWFAY, RASQSISDYLH, YASQSIS, and QNGHSFPLT.

10 Claims, 41 Drawing Sheets

(56) References Cited

FOREIGN PATENT DOCUMENTS

Figure 1:
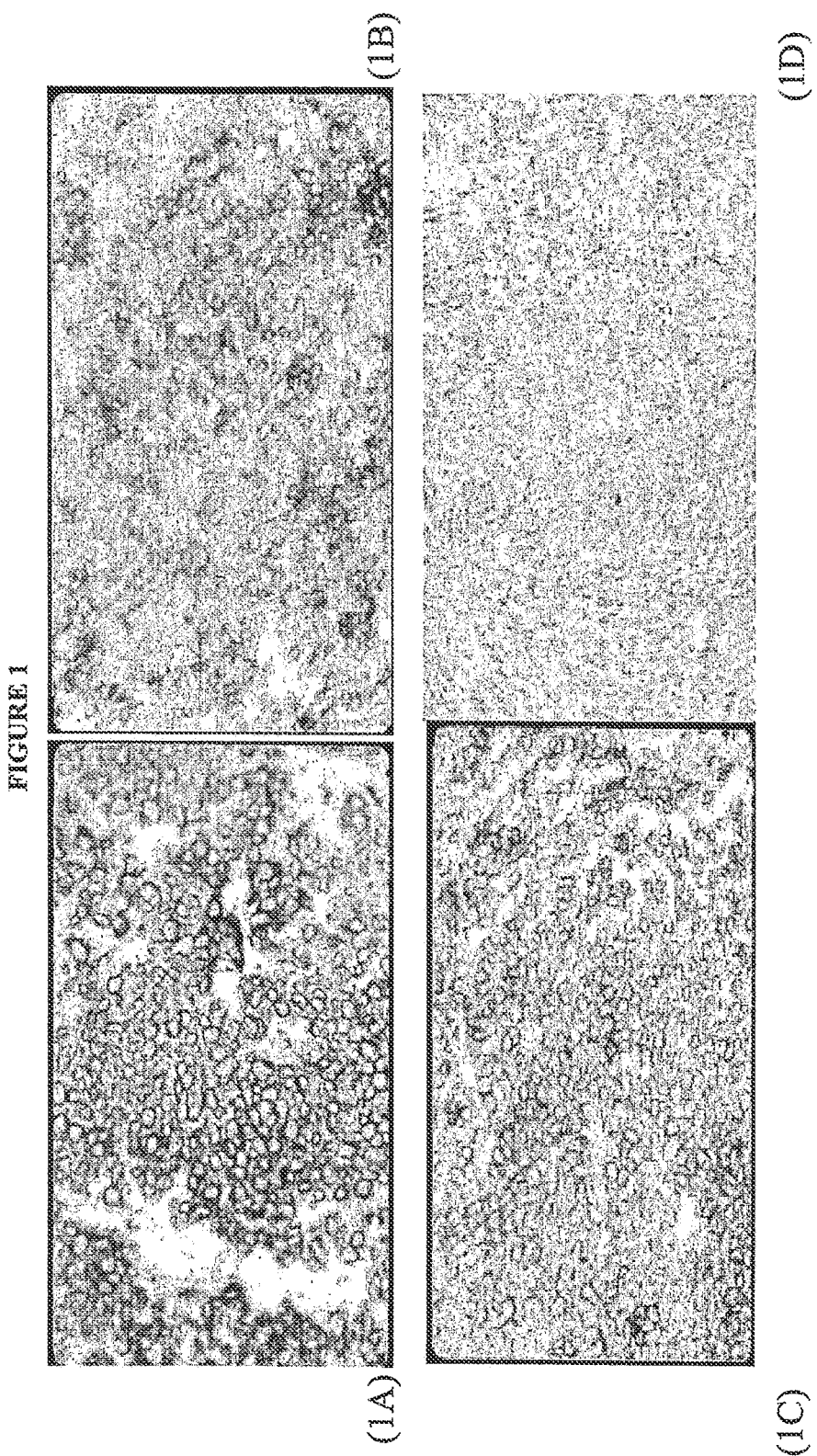

| WO | WO 03/075846 | 9/2003 |
|---|---|---|
| WO | WO 2004/050849 | 6/2004 |

OTHER PUBLICATIONS

Czuczman, M. S. et al., Treatment of patients with low-grade B-cell lymphoma with the combination of chimeric anit-CD20 monoclonal antibody and CHOP chemotherapy. J. Clin. Oncol., 17:268-276, 1999. (Exhibit 4).

Garin-Chesa, P. et al, Immunohistochemical analysis of neural cell adhesion molecules. Differential expressionin small round cell tumors of childhood and adolescence. Am. J. Pathol., 139:275-286, 1991. (Exhibit 5).

Ritter, G. et al, Ganglioside antigens expressed by human cancer cells. Semin. Cancer. Biol., 2:401-409, 1991. (Exhibit 6).

Ylagan et al., CD44 expression in astrocytic tumors. Modern Pathology, 10:1239-1246, 1997. (Exhibit 7).

Kuan, C. T. et al., 125I-labeled anti-epidermal growth factor receptor vIII single-chain Fv exhibits specific and high-level targeting of glioma xenografts. Clin. Can. Res., 5:1539-1549, 1999. (Exhibit 8).

Richardson, R. B. et al., Radioimmunolocalization of human brain tumors. Biodistribution of radiolabelled monoclonal antibody UJ13A. Eur J Nucl Med, 12:313-320, 1986. (Exhibit 9).

Papanastassiou, V. et al., Treatment of recurrent and cystic malignant gliomas by a single intracavitary injection of 131I-monoclonal antibody: Feasibility, pharmocokinetics and dosimetry. Br. J. Cancer, 67:144-151, 1993. (Exhibit 10).

Celis, E. et al., Induction of anti-tumor cytoxic T lymphocytes in normal humans using primary cultures and synthetic peptide epitopes. Proc. Natl. Acad. Sci. USA, 91:2105-2109, 1994. (Exhibit 11).

Riva, P. et al., 131I radioconjugated antibodies for the locoregional radioimmunotherapy of high-grade malignant glioma-phase I and II study. Acta Oncol, 38:351-359 1999. (Exhibit 12).

Heiner, J. et al., Localization of GD2 specific monoclonal antibody in human osteogenic sarcoma. Cancer Res., 47:5377-5381, 1987. (Exhibit 13).

Spendlove, I. et al., Decay accelerating factor (CD55): a target for cancer vaccines? Cancer Res., 59:2282-2286, 1999. (Exhibit 14).

Weidner, N. et al., Immunohistochemical profile of monoclonal antibody O13 that recognizes glycoprotein 930/32MIC2 and is useful in diagnosing ewing's sarcoma and peripheral neuroepithelioma. American Journal on Surgical Pathology, 18:486-494, 1994. (Exhibit 15).

Hatzubai, A. et al., The use of a monoclonal anti-idiotype antibody to study the biology of human B-cell lymphoma. J. Immunol., 126:3297-2402, 1981. (Exhibit 16).

Cheung, N. K. et al., Monoclonal antibodies to a glycolipid antigen on human neuroblastoma cells. Cancer Res., 45:2642-2649, 1985. (Exhibit 17).

Kramer, K. et al., Prognostic value of TrkA protein detection my monoclonal antibody 5C3 in Neuroblastoma. Clin. Can. Res., 2:1361-1367, 1996. (Exhibit 18).

Hecht, T. T. et al., Production and characterization of a monoclonal antibody that binds reed-sternberg cells. J. Immunol., 134:4231-4236, 1985. (Exhibit 19).

Seeger, R. C. et al., Danon, Y. L., Rayner, S. A., Hoover, F. Definition of Thy-1 determinant on human neuroblastoma, glioma, sarcoma, and teratoma cells with a monoclonal antibody. J. Immunol., 128:983-989, 1982. (Exhibit 20).

Kaaijk, P. et al., Expression of CD44 splice variants in human primary brain tumors. Journal of Neuro-Oncology, 26:185-190, 1995. (Exhibit 21).

Wikstrand, C. J. et al., Lactotetraose seris ganglioside 3', 6'-isoLD1 in tumors of central nervous and other systems in vitro and in vivo. Cancer Res., 53:120-126, 1993. (Exhibit 22).

Pappo, A. et al., Biology and treatment. Pediatr. Clin. North Am., 44:953-972, 1997. (Exhibit 23).

Fujisawa, T. et al., A monoclonal antibody with selective immunoreactivity for neuroblastoma and rhabdomyosarcoma. Proc. Am. Assoc. Cancer Res., 30:345, 1989, (Exhibit 24).

Wikstrand, C. J. et al., Monoclonal Antibodies against EGFRvIII are Tumor Specific and React with Breast and Lung Carcinomas and Malignant Gliomas. Cancer Res., 44:3140-48, 1995. (Exhibit 25).

Kishima, H. et al., Monoclonal antibody ONS-21 recognizes integrin a3 in gliomas and gliomas and medulloblastomas. Br. J. Cancer, 79:333-339, 1998. (Exhibit 26).

Moriuchi, S. et al., Characterizaton of a new mouse monoclonal antibody (ONS-M21) reactive with both medulloblastomas and gliomas. Br. J. Cancer, 68:831-837, 1993. (Exhibit 27).

Kondo, S. et al., Human glioma-specific antigens detected by monoclonal antibodies. Neurosurgery, 30:506-511, 1992. (Exhibit 28).

Dastidar, S. G. et al., Monoclonal antibody against human glioblastoma multiforme (U-87Mg) immunoprecipitates a protein of monoclonal mass 38Kda and inhibits tumor growth in nude mice. J. Neuroimmuno, 56:91-98, 1995. (Exhibit 29).

Mihara, Y. et al., Monoclonal antibody against ependymoma-derived cell line. Journal of Neuro-Oncology, 12:1-11, 1992. (Exhibit 30).

Daghighian, F. et al., Development of a method to measure kinetics of radiolabeled monoclonal antibody in human tumour with applications to microdosimetry: positron emission tomography studies of iodine-124 labeled 3F8 monoclonal antibody in glioma. Eur J Nucl Med, 20:402-409, 1993. (Exhibit 31).

Plate, K. H. et al., Platelet derived growth factor b is induced during tumor development and upregulated during tumor progressing in endothelial cells in human gliomas. Lab. Invest., 67:529-534, 1992. (Exhibit 32).

Yang, H. S. et al., Expression of 300-kilodalton intermediate filament-associated protein distinguishes human glioma cells from normal astrocytes. Proceedings of the National Academy of Sciences of the United States of America, 90:8534-8537, 1993. (Exhibit 33).

Koehler G et al., Continuous culture of fused cells secreting antibody of pre-defined specificity. Nature 256:495-496, 1975 (Exhibit 34).

Moffat R et al., Clinical utility of external immunoscintigraphy with the IMMU-4 techetium-99m Fab' antibody fragment in patients undergoing surgery for carcinoma of the colon and rectum:results of a pivotal, phase III trial. The Immunomedics Study Group. J Clin Oncol 14(8): 2295-2305, 1996 (Exhibit 35).

Maloney DG et al., IDEC-C2B8: Results of a phase I multiple-dose trial in patients with relapsed non-hodgkin's lymphoma. J Clin Oncol 15:3266-3274, 1997 (Exhibit 36).

Cobleigh MA et al., Multinational study of the efficacy and safety of humanized anti-HER2 monoclonal antibody in women who have HER2-overexpressing metastatic breast cancer that has progressed after chemotherapy for metastatic disease. J Clin Oncol 17:2639-2648, 1999 (Exhibit 37).

Meredith RF et al., Phase II study of dual 131I-labeled monoclonal antibody therapy with interferon in patients with metastatic colorectal cancer. Clin Can Res 2:1811-1818, 1996 (Exhibit 38).

Yeh SD et al., Radioimmunodetection of neuroblastoma with iodine-131-3F8: Correlation with biopsy, iodine-131-Metaiodobenzylguanidine (MIBG) and standard diagnostic modalities. J Nucl Med 32:769-776, 1991 (Exhibit 39).

Wheldon TE et al., The curability of tumors of differing size by targeted radiotherapy using 131-I or 90-Y. Radiother Oncol 21:91-99, 1991 (Exhibit 40).

Wilder RB et al., Radioimmunotherapy: recent results and future directions. J Clin Oncol 14:1383-1400, 1996 (Exhibit 41).

Zalutsky MR et al., Radioimmunotherapy of neoplastic meningitis in rats using an alpha-particle-emitting immunoconjugate. Cancer Res 54:4719-4725, 1994 (Exhibit 42).

McDevitt MR et al., Radioimmunotherapy with alpha-emitting nuclides. Eur J Nucl Med 25:1341-1351, 1998 (Exhibit 43).

DeNardo SJ et al., Antibody phage libraries for the next generation of tumor targeting radioimmunotherapeutics. Clin Can Res 5:3213s-3218s, 1999 (Exhibit 44).

DeNardo SJ et al., Phage Library-derived human anti-TETA anti anti-DOTA ScFv for pretargeting RIT. Hybridoma 18:13-21, 1999 (Exhibit 45).

(56) References Cited

OTHER PUBLICATIONS

Eshhar Z et al., Specific activation and targeting of cytotoxic lymphocytes through chimeric single chains consisting of antibody-binding domains and the or zeta subunits of the immunoglobulin and T-cell receptors. Proc Natl Acad Sci USA 90:720-24, 1993 (Exhibit 46).

Altenschmidt U et al., Cytolysis of tumor cells expressing the Neu/erbB-2, erbB-3, and erbB-4 receptors by genetically targeted I T lymphocytes. Clin Can Res 2:1001-1008, 1996 (Exhibit 47).

Krause A et al., Antigen-dependent CD-28 signaling enhances survival and proliferation in genetically modified activated human primary T lymphocytes. J Exp Med 188:619-626, 1998 (Exhibit 48).

Price MR et al., Characteristics of the cell surface antigen p72, associated with a variety of human tumors and mitogen-stimulated T-lymnphoblasts. FEBS Letters 171:31-35, 1984 (Exhibit 49).

Gorlick R et al., Expression of HER2/erbB-2 correlates with survival in osteosarcoma. J Clin Oncol 17:2781-2788, 1999 (Exhibit 50).

Cheung NK et al., Detection of metastatic neuroblastoma in bone marrow: when is routine marrow histology insensitive? J Clin Oncol 15:2807-2817, 1997 (Exhibit 51).

Ghossein RA et al., Detection of circulating prostatic tumor cells using immunobead reverse transcriptase polymerase chain reaction for prostatic specific membrane antigen mRNA. Diag Mol Path 8:59-65, 1999 (Exhibit 52).

Leung W et al., Frequent detection of tumor cells in hematopoietic grafts in Neuroblastoma and ewing's sarcoma. Bone Marrow Transpl 22:971-979, 1998 (Exhibit 53).

Mueller BM et al., Enhancement of antibody-dependent cytotoxicity with a chimeric anti-GD2 antibody. J Immunol 144:1382-1386, 1990 (Exhibit 54).

Santos AD et al., Generation and characterization of a single gene-encoded single-chain-tetravalent antitumor antibody. Clin Can Res 5:3118s-3123s, 1999 (Exhibit 55).

Guo HF et al., Recombinant anti-ganglioside GD2 scFv-streptavidin fusion protein for tumor pretargeting. Proc Am Assoc Cancer Res 37:469, 1996 (abstract) (Exhibit 56).

Fagnou C et al., Presence of tumor cells in bone marrow but not in blood is associated with adverse prognosis in patients with ewing's tumor. J Clin Oncol 15:1707-1711, 1998 (Exhibit 57).

Munn DH et al., Interleukin-2 enhancement of monoclonal antibody-mediated cellular cytotoxicity (ADCC) against human melanoma. Cancer Res 47:6600-6605, 1987 (Exhibit 58).

Hank JA et al., Augmentation of antibody dependent cell mediated cytotoxicity following in vivo therapy with recombinant interleukin-2. Cancer Res 50:5234-5239, 1990 (Exhibit 59).

Kushner BH et al., GM-CSF enhances 3F8 monoclonal antibody-dependent cellular cytotoxicity against human melanoma and neuroblastoma. Blood 73:1936-1941, 1989 (Exhibit 60).

Saarinen UM et al., Eradication of neuroblastoma cells in vitro by monoclonal antibody and human complement: method for purging autologous bone marrow. Cancer Res 45:5969-5975, 1985 (Exhibit 62).

Munn DH et al., Antibody-dependent antitumor cytotoxicity by human monocytes cultured with recombinant macrophage colony-stimulating factor. Induction of efficient antibody-mediated antitumor cytotoxicity not detected by isotope release assays. J Exp Med 170:511-526, 1989 (Exhibit 63).

Munn DH et al., Phagocytosis of tumor cells by human monocytes cultured in recombinant macrophage colony-stimulating factor. J Exp Med 172:231-237, 1990 (Exhibit 64).

Sabzevari H et al., A recombinant antibody-interleukin 2 fusion protein suppresses growth of hepatic human neuroblastoma metastases in severe combined immunodeficient mice. Proceeds of the National Academy of Science USA 91:9626-9630, 1994 (Exhibit 65).

Mujoo K et al., A potent and specific immunotoxin for tumor cells expressing disialoganglioside GD2. Cancer Imumnol Immunother 34:198-204, 1991 (Exhibit 66).

Gottstein C et al., Antidisialoganglioside Ricin A-chain immunotoxins show potent anti-tumor effects in vitro and in a disseminated human neuroblastoma severe combined immunodeficiency mouse model. Cancer Res 54:6186-6193, 1994 (Exhibit 67).

Holzer U et al., Superantigen-staphylococcal-enterotoxin-A-dependent and antibody-targeted lysis of GD2-positive neuroblastoma cells. Cancer Immunol Immunother 41:129-136, 1995 (Exhibit 68).

Cheung NK et al., Ganglioside GD2 specific monoclonal antibody 3F8—a phase I study in patients with neuroblastoma and malignant melanoma. J Clin Oncol 5:1430-1440, 1987 (Exhibit 69).

Cheung NK et al., Reassessment of patient response to monoclonal antibody 3F8. J Clin Oncol 10:671-672, 1992 (Exhibit 70).

Murray JL et al., Phase I trial of murine monoclonal antibody 14G2a administered by prolonged intravenous infusion in patients with neuroectodermal tumors. J Clin Oncol 12:184-193, 1994 (Exhibit 71).

Uttenreuther-Fischer MM et al., Pharmacokinetics of anti-ganglioside GD2 mAb 14G2a in phase 1 trial in pediatric cancer patients. Cancer Immunol Immunother 41:29-36, 1995 (Exhibit 72).

Handgretinger R et al., A phase I study of neuroblastoma with the anti-ganglioside GD2 antibody 14.G2a. Cancer Immunol Immunother 35:199-204, 1992 (Exhibit 73).

Miraldi FD et al., Diagnostic imaging of human neuroblastoma with radiolabeled antibody. Radiology 161:413-418, 1986 (Exhibit 74).

Arbit E et al., Quantitative Immunoimaging of gliomas in humans with anti-ganglioside monoclonal antibodies. J Neurosurg 76:399a, 1991 (Exhibit 75).

Grant SC et al., Radioimmunodetection of small-cell lung cancer using the anti-GD2 ganglioside monoclonal antibody 3F8: a pilot trial. Eur J Nucl Med 23:145-149, 1996 (Exhibit 76).

Larson SM et al., PET scanning of iodine-124-3F8 as an approach to tumor dosimetry during treatment planning for radioimmunotherapy in a child with neuroblastoma. J Nucl Med 33:2020-2023, 1992 (Exhibit 77).

Pentlow KS et al., Quantitative imaging of I-124 using positron emission tomography with applications to radioimmunodiagnosis and radioimmunotherapy. Medical Physics 18:357-366, 1991 (Exhibit 78).

Pentlow KS et al., Quantitative imaging of iodine-124 with PET. J Nucl Med 37:1557-1562, 1996 (Exhibit 79).

Saleh MN et al., A phase I trial of the murine monoclonal anti-GD2 antibody 14.G2a in metastatic melanoma. Cancer Res 52:4342-4347, 1992 (Exhibit 80).

Cheung NK et al., Antibody response to murine anti-G132 monoclonal antibodies: Correlation with patient survival. Cancer Res 54:2228-2233, 1994 (Exhibit 81).

Drengler RL et al., Phase I and pharmacokinetic trial of oral irinotecan administered daily for 5 days every 3 weeks in patients with solid tumors. J Clin Oncol 17:685-696, 1999 (Exhibit 82).

Cheung NK et al., Complete tumor ablation with iodine 131-radiolabeled disialoganglioside GD2 specific monoclonal antibody against human neuroblastoma xenografted in nude mice. J Natl Cancer Inst 77:739-745, 1986 (Exhibit 83).

Cheung NK et al., Disialoganglioside GD2 anti-idiotypic monoclonal antibodies. Int J Cancer 54:499-505, 1993 (Exhibit 84).

Loh A et al., A pharmacokinetic model of 131I-G250 antibody in patients with renal cell carcinoma. J Nucl Med 3:484-489, 1998 (Exhibit 85).

Kolbert KS et al., Implementation and evaluation of patient-specific three dimensional internal dosimetry. J Nucl Med 38:301-308, 1997 (Exhibit 86).

Sgouros G et al., Bone marrow dosimetry: Regional variability of marrow-localizing antibody. J Nucl Med 37:695-698, 1996 (Exhibit 87).

Sgouros G et al., Marrow and whole-body absorbed dose vs marrow toxicity following 131I-G250 antibody therapy in patients with renal-cell carcinoma. J Nucl Med 38:252P, 1997 (Exhibit 88).

Furhang EE et al., Radionuclide photon dose kernels for internal emitter dosimetry. Medical Physics 23:759-764, 1996 (Exhibit 89).

Furhang EE et al., A monte carlo approach to patient-specific dosimetry. Medical Physics 23:1523-1529, 1996 (Exhibit 90).

Furhang EE et al., Implementation of a monte carlo dosimetry method for patient-specific internal emitter therapy. Medical Physics 24:1163-1172, 1997 (Exhibit 91).

(56) References Cited

OTHER PUBLICATIONS

Scott AM et al., Image registration of SPECT and CT images using an external fiduciary band and three-dimensional surface fitting in metastatic thyroid cancer. J Nucl Med 36:100-103, 1995 (Exhibit 92).

Sgouros G et al., Three-dimensional dosimetry for radioimmunotherapy treatment planning. J Nucl Med 34:1595-1601, 1993 (Exhibit 93).

Arndt CA et al., Common musculoskeletal tumors of childhood and adolescence. N Engl J Med. 1999;341:342-52 (Exhibit 94).

West DC et al., Detection of circulating tumor cells in patients with Ewing's sarcoma and peripheral primitive neuroectodermal tumor. J Clin Oncol. 1997;15:583-8 (Exhibit 95).

de Alava E et al., Ewing family tumors: potential prognostic value of reverse-transcriptase polymerase chain reaction detection of minimal residual disease in peripheral blood samples. Diagn Mol Pathol. 1998;7:152-7 (Exhibit 96).

Toretsky JA et al., Detection of (11;22)(q24;q12) translocation-bearing cells in peripheral blood progenitor cells of patients with Ewing's sarcoma family of tumors. J Natl Cancer Inst. 1995;87:385-6. (Exhibit 97).

Burdach S et al., Myeloablative radiochemotherapy and hematopoietic stem-cell rescue in poor prognosis Ewing's sarcoma. J Clin Oncol. 1993;11:1482-8. (Exhibit 98).

Chan KW et al., High-dose sequential chemotherapy and autologous stem cell reinfusion in advanced pediatric solid tumors. Bone Marrow Transplant. 1997;20:1039-43. (Exhibit 99).

Fischmeister G et al., Low incidence of molecular evidence for tumour in PBPC harvests from patients with high risk Ewing tumours. Bone Marrow Transplant. 1999;24:405-9. (Exhibit 100).

Horowitz ME et al., Total-body irradiation and autologous bone marrow transplant in the treatment of high-risk Ewing's sarcoma and rhabdomyosarcoma. J Clin Oncol. 1993;11:1911-8. (Exhibit 101).

Perentesis J et al., Autologous stem cell transplantation for high-risk pediatric solid tumors. Bone Marrow Transplant. 1999;24:609-15. (Exhibit 102).

Chirgwin JM et al., Isolation of biologically active ribonucleic acid from sources enriched in ribonuclease. Biochemistry. 1979;18:5294-9. (Exhibit 103).

Mackall CL, et al., Pathways of T-cell regeneration in mice and humans: implications for bone marrow transplantation and immunotherapy. Immunol Rev. 1997;157:61-72. (Exhibit 104).

Vogel W et al., Clinical applications of CD34 (+) peripheral blood progenitor cells (PBPC). Stem Cells. 2000;18:87-92. (Exhibit 105).

Dyson PG et al., CD34+ selection of autologous peripheral blood stem cells for transplanation following sequential cycles of high-dose therapy and mobilization in multiple myeloma [In Process Citation]. Bone Marrow Transplant. 2000;25:1175-84. (Exhibit 106).

Emig M et al., Accurate and rapid analysis of residual disease in patients with CML using specific fluorescent hybridization probes for real time quantitative RT-PCR. Leukemia. 1999;13:1825-32. (Exhibit 107).

Mensink E et al., Quantitation of minimal residual disease in Philadelphia chromosome positive chronic myeloid leukaemia patients using real-time quantitative RT-PCR. Br J Haematol. 1998;102:768-74. (Exhibit 108).

Pongers-Willemse MJ et al., Real-time quantitative PCR for the detection of minimal residual disease in acute lymphoblastic leukemia using junctional region specific TaqMan probes. Leukemia. 1998;12:2006-12. (Exhibit 109).

Branford S et al., Monitoring chronic myeloid leukaemia therapy by real-time quantitative PCR in blood is a reliable alternative to bone marrow cytogenetics. Br J Haematol. 1999;107:587-99. (Exhibit 110).

Chang H.R. et al., Expression of disialogangliosides $G_{D2}$ and $G_{D3}$ on human soft tissue sarcomas. Cancer 70: 633-8, (1992) (Exhibit 111).

Froberg, K. et al., Intra-abdominal desmoplastic small round cell tumor: immunohistochemical evidence for up-regulation of autocrine and paracrine growth factors. Ann Clin Lab Sci 29: 78-85, 1999 (Exhibit 112).

Heiner, J.P. et al., Localization of $G_{D2}$-specific monoclonal antibody 3F8 in human osteosarcoma. Cancer Res. 47: 5377-81 (1987) (Exhibit 113).

Kushner, B.H. et al., Desmoplastic small round-cell tumor: prolonged progression-free survival with aggressive multimodality therapy. J.Clin. Oncol. 14: 1526-31, (1996) (Exhibit 114).

Ladanyi, M. et al., Fusion of EWS and WT1 genes in the demoplastic small round cell tumor. Cancer Res. 54: 2837-40, (1994) (Exhibit 115).

Gerald, W.L. et al., Intrabdominal demoplastic small round cell tumor. Report of 19 cases of a distinctive type of high-grade polyphenotypic malignancy affecting young individuals. Am. L. Surg. Pathol. 15, 499-513, (1991) (Exhibit 116).

Gerald, W.L. et al., Clinical patholgic, and molecular spectrum of tumors associated with t(11;22) (p13;q12): demoplastic small round-cell tumor and its variants. J. Clin. Oncol., 16: 3028-36, (1998) (Exhibit 117).

Ordonez, N.G. et al., Intra-abdominal desmoplastic small cell tumor: a light microscopic, immunocytochemical, ultrastructural, and flow cytometric study. Hum. Pathol. 24, 850-65, (1993) (Exhibit 118).

Ordonez, N.G. et al., Desmoplastic small round cell tumor: II: an ultrastructural and immunohistochemical study with emphasis on new immunohistochemical markers. Am. J. Surg. Pathol. 22: 1314-27, (1998) (Exhibit 119).

Stancovski, I. et al., Targeting of T lymphocytes to Neu/HERe-expressing cells using chimeric single chain Fv receptors. J Immunol, 151: 6577-6582, 1993. (Exhibit 146).

Moritz, D. et al., Cytotoxic T lymphocytes with a grafted recognition specificity for ERBB2-expressing tumor cells. Proc. Natl Acad Sci, USA, 91: 4318-4322, 1994. (Exhibit 147).

Wels, W. et al., Biotechnological and gene therapeutic strategies in cancer treatment. Gene, 159: 73-80, 1995. (Exhibit 148).

Eshhar, Z. et al., Functional expression of chimeric receptor genes in human T cells. J Immunol Methods, 248: 67-76, 2001. (Exhibit 149).

Wei, M. X. et al., Experimental tumor therapy in mice using the cyclophosphamide-activating cytochrome P450 2B1 gene. Hum Gene Ther, 5: 969, 1994. (Exhibit 150).

Weijtens, M. E. et al., Single chain Ig/gamma gene-redirected human T lymphocytes produce cytokines, specifically lyse tumor cells, and recycle lytic capacity. J Immunol, 157: 836-843, 1996. (Exhibit 151).

Finney, H. M. et al., Chimeric receptors providing both primary and costimulatory signaling in T cells from a single gene product. J Immunol, 161: 2791-2797, 1998. (Exhibit 152).

Koehne, G. et al., Rapid selection of antigen-specific T lymphocytes by retroviral transduction. Blood, 96: 109-117, 2000. (Exhibit 153).

Bunnell, B. A. et al., National High-efficiency retroviral-mediated gene transfer into human nonhuman primate peripheral blood lymphocytes. Proceeds of the Academy of Science,USA, 92: 7739-7743, 1995. (Exhibit 154).

Miller, A. D. et al., Construction and properties of retrovirus packaging cells based on gibbon ape leukemia virus. J Virol, 1991: 2220-2224, 1991. (Exhibit 155).

Lam, J. S. et al., Improved gene transfer into human lymphocytes using retroviruses with gibbon ape leukemia virus envelope. Hum Gene Ther, 7: 1415-1422, 1996. (Exhibit 156).

Bonini, C. et al., HSV-TK gene transfer into donor lymphocytes for control of allogeneic graft-versus-leukemia. Science, 276: 1719-1723, 1997. (Exhibit 157).

Pollok, K. E. et al., High-efficiency gene transfer into normal and adenosine deaminase-deficient T lymphocytes is mediated by transduction on recombinant fibronectin fragments. J Virol, 72: 4882-4892, 1998. (Exhibit 158).

Galea-Lauri, J. et al., Expression of a variant of CD28 on a subpopulation of human NK cells: implications for B7-mediated stimulation of NK cells. J Immunol, 163: 62-70, 1999. (Exhibit 159).

Patel, S. D. et al., Impact of chimeric immune receptor extracellular protein domains on T cell function. Gene Therapy, 6: 412-419, 1999. (Exhibit 160).

Fitzer-Attas, C. J. et al., Harnessing Syk familytyrosine kinases as signaling domains for chimeric single chain of the variable domain receptors: optional design for T cell activation. J Immunol, 160: 145-154, 1998. (Exhibit 161).

(56) References Cited

OTHER PUBLICATIONS

Varez-Vallina, L. et al., Efficient discrimination between different densities of target antigen by tetracycline-regulatable T bodies. Hum Gene Ther, 10: 559-563, 1999. (Exhibit 162).
Yee, C. et al., In vivo tracking of tumor-specific T cells. Curr Opin Immunol, 13: 141-146, 2001. (Exhibit 163).
Xiaoning, R. T. et al., Rapid death of adoptively transferred T cells in acquired immunodeficiency syndrome. Blood, 93: 1506-1510, 1999. (Exhibit 164).
Riddell, S. R. et al., T-cell mediated rejection of gene-modified HIV-specific cytotoxic T lymphocytes in HIV-infected patients. Nat Med, 2: 216-223, 1996. (Exhibit 165).
Crist W et al., The Third Intergroup Rhabdomyosarcoma Study J Clin Oncol 13:610-30, 1995 (Exhibit 166).
Maurer HM et al., The Intergroup Rhabdomyosarcoma Study-II. Cancer 71:1904-22, 1993 (Exhibit 167).
Weigel BJ et al., Role of high-dose chemotherapy with hematopoietic stem cell rescue in the treatment of metastatic or recurrent rhabdomyosarcoma. J Pediatr Hematol Oncol 23:272-276, 2001 (Exhibit 168).
Kramer K et al., Targeted radioimmunotherapy for leptomeningeal cancer using (131)I-3F8. Med Pediatr Oncol 35:716-8, 2000 (Exhibit 169).
Kumar S et al., Myogenin is a specific marker for rhabdomyosarcoma: an immunohistochemical study in paraffin embedded tissues. Mod Pathol 13: 988-93, 2000 (Exhibit 170).
Gattenloehner S et al., The fetal form of the acetylcholine receptor distinguishes rhabdomyosarcomas from other childhood tumors. Am J Pathol. 152:437-44 1998 (Exhibit 171).
Truong LD et al., A study of 584 cases and review of the literature Am J Clin Pathol 93:305-14, 1990 (Exhibit 172).
Qualman SJ et al., Intergroup Rhabdomyosarcoma Study: update for pathologists Pediatr Dev Pathol 1:550-61, 1998 (Exhibit 173).
Strother DR et al., Expression of the 5.1 H11 antigen, a fetal muscle surface antigen, in normal and neoplastic tissue. Arch Pathol Lab Med 114:593-596, 1990 (Exhibit 174).
Merino ME et al., Immunomagnetic purging of ewing's sarcoma from blood and bone marrow: quantitation by real-time polymerase chain reaction. J Clin Oncol 19:3649-3659, 2001 (Exhibit 175).
International Search Report, Apr. 2, 2002 International Search Report from Patent Cooperation Treaty for International Patent Application Uses of Monoclonal Antibody 8H9 for Sloan-Kettering Institute for Cancer Research, et al. International application No. PCT/US01/32565, International Filing Date Oct. 18, 2001, claiming benefit of U.S. Appl. No. 60/241,344, filed Oct. 18, 2000, and U.S. Appl. No. 60/330,396, filed Oct. 17, 2001. (Exhibit 1).
Juhl, et al., Additive Cytotoxicity of Different Monoclonal Antibody-Cobra Venom Factor Conjugates for Human Neuroblastoma Cells, Immunobiology, Nov. 1997, vol. 197, pp. 444-459 (Exhibit 2).
Modak, et al., Radioimmunotargeting to Human Rhabdomyosarcoma (RMS) using Monoclonal-Antibody (MOAB) 8H9, Proceedings of the American Association for Cancer Research Annual Meeting, Mar. 2000 vol. 41 pp. 724, Abstract 4600. (Exhibit 3).
Xu, et al., Targeting and therapy of carcinoembryonic antigen-expressing tumors in transgenic mice with an antibody-interleukin 2 fusion protein, Cancer Res Aug. 15, 2000, vol. 60. No. 16, pp. 4475-4484, abstract only. (Exhibit 4).
Pegram, M. D., Slamon, D. J., Combination therapy with trastuzumab (Herceptin) and ciplatin for chemoresistant metastatic breast cancer: evidence for receptor-enhanced chemosensitivity. Sem. Oncol., 26:89-95, 1999. (Exhibit 5).
Bigner, D. D., et al., Iodine-131-labeled antitenascin monoclonal antibody 81C6 treatment of patients with recurrent malignant gliomas:phase I trial results. Journal Clincal Oncology, 16:2202-2212, 1998. (Exhibit 6).
Bruland, O. et al., New monoclonal antibodies specific for human sarcomas. Int J Cancer, 15:27-31, 1986. (Exhibit 7).
Wang, N. P. et al., Expression of myogenic regulatory proteins (myogenin and MyoD1) in small blue round cell tumors of childhood. Am. J. Pathol., 147:1799-1810, 1995. (Exhibit 8).
Bigner, D. D. et al., Phase I studies of treatment of malignant gliomas and neoplastic meningitis with 131 I radiolabeled monoclonal antibodies anti-tenascin 81C6 and anit-chondroitin proteoglycan sulfate Mel-14 (ab') 2—a preliminary report. J Neuro Oncol, 24:109-122, 1995. (Exhibit 9).
Mariani, G. et al., A pilot pharmacokinetic and immunoscintigraphic study with the technetium-99m-labeled monoclonal antibody BC-1 directed against oncofetal fibronectin in patients with brain tumors. Cancer Supplement, 80:2484-2489, 1997. (Exhibit 10).
DiMaggio JJ et al., Monoclonal antibody therapy of cancer. In: Pinedo HM, Chabner BA, Longo DL, (eds.): Cancer Chemotherapy and Biological Response Modifiers, Annual 11, Elsevier Science Publishers B.V., (Biomedical Division), 1990, pp. 177-203 (Exhibit 11).
Schlom J., Monoclonal Antibodies in cancer therapy: Basic principles. In: DeVita VT, Hellman S, Rosenberg SA, (eds.): Biologic therapy of cancer, 2nd ed. Philadelphia, J.B.Lippincott Co, 1995, pp. 507-520 (Exhibit 12).
Lode HN. et al., Immunocytokines: A promising approach to cancer immunotherapy. Pharmacology Therapeutics 80:277-292, 1998 (Exhibit 13).
Erikson HP. et al., Hexabrachion protein (tenascin, cytotactin, brachionectin) in connective tissues, embryonic tissues and tumors. Adv Cell Biol 2:55-90, 1988 (Exhibit 24).
Modak S. et al., Novel tumor-associated surface antigen: broad distribution among neuroectodermal, mesenchymal and epithelial tumors, with restricted distribution in normal tissues. Proceedings of ASCO 17:449a, 1998, Abstract 1716 (Exhibit 15).
Cheung NK. et al., Treatment of advanced stage neuroblastoma. In: Reghavan D, Scher HI, Leibel SA, Lange P, (eds.): Principles and Practce of Genitourinary Oncology. Philadelphia, J.B. Lippincott Company, 1997, pp. 1101-1111 (Exhibit 16).
Brodeur G.M. et al., Neuroblastoma. In: Pizzo PA, Poplack DG, (eds.): Principles and Practice of Pediatric Oncology, 3rd ed. Philadelphia. J.B. Lippincott Company, 1997, pp. 761-797 chapter 2 (Exhibit 17).
Cheung N.K.V. et al., Biological and molecular approaches to diagnosis and treatment. section I. Principles of Immunotherapy. In: Pizzo PA, Poplack DG, (eds.): Principles and Practice of Pediatric Oncology, 3rd ed. ed. Philadelphia, J.B. Lippincott Company, 1997, pp. 323-342 (Exhibit 18).
Larson S.M. et al., Antibodies in cancer therapy: Radioisotope conjugates. In: DeVita VT. Hellman S, Rosenberg SA, (eds.): Biologic Therapy of Cancer, 2nd ed. Philadelphia, J.B. Lippincott Co., 1995, pp. 534-552 (Exhibit 19).
Reisfeld R.A. et al., Potential of genetically engineered anti-ganglioside GD2 antibodies for cancer immunotherapy. In: Progress in Brain Search (Svennerhol,L, Asbury,AK, Reisfeld,RA, Sandhoff,K, Suzuki,K, Tettamani,G, Toffano,G, vol. 101. Cambridge, UK, Elsevier Trends Journals, 1994, pp. 201-212 (Exhibit 20).
Cheung N.K.V. et al., Decay-accelerating factor protects human tumor cells from complement-mediated cytotoxicity in vitro. J Clin Invest 81:1122-1128, 1988 (Exhibit 21).
Murray J.L. et al., Phase I trial of murine monoclonal antibody 14G2a administered by prolonged intravenous infusion in patients with neuroectodermal tumors. J Biol Resp Modif 1991 (Soc. Biol. Therapy Meeting Abstract 1991.) Journal of Clinical Oncology, vol. 12, No. 1 Jan. 1994; pp. 184-193 (Exhibit 22).
Ugur O. et al., Comparison of the targeting characteristics of various radioimmunoconjugates for radioimmunotherapy of neuroblastoma: Dosimetry calculations incorporating cross-organ beta doses. Nucl Med Biol 23:1-8 ,1996 (Exhibit 23).
Saleh M.N. et al., Phase I trial of the murine monoclonal anti-GD2 antibody 14G2a in metastatic melanoma. Cancer Research 52, 4342-4347, Aug. 15, 1992 (Exhibit 24).
Handgretinger R. et al., A phase I study of human/mouse chimeric antiganglioside GD2 antibody ch14.18 in patients with neuroblastoma. Eur J Cancer 31:261-267, 1995 (Exhibit 25).

(56) References Cited

OTHER PUBLICATIONS

Cheung N.K.V. et al., 3F8 monoclonal antibody treatment of patients with stage IV neuroblastoma: a phase II study. In: Evans AE, Guillio JD, Biedler JL, et al, (eds.): Advances in Neuroblastoma Research, vol. 4. New York, Wiley Liss, 1994, pp. 319-329 (Exhibit 26).

Yu A.L. et al., Phase I clinical trial of ch14.18 in patients with refractory neuroblastoma. Proc Am Soc Clin Oncol 10:318, 1991, Abstract 1118 (Exhibit 27).

Cheung N.K., Biological and Molecular Approaches to Diagnosis and Treatment. Immunotherapy. In: Pizzo PA, Poplack DG. (eds.): Principles and Practice of Pediatric Oncology, 2nd ed. Philadelphia, J.B.Lippincott Company, 1992, pp. 357-370 (Exhibit 28).

Cheung N.K.V. et al., 3F8 monoclonal antibody treatment of patients with stage IV neuroblastoma: A phase II Study. Int J Oncol 12:1299-1306, 1998 (Exhibit 29).

Cheung N.K. et al., Phase I study of radioimmunotherapy of neuroblastoma using iodine 131 labeled 3F8. In: Prog. Clin. Biol. Res: Advances in Neuroblastoma Research 4. New York, Wiley Liss, 1994, pp. 329 (Exhibit 30).

Kramer K. et al., Pharmacokinetics and acute toxicology of intraventricular $^{131}$I-monoclonal antibody targeting disialoganglioside in non-human primates. J Neuro Oncol 1996 (Exhibit 31).

Saleh M.N. et al., Phase I trial of chimeric anti-GD2 monoclonal antibody C14.18 in patients with metastatic melanoma. Hum. Antibod. Hybridomas, 1992, vol. 3, January (Exhibit 32).

Cheung I.Y. et al., Induction fo Ab3' following anti-GD2 monoclonal antibody 3F8 therapy predicts survival among patients (pts) with advanced neuroblastoma. Proc Am Assoc Cancer Res 40:574, 1999, Abstract 3787 (Exhibit 33).

Chen S. et al., Surface antigen expression and complement susceptibility of differentiated neuroblastoma clones. Am J Pathol In press:, 1999 (Exhibit 34).

Sgouros G. et al., Hematolgoic toxicity in radioimmunotherapy: An evaluation of different predictive measures. J Nucl Med 37:43P-44P, 1996, Abstract 165 (Exhibit 35).

Sgouros G. et al., Treatment planning for internal emitter therapy: methods, applications and clinical implications. 1996 (Exhibit 36).

Sgouros G. et al., Yttrium-90 biodistribution by yttrium-87 imaging: a feasibility analysis. Medical Physics 25(8), Aug. 1998 (Exhibit 37).

Meyer C.R. et al., Demonstration of accuracy and clinical versatility of mutual information for automatic multimodality image fusion using affine and thin-plate spline warped geometric deformations. Medical Image Analysis 1:195-206, 1997 (Exhibit 38).

Burdach S. et al., Myeloablative therapy, stem cell rescue and gene transfer in advanced Ewing tumors. Bone Marrow Transplant. 1996;18 Suppl 1:S67-8. (Exhibit 39).

Ladenstein R. et al., Impact of megatherapy in children with high-risk Ewing's tumours in complete remission: a report from the EBMT Solid Tumour Registry [published erratum appears in Bone Marrow Transplant Sep. 1996;18(3):675]. Bone Marrow Transplant. 1995;15:697-705. (Exhibit 40).

Ladenstein R. et al., Autologous stem cell transplantation for solid tumors in children. Curr Opin Pediatr. 1997; 9:55-69. (Exhibit 41).

Laws H.J. et al., Multimodality diagnostics and megatherapy in poor prognosis Ewing's tumor patients. A single-center report. Strahlenther Onkol. 1990;175:488-94. (Exhibit 42).

Pape H. et al., Radiotherapy and high-dose chemotherapy in advanced Ewing's tumors. Strahlenther Onkol. 1999; 175:484-7. (Exhibit 43).

Pession A. et al., Phase I study of high-dose thiotepa with busulfan, etoposide, and autologous stem cell support in children with disseminated solid tumors. Med Pediatr Oncol. 1999; 33:450-4. (Exhibit 44).

Stewart D.A. et al., High-dose melphalan +/− total body irradiation and autologous hematopoietic stem cell rescue for adult patients with Ewing's sarcoma or peripheral neuroectodermal tumor. Bone Marrow Transplant. 1996; 18:315-8. (Exhibit 45).

Rill D.R. et al., Direct demonstration that autologous bone marrow transplantation for solid tumors can return a multiplicity of tumorigenic cells. Blood. 1994; 84:380-3. (Exhibit 46).

Brenner M.K. et al., Gene-marking to trace origin of relapse after autologous bone-marrow transplantation. Lancet. 1993; 341:85-6. (Exhibit 47).

Mackall C. et al., Combined Immune Reconstitution/Tumor Vaccination to induce anti-tumor immune responses in the setting of minimal residual neoplastic disease [abstract]. Blood. 1999; 94:133a, Abstract 586 (Exhibit 48).

Quinones R.R. et al., Extended-cycle elutriation to adjust T-cell content in HLA-disparate bone marrow transplantation. Blood. 1993; 82:307-17. (Exhibit 49).

Kontny H.U. et al., Simultaneous expression of Fas and nonfunctional Fas ligand in Ewing's sarcoma. Cancer Res. 1998; 58:5842-9. (Exhibit 50).

de Wynter R.A. et al., Comparison of purity and enrichment of CD34+ cells from bone marrow, umbilical cord and peripheral blood (primed for apheresis) using five separation systems. Stem Cells. 1995; 13:524-32. (Exhibit 51).

Dworzak M.N. et al., Plow cytometric assessment of human MIC2 expression in bone marrow, thymus, and peripheral blood. Blood. 1994; 83:415-25. (Exhibit 52).

De Leij, et al., SCLC-cluster-2 antibodies detect the pancarcinoma/epithelial glycoprotein E GP-2 (supplement) Int. J. Cancer 8: 60-3, 1994 (Exhibit 53).

Willian L. et al., Intra-abdominal desmoplastic small round-cell tumors: report of 19 cases of distinctive type of high-grade polyphenotypic malignancy affecting young individuals Am. J. Surg. Pathol. 15(6): 499-513, (1991) (Exhibit 54).

Lee, S.B. et al., The EWS-WT1 translocation product induces PDGFA in desmoplastic small round-cell tumour. Nat Genet 17, 309-13, 1997 (Exhibit 55).

Daniel, P. T. et al., Costimulatory signals through B7.1/CD28 prevent T cell apoptosis during target cell lysis. J Immunol, 159: 3808-3815, 1997. (Exhibit 60).

Hwu, P. et al., Lysis of ovarian cancer cells by human lymphocytes redirected with a chimeric gene comosed of an antibody variable region and the Fc-receptor gamma-chain. J. Exp. Med., 178: 361-369, 1993. (Exhibit 61).

Rosenberg, S. A., Cell transfer therapy: clinical applications. In: V. T. J. DeVita, S. Hellman, and S. A. Rosenberg (eds.), Biologic therapy of cancer, second edition, pp. 487-506. Philadelphia: J.B.Lippincott Company, 1995. (Exhibit 62).

Yang, A.-G. et al., A new class of antigen-specific killer cells. Nat Biotechnol, 15: 46-51, 1997. (Exhibit 63).

Culver, K. W. et al., In vivo gene transfer with retroviral vector-producer cells for treatment of experimental brain tumors. Science, 256: 1550, 1992. (Exhibit 64).

Jensen, M. et al., CD20 is a molecular target for scFvFc: receptor redirected T cells: implications for cellular immunotherapy of CD20+ malignancy. Biol Blood Marrow Transplant, 4: 75-83, 1998. (Exhibit 65).

Eshhar, Z. et al., Tyrosine kinase chimeras for antigen-selective T-body therapy. Adv Drug Deliv Rev, 31: 171-182, 1998. (Exhibit 66).

Valitutti, S. et al., Serial triggering of TCRs: a basis for the sensitivity and specificity of antigen recognition. Immunology Today, 18: 299-304, 1997. (Exhibit 67).

Ruymann F.B. et al., Progress in the diagnosis and treatment of rhabdomyosarcoma and related soft tissue sarcomas. Cancer Invest 18:223-241, 2000 (Exhibit 68).

Cheung N.K. et al., Targeting of ganglioside GD2 monoclonal antibody to neuroblastoma J Nuc Med 28:1577-83, 1987 (Exhibit 69).

Thomson B. et al., RT-PCR evaluation of peripheral blood, bone marrow and peripheral blood stem cells in children and adolescents undergoing VACIME chemotherapy for Ewing's sarcoma and alveolar rhabdomyosarcoma. Bone Marrow Transplant 24:527-33, 1999 (Exhibit 70).

Athale U.H. et al., Use of Reverse Transcriptase Polymerase Chain Reaction for Diagnosis and Staging of Alveolar Rhabdomyosarcoma, Ewing Sarcoma Family of Tumors, and Desmoplastic Small Round Cell Tumor. Am J Pediatr Hematol Oncol 23(2):99-104, 2001 (Exhibit 71).

(56) References Cited

OTHER PUBLICATIONS

Mackall C. et al., Targeting tumor specific translocations in sarcomas in pediatric patients for immunotherapy. Clin Orthop. 373:25-31, 2000 (Exhibit 72).
Gruchala A. et al., Rhabdomyosarcoma. Morphologic, immunohistochemical, and DNA study. Gen Diagn Pathol 1142:175-84, 1997 (Exhibit 73).
Kalebic T. et al., In vivo treatment with antibody against IGF-1 receptor suppresses growth of human rhabdomyosarcoma and down-regulates p34$^{cdc2}$. Cancer Res 54:5531-4, 1994 (Exhibit 74).
International Search Report for PCT/US03/07004, filed Mar. 6, 2003 for Sloan-Kettering Institute for Cancer Research et al., dated Jun. 7, 2005.
Supplemental European Search Report for EP 01 98 3999, filed May 16, 2003, for Sloan-Kettering Institute for Cancer Research et al., dated Jul. 26, 2005.
Modak, et al., "Disialoganglioside GD2 and antigen 8H9: Potential targets for antibody-based immunotherapy against desmoplastic small round cell tumor (DSRCT) and rhabdomyosarcoma (RMS)", Proceedings of the American Assosciation for Cancer Search Annual Meeting, vol. 40, Mar. 1999, p. 474.
Anja Krause, Hong Fen Guo, Jean-Baptiste Latouche, Cuiwen Tan, Nai-Kong V. Cheung, Michael Sadelain, Antigen-Dependent CD28 Signaling Selectively Enhances Survival and Proliferation in Genetically Modified Activated Human Primary T Lymphocytes, J. Exp. Med, vol. 188, No. 4, pp. 619-626 (1998).
Cheung Nai-Kong V. et al., "Anti-idiotypic Antibody Facilitates scFv Chimeric Immune Receptor Gene Transduction and Clonal Expansion of Human Lymphocytes for Tumor Therapy", Hybridoma and Hybridomics vol. 22, No. 4, pp. 209-218 (2003).
Cheung Nai-Kong V. et al., "Anti-idiotypic Antibody as the Surrogate Antigen for Cloning scFv and its Fusion Proteins", Hybridoma and Hybridomics vol. 21, No. 6, pp. 433-443 (2002).
Cheung Nai-Kong V., "Monoclonal Antibody-based Therapy for Neuroblastoma", Current Oncology Reports, vol. 2, No. 6, pp. 547-553 (2000).
International Patent Publication No. WO 02/32375 for Sloan-Kettering Institute for Cancer Research, Filed Oct. 18, 2001 for "Uses of Monoclonal Antibody 8H9".
Modak S., Guo H.F., Humm J.L., Smith-Jones P.M., Larson S.M., Cheung N.K., "Radioimmunotargeting of Human Rhabdomyosarcoma Using Monoclonal Antibody 8H9", Cancer Biother Radiopharm, 20(5):534-46 (2005).
Modak S., Guo H.F., Humm J., Larson S.M., Cheung N.K., "Novel Tumor Target for Antibody-based Therapy of Rhabdomyosarcoma and Other Pediatric Solid Tumors", Journal of Pediatric Hematology/Oncology 22(4) (2000).
Modak S., Gultekin S.H., Kramer K., Guo H.F., Rosenfeld M.R Ladanyi M., Larson S.M., Cheung Nai Kong V., "Novel Tumor-associated Surface Antigen: Broad Distribution among Neuroectodermal Mesenchymal and Epithelial Tumors with Restructured Distribution in Normal Tissues", Proceedings of ASCO vol. 17 (1998).
Modak S., Kramer K Gultekin S.H., Guo H.F., Larson S.M., Cheung N.K., "Monoclonal Antibody 8H9: Specific for a Novel Tumor Antigen on Human Neuroblastoma", Medical and Pediatric Oncology, vol. 35, No. 6 (2000).
Queen, et al. "A humanized antibody that binds to the interleukin receptor", Proc. Natl. Acad. Sci USA, vol. 86, pp. 10029-10033, Dec. 1989.
PCT International Preliminary Examination Report for Sloan-Kettering Institute for Cancer Research, Int'l Application No. PCT/US01/32565, Filed Oct. 18, 2001, Dated Apr. 27, 2006.
PCT Written Opinion of the International Preliminary Examining Authority for Sloan-Kettering Institute for Cancer Research, Int'l Application No. PCT/US01/32565, Filed Oct. 18, 2001, Dated Oct. 25, 2005.

PCT Application Publication No. PCT/US97/04427 for Sloan-Kettering Institute for Cancer Research et al., Filed Mar. 20, 1997 for "Single Chain FV Constructs of Anti-ganglioside GD", Published with International Search Report.
European Patent Office Supplementary Search Report for Sloan-Kettering Institute for the Cancer Research, Int'l No. PCT/US03/07004, Filed Mar. 4, 2003 Dated Oct. 25, 2005.
PCT Notification of Transmittal of International Search Report, Apr. 2, 2002, for Sloan-Kettering Institute for Cancer Research, Int'l App'l No. PCT/US01/32565, filed Oct. 18, 2001.
PCT Notification of Transmittal of the International Search Report, Dec. 22, 2003, for Sloan-Kettering Institute for Cancer Research, Int'l App'l No. PCT/US02/33331, filed Oct. 17, 2002.
Supplementary European Search Report, Oct. 12, 2005, for Sloan-Kettering Institute for Cancer Research, European App'l No. EP 02 80 1782, filed Apr. 23, 2004.
Supplementary European Search Report, Jul. 26, 2005, for Sloan—Kettering Institute for Cancer Research, European App'l No. EP 01 98 3999 filed May 16, 2003.
Supplementary European Search Report, Oct. 14, 2005, for Sloan-Kettering Institute for Cancer Research, European App'l No. EP 03 71 6369 filed Oct. 8, 2004.
EPO Communication, Jan. 16, 2006, Sloan-Kettering Institute for Cancer Research, European App'l No. EP 03 716 369.8 filed Oct. 8, 2004.
Alvarez-Vallina et al., 1996, "Antigen-specific targeting of CD28 receptors," European Journal of Immunology, 26(10):2304-2309.
Baxevanis et al., 2004, "Targeting of tumor cells by lymphocytes engineered to express chimeric receptor genes", Cancer Immunol Immunother, 53:893-903.
Botti et al., 1997, "Comparison of three different methods for radiolabelling human activated T lymphocytes", Eur. J. Nucl. Med. 24:497-504.
Curti, 1993, "Physical barriers to drug delivery in tumors", Crit. Rev. in Oncology/Hematology, 14:29-39.
Elliott et al., 1999, "SSTR2A is the dominant somatostatin receptor subtype expressed by inflammatory cells, is widely expressed and directly regulates T cell IFN-gamma release", Eur. J. Immunol. 29:2454-63.
Fisher et al., 1989, "Tumor localization of adoptively transferred indium-111 labeled tumor infiltrating lymphocytes in patients with metastatic melanoma", J. Clin. Oncol. 7:250-261.
Gong et al.,1994, "Characterization of a human cell line (NK-92) with phenotypical and functional characteristics of activated natural killer cells", Leukemia, 8:652-8.
Gura, T., 1998, "Systems for identifying new drugs are often faulty", Science, 278:1041-1042.
Heppeler et al., 1999, "Radiometal-labelled macrocyclic chelator-derivatized somatostatin analogue with superb tumour-targetting properties and potential for receptor-mediated internal radiotherapy," Chemistry—A European Journal, 5(7):1974-1981.
Heslop et al., 1997, "Adoptive cellular immunotherapy for EBV lymphoproliferative diseases", Immunological Reviews 157:217-222.
Heslop et al., 1996, "Long-term restoration of immunity against Epstein-barr virus infection by adoptive transfer of gene-modified virus-specific T lymphocytes", Nature Med., 2:551-555.
Hombach, A. et al., 1998, "Isolation of Single Chain Antibody Fragments with Specificity for Cell Surface Antigens by Phage Display Utilizing Internal Image Anti-Idiotypic Antibodies", J. Immunol. Methods, 218:53-61.
Jain, R.K., 1994, "Barriers to drug delivery in solid tumors", Sci. Am., 271:58-65.
Koehne et al, 2003, "Serial in vivo imaging of the targeted migration of human HSV-TK-transduced antigen-specific lymphocytes ", Nature Biotechnology, 21:405-413.
Koehne et al,, 2000, "Noninvasive Imaging of human radiolabeled antigen-specific donor T lymphocytes after adoptive immunotherapy in SCID-mice", Blood, 96:516a, abstract #2222.
Koprowski et al., 1984, "Human anti-idiotype antibodies in cancer patients: Is the modulation of the immune response beneficial for the patient?", Proc. Natl. Acad. Sci, USA, 81:216-219.

(56) References Cited

OTHER PUBLICATIONS

Kramer et al., 1997, "Pharmacokinetics and acute toxicology of intraventricular 131I-monoclonal antibody targeting disialoganglioside in non-human primates," J. Neuro. Oncol., 35:101-111.
Kundra et al., 2002, "Noninvasive monitoring of somatostatin receptor type 2 chimeric gene transfer", J. Nucl. Med. 43:405-12.
Lacerda et al., 1996, "Human Epstein-Barr virus (EBV)-specific cytoxic T lymphocytes home preferentially to and induce selective regressions of autologous EBV-induced B cell lymphoproliferations in xenografted C.B-17 Scid/Scid mice", J. Exp. Med., 183:1215-1228.
Ma et al., 2002, "Genetically engineered T cell as adoptive immunotherapy of cancer", in Giaccone G, Schilsky, R, Sondel, P. (ed), Cancer Chemotherapy and Biological Response Modifiers. Amsterdam, Elsevier Science B.V., chapter 15, pp. 315-341.
Maher et al., 2002, "Human T-lymphocyte cytoxity and proliferation directed by a single chimeric TCRzeta/CD28 receptor", Nat. Biotechnol. 20:70-5.
Maki et al., 2001, "Factors regulating the cytoxic activity of the human natural killer cell line, NK-92", J. Hematother. Stem Cell Res. 10:369-83.
McGuiness et al., 1999, "Anti-tumor activity of human T cells expressing the CC49-zeta chimeric immune receptor", Human Gene Therapy, 10:165-173.
Modak, et al., 1999, "Disialoganglioside GD2 and antigen 8H9: Potential targets for antibody-based immunotherapy against desmoplastic small round cell tumor (DSRCT) and rhabdomyosarcoma (RMS)", Proceedings of the American Association for Cancer Research Annual Meeting, #3133.
Papadopoulos et al., 1994, "Infusions of donor leukocytes to treat Epstein-Barr virus-associated lymphoproliferative disorders after allogeneic bone marrow transplantation", N. Engl. J. Med., 330:1185-1191.
Reinhold et al., 1999, "Specific lysis of melanoma cells by receptor grafted T cells is enhanced by anti-idiotypic monoclonal antibodies directed to scFv domain of the receptor", Journal of Investigative Dermatology, 112: 744-750.
Riddell et al., 1992, "Restoration of viral immunity in immunodeficient humans by the adoptive transfer of T cell clones", Science, 257:238-241.
Rosenberg et al., 1988, "A progress report on the treatment of 157 patients with advanced cancer using lymphokine-activated killer cells and interleukin-2 or high-dose interleukin-2 alone", N. Engl. J. Med., 316: 889-897.
Rossig et al., 2002, "Epstein-Barr virus=-specific human T lymphocytes expressing antitumor chimeric T-cell receptors potential for improved immunotherapy", Blood, 99:2009-16.
Rossig et al., 2001, "Targeting of G(D2)—positive tumor cells by human T lymphocytes engineered to express chimeric T-cell receptor genes", Int. J. Cancer, 94:228-36.
Schlebusch H., et. al., 1997, "Production of a Single-Chain Fragment of the Murine Anti-Idiotypic Antibody ACA125 as Phage-Displayed and Soluble Antibody by Recombinant Phage Antibody Technique", Hybridoma, 16(1):47-52.
Smanik et al., 1996, "Cloning of the human sodium iodide symporter", Biochem. Biophys. Res. Comm., 226:339-345.
Tonn et al., 2001, "Cellular immunotherapy of malignancies using the clonal natural killer cell line NK-92", J. Hematother. Stem Cell Res., 10:535-44.
Tsutsumi et al.,1997, "Expression of somatostatin receptor subtype 2 mRNA in human lymphoid cells", Cell Immunol., 181:44-9.
Ugur et al., 2002, "ga-66 labeled somatostatin analogue DOTA-DPhel-Tyr3-octreotide as a potential agent for positron emission tomography imaging and receptor mediated internal radiotherapy of somatostatin receptive positive tumors", Nucl. Med. Biol. 29:147-57.
Walter et al., 1995, "Reconstitution of cellular immunity against cytomegalovirus in recipients of allogeneic bone marrow by transfer of T-cell clones from the donor", N. Engl. J. Med., 333:1038-1044.
Zhang W., et. al., 2002, "Production and Characterization of Human Monoclonal Anti-Idiotype Antibodies to Anti-dsDNA Antibodies", Lupus, 11(6):362-369.
Zinn et al., 2002, "Gamma camera dual imaging with a somatostatin receptor and thymidine kinase after gene transfer with a bicistronic adenovirus in mice", Radiology, 223:417-25.
U.S. Office Action, Jul. 26, 2006, for Nai-Kong V. Cheung, U.S. Appl. No. 10/097,558, filed Mar. 8, 2002.
U.S. Office Action, Dec. 27, 2007, for Nai-Kong V. Cheung, U.S. Appl. No. 10/097,558, filed Mar. 8, 2002.
U.S. Office Action, May 16, 2008, for Nai-Kong V. Cheung, U.S. Appl. No. 10/097,558, filed Mar. 8, 2002.
U.S. Office Action, Apr. 5, 2006, for Nai-Kong V. Cheung, U.S. Appl. No. 10/273,762, filed Oct. 17, 2002.
U.S. Office Action, Sep. 7, 2006, for Nai-Kong V. Cheung, U.S. Appl. No. 10/273,762, filed Oct. 17, 2002.
U.S. Office Action, Mar. 23, 2007, for Nai-Kong V. Cheung, U.S. Appl. No. 10/273,762, filed Oct. 17, 2002.
U.S. Office Action, Jul. 10, 2007, for Nai-Kong V. Cheung, U.S. Appl. No. 10/273,762, filed Oct. 17, 2002.
U.S. Office Action, Jan. 14, 2008, for Nai-Kong V. Cheung, U.S. Appl. No. 10/273,762, filed Oct. 17, 2002.
U.S. Notice of Allowance, Oct. 30, 2008, for Nai-Kong V. Cheung, U.S. Appl. No. 10/097,558, filed Mar. 8, 2002.
U.S. Office Action, Sep. 22, 2004, for Nai-Kong V. Cheung, U.S. Appl. No. 10/097,558, filed Mar. 8, 2002.
U.S. Office Action, Aug. 24, 2004, for Nai-Kong V. Cheung, U.S. Appl. No. 10/097,558, filed Mar. 8, 2002.
U.S. Office Action, Nov. 17, 2005, for Nai-Kong V. Cheung, U.S. Appl. No. 10/273,762, filed Oct. 17, 2002.
U.S. Advisory Action, Dec. 13, 2006, for Nai-Kong V. Cheung, U.S. Appl. No. 10/273,762, filed Oct. 17, 2002.
U.S. Advisory Action, Jan. 22, 2007, for Nai-Kong V. Cheung, U.S. Appl. No. 10/273,76, filed Oct. 17, 2002.
U.S. Office Action, Sep. 15, 2008, for Nai-Kong V. Cheung, U.S. Appl. No. 10/273,762, filed Oct. 17, 2002.
U.S. Office Action, Feb. 20, 2009, for Nai-Kong V. Cheung and Hong-fen Guo, U.S. Appl. No. 10/273,762, filed Oct. 17, 2002.
Kawai et al., 1999, "Occurrence of ganglioside GD3 in neoplastic astrocytes", Virchows Arch, 434:201-205.
PCT International Search Report for the Government of The United States of America as represented by the Secretary, Department of Health and Human Services and Memorial Sloan-Kettering Cancer Center, Nov. 22, 2004, Int'l Application No. PCT/US03/38227.
Australian Office Action, Mar. 24, 2009, for Ira Pastan, Australian Application No. EP 2003298794.
Canadian Office Action, Jul. 8, 2009, for Sloan-Kettering Institute for Cancer Research, Canadian Application No. 2,423,843.
European Office Action, May 19, 2006, for Sloan-Kettering Institute for Cancer Research, European Application No. 01 98 3999.
European Office Action, Jan. 26, 2007, for Sloan-Kettering Institute for Cancer Research, European Application No. 02801782.
European Office Action, May 23, 2007, for Sloan-Kettering Institute for Cancer Research, European Application No. 03 716 369.8.
European Office Action, Aug. 16, 2006, for Sloan-Kettering Institute for Cancer Research, European Application No. 03 716 369.8.
European Communmication (Interview Summary), Sep. 13, 2007, for Sloan-Kettering Institute for Cancer Research, European Application No. 03 716 369.8.
European Office Action, Jun. 25, 2007, for Ira Pastan, European Application No. EP 03 796 552.2.
U.S. Office Action, Feb. 22, 2007, for Ira Pastan, U.S. Appl. No. 10/537,061, filed Jun. 1, 2005.
U.S. Office Action, Aug. 14, 2007, for Ira Pastan, U.S. Appl. No. 10/537,061, filed Jun. 1, 2005.
U.S. Office Action, Jan. 24, 2008, for Ira Pastan, U.S. Appl. No. 10/537,061, filed Jun. 1, 2005.
Modak et al., 2002, "Disialoganglioside GD2 and a novel tumor antigen: potential targets for immunotherapy of desmoplastic small round cell tumor", Med. Pediatr. Oncol., 39:547-551.

(56) References Cited

OTHER PUBLICATIONS

Onda et al., 2004, "In vitro and in vivo cytoxic activities of recombinant immunotoxin 8H9(Fv)-PE38 against breast cancer, osteosarcoma, and neuroblastoma", Cancer Research, 64:1419-1424.
Luther et al., 2008, "Intraparenchymal and Intratumoral Interstitial Infusion of Anti-Glioma Monoclonal Antibody 8H9", Neurosurgery, 63:1166-1174.
Xu et al., 2009, "MicroRNA miR-29 Modulates Expression of Immunoinhibitory Molecule B7-H3: Potential Implications for Immune Based Therapy of Human Solid Tumors", Cancer Research, 69(15).
European Office Action (FER), Mar. 30, 2006, for The Government of the United States of America as represented by The Secretary, Department of Health and Human Services and Memorial Sloan-Kettering Cancer Center, European Application No. EP 03 796 552.2.
Supplementary Partial European Search Report for The Government of the United States of America as represented by the Secretary, Department of Health and Human Services and Memorial Sloan-Kettering Cancer Center, Feb. 3, 2006, European Application No. EP 03 796 552.2.
Cheung et al., 2004, "Single chain Fv-streptavidIn substantially improved therapeutic index in multi-step targeting directed at disialoganglioside GD2", J. Nucl. Med., 867-877.
Murray et al., 1996, "Phase Ia/Ib trial of anti-GD2 chimeric monoclonal antibody 14.18 (ch14.18) and recombinant human granulocyte-macrophage colony-stimulating factor (rhGM-CSF) in metastatic melanoma", J. Immunother. Emphasis Tumor Immunol., 19:206-17.
U.S. Notice of Allowance, Sep. 23, 2009, for Nai-Kong V. Cheung, U.S. Appl. No. 10/097,558, filed Mar. 8, 2002.
U.S. Decision Granting Petition Under 37 CFR 1.313(c)(2), Jul. 28, 2009, for Nai-Kong V. Cheung, U.S. Appl. No. 10/097,558, filed Mar. 8, 2002.
U.S. Notice of Allowance, Sep. 25, 2009, for Nai-Kong V. Cheung, U.S. Appl. No. 10/273,762, filed Oct. 17, 2002.
U.S. Interview Summary, Aug. 11, 2009, for Nai-Kong V. Cheung, U.S. Appl. No. 10/273,762, filed Oct. 17, 2002.
PCT Notification Concerning Transmittal of International Preliminary Report on Patentability for Sloan-Kettering Institute for Cancer Research et al., Sep. 22, 2009, Int'l Application No. PCT/US2008/058030.
U.S. Office Action, Dec. 13, 2006, for Nai-Kong V. Cheung, U.S. Appl. No. 10/505,658, filed Aug. 20, 2004.
U.S. Office Action, Apr. 2, 2007, for Nai-Kong V. Cheung, U.S. Appl. No. 10/505,658, filed Aug. 20, 2004.
U.S. Office Action, Jan. 17, 2007, for Nai-Kong V. Cheung, U.S. Appl. No. 10/505,658, filed Aug. 20, 2004.
U.S. Office Action, Sep. 24, 2008, for Nai-Kong V. Cheung, U.S. Appl. No. 10/505,658, filed Aug. 20, 2004.
U.S. Office Action, Mar. 20, 2008, for Nai-Kong V. Cheung, U.S. Appl. No. 10/505,658, filed Aug. 20, 2004.
U.S. Office Action, Mar. 2, 2009, for Nai-Kong V. Cheung, U.S. Appl. No. 10/505,658, filed Aug. 20, 2004.
U.S. Notice of Allowance, Aug. 21, 2009, for Nai-Kong V. Cheung, U.S. Appl. No. 10/505,658, filed Aug. 20, 2004.
Canadian Office Action, Nov. 2, 2009, for Sloan-Kettering Institute for Cancer Research, Canadian Application No. 2,463,017.
U.S. Notice of Allowance, Dec. 14, 2009, for Nai-Kong V. Cheung, U.S. Appl. No. 10/505,658, filed Aug. 20, 2004.
Supplementary Partial European Search Report for Sloan-Kettering Institute for Cancer Research, Mar. 1, 2010, European Application No. EP 08 74 4263.
European Result of Consultation, Mar. 12, 2010, for Sloan-Kettering Institute for Cancer Research, for for EP 03 716 369.8, filed Oct. 18, 2004, National Stage of PCT/US03/07004, Filed Mar. 6, 2003.
European Communication under Rule 71(3) EPC, Apr. 28, 2010, for Sloan-Kettering Institute for Cancer Research, for for EP 03 716 369.8, Filed Oct. 18, 2004, National Stage of PCT/US03/07004, Filed Mar. 6, 2003.
European Office Action, Jul. 1, 2010, for Sloan-Kettering Institute for Cancer Research, for EP 01 98 3999, Filed May 16, 2003, National Stage of PCT/US01/32565, Filed Oct. 18, 2001.
Canadian Office Action, Sep. 20, 2010, for Sloan-Kettering Institute for Cancer Research, Canadian Application No. 2,423,843.
Canadian Office Action, Nov. 18, 2010, for Sloan-Kettering Institute for Cancer Research, Canadian Application No. 2,478,082.
U.S. Office Action, Nov. 26, 2010, for Nai-Kong V. Cheung, U.S. Appl. No. 12/709,848, filed Feb. 22, 2010.
European Office Action, Nov. 15, 2010, for Sloan-Kettering Institute for Cancer Research, for for EP 01 983 999.2, Filed May 16, 2003, National Stage of PCT/US01/32565, Filed Oct. 18, 2001.
Adams et al., 1993, "Highly specific in vivo tumor targeting by monovalent and divalent forms of 741F8 anti-c-erbB-2 single-chain Fv", Cancer Research, 53:4026-4034.
Alt et al., 1999, "Novel tetravalent and bispecific IgG-like antibody molecules combining single-chain diabodies with the immunoglobulin y1 Fc or CH3 region", FEBS Letters, 454:90-94.
Bird et al., 1988, "Single-chain antigen-binding proteins", Science, 242:423-426.
Brocks et al., 1997, "A TNF receptor antagonistic scFv, which is not secreted in mammalian cells, is expressed as a soluble mono- and bivalent scFv derivative in insect cells", Immunotechnology, 3:173-84.
Burton, D.R. and Barbas III, C.G., 1994, "Human antibodies from combinatorial libraries", Advances in Immunology, 57:191-280.
Cheung NK, 2007, "Therapeutic antibodies and immunologic conjugates" in Abeloff MD, Armitage JO, Niederhuber JE, et al (eds): Clinical Oncology (ed 4th). Philadelphia, Elsevier Churchill Livingstone, Chapter 34, pp. 531-544.
Cai, X. and Garen, A., 1995, "Anti-melanoma antibodies from melanoma patients immunized with genetically modified autologous tumor cells: selection of specific antibodies from single-chain Fv fusion phage libraries", Proceedings of the National Academy of Sciences of the United States of America, 92:6537-41.
George, A.J.T., Spooner, R.A. and Epenetos, A.A. (1994) Applications of Monoclonal Antibodies in Clinical Oncology. Immunology Today 15, 559-561.
Ghetie et al., 1997, "Homodimerization of tumor-reactive monoclonal antibodies markedly increases their ability to induce growth arrest or apoptosis of tumor cells", Proceedings of the National Academy of Sciences of the United States of America, 94:7509-14.
Huston et al., 1988, "Protein engineering of antibody binding sites: recovery of specific activity in an anti-digoxin single-chain Fv analogue produced in *Escherichia coli*", Proceedings of the National Academy of Sciences of the United States of America, 85:5879-83.
Kato et al., 1995, "Mammalian expression of single chain variable region fragments dimerized by Fc regions", Molecular Biology Reports, 21:141-146.
Kipriyanov et al., 1995, "Single-chain antibody streptavidin fusions: tetrameric bifunctional scFv-complexes with biotin binding activity and enhanced affinity to antigen", Human Antibodies Hybridomas, 6:93-101.
Kushner, B. H. and Cheung, N. K., 1992, "Absolute requirement of CD11/CD18 adhesion molecules, FcRII and phosphatidylinositol-linked FcRIII for monoclonal antibody-mediated neutrophil anti-human tumor cytotoxicity", Blood, 79:1484-1490.
Laemmli, U.K., 1970, "Cleavage of structural proteins during the assembly of the head of bacteriophage T4", Nature, 227:680-85.
Lu, J. and Sloan, S.R., 1999, "An alternating selection strategy for cloning phage display antibodies", Journal of Immunological Methods, 228:109-119.
Michael et al., 1996, "In vitro and in vivo characterisation of a recombinant carboxypeptidase G2::anti-CEA scFv fusion protein", Immunotechnology, 2:47-57.
Modak et al., 2001, "Monoclonal antibody 8H9 targets a novel cell surface antigen expressed by a wide spectrum of human solid tumors", Cancer Res., 61:4048-54.
Powers et al., 2001, "Expression of single-chain Fv-Fc fusions in *Pinchia pastoris*", Journal of Immunological Methods, 251:123-135.
Raag, R. and Whitlow, M., 1995, "Single-chain Fvs", FASEB Journal, 9:73-80.

(56) References Cited

OTHER PUBLICATIONS

Schultz et al., 2000, "A tetravalent single-chain antibody-streptavidin fusion protein for pretargeted lymphoma therapy", Cancer Research, 60:6663-6669.

Shu et al., 1993, "Secretion of a single-gene-encoded immunoglobulin from myeloma cells", Proceedings of the National Academy of Sciences of the United States of America, 90:7995-9.

Thanavala et al., 1986, "A surrogate hepatitis B virus antigenic epitope represented by a synthetic peptide and an internal image antiidiotype antibody", Journal of Experimental Medicine, 164:227-236.

Towbin et al., 1979, "Electrophoretic transfer of proteins from polyacrylamide gels to nitrocellulose sheets: procedure and some applications", Proceedings of the National Academy of Sciences of the United States of America, 76:4350-4.

Tur at al., 2001, "Selection of scFv phages on intact cells under low pH conditions leads to a significant loss of insert-free phages", Biotechniques, 30:404-413.

Umana et al., 1999, "Engineered glycoforms of an antineuroblastoma IgG1 with optimized antibody-dependent cellular cytotoxic activity", Nature Biotechnology, 17:176-180.

Wagner et al., 1997, "Immunological responses to the tumor-associated antigen CA125 in patients with advanced ovarian cancer induced by the murine monoclonal anti-idiotype vaccine ACA125", Hybridoma, 16:33-40.

Wang et al., 1999, "Human single-chain Fv immunoconjugates targeted to a melanoma-associated chondroitin sulfate proteoglycan mediate specific lysis of human melanoma cells by natural killer cells and complement", Proceedings of the National Academy of Sciences of the United States of America, 96:1627-32.

Watters et al., 1997, "An optimized method for cell-based phage display panning", Immunotechnology, 3:21-9.

Winter, G. and Milstein, C., 1991, "Man-made antibodies", Nature, 349:293-299.

Winter et al., 1994, "Making antibodies by phage display technology", Annual Review of Immunology, 12: 433-55.

Wright, A. and Morrison, S.L., 1997, "Effect of glycosylation on antibody function: implications for genetic engineering", Trends in Biotechnology, 15:26-31.

Wu et al., 1996, "Tumor localization of anti-CEA single-chain Fvs: improved targeting by non-covalent dimers", Immunotechnology, 2:21-36.

European Office Action, Apr. 8, 2013, for Sloan-Kettering Institute for Cancer Research, European App'l No. 01983999.2, Filed May 16, 2003.

European Office Action, Feb. 4, 2013, for Sloan-Kettering Institute for Cancer Research, European App'l No. 02801782.0, Filed Apr. 23, 2004.

U.S. Notice of Allowance, Apr. 4, 2013, for Nai-Kong V. Cheung, U.S. Appl. No. 12/797,081, filed Jun. 9, 2010.

U.S. Notice of Allowance, Nov. 13, 2012, for Nai-Kong V. Cheung, U.S. Appl. No. 12/721,798, filed Mar. 11, 2010.

U.S. Office Action, Jul. 10, 2012, for Nai-Kong V. Cheung, U.S. Appl. No. 12/721,798, filed Mar. 11, 2010.

U.S. Office Action, Jul. 28, 2011, for Nai-Kong V. Cheung, U.S. Appl. No. 12/721,798, filed Mar. 11, 2010.

U.S. Office Action, Feb. 3, 2011, for Nai-Kong V. Cheung, U.S. Appl. No. 12/721,798, filed Mar. 11, 2010.

Savage et al., 1993, "Construction, characterisation and kinetics of a single chain antibody recognising the tumour associated antigen placental alkaline phosphate", Br. J. Cancer, 68:738-742.

European Office Action, Aug. 26, 2013, for Sloan-Kettering Institute for Cancer Research, European App'l No. 01983999.2, Filed May 16, 2003.

Canadian Office Action, Jul. 17, 2014, for Sloan-Kettering Institute for Cancer Research, Canadian App'l No. 2,680,111, Filed Mar. 24, 2008.

European Office Action, Aug. 12, 2014, for Sloan-Kettering Institute for Cancer Research, European App'l No. 01983999.2, Filed May 16, 2003.

European Office Action, Dec. 11, 2013, for Sloan-Kettering Institute for Cancer Research, European App'l No. 08744263.8, Filed Sep. 1, 2009.

Indian Office Action, Feb. 13, 2013, for Sloan-Kettering Institute for Cancer Research, Indian App'l No. 1826/MUMNP/2009, Filed Jan. 10, 2009.

U.S. Office Action, Sep. 9, 2014, for Nai-Kong V. Cheung, U.S. Appl. No. 12/531,828, filed Sep. 17, 2009.

* cited by examiner

Figure 33: 8H9-scFv sequence

```
        Q  V  K  L  Q  Q     S  G  A  E  L  V     K  P  G  A  S  V  K  L  S  C  K  A  S  G  Y  T  F  T
    1   CAGGTCAAA CTGCAGCAG TCTGGGGCT GAACTGGTA AAGCCTGGG GCTTCAGTG AAATTGTCC TGCAAGGCT TCTGGCTAC ACCTTCACA
        GTCCAGTTT GACGTCGTC AGACCCCGA CTTGACCAT TTCGGACCC CGAAGTCAC TTTAACAGG ACGTTCCGA AGACCGATG TGGAAGTGT

N  Y  D  I  N  W     V  R  Q  R  P  E  Q  G  L  E  W  I  G  W  I     F  P  G  D  G  S  T  Q  Y
   91   AACTATGAT ATAAACTGG GTGAGGCAG AGGCCTGAA CAGGGACTT GAGTGGATT GGATGGATT TTTCCTGGA GATGGTAGT ACTCAATAC
        TTGATACTA TATTTGACC CACTCCGTC TCCGGACTT GTCCCTGAA CTCACCTAA CCTACCTAA AAAGGACCT CTACCATGA TGAGTTATG

N  E  K  F  K  G  K  A  T  L  T  T  D  T  S  S  S  T  A  Y  M  Q  L  S  R  L  T  S  E  D
  181   AATGAGAAG TTCAAGGGC AAGGCCACA CTGACTACA GACACATCC TCCAGCACA GCCTACATG CAGCTCAGC AGGCTGACA TCTGAGGAC
        TTACTCTTC AAGTTCCCG TTCCGGTGT GACTGATGT CTGTGTAGG AGGTCGTGT CGGATGTAC GTCGAGTCG TCCGACTGT AGACTCCTG

S  A  V  Y  F  C  A  R  Q  T  T  A  T  W  F  A  Y  W  G  Q  G  T  T  V  T  V  S  G  G
  271   TCTGCTGTC TATTTCTGT GCAAGACAG ACTACGGCT ACCTGGTTT GCTTACTGG GGCCAAGGG ACCACGGTC ACCGTCTCC TCAGGTGGA
        AGACGACAG ATAAAGACA CGTTCTGTC TGATGCCGA TGGACCAAA CGAATGACC CCGGTTCCC TGGTGCCAG TGGCAGAGG AGTCCACCT

G  G  S     G  G  G     G  S  G  G  G  G  S  D  I  E  L  T  Q  S  P  T  T  L  S  V  T  P  G  D
  361   GGCGGTTCA GGCGGAGGT GGCTCTGGC GGTGGCGGA TCGGACATC GAGCTCACT CAGTCTCCA ACCACCCTG TCTGTGACT CCAGGAGAT
        CCGCCAAGT CCGCCTCCA CCGAGACCG CCACCGCCT AGCCTGTAG CTCGAGTGA GTCAGAGGT TGGTGGGAC AGACACTGA GGTCCTCTA

R  V  S  L  S  C  R  A  S  Q  S  I  S  D  Y  L  H  W  Y  Q  Q  K  S  H  E  S  P  R  L  L
  451   AGAGTCTCT CTTTCCTGC AGGGCCAGC CAAAGTATT AGCGACTAT TTACATTGG TACCAACAA AAATCACAT GAGTCTCCA AGGCTTCTC
        TCTCAGAGA GAAAGGACG TCCCGGTCG GTTTCATAA TCGCTGATA AATGTAACC ATGGTTGTT TTTAGTGTA CTCAGAGGT TCCGAAGAG

I  K  Y  A  S  Q  S  I  S  G  I  P  S  R  F  S  G  S  G  S  D  F  T  L  S  I  N  S
  541   ATCAAATAT GCTTCCCAG TCCATCTCT GGGATCCCC TCCAGGTTC AGTGGCAGT GGATCAGGG TCAGATTTC ACTCTCAGT ATCAACAGT
        TAGTTTATA CGAAGGGTC AGGTAGAGA CCCTAGGGG AGGTCCAAG TCACCGTCA CCTAGTCCC AGTCTAAAG TGAGAGTCA TAGTTGTCA

V  E  P  E  D  V  G  V  Y  Y  C  Q  N  G  H  S  F  P  L  T  F  G  A  G  T  K  L  E  L  K
  631   GTGGAACCT GAAGATGTT GGAGTGTAT TACTGTCAA AATGGTCAC AGCTTTCCG CTCACGTTC GGTGCTGGG ACCAAGCTG GAGCTGAAA
        CACCTTGGA CTTCTACAA CCTCACATA ATGACAGTT TTACCAGTG TCGAAAGGC GAGTGCAAG CCACGACCC TGGTTCGAC CTCGACTTT

Q  A  A                  (SEQ ID NO.35)
  721   CAGGCGGCC GC            (SEQ ID NO.36)
        GTCCGCCGG CG            (SEQ ID NO.37)
```

Figure 34:

8H9scfv cDNA sequence:
CAGGTCAAACTGCAGCAGTCTGGGGCTGAACTGGTAAAGCCTGGGGCTTCAGTGAAATTGTC
CTGCAAGGCTTCTGGCTACACCTTCACAAACTATGATATAAACTGGGTGAGGCAGAGGCCTG
AACAGGGACTTGAGTGGATTGGATGGATTTTTCCTGGAGATGGTAGTACTCAATACAATGAG
AAGTTCAAGGGCAAGGCCACACTGACTACAGACACATCCTCCAGCACAGCCTACATGCAGCT
CAGCAGGCTGACATCTGAGGACTCTGCTGTCTATTTCTGTGCAAGACAGACTACGGCTACCTG
GTTTGCTTACTGGGGCCAAGGGACCACGGTCACCGTCTCCTCAGATGGAGGCGGTTCAGGCG
GAGGTGGCTCTGGCGGTGGCGGATCGGACATCGAGCTCACTCAGTCTCCAACCACCCTGTCTG
TGACTCCAGGAGATAGAGTCTCTCTTTCCTGCAGGGCCAGCCAGAGTATTAGCGACTACTTAC
ACTGGTACCAACAAAAATCACATGAGTCTCCAAGGCTTCTCATCAAATATGCTTCCCAATCCA
TCTCTGGGATCCCCTCCAGGTTCAGTGGCAGTGGATCAGGGTCAGATTTCACTCTCAGTATCA
ACAGTGTGGAACCTGAAGATGTTGGAGTGTATTACTGTCAAAATGGTCACAGCTTTCCGCTCA
CGTTCGGTGCTGGGACCAAGCTGGAGCTGAAACAGGCGGCCGC (SEQ ID NO.38)

8H9scfv amino acid sequence:
QVKLQQSGAELVKPGASVKLSCKASGYTFTNYDINWVRQRPEQGLEWIGWIFPGDGSTQYNEKF
KGKATLTTDTSSSTAYMQLSRLTSEDSAVYFCARQTTATWFAYWGQGTTVTVSSDGGGSGGGGS
GGGGSDIELTQSPTTLSVTPGDRVSLSCRASQSISDYLHWYQQKSHESPRLLIKYASQSISGIPSRFSG
SGSGSDFTLSINSVEPEDVGVYYCQNGHSFPLTFGAGTKLELKQAA (SEQ ID NO.39)

Mutated 8H9 scFv with decreased normal tissue adherence
QVKLQQSGAELVEPGASVKLSCKASGYTFTNYDINWVRQRPEQGLEWIGWIFPGDGSTQYNEKFK
GKATLTTDTSSSTAYMQLSRLTSEDSAVYFCARQTTATWFAYWGQGTTVTVSSDGGGSGGGGSG
GGGSDIELTQSPTTLSVTPGDQVSLSCRASQSISDYLHWYQQKSHESPQLLIKYASQSISGIPSRFSGS
GSGSDFTLSINSVEPEDVGVYYCQNGHSFPLTFGAGTELELEQAA (SEQ ID NO.40)

USES OF MONOCLONIAL ANTIBODY 8H9

This application is a Continuation application of U.S. Ser. No. 12/721,798, filed Mar. 11, 2010 (now U.S. Pat. No. 8,414,892), which is a Divisional application of U.S. Ser. No. 10/505,658, filed Aug. 20, 2004 (now U.S. Pat. No. 7,737,258), which is a National Stage application of PCT/US03/07004, filed Mar. 6, 2003, which is a continuation-in-part of U.S. Ser. No. 10/273,762, filed Oct. 17, 2002 (now U.S. Pat. No. 7,666,424) and PCT/US02/33331, filed Oct. 17, 2002, which are both continuation-in-part of U.S. Ser. No. 10/097,558, filed Mar. 8, 2002 (now U.S. Pat. No. 7,737,258), which is a continuation-in-part of PCT/US01/32565, filed Oct. 18, 2001, which claims benefit of U.S. Ser. No. 60/241,344, filed Oct. 18, 2000, and U.S. Ser. No. 60/330,396, filed Oct. 17, 2001. The contents of which are incorporated by reference hereinto this application.

The invention disclosed herein was made with government support under Department of Energy Grant No. DE-FG-02-93ER61658 (1997-2002), the National Cancer Institute Grant No. NCI CA 89936 (12/1/00-11/30/02), and National Institutes of Health Grant No. CA61017. Accordingly, the U.S. Government has certain rights in this invention.

Throughout this application, various references are cited. Disclosures of these publications in their entireties are hereby incorporated by reference into this application to more fully describe the state of the art to which this invention pertains.

BACKGROUND OF THE INVENTION

Tumor-restricted surface antigens may be targets for diagnosis and immune-based therapies. Monoclonal antibody 8H9 is a murine IgG1 hybridoma derived from the fusion of mouse myeloma SP2/0 cells and splenic lymphocytes from BALB/c mice immunized with human neuroblastoma. By immunohistochemistry, 8H9 was highly reactive with human brain tumors, childhood sarcomas, neuroblastomas and less so with adenocarcinomas. Among primary brain tumors, 15/17 glioblastomas, 3/4 mixed gliomas, 4/11 oligodendrogliomas, 6/8 astrocytomas, 2/2 meningiomas, 3/3 schwannomas, 2/2 medulloblastomas, 1/1 neurofibroma, 1/2 neuronoglial tumors, 2/3 ependymomas and 1/1 pineoblastoma were tested positive. Among sarcomas, 21/21 Ewing's/PNET, 28/29 rhabdomyosarcoma, 28/29 osteosarcomas, 35/37 desmoplastic small round cell tumors, 2/3 synovial sarcomas, 4/4 leiomyosarcomas, 1/1 malignant fibrous histiocytoma and 2/2 undifferentiated sarcomas tested positive with 8H9. 87/90 neuroblastomas, 12/16 melanomas, 3/4 hepatoblastomas, 7/8 Wilm's tumors, 3/3 rhabdoid tumors and 12/27 adenocarcinomas also tested positive. In contrast 8H9 was nonreactive with normal human tissues including bone marrow, colon, stomach, heart, lung, muscle, thyroid, testes, pancreas, and human brain (frontal lobe, cerebellum, pons and spinal cord). Reactivity with normal cynomolgus monkey tissue was similarly restricted. Indirect immunofluorescence localized the antigen recognized by 8H9 to the cell membrane. The antigen is proteinase-sensitive and is not easily modulated off cell surface. 8H9 immuno-precipitated a 58 kD band following N-glycanase treatment, most likely a protein with heterogeneous degree of glycosylation. This novel antibody-antigen system may have potential for tumor targeting.

Monoclonal antibodies such as 3F8 (1) and 14.18 (2) against $G_{D2}$ in neuroblastoma, M195 against CD33 in acute leukemia (3), anti-HER2 antibodies in breast cancer (4) and anti-CD20 antibodies in lymphoma (5) have shown efficacy in recent clinical trials. The prognosis in glial brain tumors and metastatic mesenchymal and neuroectodermal tumors remains dismal despite innovations in chemotherapy and radiation therapy. Immunotherapy may offer new possibilities for improving the outcome in these patients.

Tumor antigens expressed on cell membrane are potential targets in immunotherapy. Examples of tumor antigens expressed on glial tumors include neural cell adhesion molecules (6), gangliosides such as $G_{D2}$ and $G_{M2}$ (7), and neuro-hematopoeitic antigens (8). Recent investigations have focused on growth factor receptors as immune targets, in particular type III mutant epidermal growth factor receptor (EGFRvIII) which has been shown to be expressed on 50% of glial brain tumors (9). Notwithstanding the universal expression of NCAM by neuronal cells, two clinical studies have utilized anti-NCAM antibodies in patients. MAb UJ13A was shown to accumulate in gliomas by virtue of disruption of blood brain bather locally (10) and another antibody, ERIC-1 was used in a therapeutic setting in resected glioma cavities with some clinical benefit (11)

Recent studies have targeted immunotherapy to extracellular matrix around tumor cells. Tenascin has been reported to be expressed in 50-95% of glial brain tumors as well as on mesenchymal tumors, carcinomas and normal human glial, liver and kidney cells (12). Anti-tenascin monoclonal antibodies 8106 (13) and BC-2 and BC-4 (14) administered intracavity have recently been reported to show efficacy in the treatment of patients with malignant gliomas. However, since these antigens are also present to varying degrees on normal human neural and non-neural cells, their clinical utility would depend on their overexpression by brain tumors when compared to normal tissues. With the exception of EGFRvIII, the glial tumors antigens described to date are generally found on normal brain tissue, or are restricted to intracellular compartments, thus with limited clinical utility for antibody targeting.

Membrane antigens that have been targeted on osteosarcoma include $G_{D2}$ (15), CD55 (16) and an as yet undefined osteosarcoma-associated antigen recognized by the MoAbs TP-1 and TP-3 (17). However, these antigens are present to varying degrees on normal tissues. Similarly the glycoprotein p30/32 coded by the MIC2 oncogene and recognized by the monoclonal antibody 013 in the Ewing's family of tumors is expressed on normal tissues (18). In rhabdomyosarcoma, the MyoD family of oncofetal proteins is nuclear in localization (19) and therefore inaccessible to antibody-targeted immunotherapy.

An ideal tumor antigen for targeted immunotherapy should be absent on normal tissues and abundantly expressed on tumor cell surface. Such tumor-specific antigens e.g. idiotypes in B cell lymphoma are rare (20). Moreover, a "generic" tumor-specific antigen expressed on tumor cells of varying lineage recognized by monoclonal antibodies may have broader utility in antibody-based strategies. We describe here a novel tumor-associated antigen, recognized by a murine monoclonal antibody 8H9, expressed on cell membranes of a broad spectrum of tumors of neuroectodermal, mesenchymal and epithelial origin, with restricted distribution on normal tissues.

SUMMARY OF THE INVENTION

This invention provides a composition comprising an effective amount of monoclonal antibody 8H9 or a derivative thereof and a suitable carrier. This invention provides a pharmaceutical composition comprising an effective amount of monoclonal antibody 8H9 or a derivative thereof and a pharmaceutically acceptable carrier.

This invention also provides an antibody other than the monoclonal antibody 8H9 comprising the complementary determining regions of monoclonal antibody 8H9 or a derivative thereof, capable of binding to the same antigen as the monoclonal antibody 8H9.

This invention provides a substance capable of competitively inhibiting the binding of monoclonal antibody 8H9. In an embodiment of the substance, it is an antibody.

This invention provides an isolated antibody, wherein the Complementary Determining Region is NYDIN, for CDR1, WIFPGDGSTQY for CDR2, QTTATWFAY for CDR3 for the heavy chain, and RASQSISDYLH for the CDR1, YASQSIS for CDR2, QNGHSFPLT for CDR3 for the light chain. This invention further provides the above antibody, wherein the other sequences are of human origin.

The invention also provides a composition comprising an effective amount of monoclonal antibody 8H9 or a derivative thereof and a suitable carrier, which includes sequences as set forth in FIG. 33. In an embodiment, the sequences are mutated. This invention also provides the mutated form of 8H9, so as to reduce background and cytotoxicity. Other mutations could be established which could achieve the above-described function. In a further embodiment, the antibody includes sequences as set forth in FIG. 34.

Furthermore, the invention provides a composition comprising the above antibodies and an isolated nucleic acid molecule encoding the antibodies above. This invention also provides the isolated nucleic acid molecule above, wherein the sequences are set forth in FIG. 33.

In addition, this invention provides a vector comprising the above nucleic acid molecules. The invention also provides a cell comprising the above vector.

This invention provides an isolated scFv of monoclonal antibody 8H9 or a derivative thereof. In an embodiment, the scFv is directly or indirectly coupled to a cytotoxic agent.

This invention provides a cell comprising 8H9-scFv. In an embodiment, it is a red cell. This invention also provides a 8H9-scFv-gene modified cell. This invention provides a liposome modified by 8H9-scFv.

This invention provides a method for directly kill, or deliver drug, DNA, RNA or derivatives thereof to cell bearing the antigen recognized by the monoclonal antibody 8H9 or to image cells or tumors bearing said antigen using the isolated 8H9-scFv or cell or liposome comprising the 8H9-scFv.

This invention provides a protein with about 58 kilodaltons in molecular weight, reacting specifically with the monoclonal antibody 8H9. When this 58 kd protein is glycosylated, the apparent molecular weight is about 90 kilodaltons.

This invention also provides an antibody produced by immunizing the 8H9 antigen or specific portion thereof, which is immunogenic.

This invention also provides a nucleic acid molecule encoding the 8H9 antigen. In addition, this invention provides a nucleic acid molecule capable of specifically hybridizing the molecule encoding the 8H9 antigen. The nucleic acid molecule includes but is not limited to synthetic DNA, genomic DNA, cDNA or RNA.

This invention provides a vector comprising the nucleic acid molecule encoding 8H9 antigen or a portion thereof. This invention provides a cell comprising the nucleic acid molecule encoding 8H9 antigen.

This invention provides a method for producing the protein which binds to the monoclonal antibody 8H9 comprising cloning the nucleic acid molecule encoding the 8H9 antigen in an appropriate vector, expressing said protein in appropriate cells and recovery of said expressed protein.

This invention also provides a method for production of antibody using the protein produced by the above method. This invention also provides antibodies produced by the above method. In an embodiment, the antibody is a polyclonal antibody. In another embodiment, the antibody is a monoclonal.

This invention provide a method of inhibiting the growth of tumor cells comprising contacting said tumor cells with an appropriate amount of monoclonal antibody 8H9 or a derivative thereof, or the antibody of claim produced by the expressed 8H9 antigen or a derivative of the produced antibody thereof.

This invention provides a method of inhibiting the growth of tumor cells in a subject comprising administering to the subject an appropriate amount of monoclonal antibody 8H9 or a derivative thereof, or the antibody produced by the expressed 8H9 antigen or a derivative thereof.

This invention provides a method for imaging a tumor in a subject comprising administering to the subject a labeled monoclonal antibody 8H9 or labeled derivatives, or a labeled antibody produced by the expressed 8H9 antigen or a labeled derivative. In embodiment, the antibodies or derivatives are labeled by a radioisotope.

This invention provides a method of reducing tumor cells in a subject comprising administering to the subject monoclonal antibody 8H9 or a derivative thereof, or a monoclonal antibody produced by the expressed 8H9 antigen or a derivative thereof wherein the antibody or derivative is coupled to a cytotoxic agent to the subject.

This invention provides a method to evaluate the tumor bearing potential of a subject comprising measuring the expression the 8H9 antigen in the subject, wherein the increased expression of said antigen indicates higher tumor bearing potential of the subject.

This invention provides a transgenic animal comprising an exogenous gene encoding the 8H9 antigen. This invention also provides a knock out animal wherein the gene encoding the 8H9 mouse analogous antigen has been knocked out.

Finally, this invention provides a method to screening new anti-tumor compound comprising contacting the above transgenic animal with the tested compound and measuring the level of expression of the 8H9 antigen in said transgenic animal, a decrease in the level of expression indicating that the compound can inhibit the expression of the 8H9 antigen and is a anti-tumor candidate.

DETAILED DESCRIPTION OF THE FIGURES

First Series of Experiments

FIG. 1. (1A) Desmoplastic small round cell tumor (10×) immunostained with 8H9 showing strong membrane positivity and typical histology (1B) Glioblastoma multiforme stained with 8H9 showing binding to cell membranes and fibrillary stroma (1C) Embryonal rhabdomyosarcoma stained with 8H9 showing cell membrane reactivity (1D) Negative staining of embryonal rhabdomyosarcoma with MOPC21, an irrelevant IgG1 control antibody FIG. 2. Persistence of 8H9 binding to U2OS cells (2A) and NMB7 cells (2B) as studied by indirect immunofluorescence. X-axis: relative immunofluorescence, y-axis: hours of incubation. U2OS cells were reacted with 8H9 and HB95, and NMB7 cells with 8H9 and 3F8. After washing, cells were recultured and persistence of immunoreactivity of the primary antibodies evaluated by indirect immunofluorescence using I-TIC-conjugated secondary antibody. Relative immunofluorescence of 8H9 on U2OS cells dropped to 80% after 48hrs (HB95 to 11%), while that on NMB7 cells showed no significant drop off at 36 hrs (3F8 dropped to 39%)

Figure 3:
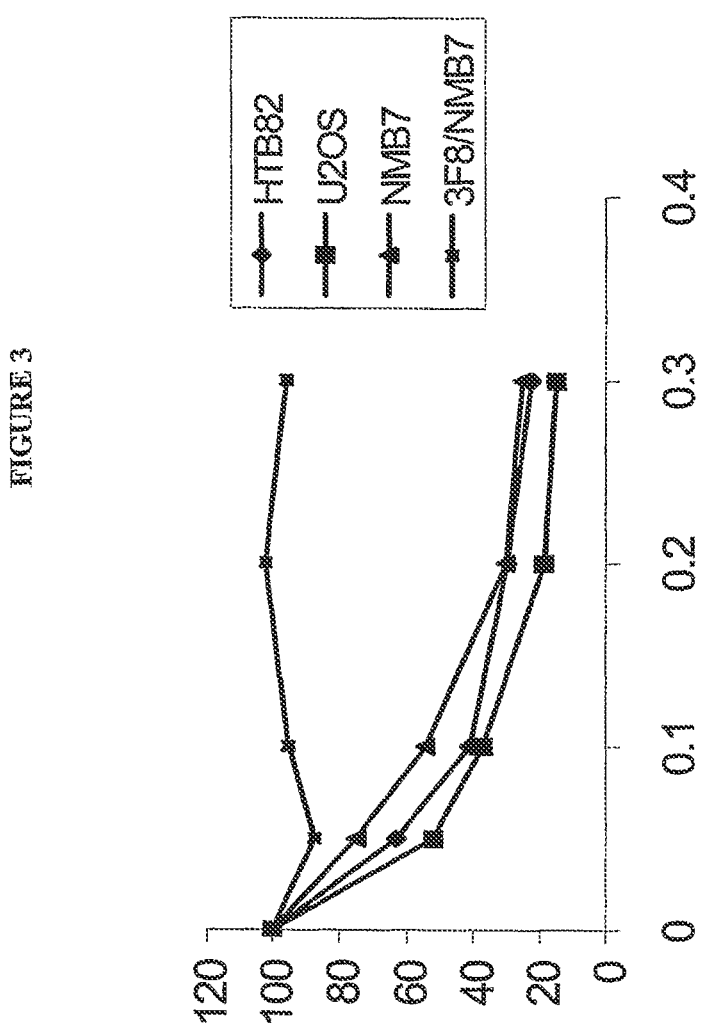

FIG. 3. Effect of Pronase E on 8H9 immunoreactivity with HTB82, U2OS and NMB7 cells and on 3F8 immunoreactivity with NMB7 cells as studied by indirect immunofluorescence. X-axis: concentration of Pronase E (mg/ml); y-axis: relative immunofluorescence.

Second Series Experiments

Figure 4:
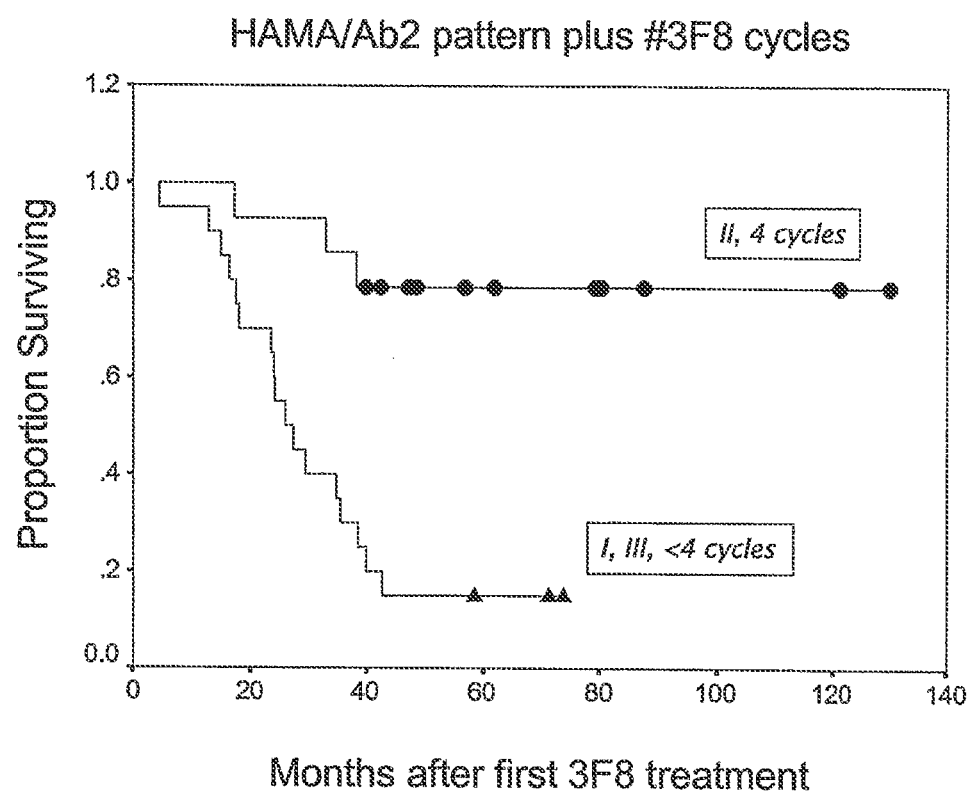

FIG. 4. 4 cycles of 3F8 and low level HAMA response are associated with prolonged survival.

Figure 5:
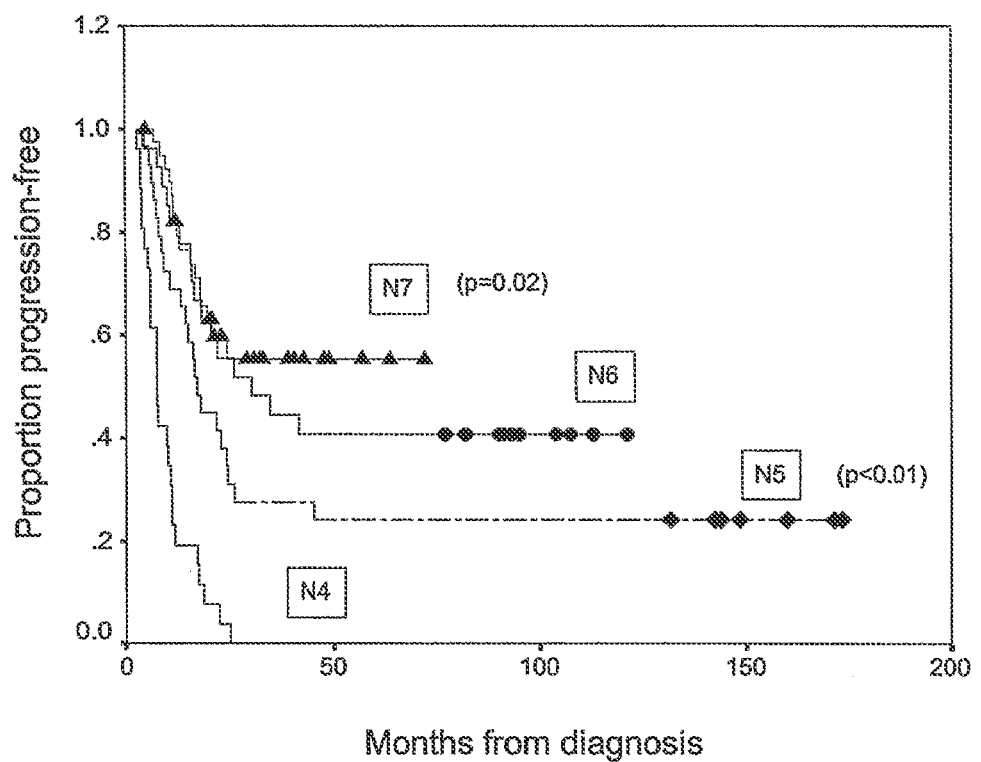

FIG. 5. Improved long-term survival after MoAb 3F8 in patients with stage 4 NB newly diagnosed >1 year of age at Memorial Sloan-Kettering Cancer Center. N4 to N7 are sequential protocols over 15 years. N4 and N5 are chemotherapy+ABMT, N6 is chemotherapy+3F8, and N7 is N6+$^{131}$I-3F8.

Figure 6:
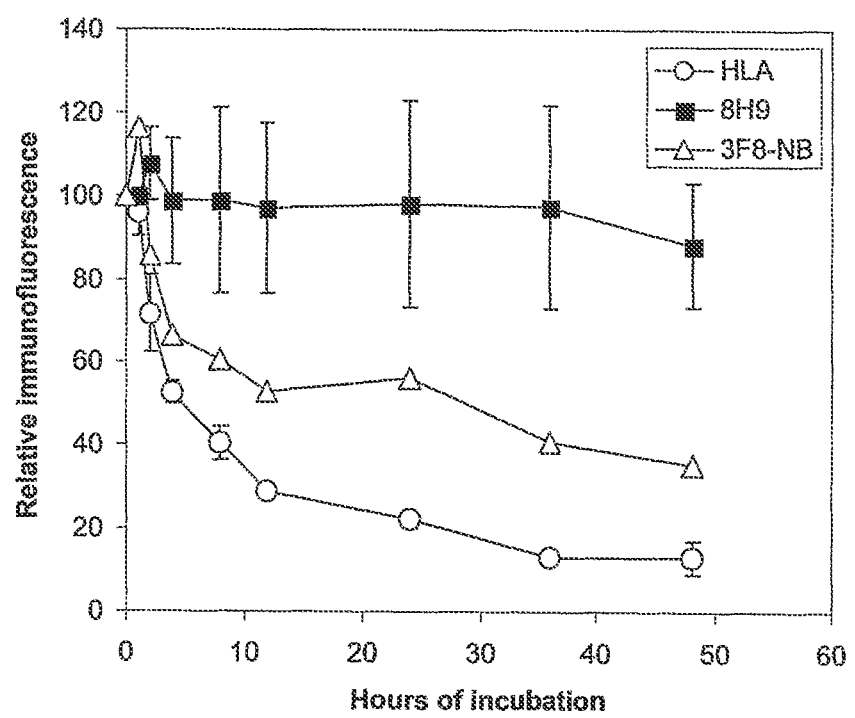

FIG. 6. Antigen modulation following binding to 8H9.

Figure 7:
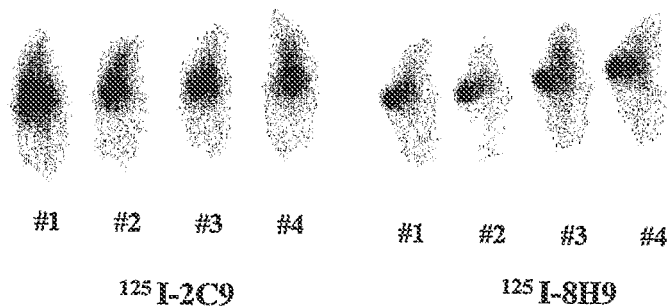

FIG. 7. At 120 h: $^{125}$I8H9 localized to tumors (N=4) while control antibody 2C9 (mouse IgG1) remained in blood pool/liver (N=4).

Figure 8:
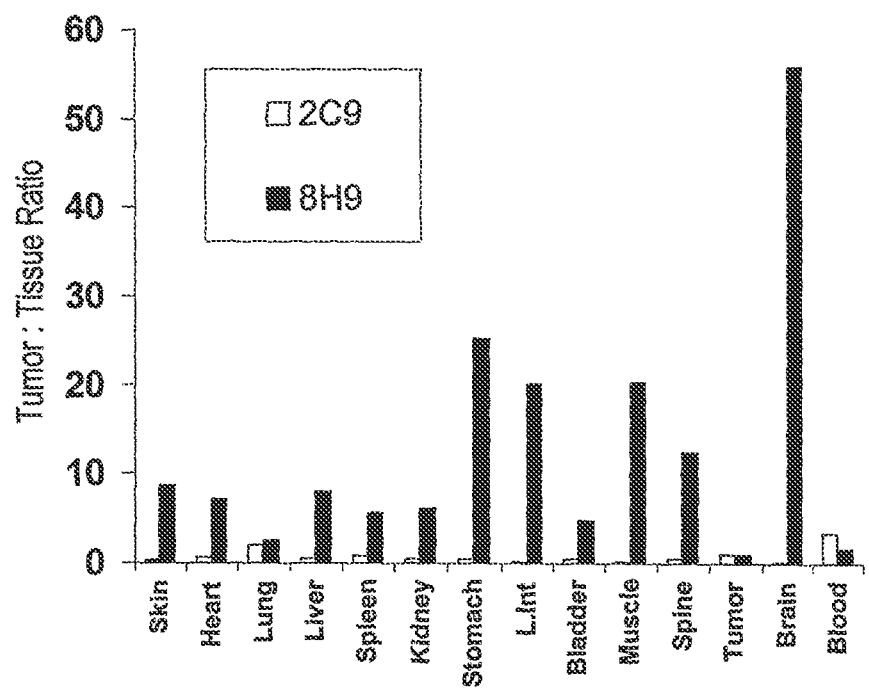

FIG. 8. High tumor-tissue ratio was specific for $^{125}$I-8H9 vs control MoAb $^{125}$I-2C9 in RMS xenografts.

Third Series of Experiments

Figure 9:
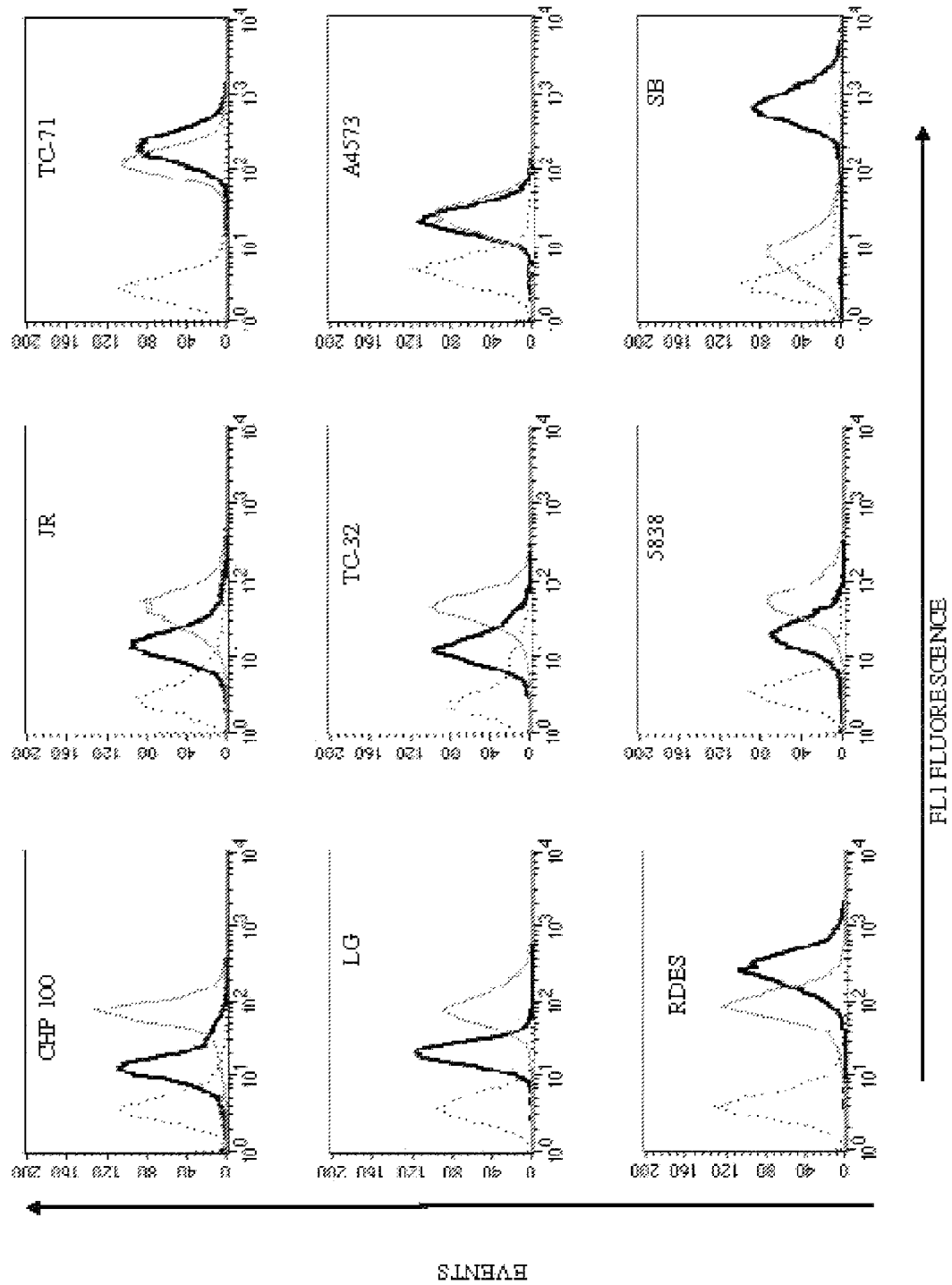

FIG. 9. Reactivity of 8H9 with Ewing's sarcoma cell lines.

Flow cytometric analysis of 8H9 binding to nine Ewing's sarcoma cell lines is shown. The designation for each line is shown in the upper right corner. FL1 fluorescence of isotype (dashed black line) CD99 (thin black line) and 8H9 (thick black line) is shown.

Figure 10:
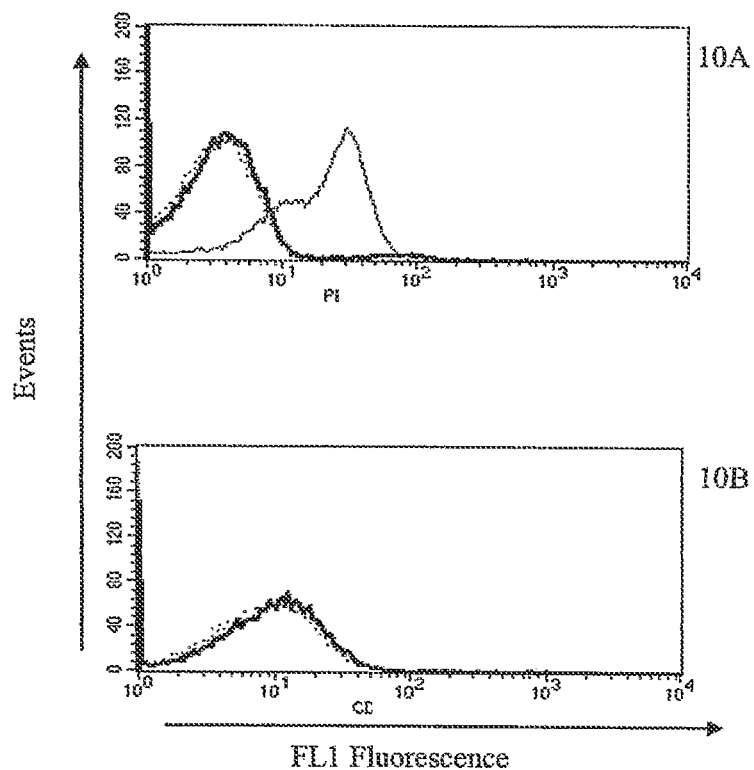

FIG. 10. Lack of Reactivity of 8119 with T cells or bone marrow progenitor cells. Electronically gated Cd3+ cells from peripheral blood of a normal donor (top panel) are analyzed for isotype (dashed line), CD99 (thin black line) and 8H9 (thick black line). Electronically gated CD34+ cells from fresh human bone marrow from a normal donor (bottom panel) are analyzed for isotype (dashed line) and 8H9 (thick black line) staining.

Figure 11A:
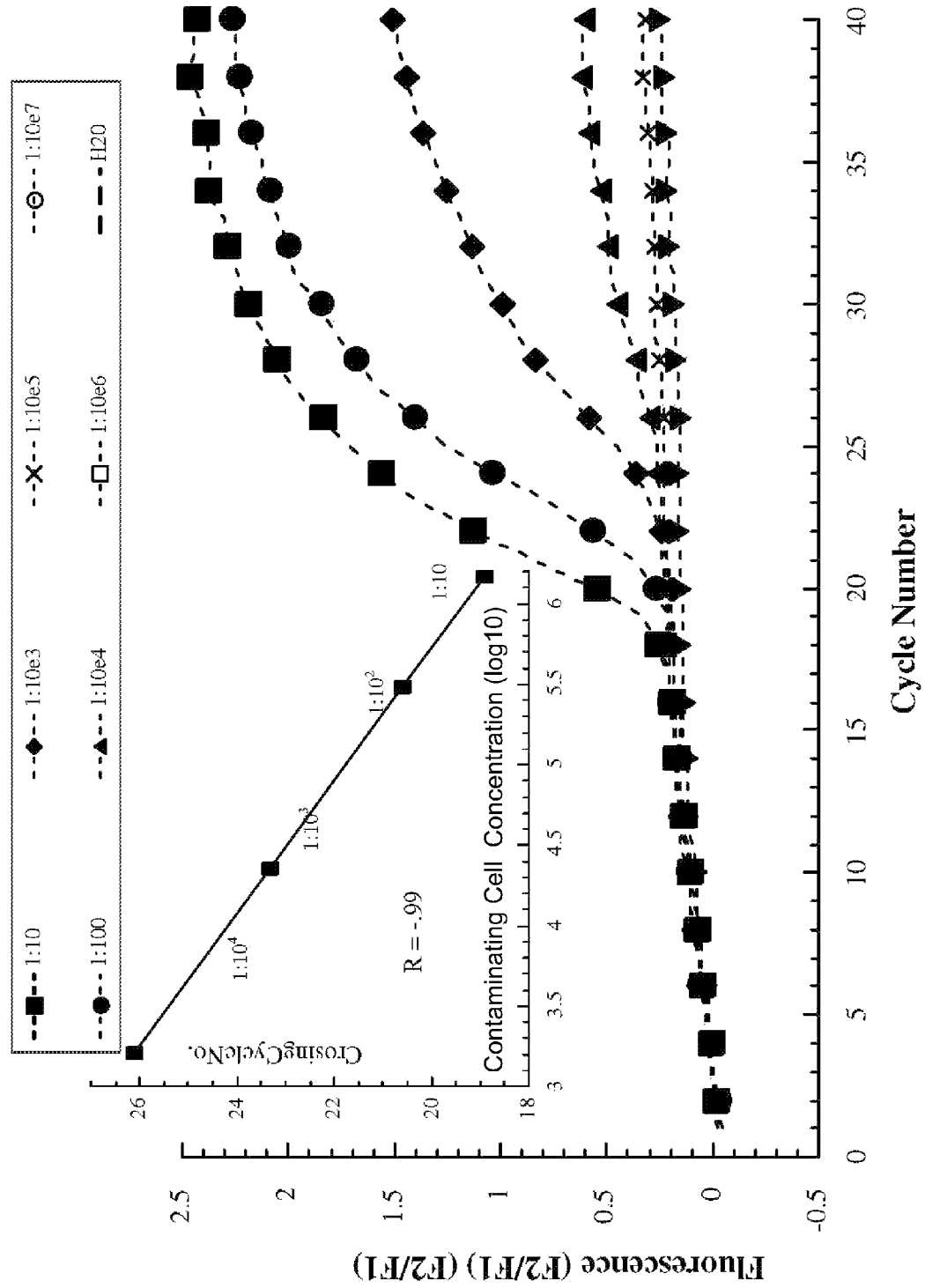
Figure 11B:
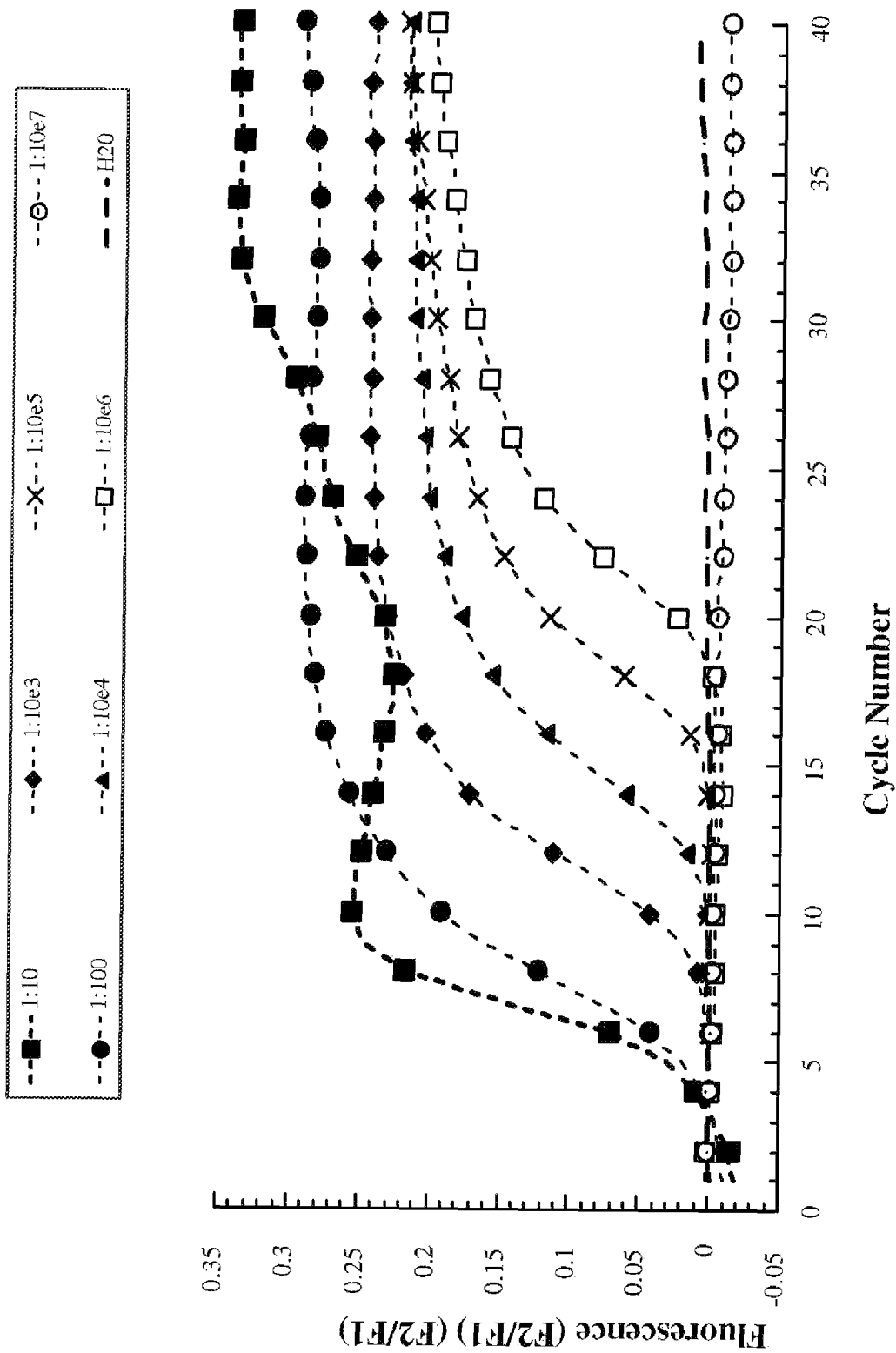

FIG. 11. Real-time PCR analysis of t(11,22) in artificially contaminated PBMCs accurately quantifies EWS/FII 1 transcript over up to five log dilutions of tumor. Crossing time (x axis) is plotted vs. fluorescence (y axis) 11a: Non-nested PCR of 10×10$^6$ PBMCs contaminated from 1:10 to 1:10$^6$. In the inset, a linear relationship between crossing time and log cell concentration over 4 log dilutions of tumor is shown. Samples contaminated at less that 1:10$^4$ show no detectable postivity in this assay. 11b: Nested PCR of 10×10$^6$ PBMCs contaminated from 1:10 to 1:10$^7$. A linear relationship is observed over 5 log dilutions of tumor from 1:100 to 1:10$^6$.

FIG. 12. Quantitative PCR analyis of purging demonstrates 2-3 log reduction in peripheral blood and progenitor cells spikes with Ewing's Sarcoma cells. Cycle number (x axis) is plotted vs. fluorescence (y axis). Experimental samples were run with standard contaminated dilutions shown in the inset 12a: Non-nested PCR analysis of 1×10$^6$ pre-purged and post-purged non-CD34 selected bone marrow from a normal healthy donor contaminated at a level of 1:100. A two-log reduction in tumor burden is demonstrated in the post-purged sample which shows a level of contamination at 1:10$^4$. 12b: Nested PCR analysis of pre-purged and post-purged CD34 selected cells harvested following G-CSF mobilization from a patient with Ewing's sarcoma. Since this patient was negative for EWS/FLI, CD34 cells were spike with Ewing's sarcoma at a level of 1:10$^3$. A three-log reduction in tumor burden is demonstrated in the post-purged sample which shows a level of contamination at 1:10$^6$. 12c: Nested PCR analysis of pre-purged and post-purged PBMCc from a normal healthy donor buffy coat contaminated at a level of 1:100.

A greater than 3-log reduction in tumor burden is demonstrated in the post-purged sample which shows a level of contamination of less than 1:10$^6$. 12d: Nested PCR analysis of pre-purged and post-purged non PBMCs from a normal healthy donor buffy coat contaminated at a level of 1:10$^3$. A 3 log reduction in tumor burden is demonstrated in the post-purged sample which shows a level of contamination at 1:10$^6$.

Figure 13A:
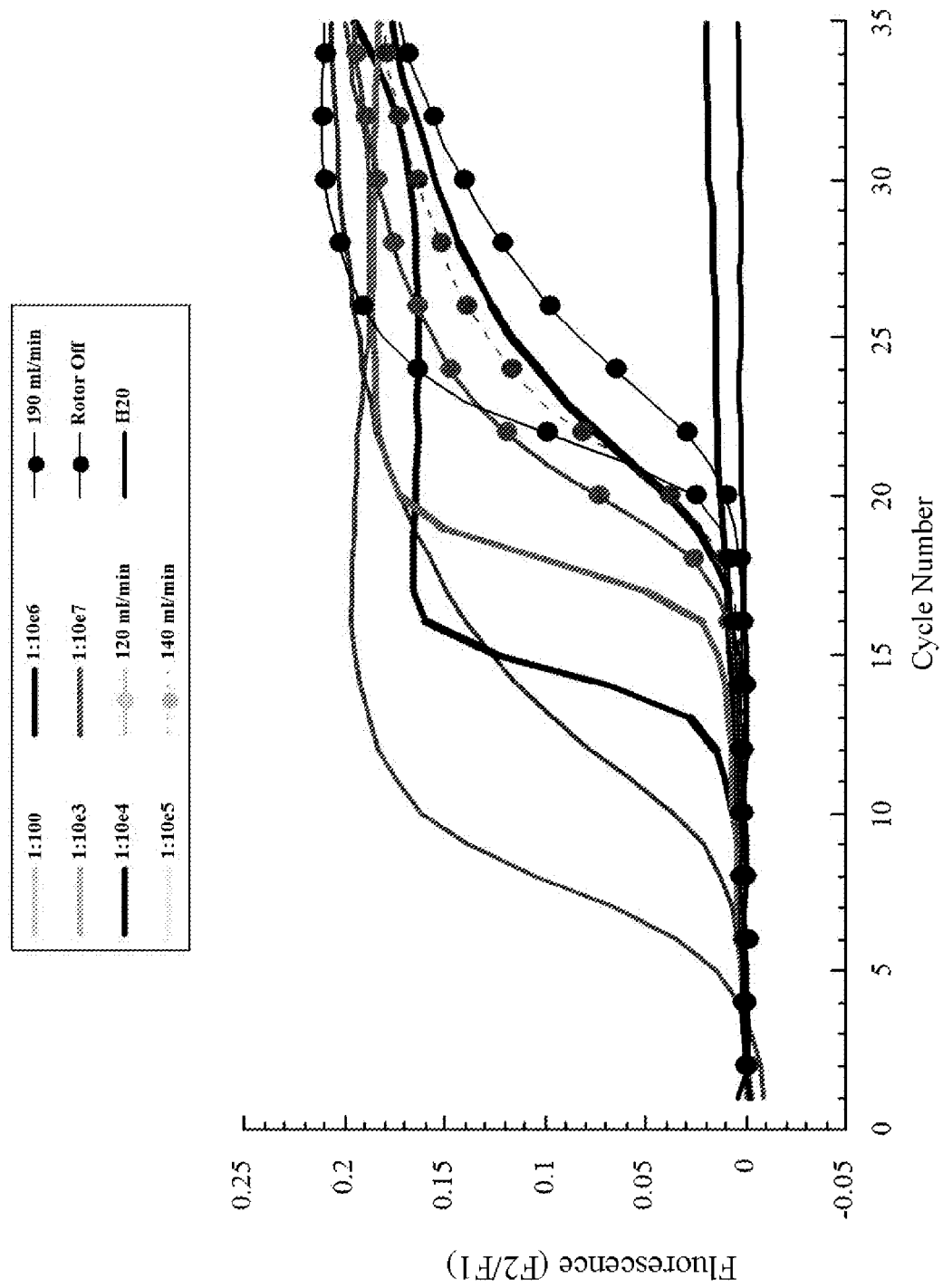
Figure 13B:
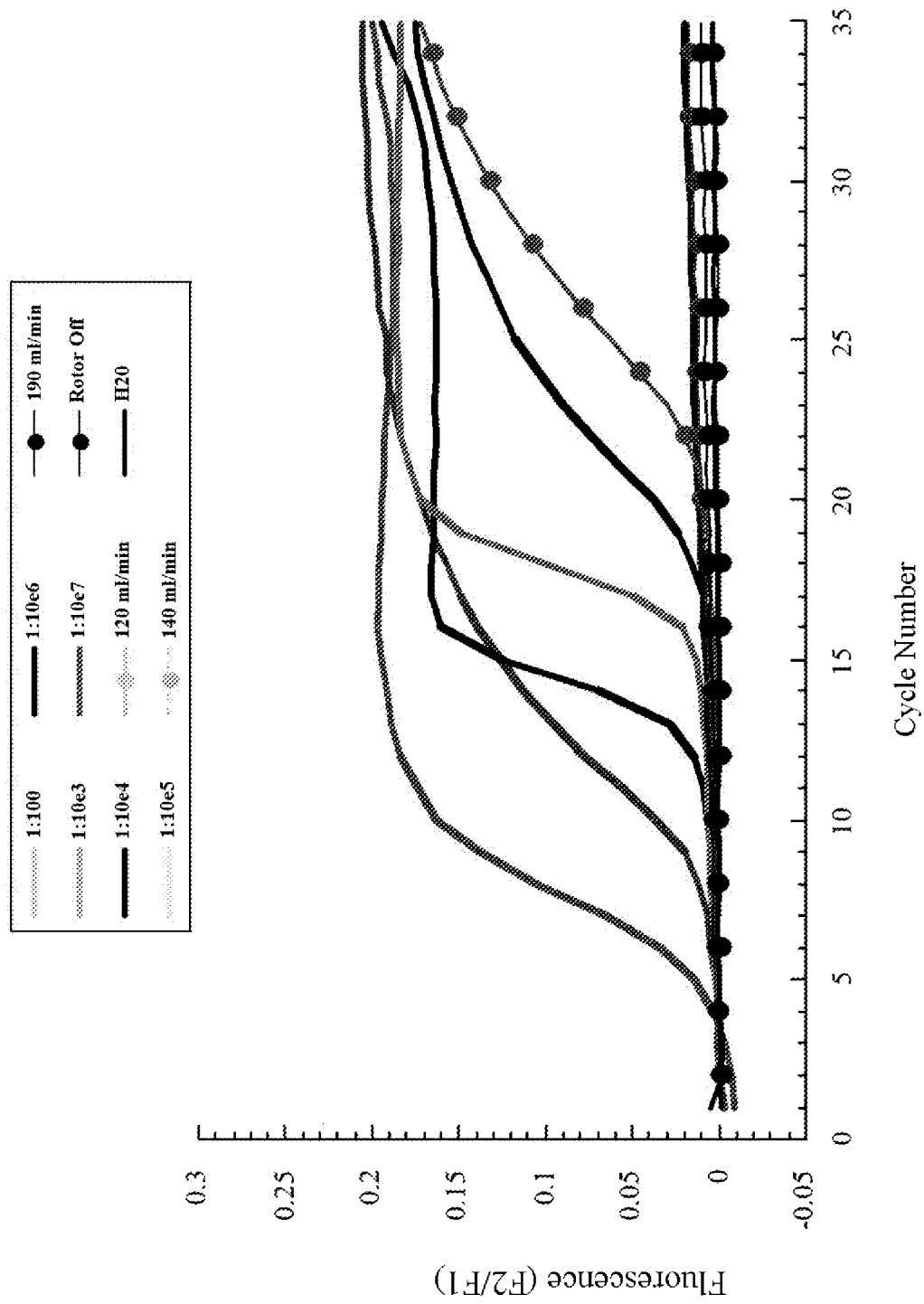
Figure 13C:
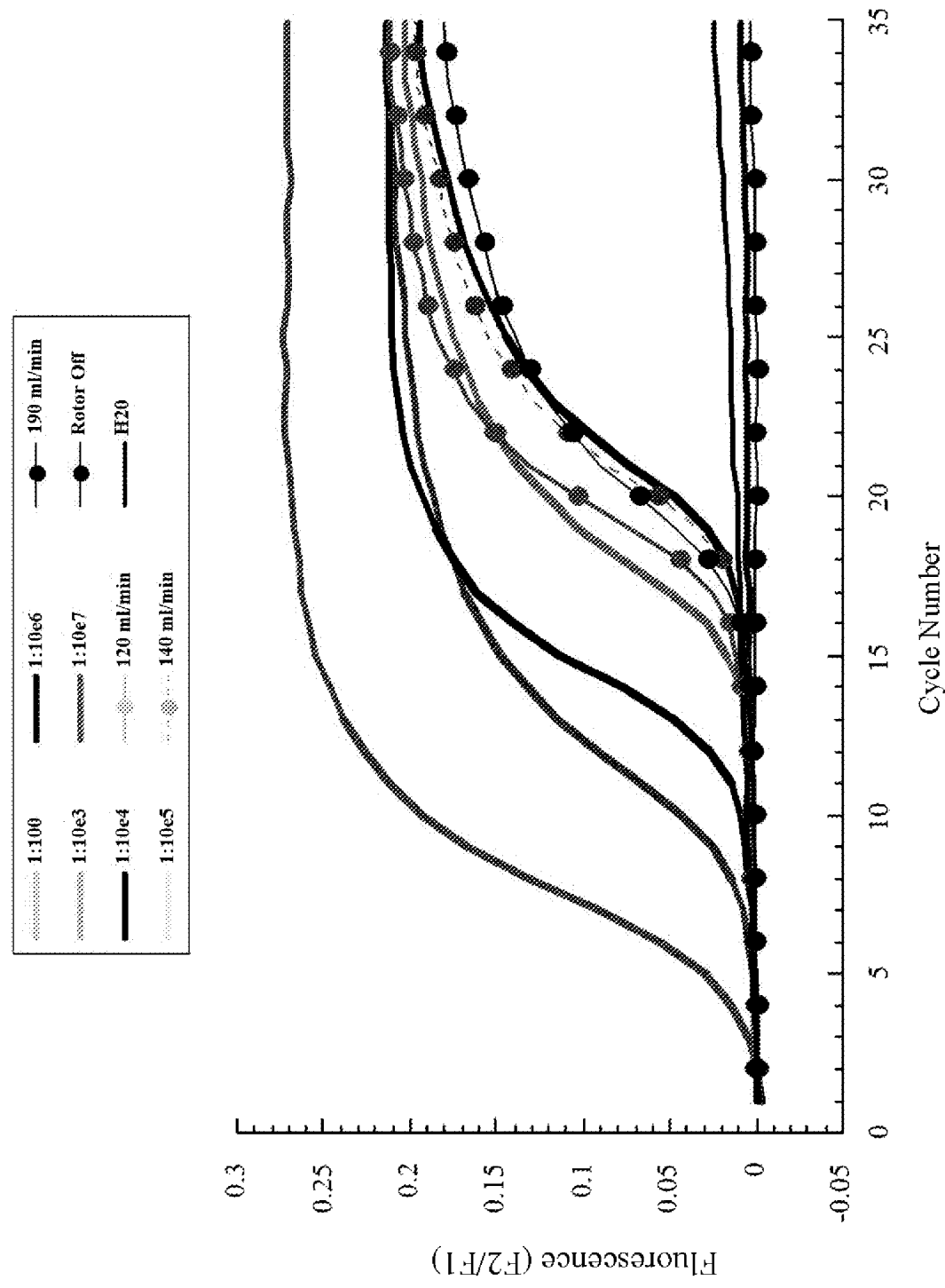

FIG. 13. Contamination of patient elutriated apheresis fractions is demonstrated at at level of 1:10$^5$-1:10$^6$. Quantitative PCR analysis of apheresis fractions from patients presenting with disseminated Ewing's sarcoma. Cycle number (x axis) is plotted vs. fluorescence (y axis) Patient samples are compared to standard contaminated dilutions. Patient a (top panel) shows contamination of all fractions at a level of 1:10$^5$-1:10$^6$. Patient B (middle panel) shows contamination in the leukocyte fraction only at a level of approximately 1:10$^6$, Patient C (bottom panel) shows contamination in several fractions at a similar level.

Figure 14:
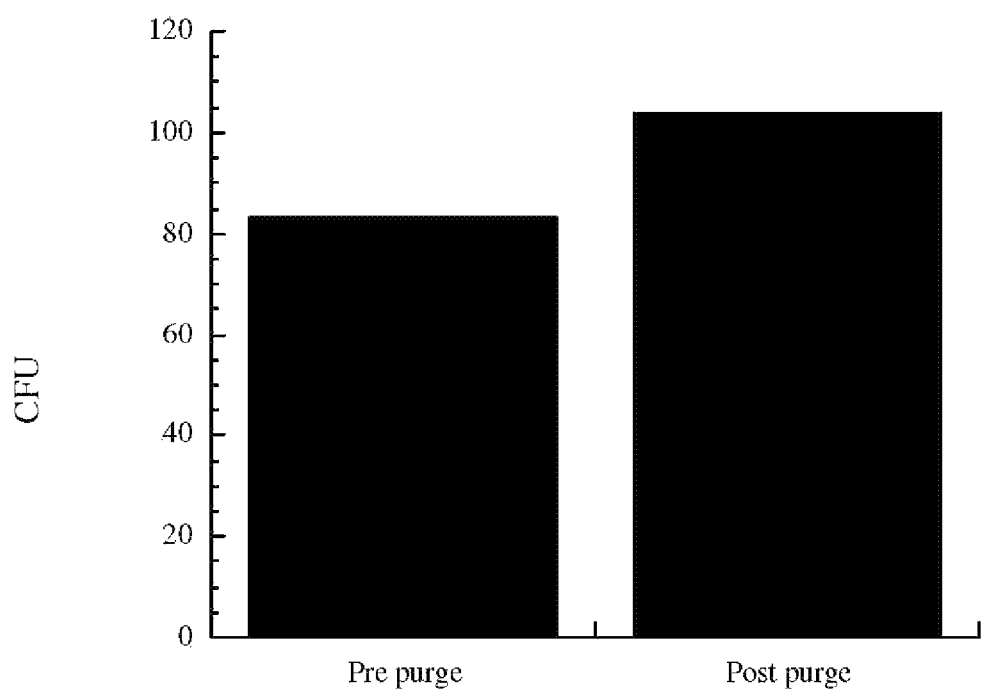

FIG. 14. Progenitor CFU capability is not affected by 8H9 based purging. Colony formy units from CD34 selected cells from bone marrow from a normal healthy donor (x axis) are plotted for pre- and post purged samples.

Figure 15:
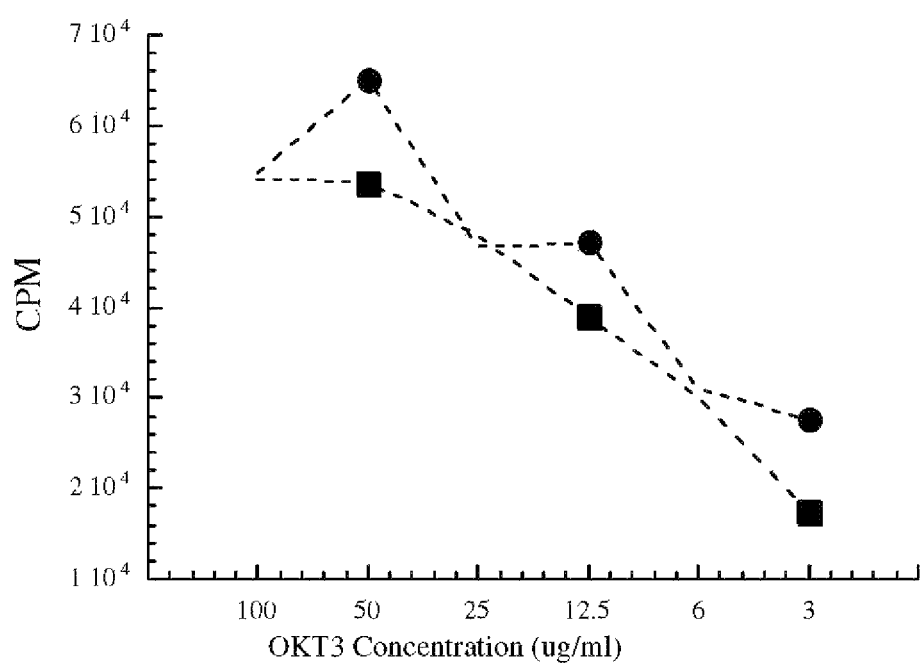

FIG. 15. OKT3 mediated T cell proliferation is unchanged after purging when compared to pre-purged proliferation. T cells from normal healthy donor buffy coat were evalauted for [$^3$H] Thymidine uptake as a measure of T cell proliferation with a decreasing concentration of OKT3. Uptake is measured as counts per million (y axis) and is plotted vs. OKT3 concentration for pre-purged (solid square), and post purged (solid circle).

Fourth Series of Experiments

Figure 16:
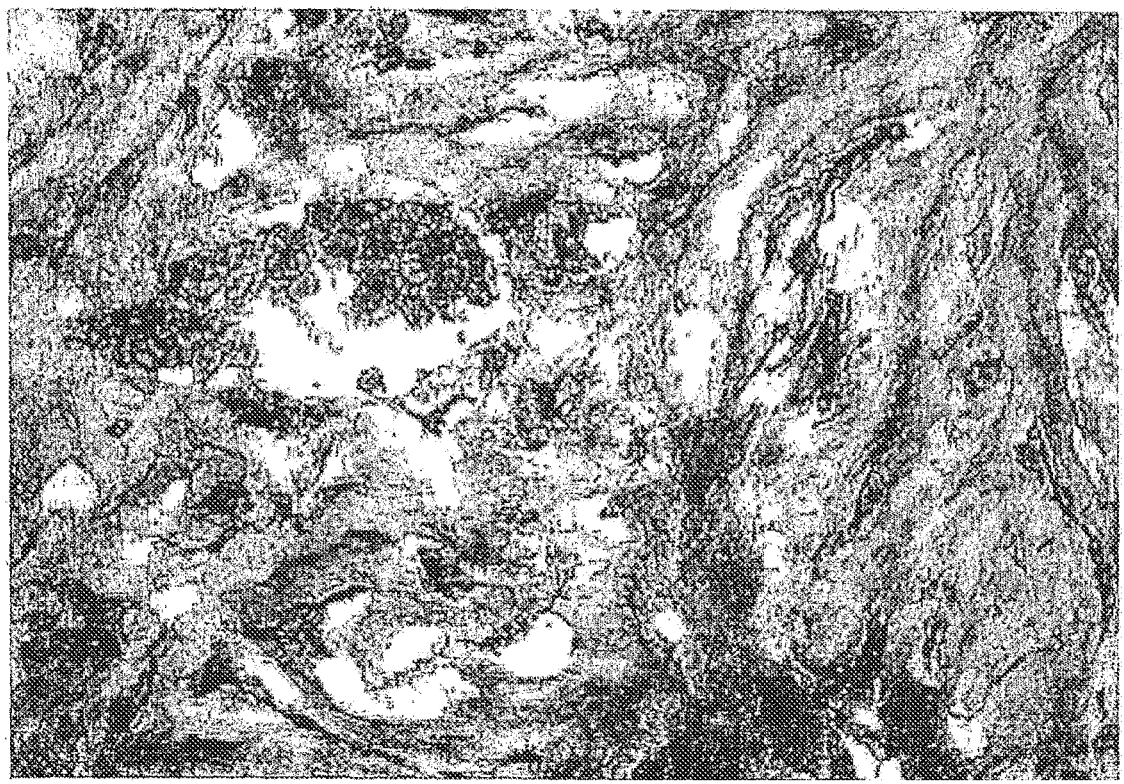

FIG. 16. DSRCT (40X) demonstrating cell membrane and stromal reactivity with 3F8

Figure 17:
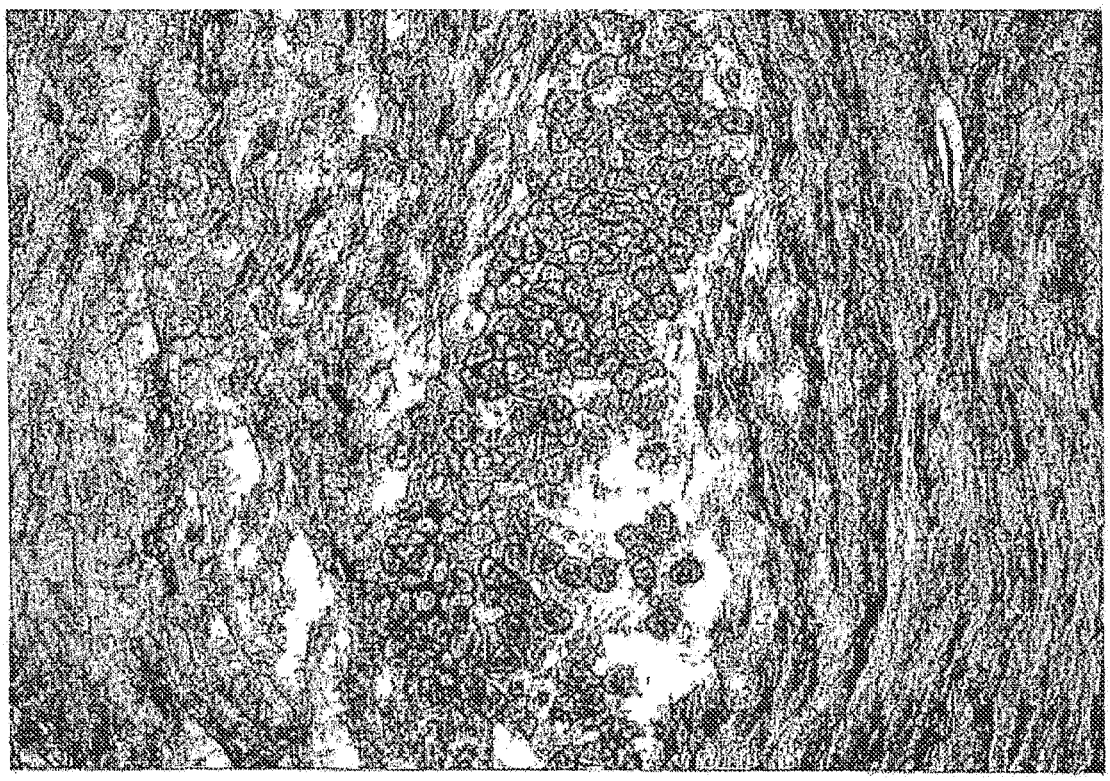

FIG. 17. DSRCT (40X) showing strong, homogeneous, cell membrane and stromal reactivity with 8H9

Fifth Series of Experiments

Figure 18A:
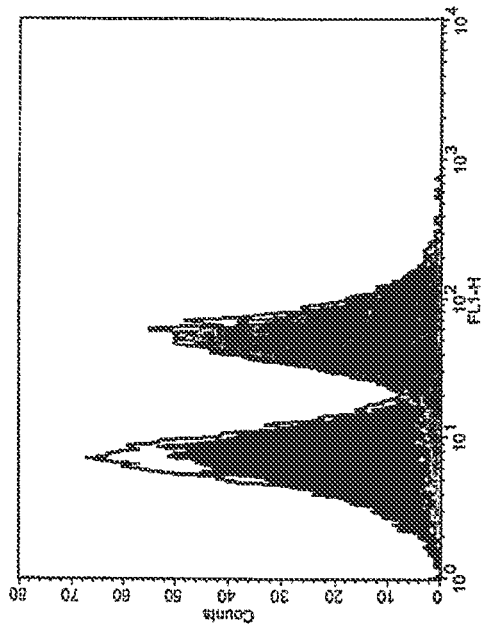
Figure 18B:
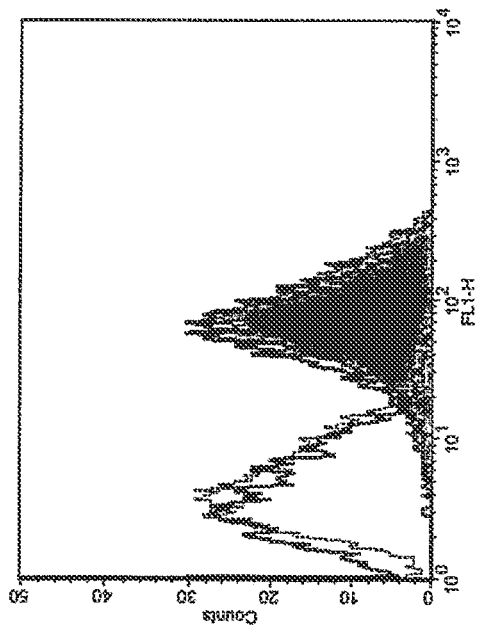

FIG. 18. Inhibition of 8119 by anti-idiotype 2E9 by FACS analysis. 18A: Staining of LAN-1 neuroblastoma cells with 5 ug/ml of 8H9 (shaded peak) was not inhibited at low concentration of 2E9 (2 ug/ml, solid line), but almost completely at concentration of 10 ug/ml (dotted line) superimposable with the negative antibody control (solid line). 18B: Staining of LAN-1 neuroblastoma cells with 5 ug/ml of 3F8 (anti-GD2, shaded peak) was not inhibited by any concentrations (2 ug/ml, solid line, or 200 ug/ml, dotted line) of 2E9. 18C Staining of HTB-82 rhabdomyosarcoma cells with 5 ug/ml of 8H9 (grey peak) was not inhibited at low concentration (2 ug/ml, solid line), but completely at 10 ug/ml of 2E9 (solid line) superimposable with negative antibody control (black peak).

Figure 19:
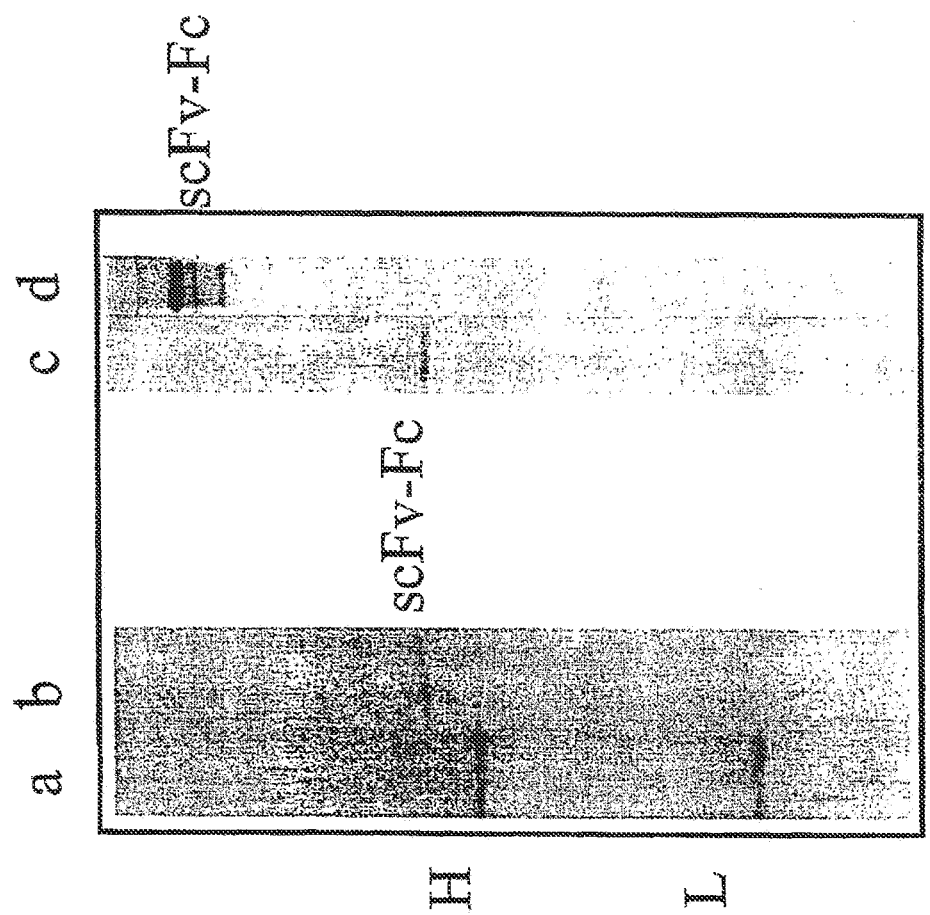

FIG. 19. SDS-PAGE (lanes a and b) and Western blot (c and d) of 8H9 scFv-Fc. H=heavy chain of 8H9, L=light chain of 8H9, scFv-Fc=chimeric fusion protein between 8H9 scFv and the human 1-CH2—CH3 domain. With 2-mercaptothanol: lanes a, b and c. Native gel : lane d. SDS-PAGE was stained with Comassie Blue; western blot with 2E9 anti-idiotypic antibody.

Figure 20A:
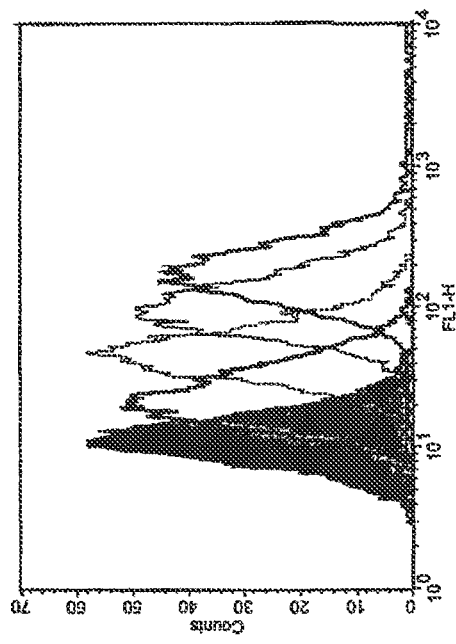
Figure 20B:
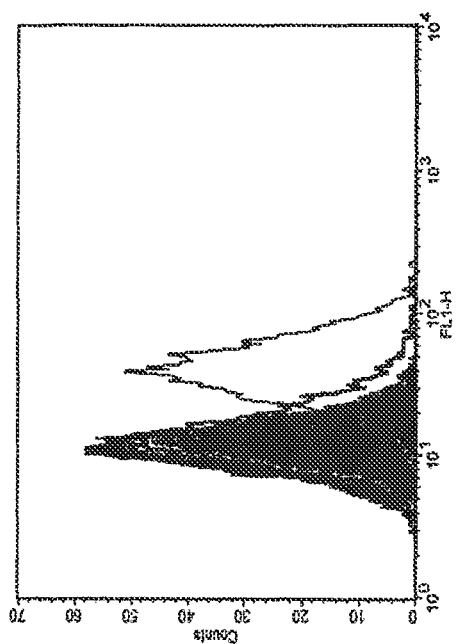

FIG. 20. FACS analysis of 8h9-scFv-Fc staining of HTB82 rhabdomyosarcoma cells. 20A Immunofluorescence increased with concentrations of 8H9-scFv-Fc (1, 5, 25, 125 ug/ml), shaded peak is no antibody control. 20B: Cell staining (5 ug/ml of 8H9-scFv-Fc, thin solid line) was completely inhibited (thick solid line) at 1 ug/ml of anti-idiotypic antibody 2E9, shaded peak is no antibody control.

Figure 21:
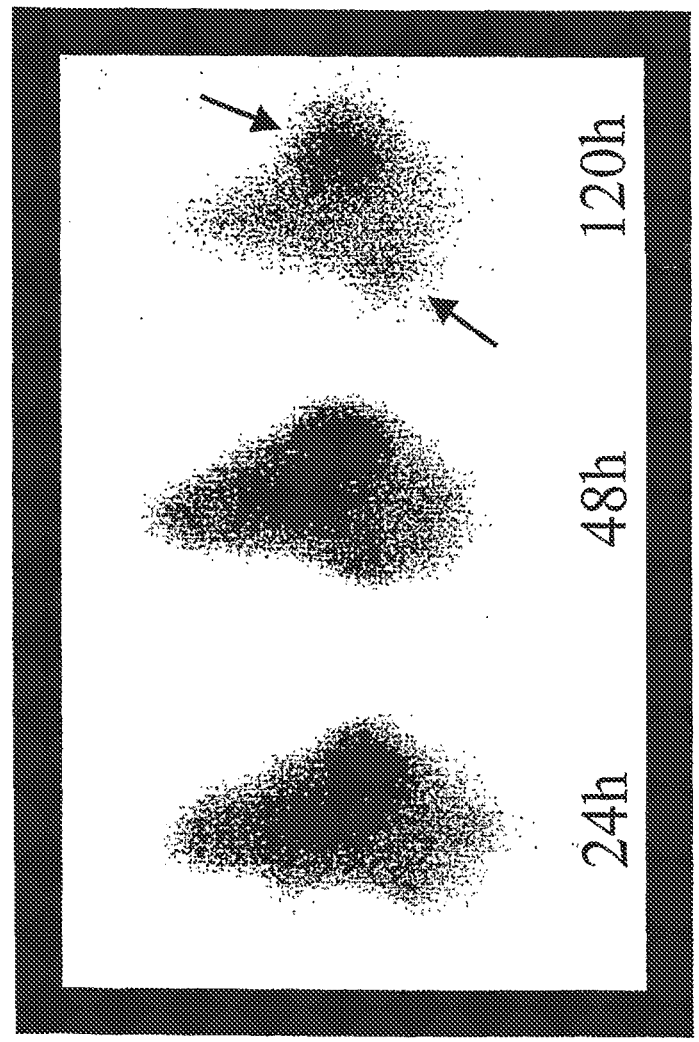

FIG. 21. Immunoscintigraphy of human tumors using $^{125}$I-labeled 8H9 scFv-Fc. Mice xenografted with human LAN-1 neuroblastoma received retroorbital injections of 25 uCi of 125I-labeled antibody. 24 h, 48 h and 7 days after injection, the animals were anesthesized and imaged with a gamma camera.

Figure 22:
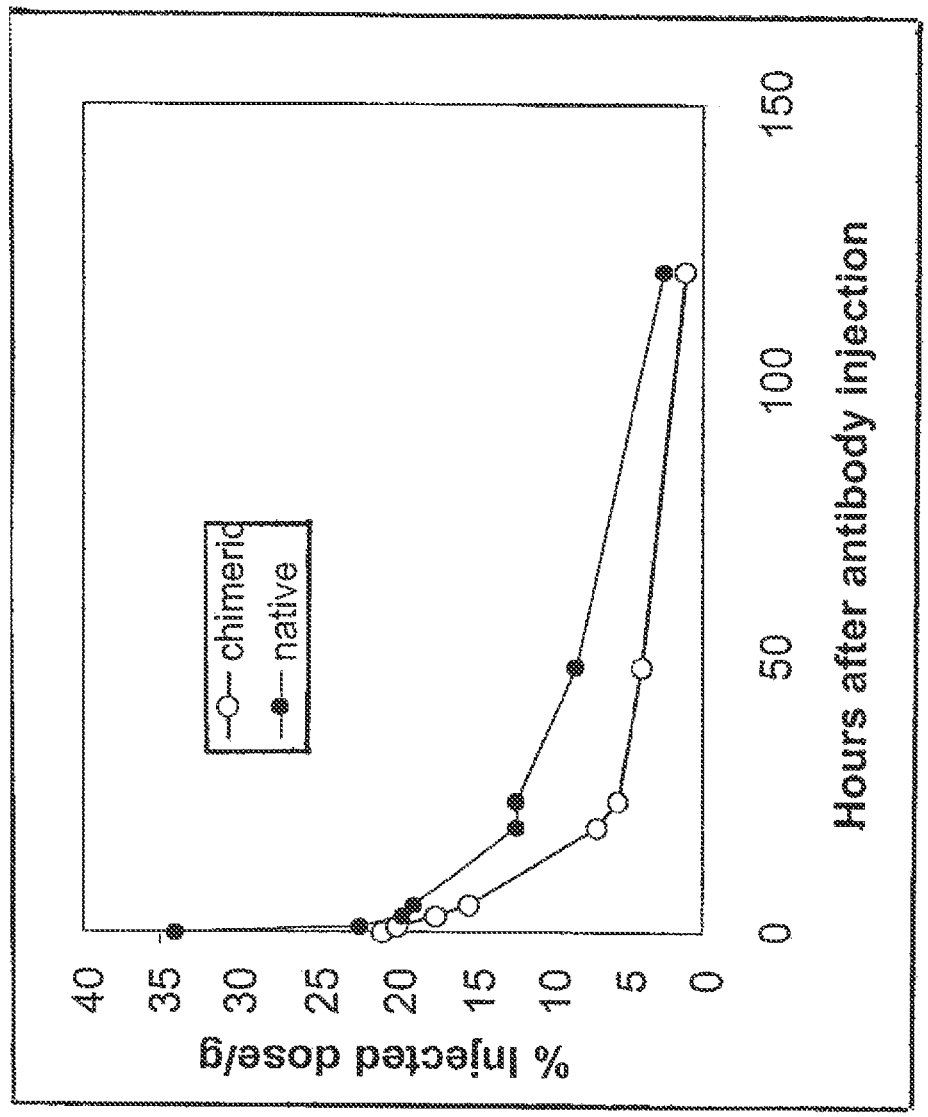

FIG. 22. Blood clearance of $^{125}$I-labeled chimeric 8H9 and $^{125}$I-native 8H9. Mice xenografted with human LAN-1 neuroblastoma received retroorbital injections of $^{125}$I-labeled antibody. Percent injected dose/gm of serial blood samples were plotted over time.

Sixth Series of Experiments

Figure 23:
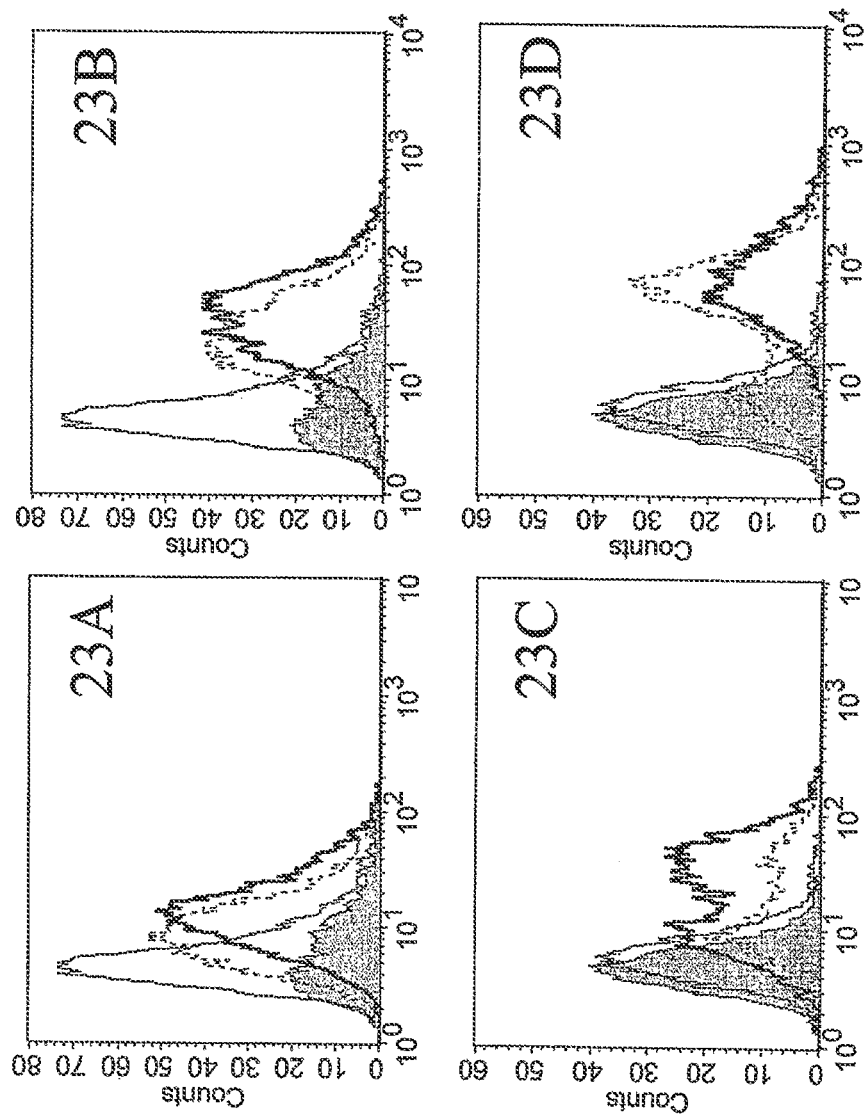

FIG. 23. Anti-idiotype affinity enrichment of producer lines. Producer lines were stained with anti-idiotypic MoAb 2E9 before (shaded peak, A and B), and after first (dotted line peak, A) and second (thick solid line, A) affinity purification, and after first (dotted line, B) and second (solid line B) subcloning, showing improved scFv expression. By FACS indicator line K562 showed improved scFv expression after first (dotted line, C) and second (thick solid line, C) affinity purification of the producer line, and subsequent first (dotted line, C) and second (thick solid line, D) subcloning of the producer line, when compared to unpurified producer lines (shaded peaks, C and D), consistent with improvement in gene transduction efficiency. The thin solid line curves in each figure represents nonproducer line (A and B) or uninfected K562 (C and D).

Figure 24:
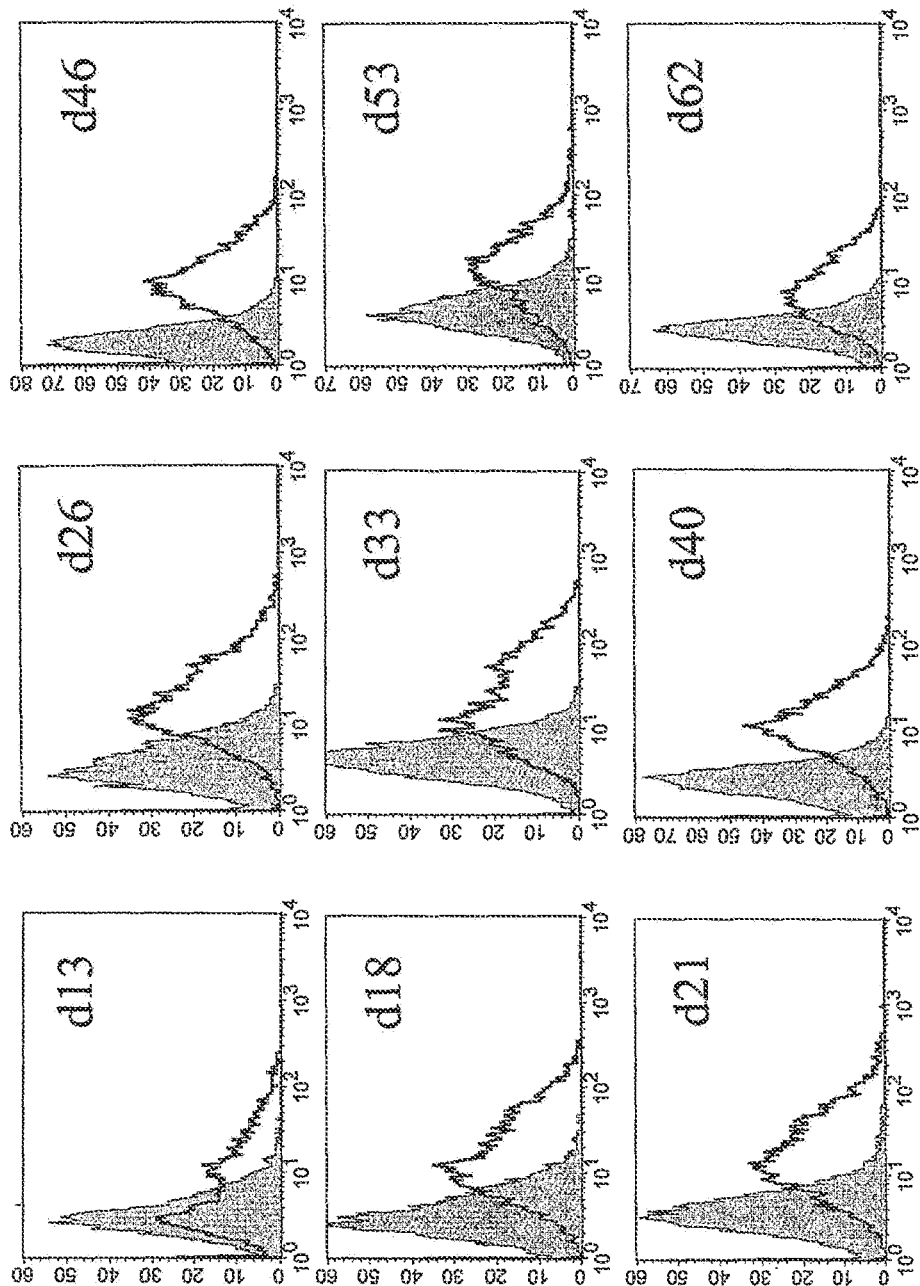

FIG. 24. Flow cytometry analysis of scFv expression. Cultured 8H9-scFv-CD28-. gene-modified lymphocytes were assayed for their scFv expression using anti-idiotypic MoAb 2E9 (solid curves) and control rat IgG1 MoAb as control (shaded histograms) from day 13 through day 62. Although a substantial proportion of cells were positive by day 13, they became homogeneous by day 21 and persisted till day 62, when the overall mean fluorescence appeared to decrease.

Figure 25:
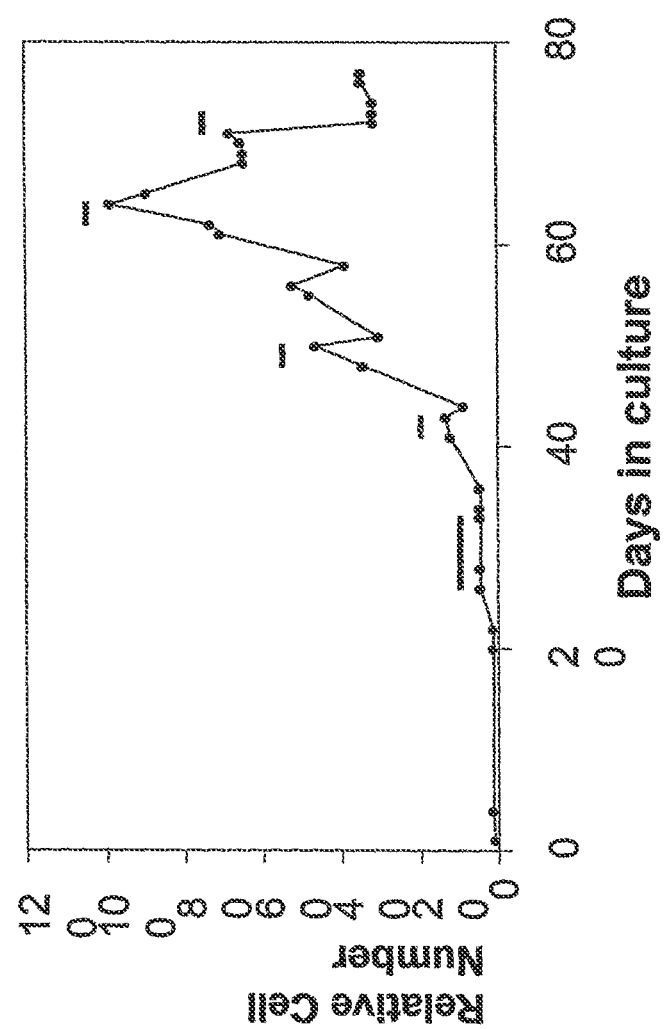

FIG. 25. In vitro expansion of 8H9-scFv-CD28- gene-modified primary human lymphocytes. Clonal expansion was expressed as a fraction of the initial viable cell number. IL-2 (100 U/ml) was added after retroviral infection and was present throughout the entire in vitro culture period. Short bars depict the days when soluble anti-idiotypic antibody 2E9 (3-10 ug/ml) was present in the culture.

Figure 26:
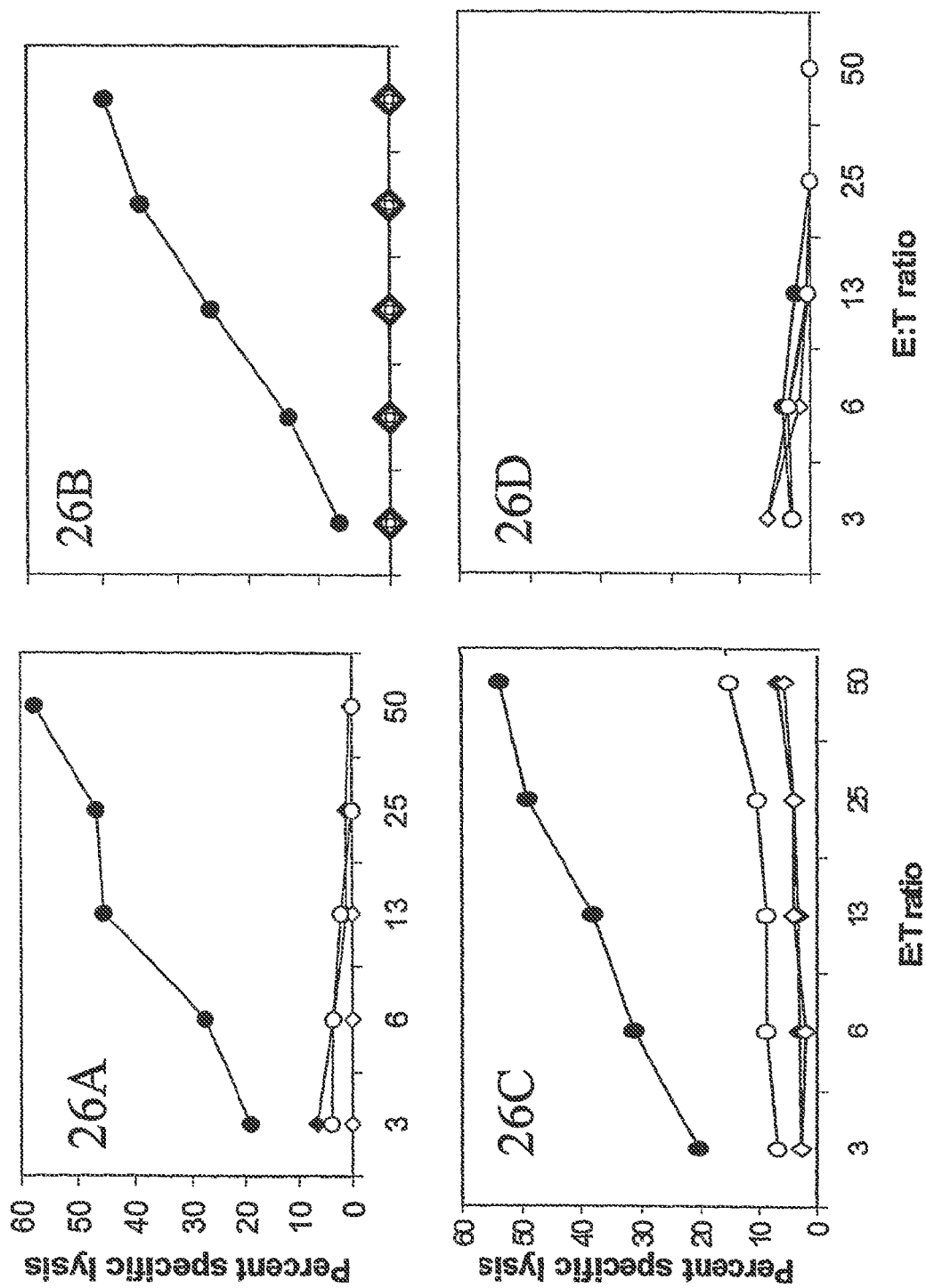

FIG. 26. Cytotoxicity against tumor cell lines: 8H9-scFv-CD28- gene-modified lymphocytes from day 56 of culture (scFv-T) were assayed by $^{51}$Cr release assay in the presence or absence of 8H9 (50 ug/ml final concentration) as an antigen blocking agent. Control lymphocytes (LAK) from the same donor but not gene-modified, were cultured under the same conditions as the gene-modified cells. 26A: NMB-7 neuroblastoma. 26B: LAN-1 neuroblastoma. 26C: HTB-82 rhabdomyosarcoma. 26D: Daudi lymphoma.

Figure 27:
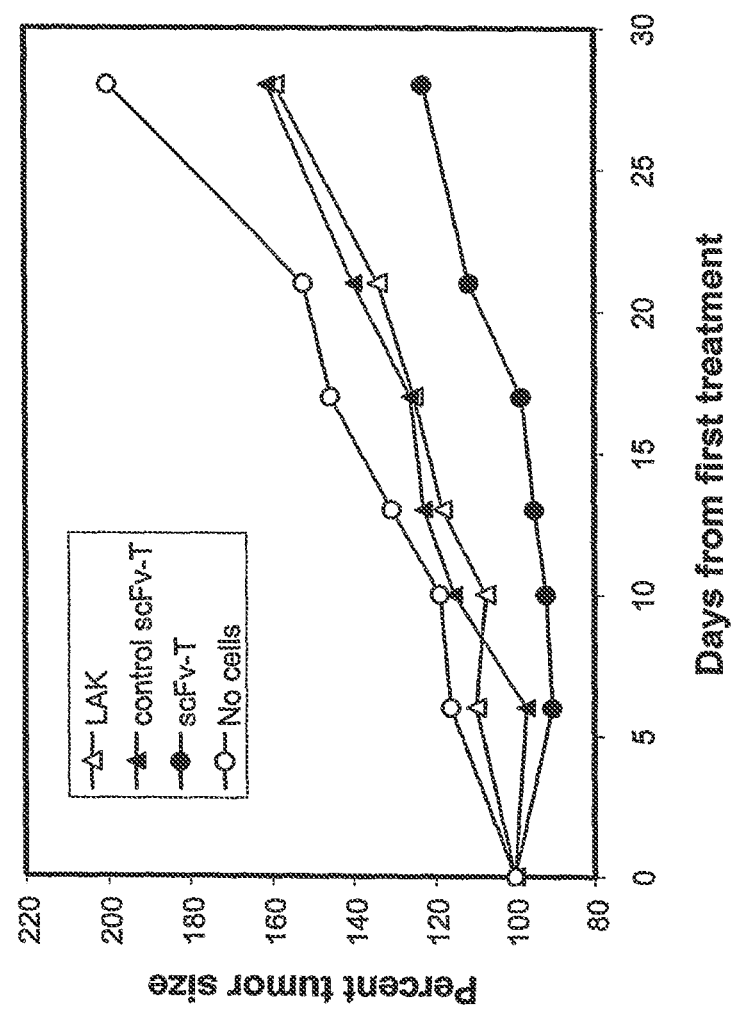

FIG. 27. Suppression of rhabdomyosarcoma tumor growth in SCID mice. Human rhabdomyosarcoma HTB-82 was strongly reactive with 8H9, but not with 5F11 (anti-GD2) antibodies. Experimental group: 8H9-scFv-CD28- gene-modified human lymphocytes (solid circles). Control groups: no cells +2E9 (open circles), cultured unmodified lymphocytes (LAK) +2E9 (open triangles), or 5F11scFv-CD28-modified lymphocytes +1G8 [rat anti-5F11 anti-idiotype MoAb] (solid triangles).

Seventh Series of Experiments

Figure 28:

FIG. 28. Sequential imaging of nude mouse bearing RMS xenograft 24, 48 and 172 h after injection with 4.4 MBq $^{125}$I-8H9 as compared to a RMS xenograft-bearing mouse imaged 172 h after injection with 4.4 MBq$^{125}$I-2C9.

Figure 29:
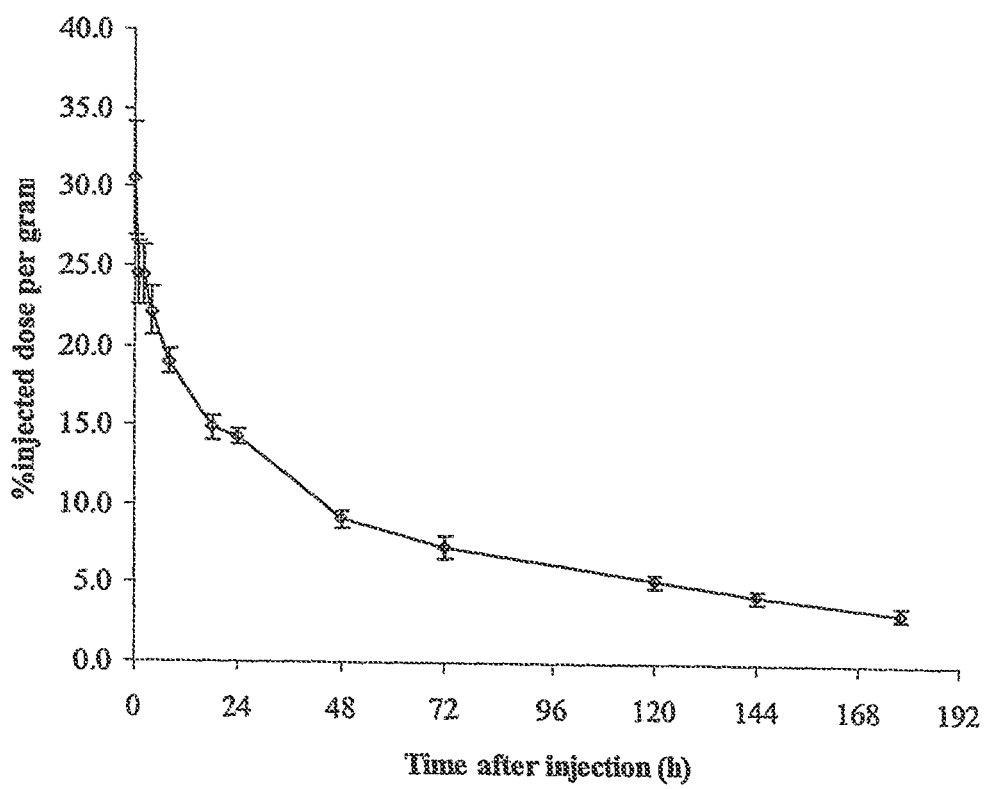

FIG. 29. Blood kinetics of $^{125}$I-8H9 in nude mice with RMS xenografts. Error bars represent SEM.

Figure 30:
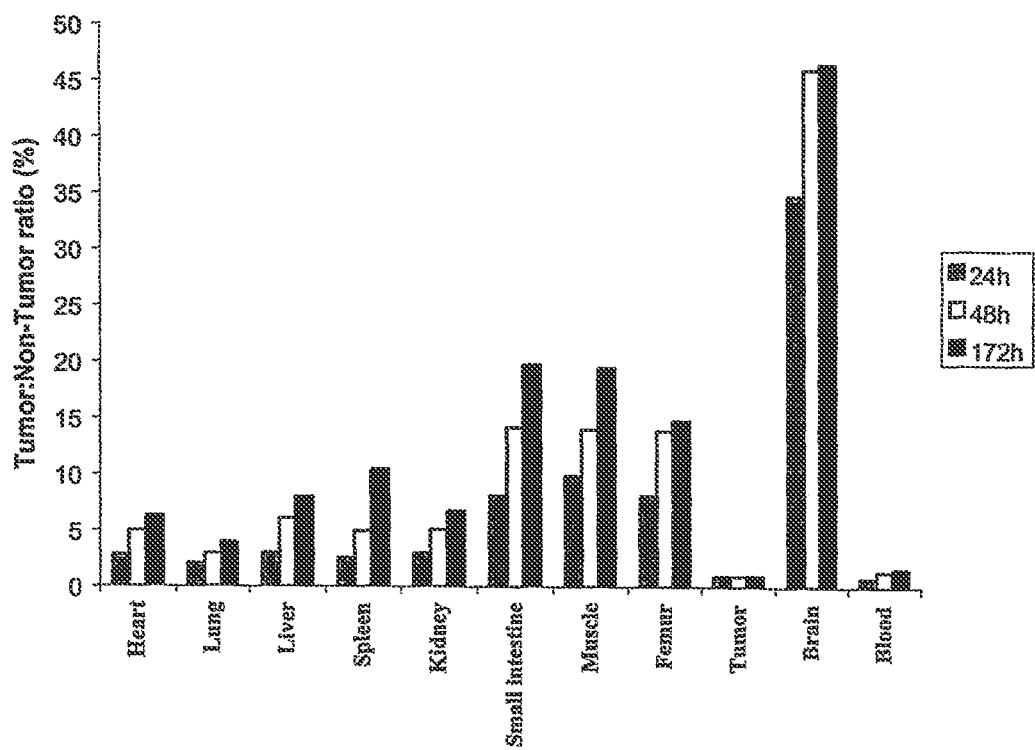

FIG. 30. Comparison of biodistribution of $^{125}$I-8H9 at 24, 48 and 172 h after injection in xenograft and normal tissues.

Figure 31:
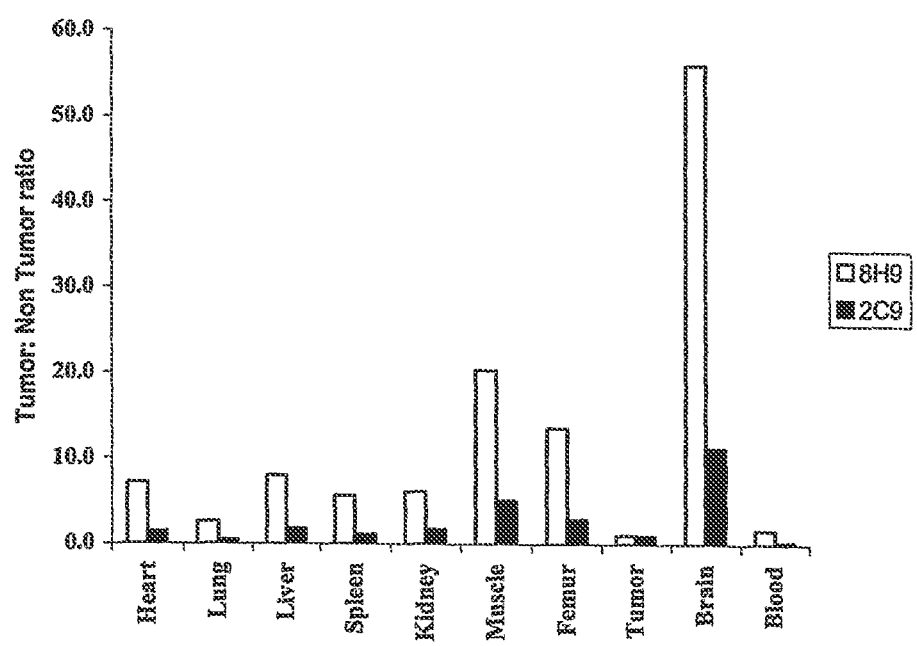

FIG. 31. Comparison of biodistribution of $^{125}$I-8H9 with that of the nonspecific anticytokeratin MoAb $^{125}$I-2C9 (solid bars) in xenografts and normal tissues.

Figure 32:
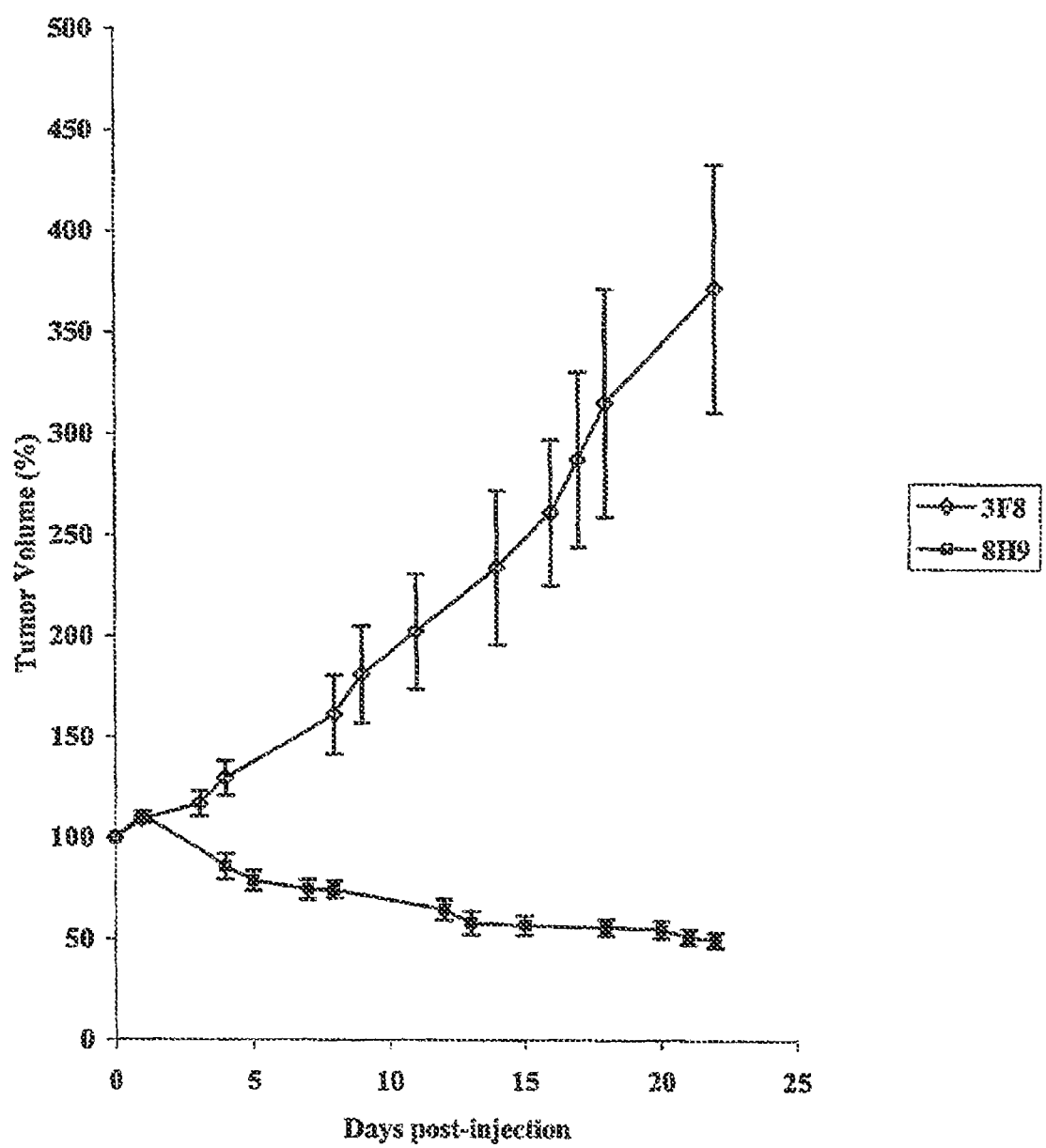

FIG. 32. Anti tumor effect on RMS xenografts: $^{131}$I-8H9 versus negative control MoAb$^{131}$I-3F8. Each mouse received 18.5 MBq radiolabeled MoAb (5 mice per group).

FIG. 33: 8H9 scFv gene sequence (sense and complementary). Complementary determining regions (CDR) are marked in boxes in the following order : CDR-1 (HC, heavy chain), CDR-2 (HC), CDr-3 (HC), CDR-1 (LC, light chain), CDR-2 (LC), CDR-3 (LC).

FIG. 34: Gene and amino acid sequences of 8H9scFv is depicted. Mutated 8H9 scFv carries the following site-directed mutagenesis (VH: K13E and VL: R18Q, R45Q, K103E, K107E) to decrease PI from 6.4 to 4.8, and net charge from −1 to −9, a strategy to decrease nonspecific normal tissue adherence.

DETAILED DESCRIPTION OF THE INVENTION

This invention provides a composition comprising an effective amount of monoclonal antibody 8H9 or a derivative thereof and a suitable carrier. This invention provides a pharmaceutical composition comprising an effective amount of monoclonal antibody 8H9 or a derivative thereof and a pharmaceutically acceptable carrier. In an embodiment of the above composition, the derivative is a scFv. In a separate embodiment, the antibody is an antibody-fusion construct. In another embodiment, the antibody is an scFvFc.

This invention provides an isolated antibody, wherein the Complementary Determining Region is NYDIN, for CDR1, WIFPGDGSTQY for CDR2, QTTATWFAY for CDR3 for the heavy chain, and RASQSISDYLH for the CDR1, YASQSIS for CDR2, QNGHSFPLT for CDR3 for the light chain. This invention further provides the above antibody, wherein the other sequences are of human origin.

The invention also provides a composition comprising an effective amount of monoclonal antibody 8H9 or a derivative thereof and a suitable carrier, which includes sequences as set forth in FIG. 33. In an embodiment, the sequences are mutated. This invention also provides the mutated form of 8H9, so as to reduce background and cytotoxicity. Other mutations could be established which could achieve the above-described function. In a further embodiment, the antibody includes sequences as set forth in FIG. 34.

Furthermore, the invention provides a composition comprising the above antibodies and an isolated nucleic acid molecule encoding the antibodies above. This invention also provides the isolated nucleic acid molecule above, wherein the sequences are set forth in FIG. 33.

This invention also provides a peptide or polypeptide comprising: NYDIN, WIFPGDGSTQY, QTTATWFAY, RASQSISDYLH, YASQSIS, QNGHSFPLT alone or in combination thereof. The peptide or polypeptide functions similarly to the 8H9 antibody and therefore, for the below uses, this peptide or polypeptide may be used similarly. In an embodiment, the invention provides an isolated nucleic acid encoding the above peptide.

In addition, this invention provides a vector comprising the above nucleic acid molecules. The invention also provides a cell comprising the above vector. This invention further provides cells expressing the 8H9 or derivative of 8H9 antibodies.

This invention provides an antibody other than the monoclonal antibody 8H9 comprising the complementary determining regions of monoclonal antibody 8H9 or a derivative thereof, capable of binding to the same antigen as the monoclonal antibody 8H9.

This invention also provides a substance capable of competitively inhibiting the binding of monoclonal antibody 8H9. In an embodiment, the substance is an antibody. In another embodiment, the substance is a peptide.

This invention further provides an isolated single chain antibody of 8H9 or a derivative thereof. This invention also provides an isolated scFv of monoclonal antibody 8H9 or a derivative thereof. Single chain antibodies or derivatives are known in the antibody field. In an embodiment, the scFv is directly or indirectly coupled to a cytotoxic agent. In a further embodiment, the scFv is linked to a first protein capable of binding to a second protein which is coupled to a cytotoxic agent. Same rationale applies to the imaging uses of the 8H9 monoclonal antibody or its derivative. In the case of imaging, instead of a cytotoxic agent, the antibody or its derivative will be coupled to an imaging agent. Both cytotoxic or imaging agents are known in the art.

This invention provides a cell comprising 8H9-scFv. In an embodiment, the cell is a red cell. This invention also provides a 8H9-scFv-gene modified cell.

This invention also provides a liposome modified by 8H9-scFv. It is one intention of the disclosure to deliver 8H9 via liposomes or via other delivery technologies.

This invention provides a method to directly kill, or deliver drug, DNA, RNA or derivatives thereof to cell bearing the antigen recognized by the monoclonal antibody 8H9 or to image cells or tumors bearing said antigen using the isolated 8H9-scFv or 8H9-scFv modified cell or liposome.

This invention provides a protein with about 58 kilodaltons in molecular weight, reacting specifically with the monoclonal antibody 8H9. When this protein is glycosylated, the apparent molecular weight is about 90 kilodaltons.

This invention provides an antibody produced by immunizing the expressed 8H9 antigen or specific portion thereof. The specific portion is the region which is recognized by 8H9. Another region is the region which performs its specific function.

This invention provides a nucleic acid molecule encoding 8H9 antigen.

This invention provides a nucleic acid molecule capable of specifically hybridizing the nucleic acid molecule which encodes the 8H9 antigen. The nucleic acid molecule includes but is not limited to synthetic DNA, genomic DNA, cDNA or RNA.

This invention also provides a vector comprising the nucleic acid molecule encoding the 8H9 antigen or a portion thereof. The portion could be a functional domain of said antigen. This invention provides a cell comprising the nucleic acid molecule encoding the 8H9 antigen.

This invention provides a method for producing the protein which binds to the monoclonal antibody 8H9 comprising cloning the nucleic acid molecule which encodes the 8H9 antigen in an appropriate vector, expressing said protein in appropriate cells and recovery of said expressed protein.

This invention provides a method for production of antibody using the expressed 8H9 antigen or the portion which is immunogenic. This invention also provides an antibody produced by the above described method. In an embodiment, the antibody is polyclonal. In another embodiment, the antibody is a monoclonal.

This invention provides a method of inhibiting the growth of tumor cells comprising contacting said tumor cells with an appropriate amount of monoclonal antibody 8H9 or a derivative thereof, or the antibody produced using the expressed 8H9 antigen or a derivative thereof.

This invention provides a method of inhibiting the growth of tumor cells in a subject comprising administering to the subject an appropriate amount of monoclonal antibody 8H9 or a derivative thereof, or the antibody produced using the expressed 8H9 antigen or a derivative thereof.

This invention provides a method for imaging a tumor in a subject comprising administering to the subject a labeled monoclonal antibody 8H9 or a labeled derivatives, or a labeled antibody produced using the expressed 8H9 antigen or a labeled derivative. In an embodiment, the antibody or the derivative is labeled with radioisotope.

This invention provides a method of reducing tumor cells in a subject comprising administering to the subject monoclonal antibody 8H9 or a derivative thereof, or a monoclonal antibody produced using the expressed 8H9 antigen or a derivative thereof wherein the antibody or derivative is coupled to a cytotoxic agent to the subject. In an embodiment, the coupling to a cytotoxic agent is indirect. In another embodiment, the coupling is first directly linking the antibody or derivative with a first protein which is capable of bind to a second protein and the second protein is covalently couple to a cytotoxic agent. In a further embodiment, the cytotoxic agent is a radioisotope.

This invention also provides a method to evaluate the tumor bearing potential of a subject comprising measuring the expression the 8H9 antigen in the subject, wherein the increased expression of said antigen indicates higher tumor bearing potential of the subject.

This invention provides a transgenic animal comprising an exogenous gene encoding the 8H9 antigen. The transgenic animal may also carried an knock out gene encoding the 8H9 mouse analogous antigen. In an embodiment, it is a transgenic mouse.

This invention provides a method to screening new anti-tumor compound comprising contacting the transgenic animal with the tested compound and measuring the level of expression of the 8H9 antigen in said transgenic animal, a decrease in the level of expression indicating that the compound can inhibit the expression of the 8H9 antigen and is a anti-tumor candidate.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

First Series of Experiments
Monoclonal Antibody 8H9 Targets a Novel Cell Surface Antigen Expressed by a Wide Spectrum of Human Solid Tumors Tumor-restricted surface antigens may be targets for diagnosis and immune-based therapies. Monoclonal antibody 8H9 is a murine IgG1 hybridoma derived from the fusion of mouse myeloma SP2/0 cells and splenic lymphocytes from BALB/c mice immunized with human neuroblastoma. By immunohistochemistry, 8H9 was highly reactive with human brain tumors, childhood sarcomas, neuroblastomas and less so with adenocarcinomas. Among primary brain tumors, 15/17 glioblastomas, 3/4 mixed gliomas, 4/11 oligodendrogliomas, 6/8 astrocytomas, 2/2 meningiomas, 3/3 schwannomas, 2/2 medulloblastomas, 1/1 neurofibroma, 1/2 neuronoglial tumors, 2/3 ependymomas and 1/1 pineoblastoma were tested positive. Among sarcomas, 21/21 Ewing's/

PNET, 28/29 rhabdomyosarcoma, 28/29 osteosarcomas, 35/37 desmoplastic small round cell tumors, 2/3 synovial sarcomas, 4/4 leiomyosarcomas, 1/1 malignant fibrous histiocytoma and 2/2 undifferentiated sarcomas tested positive with 8H9. 87/90 neuroblastomas, 12/16 melanomas, 3/4 hepatoblastomas, 7/8 Wilm's tumors, 3/3 rhabdoid tumors and 12/27 adenocarcinomas also tested positive. In contrast 8H9 was nonreactive with normal human tissues including bone marrow, colon, stomach, heart, lung, muscle, thyroid, testes, pancreas, and human brain (frontal lobe, cerebellum, pons and spinal cord). Reactivity with normal cynomolgus monkey tissue was similarly restricted. Indirect immunofluorescence localized the antigen recognized by 8H9 to the cell membrane. The antigen is proteinase-sensitive and is not easily modulated off cell surface. 8H9 immuno-precipitated a 58 kD band following N-glycanase treatment, most likely a protein with heterogeneous degree of glycosylation. This novel antibody-antigen system may have potential for tumor targeting.

Monoclonal antibodies such as 3F8 (1) and 14.18 (2) against $G_{D2}$ in neuroblastoma, M195 against CD33 in acute leukemia (3), anti-HER2 antibodies in breast cancer (4) and anti-CD20 antibodies in lymphoma (5) have shown efficacy in recent clinical trials. The prognosis in glial brain tumors and metastatic mesenchymal and neuroectodermal tumors remains dismal despite innovations in chemotherapy and radiation therapy. Immunotherapy may offer new possibilities for improving the outcome in these patients.

Tumor antigens expressed on cell membrane are potential targets in immunotherapy. Examples of tumor antigens expressed on glial tumors include neural cell adhesion molecules (6), gangliosides such as $G_{D2}$ and $G_{M2}$ (7), and neuro-hematopoeitic antigens (8). Recent investigations have focused on growth factor receptors as immune targets, in particular type III mutant epidermal growth factor receptor (EGFRvIII) which has been shown to be expressed on 50% of glial brain tumors (9). Notwithstanding the universal expression of NCAM by neuronal cells, two clinical studies have utilized anti-NCAM antibodies in patients. MAb UJ13A was shown to accumulate in gliomas by virtue of disruption of blood brain bather locally (10) and another antibody, ERIC-1 was used in a therapeutic setting in resected glioma cavities with some clinical benefit (11)

Recent studies have targeted immunotherapy to extracellular matrix around tumor cells. Tenascin has been reported to be expressed in 50-95% of glial brain tumors as well as on mesenchymal tumors, carcinomas and normal human glial, liver and kidney cells (12). Anti-tenascin monoclonal antibodies 8106 (13) and BC-2 and BC-4 (14) administered intracavity have recently been reported to show efficacy in the treatment of patients with malignant gliomas. However, since these antigens are also present to varying degrees on normal human neural and non-neural cells, their clinical utility would depend on their overexpression by brain tumors when compared to normal tissues. With the exception of EGFRvIII, the glial tumors antigens described to date are generally found on normal brain tissue, or are restricted to intracellular compartments, thus with limited clinical utility for antibody targeting.

Membrane antigens that have been targeted on osteosarcoma include $G_{D2}$ (15), CD55 (16) and an as yet undefined osteosarcoma-associated antigen recognized by the MoAbs TP-1 and TP-3 (17). However, these antigens are present to varying degrees on normal tissues. Similarly the glycoprotein p30/32 coded by the MIC2 oncogene and recognized by the monoclonal antibody O13 in the Ewing's family of tumors is expressed on normal tissues (18). In rhabdomyosarcoma, the MyoD family of oncofetal proteins is nuclear in localization (19) and therefore inaccessible to antibody-targeted immunotherapy.

An ideal tumor antigen for targeted immunotherapy should be absent on normal tissues and abundantly expressed on tumor cell surface. Such tumor-specific antigens e.g. idiotypes in B cell lymphoma are rare (20). Moreover, a "generic" tumor-specific antigen expressed on tumor cells of varying lineage recognized by monoclonal antibodies may have broader utility in antibody-based strategies. We describe here a novel tumor-associated antigen, recognized by a murine monoclonal antibody 8H9, expressed on cell membranes of a broad spectrum of tumors of neuroectodermal, mesenchymal and epithelial origin, with restricted distribution on normal tissues.

Material and Methods

Tumor and Normal Tissue Samples

Frozen tumors from 330 patients with neuroectodermal, mesenchymal and epithelial neoplasia were analyzed. All diagnoses of tumor samples were confirmed by hematoxylin and eosin assessment of paraffin-embedded specimens. 15 normal human tissue samples and 8 normal cynomolgus monkey tissue samples obtained at autopsy were also analyzed.

Cell Lines

Human neuroblastoma cell lines LA-N-1 was provided by Dr. Robert Seeger, Children's Hospital of Los Angeles, Los Angeles, Calif. Human neuroblastoma cell lines LA-15-N, LA-66-N, LA-5S, LA-19-S and LA-19-N were provided by Dr. Robert Ross (Fordham University, NY) and IMR 32 and NMB7 by Dr. Shuen-Kuei Liao (McMaster University, Ontario, Canada). Breast carcinoma cell lines SW480 and ZR75-1 were provided by Dr. S. Welt (Memorial Sloan-Kettering Cancer Center, NY) and the melanoma line SKMe128 by Dr. P. Chapman (Memorial Sloan-Kettering Cancer Center, NY). Neuroblastoma cell lines SKNHM, SKNHB, SKNJD, SKNLP, SKNER, SKNMM, SKNCH and SKNSH, rhabdomyosarcoma cell line SKRJC and Ewing's/PNET cell lines SKPPR, SKPRT and SKNMC were derived from patients with metastatic disease treated at MSKCC. The following cell lines were purchased from American Type Culture Collection, Bethesda, Md.: melanoma cell lines HTB63 and HTB67, rhabdomyosarcoma cell line HTB82, small cell lung cancer cell line HTB 119, acute T-leukemia cell line Jurkat, glioblastoma multiforme cell line Glio72, breast cancer cell line HTB 22, colon carcinoma cells line SK Co-1, Hela, embryonal kidney 293, and osteosarcoma cell lines CRL1427, HTB86 and HTB 96. All cell lines were grown at 37° C. in a 6% $CO_2$ incubator using standard culture medium, which consisted of RPMI 1640 medium supplemented with 10% bovine calf serum, 2 mM glutamine, penicillin (100 IU/ml) and streptomycin (100 µg/ml). Normal human hepatocytes were purchased from Clonetics, San Diego, Calif. and processed immediately upon delivery. Normal human mononuclear cells were prepared from heparinized bone marrow samples by centrifugation across a Ficoll-Hypaque density separation gradient. EBV lymphoblastoid cell lines were derived from human mononuclear cells.

Monoclonal Antibody

Female BALB/c mice were hyperimmunized with human neuroblastoma according to previously outlined methods (21). Lymphocytes derived from these mice were fused with SP2/0 mouse myeloma cells line. Clones were selected for specific binding on ELISA. The 8H9 hybridoma secreting an $IgG_1$ monoclonal antibody was selected for further characterization after subcloning.

Immunohistochemical Studies

Eight μm cryostat frozen tumor sections were fixed in acetone and washed in PBS. Immunohistochemical studies were performed as described previously (22). Endogenous peroxidases were blocked in 0.3% $H_2O_2$ in PBS. Sections were incubated in 10% horse serum (Gibco BRL, Gaithersburg, Md.) after blocking with avidin and biotin. Incubation with purified 8H9 (2 μg/ml) in PBS was carried out at room temperature for 1 hour. An IgG1 myeloma was used as a control (Sigma Chemical, St Louis Mo.). Sections were incubated with a secondary horse anti-mouse biotinylated antibody (Vector Laboratories, Burlingame, Calif.) followed by incubation with ABC complex (Vector) and developed with Vector VIP peroxidase substrate or DAB peroxidase substrate kit (Vector). A 10% hematoxylin counterstain for 4 minutes was used. Staining was graded as positive or negative and homogeneous or heterogeneous reactivity noted.

Indirect Immunofluorescence 1 million target cells were washed in PBS and then spun at 180×g for 5 min. The pellets were then reacted with 100 μl of 15 μg/ml 8H9 at 4° C. for 1 hour. After washing the cells with PBS they were allowed to react with 100 μl FITC-conjugated goat F (ab')$_2$ anti-mouse IgG+IgM, (Biosource International, Camarillo, Calif.) at 4° C. Flow cytometric analysis was performed using FACSCalibur Immunocytometer (Becton-Dickinson Immunocytometry Systems, San Jose, Calif.).

In order to study loss of antigen after binding to 8H9, $10^6$ NMB7 and U2OS cell pellets were prepared as above and reacted with 100 μl each of 15 μg/ml of 8H9 or the anti-HLA A,B,C antibody, HB-95 (American Type Culture Collection, Bethesda, Md.) at 4° C. for 1 hour. NMB7 cells were also similarly reacted with the anti-$G_{D2}$ monoclonal antibody 3F8. After washing with PBS, cells were cultured at 37° C. in standard culture medium for 0, 1,2, 4, 8, 12, 24, 36 and 48 h. They were then reacted with FITC-conjugated secondary antibody goat F (ab')$_2$ anti-mouse IgG+IgM, (Biosource International, Camarillo, Calif.) at 4° C. Flow cytometric analysis was performed. Geometric mean immunofluorescence was compared to that of control cells incubated for similar time intervals in standard culture medium in the absence of MoAbs, and then immunostained with HB-95 (U2OS) or 3F8 (NMB7).

Antigen sensitivity to proteinase was tested by incubating 0.5×$10^6$ of HTB82, U2OS and NMB7 cells at 37° C. for 30 minutes in RPMI with increasing concentrations of neutral proteinase, Pronase E from streptomyces griseus (E. Merck, Darmstadt, Germany) After washing, cells were stained with 8H9 or 3F8 and studied by indirect immunofluorescence.

Immunoprecipitation

Immunoprecipitation was carried out using a modification of the standard technique. (23) 8H9-positive cell lines (NMB7, LAN-1, HTB82, U205, HELA, 293) and 8H9-negative cell lines (Jurkat, HTB119) were used. 2×$10^7$ viable cells were washed in TBS (0.05 M Tris-HCl, pH 8, with 0.15 M NaCl) and incubated with 10 U lactoperoxidase (Sigma) 100 ul of 100 U/ml in TBS, 1 mCi $^{125}$I (2.7 ul) and ⅙₀₀₀ dilution of 30% hydrogen peroxide for 5 min at 20° C. Five units of lactoperoxidase (50u1) and the same dilution of hydrogen peroxide (50 ul) were added every 3 min with mixing for a total of 3 times. The cells were washed extensively in TBS containing 2 mg/ml of NaI. The iodinated cells were washed three times in TBS, lysed on ice (30 min) in 500 ul of modified RIPA buffer (0.01 M Tris-HCl, pH 7.2, 0.15 M NaCl, 1% sodium deoxycholate, 1% Nonidet P-40, 0.1% sodium dodecyl sulfate (SDS), 0.01 M EDTA) containing protease inhibitors (1 mM PMSF, 50 ug/ml Bestatin, 2 ug/ml Aprotinin, 0.5 ug/ml Leupeptin, 0.7 ug/ml Pepstatin, 10 ug/ml E-64). The lysates were clarified by centrifugation at 15,000 rpm for 5 min at 4° C., then incubated with 1 mg of 8H9 or IgG1 control antibody for 16 hr at 4° C. with mixing. The antigen-antibody complex was collected by adsorption onto 100 ul Protein G-sepharose beads (Sigma) for 6 hr at 4° C. The immune complex immobilized on Protein G was washed three times with modified RIPA buffer, and then washed once with RIPA buffer containing 1 M NaCl, and then twice with modified TNN buffer (0.05 M Tris-HCl, pH 8, 0.15 M NaCl, 0.05% Nonidet P-40). Bound proteins were removed by elution with SDS-sample buffer and analyzed by 7.5% SDS-PAGE, followed by autoradiography. Deglycosylation of the radiolabeled antigen was carried out on the protein G sepharose using N-glycanase (Glyco, Novato, Calif.) and O-glycanase (Glyco) according to manufacturers' instructions. Molecular weight was estimated using Quantity One software from Bio-Rad Inc. (Hercules, Calif.).

Results

Immunohistochemical Studies

Frozen sections from 330 tumors with histologically confirmed diagnoses of cancer were analyzed for immunoreactivity with mAb 8H9 (Tables 1, 2). 15 histologically normal human tissues and 8 normal monkey tissues were also analyzed (Table 3).

TABLE 1

8H9 reactivity: neuroectodermal Tumors

| Tumors | No. | 8H9 positive | % |
|---|---|---|---|
| Neuroblastoma | 90 | 87 | 97 |
| Brain Tumors | | | |
| 1. Glial Tumors | | | |
| Glioblastoma multiforme | 17 | 15 | 88 |
| Mixed Glioma | 4 | 3 | — |
| Oligodendroglioma | 11 | 4 | 36 |
| Astrocytoma | 8 | 6 | 75 |
| Ependymoma | 3 | 2 | — |
| 2. Primitive PNET | | | |
| Medulloblastoma | 2 | 2 | — |
| 3. Mixed | | | |
| Neuronoglial tumor | 2 | 1 | — |
| 4. Other | | | |
| Schwannoma | 3 | 3 | — |
| Meningioma | 2 | 2 | — |
| Neurofibroma | 1 | 1 | — |
| Pineoblastoma | 1 | 1 | — |
| Melanoma | 16 | 12 | 75 |
| Ewing's Family of tumors | 21 | 21 | 100 |
| TOTAL | 181 | 160 | 88 |

TABLE 2

8H9 reactivity: mesenchymal, epithelial and other tumors

| Tumors | No. | 8H9 Reactive | % |
|---|---|---|---|
| A. Mesenchymal | | | |
| Rhabdomyosarcoma | 29 | 28 | 97 |
| Osteosarcoma | 29 | 28 | 97 |
| Desmoplastic small round cell tumor | 37 | 35 | 95 |
| Leiomyosarcoma | 4 | 4 | — |
| Synovial sarcoma | 3 | 2 | — |

TABLE 2-continued

8H9 reactivity: mesenchymal, epithelial and other tumors

| | | | |
|---|---|---|---|
| Malignant fibrous histiocytoma | 1 | 1 | — |
| Undifferentiated sarcoma | 2 | 2 | — |
| Fibrosarcoma | 1 | 0 | — |
| TOTAL | 106 | 100 | 94 |

B. Epithelial

| | | | |
|---|---|---|---|
| Breast | 12 | 4 | 33 |
| Bladder | 4 | 1 | — |
| Adrenal | 3 | 1 | — |
| Stomach | 1 | 1 | — |
| Prostate | 2 | 1 | — |
| Colon | 1 | 1 | — |
| Lung | 1 | 1 | — |
| Endometrium | 1 | 1 | — |
| Cervix | 1 | 0 | — |
| Renal | 1 | 1 | — |
| TOTAL | 27 | 12 | 44 |

Epithelial tumors summary

| No. | Slide | Date | Diagnosis | 8H9 |
|---|---|---|---|---|
| 1 | 7251 | Mar. 11, 1998 | Breast Ca | neg |
| 2 | 7279 | Mar. 13, 1998 | Breast Ca | neg |
| 3 | 7282/7601 | Mar. 13, 1998; Oct. 5, 1998 | Breast Ca | neg |
| 4 | 7722 | Oct. 21, 1998 | Breast Ca | NE(no cells) |
| 5 | 7261 | Mar. 11, 1998 | Breast Ca | pos |
| 6 | 6388 | Aug. 26, 1998 | Breast Ca | pos |
| 7 | 6493 | Oct. 11, 1998 | Breast Ca | neg |
| 8 | 6498 | Oct. 11, 1998 | Breast Ca | neg |
| 9 | 6499 | Oct. 11, 1998 | Breast Ca | neg |
| 10 | 6492 | Oct. 11, 1998 | Breast Ca | neg |
| 11 | 6376 | Aug. 26, 1996 | Breast Ca | pos |
| 12 | 6488 | Oct. 11, 1998 | Bladder Ca | neg |
| 13 | 6489 | Oct. 11, 1998 | Bladder Ca | weakly+ |
| 14 | 6490 | Oct. 11, 1998 | Bladder Ca | neg |
| 15 | 6491 | Oct. 11, 1998 | Bladder Ca | neg |
| 16 | 6441 | Sep. 30, 1998 | Lung Ca | pos |
| 17 | 6503 | Oct. 11, 1998 | Prostate Ca | neg |
| 18 | 6504 | Oct. 11, 1998 | Prostate Ca | pos |
| 19 | 6501 | Oct. 11, 1998 | Cervix Ca | neg |
| 20 | 6502 | Oct. 11, 1998 | Uterine Ca | pos |
| 21 | 7717 | Oct. 21, 1998 | Adrenal Ca | ne (necrotic) |
| 22 | 7250 | Mar. 11, 1998 | Adrenal Ca | neg |
| 23 | 7207 | Nov. 18, 1997 | Renal Ca | pos |
| 24 | 6505 | Oct. 11, 1998 | Stomach Ca | pos |
| 25 | 7886 | Feb. 22, 1999 | Adrenal Ca | pos |

| | Total | Evaluable | 8H9 dos. |
|---|---|---|---|
| Breast | 11 | 10 | 3 of 10 |
| Bladder | 4 | 4 | 1 of 4 |
| Prostate | 2 | 2 | 1 of 2 |
| Adrenal | 3 | 2 | 1 of 2 |
| Renal | 1 | 1 | 1 of 1 |
| Stomach | 1 | 1 | 1 of 1 |
| Uterine | 1 | 1 | 1 of 1 |
| Cervix | 1 | 1 | 0 of 1 |
| Lung | 1 | 1 | 1 of 1 |
| TOTAL | 25 | 23 | 10 of 23 |

C. Other tumors

| Tumors | No. | 8H9 reactive | % |
|---|---|---|---|
| Hepatoblastoma | 4 | 3 | — |
| Wilm's tumor | 8 | 7 | — |
| Rhabdoid tumor | 3 | 3 | — |
| Paraganglioma | 1 | 1 | — |
| TOTAL | 16 | 14 | 88 |

TABLE 3

8H9 reactivity in normal human and cynomolgus monkey tissues

| Tissues | 8H9 reactivity |
|---|---|
| A. Human | |
| Frontal lobe | Negative |
| Pons | Negative |
| Spinal cord | Negative |
| Cerebellum | Negative |
| Lung | Negative |
| Heart | Negative |
| Skeletal muscle | Negative |
| Thyroid | Negative |
| Testes | Negative |
| Pancreas | cytoplasmic staining* |
| Adrenal cortex | cytoplasmic staining* |
| Liver | cytoplasmic staining* |
| Sigmoid colon | Negative |
| Bone Marrow | Negative |
| Kidney | Negative |
| B. Cynomolgus monkey | |
| Cerebellum | Negative |
| Frontal Lobe | Negative |
| Occipital Cortex | Negative |
| Brainstem | Negative |
| Liver | cytoplasmic staining |
| Stomach | Negative |
| Adrenal Cortex | cytoplasmic staining |
| Kidney | Negative |

*non-specific background

Heterogenous, non-specific cytoplasmic staining was noticed in normal human pancreas, stomach, liver and adrenal cortex which was diminished when 8H9 F(ab')$_2$ fragments were used instead of the whole antibody for immunostaining (data not shown). None of the other human tissues showed reactivity with 8H9. In particular normal human brain tissue sections including frontal lobe, spinal cord, pons and cerebellum were completely negative. Normal tissues from cynomolgus monkey also demonstrated similarly restricted reactivity with nonspecific staining observed in stomach and liver. (Table 3)

The majority of neuroectodermal and mesenchymal tumors tested showed positive reactivity with 8H9, epithelial tumors to a lesser extent. 8H9 immunoreactivity was seen in a characteristic, homogeneous, cell membrane distribution in 286 of the 330 (87%) tumor samples examined. (FIG. 1). 88% of neuroectodermal tumors, 94% of mesenchymal tumors and 44% of epithelial tumors tested positive with 8H9. (Tables 2, 3)

Indirect Immunofluorescence

8H9 immunoreactivity in 35 neuroblastoma, melanoma, rhabdomyosarcoma, small cell lung cancer, osteosarcoma, glioblastoma, leukemia, breast cancer and colon cancer cell lines was tested using indirect immunofluorescence. Moderate to strong cell membrane reactivity with 8H9 was detected in 16/16 neuroblastoma cell lines, 3/3 melanoma cell lines, 2/2 rhabdomyosarcoma cell lines, 1/1 glioblastoma multiforme cell line, 3/3 breast cancer cell lines and 1/1 colon cancer cell lines studied. 2 of 3 Ewing's/PNET cell lines, and 2 of the 3 osteosarcoma cell lines were strongly positive while the others showed weak positivity. The small cell lung cancer cell line tested negative with 8H9 as did Jurkat T-ALL cell line and EBV transformed lymphoblastoid cells. Normal human bone marrow mononuclear cells and hepatocytes had no reactivity with 8H9. (Table 4) In the neuroblastoma cell lines studied, indirect immunofluorescence with 8H9 was weaker (mean fluorescence: 73.73; negative control: 3.95) when compared to the anti-$G_{D2}$ antibody 3F8 (mean fluorescence: 249.95).

Figure 2:
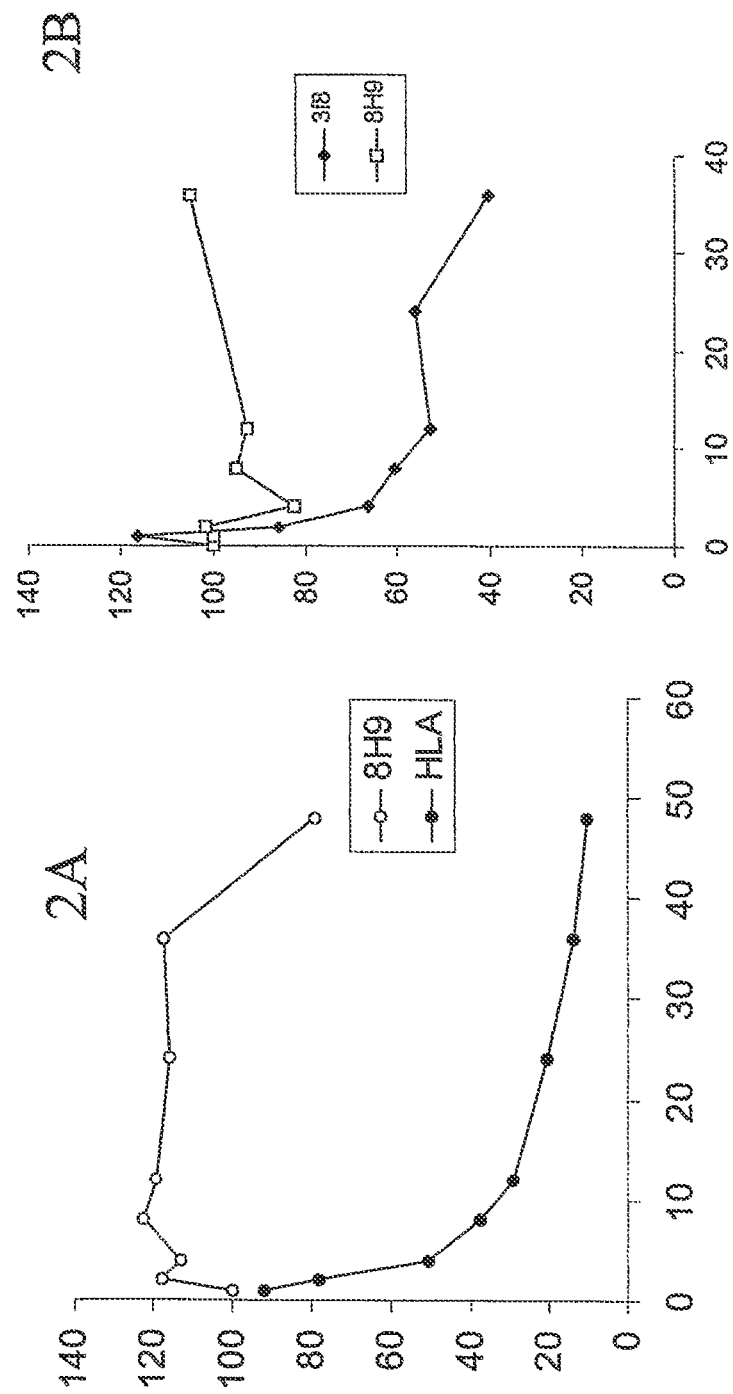

8H9 binding to U2OS as detected by indirect immunofluorescence did not diminish significantly after 48 hr of incubation at 37° C. During the same period, binding to the anti-HLA antibody HB-95 diminished by 89%. Similarly there was no significant loss of 8H9 binding to NMB7 cells. whereas 3F8 binding diminished by 61%. (FIG. 2)

There was a pronase dose-dependent reduction in reactivity with 8H9 with 75-85% loss of immunofluorescence achieved at a final Pronase concentration of 0.3 mg/ml (FIG. 3). There was no appreciable loss of reactivity with 3F8 on NMB7 cells. Furthermore, the 8H9 antigen was not sensitive to neuraminidase or phosphatidyl-inositol specific phospholipase C (data not shown).

TABLE 4

8H9 reactivity with cell lines by indirect immunofluorescence

| Cell line | 8H9 Reactivity |
| --- | --- |
| 1. Neuroblastoma | |
| LA-N-1 | positive |
| NMB7 | positive |
| LA-1-15-N | positive |
| LA-1-66N | positive |
| IMR32 | positive |
| LA-1-19N | positive |
| LA-1-5S | positive |
| LA-1-19S | positive |
| SKNHM | positive |
| SKNSH | positive |
| SKNHB | positive |
| SKNJD | positive |
| SKNLP | positive |
| SKNMM | positive |
| SKPCH | positive |
| SKNER | positive |
| 2. Melanoma | |
| HTB63 | positive |
| HTB67 | positive |
| SKMel28 | positive |
| 3. Rhabdomyosarcoma | |
| HTB 82 | positive |
| SKRJC | positive |
| 4. Small cell lung cancer | |
| HTB119 | negative |
| 5. Osteosarcoma | |
| CRL1427 | positive |
| HTB96 | positive |
| HTB86 | positive |
| 6. Ewing's/PNET | |
| SKPPR | positive |
| SKPRT | positive |
| SKNMC | positive |
| 7. Glioblastoma | |
| Glio72 | positive |

TABLE 4-continued

8H9 reactivity with cell lines by indirect immunofluorescence

| Cell line | 8H9 Reactivity |
| --- | --- |
| 8. Carcinoma Breast | |
| ZR75-1 | positive |
| SW480 | positive |
| HTB22 | positive |
| 9. Carcinoma Colon | |
| SKCo-1 | positive |
| 10. Leukemia | |
| Jurkat | negative |
| 11. Normal human cells | negative |
| Bone marrow | negative |
| Hepatocytes | negative |
| 12. EBV lymphoblastoid cells | negative |

Immunoprecipitation:

8H9 immunoprecipitated a broad band centered around 90 kD from all the 8H9-positive cell lines (HTB82, NMB7, LAN1, U2OS, Hela, 293), whether using native or reducing (2ME) conditions (data not shown). Neither control IgG1 antibody nor 8H9-negative cell lines (Jurkat or HTB 119) showed the 90kD antigen. Following N-glycanase treatment, a single 58 kD band was found. O-glycanase had no effect. We interpreted this to mean a protein with heterogeneous glycosylation pattern, without disulfide-linked subunits.

Discussion

We describe a novel 58 kD surface tumor antigen, which is detected by the monoclonal antibody 8H9. This antigen is expressed on a broad spectrum of human neuroectodermal, mesenchymal and epithelial tumors and appears to be immunohistochemically tumor specific, namely, it is expressed on cell membranes of tumor cells with no/low membrane reactivity noted on normal human tissues. The antigen was present on 88% of neuroectodermal tumors, 96% of mesenchymal tumors and 44% of epithelial cancers tested. The specific tissue distribution suggests a unique tumor antigen not previously reported.

The expression of the 8H9 antigen on several glial and nonglial brain tumors and the complete absence on normal brain tissue is unusual. This property contrasts with most of the previously described glial tumor antigens with a cell membrane distribution (Table 5). Neuroectodermal-oncofetal antigens e.g. neural cell adhesion molecules are present to varying degrees on normal adult and fetal tissues (6). Neurohematopoeitic antigens including Thy-1 determinants (24), CD-44 (8) and its splice variants (25) are present on normal and neoplastic brain tissue as well as hematopoeitic tissues, principally of the lymphoid lineage. Gangliosides, such as $G_{D2}$ and $G_{M2}$, although expressed on tumors of neuroectodermal origin, are also present on normal brain tissue (7). The lactotetraose series ganglioside 3'-6"-iso $L_{D1}$ is widely expressed on brain tumors and on epithelial cancers and germ cell tumors as well as on normal brain tissue. (26).

TABLE 5

Antigens expressed on glial tumors

| Antigen | Antibody | Crossreactivity with normal tissues |
| --- | --- | --- |
| Cell Membrane antigens | | |
| Neurohematopoeitic antigens | | |
| Thy-1 | Ab 390 (24) | Normal neuronal cells |
| CD44 | Multiple | Normal endothelium |
| CD44 splice variants | Multiple (25) | Normal neuronal cells |

TABLE 5-continued

Antigens expressed on glial tumors

| Antigen | Antibody | Crossreactivity with normal tissues |
|---|---|---|
| Cell Adhesion molecules | | |
| NCAM | ERIC-1 (11), | Normal neuronal cells |
|  | UJ13-A (10) | Normal neuronal cells |
| Integrin 3 | ONS-M21 (30) | Not reactive with normal brain |
| Gangliosides | | |
| $G_{D2}$ | 3F8 (35) | Normal neuronal cells |
| 3'-6' iso-LD1 | DMAb-22 (29) | Fetal brain, reactive astrocytes |
| Growth Factor Receptors | | |
| EGFRvIII | MR1 (9) | No normal tissues; breast and lung carcinoma |
| PDGFR- | Anti-PDGFR-7 (36) | Normal neuronal cells |
| Uncharacterized | | |
| Ependymoma-associated | MabEp-C4 (34) | Not reactive with PBL, normal brain |
| Glioma -associated | GA-17, GB-4, GC-3 (32) | Not reactive with normal adult or fetal brain |
| Glioma-associated | 6DS1 (33) | Not reactive with normal adult or fetal brain |
| Intracellular | | |
| IFAP-300 | Anti-IFAP-300 kDa (37) | Not reactive with normal brain |
| GFAP | Multiple | Normal neuronal cells |
| Interstitial matrix | | |
| Tenascin | 81C6 (13), | Normal liver, kidney; not reactive with adult brain |
|  | BC-2 (14) | Not reactive with normal brain |
| GP-240 | Mel-14 (38) | Melanoma; not reactive with normal brain |
| Oncofetal fibronectin | BC-1 (39) | Adult endometrium; not reactive with normal brain |

Another remarkable property of the 8H9 antigen is its expression on tumors of diverse lineage: neuroectodermal, mesenchymal and to a lesser degree epithelial tumors. No monoclonal antibody to date has the binding spectrum described with 8H9. This broad distribution provides MoAb 8H9 the potential of being a "generic" tumor antigen for targeted therapy. Of particular interest is its expression on 28/29 rhabdomyosarcoma tumors and the rhabdomyosarcoma cell lines tested by indirect immunofluorescence. Disseminated and high risk rhabdomyosarcomas have a very poor prognosis with <40% long term survival rate (27). Although the MYOD family of oncofetal proteins are specific to rhabdomyosarcoma, they are nuclear antigens and therefore unlikely candidates for antibody-based therapy (19). In a preliminary report, cross reactivity of the monoclonal antibody BW575 raised against small cell lung carcinoma with rhabdomyosarcoma cell lines and 2/2 rhabdomyosarcoma sections was described. However, this antibody showed cross-reactivity with normal tissues (28).

Two further groups of tumors studied were the Ewing's family of tumors and osteosarcoma. The Ewing's family of tumors can be differentiated from other small blue round cell tumors of childhood by monoclonal antibodies recognizing glycoprotein p30/32 coded by MIC2 oncogene. However, this protein is also expressed on normal tissues and on other tumors, severely limiting its utility in radioimaging and therapy (18). 100% (21/21) of Ewing's family tumors tested showed immunoreactivity with MoAb 8H9. Apart from $G_{D2}$ (15), the osteosarcoma-associated antigen recognized by the MoAbs TP-1 and TP-3 (17), and the decay accelerating factor CD55 (16), few tumor-associated antigens have been defined for osteosarcoma. In our study 28/29 (95%) osteosarcomas tested immunohistochemically positive with MoAb 8H9. The latter may therefore have clinical utility in the Ewing's family of tumors and osteosarcomas.

The 8H9 antigen appears to be a novel, previously undescribed antigen. Sensitivity to proteinase suggests that it has a protein component. Conversely, the lack of sensitivity to neuraminidase implies absence of sialic acid residues, and the lack of sensitivity to phosphatidyl-inositol specific phospholipase C implies that the 8H9 antigen is not GPI anchored. It is unlikely to be related to the neural cell adhesion molecule family due to its unique distribution and restriction of expression among normal tissues (6). Of the currently described antibodies, which bind to glial tumors, four have been reported to be restricted to tumor tissues. The mutated EGFRvIII was found to be expressed on 52% of gliomas tested and crossreacts with breast and lung carcinomas (29). However, the broad distribution of the 8H9 antigen is different from EGFRvIII. Integrin 3, a 140 kDa protein expressed on gliomas and medulloblastomas is targeted by the monoclonal antibody ONS-M21 which does not cross react with normal brain (30). However, negative immunoreactivity with neuroblastoma, melanoma and meningioma has been reported. (31). Similar data on glioma-specific antibodies with no cross reactivity with normal brain has been published. However, they do not react with other neuroectodermal or mesenchymal tumors and data regarding reactivity with other tissues is unavailable (32). A 38 kDa antigen has been targeted on glioblastoma cells by the antibody 6DS1. No cross-reactivity with human brain has been reported. Data regarding reactivity with other human tissues is unknown, although a high accumulation of the radiolabeled antibody in mouse kidney has been reported. (33). An ependymoma-specific protein antigen of 81 kDa, recognized by monoclonal antibodies which do not crossreact with normal glial cells, has also been described. These antibodies do not react with other glial tumors such as glioblastoma and crossreactivity with other tumor tissue is not known (34).

The homogeneous expression of the 8H9 antigen on cell membrane makes it an attractive candidate for targeted immunotherapy. Furthermore, the persistence of the 8H9 antigen on NMB7 cells after binding to the MoAb suggests that the antigen is not easily immunomodulated. In order to explore its potential for radioimaging we used $^{99m}$Tc conjugated 8H9 to image neuroblastoma xenografts in athymic nude mice. This revealed selective uptake in the xenografts apart from moderate uptake in the liver, % ID/gm being 50% of that achieved with the anti-$G_{D2}$ monoclonal antibody 3F8 (data not shown). The hydrazino-derivative of 8H9, therefore, retains the immunoreactive properties of the unmodified antibody, and may be useful for radioimaging of tumors. We have also demonstrated selective radioimmunolocalization of rhabdomyosarcoma xenografts in athymic mice with no significant uptake in normal tissues using $^{125}$I-labeled 8H9 (data not shown).

In summary, the monoclonal antibody 8H9 recognizes a unique 58 kD tumor-specific antigen with broad distribution across a spectrum of tumors of varying lineage: neuroectodermal, mesenchymal and epithelial, with restricted expression in normal tissues. 8H9 may have clinical utility in the targeted therapy of these human solid tumors in vitro or in vivo. Further biochemical characterization of the 8H9 antigen is warranted and may be of interest in delineating a possible role in the oncogenic process.

References

1. Cheung, N. K. V., Kushner, B. H., Cheung, I. Y., Canete, A., Gerald, W., Liu, C., Finn, R., Yeh, S. J., Larson, S. M. Anti-GD2 antibody treatment of minimal residual stage 4 neuroblastoma diagnosed at more than 1 year of age. J. Clin. Oncol., 16:3053-3060, 1998.
2. Yu, A., Uttenreuther-Fischer, M., Huang, C.-S., Tsui, C., Gillies, S., Reisfeld, R., Kung, F. Phase I trial of a human-mouse chimeric anti-disialoganglioside monoclonal antibody ch14.18 in patients with refractory neuroblastoma and osteosarcoma. J. Clin. Oncol., 16:2169-2180, 1998.
3. Jurcic, J. G., Caron, P. C., Miller, W. H., Yao, T. J., Maslak, P., Finn, R. D.,
   Larson, S. M., Warrell, R. P. J., Scheinberg, D. A. Sequential targeted therapy for acute promyelocytic leukemia with all-trans retinoic acid and anti-CD33 monoclonal antibody M195. Leuk., 9:244-248, 1995.
4. Pegram, M. D., Slamon, D. J. Combination chemotherapy with trastuzumab (Herceptin) and cisplatin for chemoresistant metastatic breast cancer: evidence for receptor-enhanced chemosensitivity. Sem. Oncol., 26:89-95, 1999.
5. Czuczman, M. S., Grilo-Lopez, A. J., White, C. A., Saleh, M., Gordon, L., LoBuglio, A. F., Jonas, C., Klippenstein, D., Dallaire, B., Yarns, C. Treatment of patients with low-grade B-cell lymphoma with the combination of chimeric anti-CD20 monoclonal antibody and CHOP chemotherapy. J. Clin. Oncol., 17:268-276, 1999.
6. Garin-Chesa, P., Fellinger, E. J., Huvos, A. G., Beresford, H. R., Melamed, M. R., Triche, T. J., Rettig, W. J Immunohistochemical analysis of neural cell adhesion molecules. Differential expressionin small round cell tumors of childhood and adolescence. Am. J. Pathol., 139:275-286, 1991.
7. Ritter, G., Livingston, P. 0. Ganglioside antigens expressed by human cancer cells. Semin Cancer. Biol., 2:401-409, 1991.
8. Ylagan, Quinn, L. R B: CD44 expression in astrocytic tumors. Modern Pathology, 10:1239-1246, 1997.
9. Kuan, C. T., Reist, C. J., Foulon, C. F., Lorimer, I. A., Archer, G., Pegram, C. N., Pastan, I., Zalutsky, M. R., Bigner, D. D. 125I-labeled anti-epidermal growth factor receptor vIII single-chain Fv exhibits specific and high-level targeting of glioma xenografts. Clin. Can. Res., 5:1539-1549, 1999.
10. Richardson, R. B., Davies, A. G., Bourne, S. P., Staddon, G. E., Jones, D. H., Kemshead, J. T., Coakham, H. B. Radioimmunolocalization of human brain tumors. Biodistribution of radiolabelled monoclonal antibody UJ13A. Eur J Nucl Med, 12:313-320, 1986.
11. Papanastassiou, V., Pizer, B. L., Coakham, H. B., Bullimore, J., Zananiri, A., Kemshead, J. T. Treatment of recurrent and cystic malignant gliomas by a single intracavitary injection of 131I-monoclonal antiobdy: Feasibility, pharmacokinetics and dosimetry. Br. J. Cancer, 67:144-151, 1993.
12. Celis, E., Tsai, V., Crimi, C., Demars, R., Wentworth, P. A., Chesnut, R. W., Grey, H. M., Sette, A., Serra, H. M. Induction of anti-tumor cytotoxic T lymphocytes in normal humans using primary cultures and synthetic peptide epitopes. Proc. Natl. Acad. Sci. USA, 91:2105-2109, 1994.
13. Bigner, D. D., Brown, M. T., Friedman, A. H., Coleman, R. E., Akabani, G., Friedman, H. S., Thorstad, W. L., Mclendon, R. E., Bigner, S. H., Zhao, X. G. Iodine-131-labeled antitenascin monoclonal antibody 8106 treatment of patients with recurrent malignant gliomas:phase I trial results. Journal Clincal Oncology, 16:2202-2212, 1998.
14. Riva, P., Frnceschi, G., Frattarelli, M., Riva, N., Guiduci, G., Cremonini, A. M., Giulaiani, G., Casi, M., Gentile, R., Jekunen, A., Kairemo, K. J. 131I radioconjugated antibodies for the locoregional radioimmunotherapy of high-grade malignant glioma-phase I and II study. Acta Oncol, 38:351-359, 1999.
15. Heiner, J., Miraldi, F. D., Kallick, S., Makley, J., Smith-Mensah, W. H., Neely, J., Cheung, N. K. V. In vivo targeting of GD2 specific monoclonal antibody in human osteogenic sarcoma xenografts. Cancer Res., 47:5377-5381, 1987.
16. Spendlove, I., James, L. L., Carmichael, J., Durrant, L. G. Decay accelerating factor (CD55): a target for cancer vaccines? Cancer Res., 59:2282-2286, 1999.
17. Bruland, O., Fodstad, O., Funderud, S., Pihl, A. New monoclonal antibodies specific for human sarcomas. Int J Cancer, 15:27-31, 1986.
18. Weidner, N., Tjoe, J Immunohistochemical profile of monoclonal antibody O13 that recognizes glycoprotein 930/32MIC2 and is useful in diagnosing ewing's sarcoma and peripheral neuroepithelioma. American Journal of Surgical Pathology, 18:486-494, 1994.
19. Wang, N. P., Marx, J., McNutt, M. A., Rutledge, J. C., Gown, A. M. Expression of myogenic regulatory proteins (myogenin and MyoD1) in small blue round cell tumors of childhood. Am. J. Pathol., 147:1799-1810, 1995.
20. Hatzubai, A., Maloney, D. G., Levy, R. The use of a monoclonal anti-idiotype antibody to study the biology of human B-cell lymphoma. J. Immunol., 126:2397-2402, 1981.
21. Cheung, N. K., Saarinen, U., Neely, J., Landmeier, B., Donovan, D., Coccia, P. Monoclonal antibodies to a glycolipid antigen on human neuroblastoma cells. Cancer Res., 45:2642-2649, 1985.
22. Kramer, K., Gerald, W., LeSauteur, L., Saragovi, H. U., Cheung, N. K. V. Prognostic value of TrkA protein detection my monoclonal antibody 5C3 in Neuroblastoma. Clin. Can. Res., 2:1361-1367, 1996.
23. Hecht, T. T., Longo, D. L., Cossman, J., Bolen, J. B., Hsu, S.-M., Israel, M., Fisher, R. I. Production and characterization of a monoclonal antibody that binds reed-sternberg cells. J. Immunol., 134:4231-4236, 1985.
24. Seeger, R. C., Danon, Y. L., Rayner, S. A., Hoover, F. Definition of a Thy-1 determinant on human neuroblastoma, glioma, sarcoma, and teratoma cells with a monoclonal antibody. J. Immunol., 128:983-989, 1982.

25. Kaaijk, P., Troost, D., Morsink, F., Keehnen, R. M., Leenstra, S., Bosch, D. A., Pals, S. T. Expression of CD44 splice variants in human primary brain tumors. Journal of Neuro-Oncology, 26:185-190, 1995.
26. Wikstrand, C. J., Longee, D. C., McLendon, R. E., Fuller, G. N., Friedman, H. S., Fredman, P., Svennerholm, L., Bigner, D. D. Lactotetraose series ganglioside 3',6'-isoLD1 in tumors of central nervous and other systems in vitro and in vivo. Cancer Res., 53:120-126, 1993.
27. Pappo, A., Shapiro, D. N., Crist, W. M. Rhabdomyosarcoma: biology and treatment. Pediatr. Clin. North Am., 44:953-972, 1997.
28. Fujisawa, T., Xu, Z. J., Reynolds, C. P., Schultz, G., Bosslet, I. V., Seeger, R. C. A monoclonal antibody with selective immunoreactivity for neuroblastoma and rhabdomyosarcoma. Proc. Am. Assoc. Cancer Res., 30:345, 1989.
29. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., et al. Monoclonal Antibodies against EGFRvIII are Tumor Specific and React with Breast and Lung Carcinomas and Malignant Gliomas. Cancer Res., 55:3140-48, 1995.
30. Kishima, H., Shimizu, K., Tamura, K., Miyao, Y., Mabuchi, E., Tominage, E., Matsuzaki, J., Hayakawa, T. Monoclonal antibody ONS-21 recognizes integrin a3 in gliomas and gliomas and medulloblastomas. Br. J. Cancer, 79:333-339, 1998.
31. Moriuchi, S., Shimuzu, K., Miyao, Y., Hayakawa, T. Characterization of a new mouse monoclonal antibody (ONS-M21) reactive with both medulloblastomas and gliomas. Br. J. Cancer, 68:831-837, 1993.
32. Kondo, S., Miyatake, S., Iwasaki, K., Oda, Y., Kikuchi, H., Zu, Y., Shomoto, M., Namba, Y. Human glioma-specific antigens detected by monoclonal antibodies. Neurosurgery, 30:506-511, 1992.
33. Dastidar, S. G., Sharma, S. K. Monoclonal antibody against human glioblastoma multiforme (U-87Mg) immunoprecipitates a protein of monoclonal mass 38 KDa and inhibits tumor growth in nude mice. J Neuroimmuno, 56:91-98, 1995.
34. Mihara, Y., Matsukado, Y., Goto, S., Ushio, Y., Tokumitsu, S., Takahashi, K. Monoclonal antibody against ependymoma-derived cell line. Journal of Neuro-Oncology, 12:1-11, 1992.
35. Daghighian, F., Pentlow, K. S., Larson, S. M., Graham, M. C., DiResta, G. R., Yeh, S. D., Macapinlac, H., Finn, R. D., Arbit, E., Cheung, N. K. Development of a method to measure kinetics of radiolabeled monoclonal antibody in human tumour with applications to microdosimetry: positron emission tomography studies of iodine-124 labeled 3F8 monoclonal antibody in glioma. Eur J Nucl Med, 20:402-409, 1993.
36. Plate, K. H., Breier, G., Farell, C. L., Risau, W. Platelet derived growth factor b is induced during tumor development and upregulated during tumor progressin in endothelial cells in human gliomas. Lab. Invest., 67:529-534, 1992.
37. Yang, H. S., Lieska, N., Glick, R., Shao, D., Pappas, G. D. Expression of 300-kilodalton intermediate filament-associated protein distinguishes human glioma cells from normal astrocytes. Proceedings of the National Academy of Sciences of the United States of America, 90:8534-8537, 1993.
38. Bigner, D. D., Brown, M., Coleman, E., Friedman, H. A., McClendon, R. E., Bigner, S. H., Zhao, X. G., Wikstrand, C. J., Pegram, C. N. Phase I studies of treatment of malignant gliomas and neoplastic meningitis with 131 I radiolabeled monoclonal antibodies anti-tenascin 8106 and anti-chondroitin proteoglycan sulfate Mel-14 (ab')2—a preliminary report. J Neuro Oncol, 24:109-122, 1995.
39. Mariani, G., Lasku, A., Pau, A., Villa, G., Motta, C., Calcagno, G., Taddei, G. Z., Castellani, P., Syrigos, K., Dorcaratto, A., et al. A pilot pharmacokinetic and immunoscintigraphic study with the technetium-99m-labeled monoclonal antibody BC-1 directed against oncofetal fibronectin in patients with brain tumors. Cancer Supplement, 80:2484-2489, 1997.

Second Series of Experiments

Recent clinical trials have shown promising potentials of monoclonal antibodies (MoAbs) in the treatment of cancer: anti-CD20 (lymphoma), anti-HER2 (breast cancer), anti-tenascin (brain tumors), anti-CD33 (leukemia), and anti-TAG-72 (colon cancer). In pediatric oncology, tumor-targeting agents are even more relevant since minimal residual disease (MRD) is often the obstacle to cure, and late effects of non-specific therapy are significant. Despite high-intensity combination therapy, most metastatic solid tumors (Ewing's sarcoma [ES], primitive neuroectodermal tumor [PNET], osteosarcoma [OS], desmoplastic small round cell tumor [DSRT], rhabdomyosarcoma [RMS], and brain tumors) remain incurable. Using metastatic neuroblastoma (NB) as proof of principle, our laboratory integrated the murine IgG3 anti-ganglioside $GD_2$ MoAb 3F8 into multi-modality therapy. 3F8 has demonstrated high selectivity and sensitivity in radioimmunodetection of metastatic tumors, and appears to be a safe and effective method of eliminating MRD, achieving a >50% progression-free survival (PFS). For most pediatric solid tumor therapeutic MoAbs do not exist. Known tumor surface antigens are often restricted to a specific tumor type, heterogeneous in its expression, or found in normal blood cells or organs. We recently described a MoAb 8H9 which recognizes a novel cell surface antigen in a wide spectrum of pediatric tumors, with no crossreactivity with blood, marrow, brain and normal organs, and minimal reactivity with hepatocyte cytoplasm. $^{131}$I or $^{99m}$Tc-labeled 8H9 can effectively image NB and RMS xenografts in SCID mice. Antigen expression was generally homogeneous within tumors, and did not modulate on MoAb binding. We propose to test the targeting potential of $^{131}$I-8H9 in a pilot imaging study. Pediatric/adolescent patients with NB, RMS, ES, PNET, OS, DSRT and brain tumors are subjects of our investigation. We have two specific aims:

1: To measure the level of agreement between conventional imaging modality (CT, MRI, and nuclear scans) and antibody 8H9 imaging in known and occult sites of disease. Sensitivity analysis of 8H9 for each disease type will be conducted.

2: To calculate the absorbed dose delivered by $^{131}$I-8H9 to tumor relative to normal organs.

Background and Significance

MoAb selective for tumors have therapeutic potential [1,2] The introduction of hybridoma technology by Kohler and Milstein in 1975[3] and the advances in molecular biologic techniques have greatly expanded the potential of MoAb in human cancers. Optimal targeting of MoAb demands high tumor antigen density with homogeneous expression, lack of antigen modulation on tumor cell surface, adequate vascularity of tumor to allow deep penetration, minimal toxicity on normal tissues, low reticulo-endothelial system (RES) uptake, noninterference by circulating free antigens, and low immunogenicity. In practice, very few MoAb-antigen-tumor model systems have fulfilled these stringent criteria. Recent clinical trials have shown promising potentials of MoAbs. Anti-CEA antibody in colorectal cancer,[4] anti-CD20 antibodies in lymphoma,[5] anti-HER2 antibodies in breast cancer,[6] anti-tenascin antibodies in glial brain tumors,[7] MoAb M195 against CD33 in acute leukemia[8] and anti-TAG-72 antibodies in colon cancer[9] have demonstrated efficacy in clinical trials. Our laboratory has developed the MoAb 3F8 which targets the ganglioside $G_{D2}$ overexpressed on NB. 3F8 has been shown to have a high specificity and sensitivity in the radioimmunodetection of minimal residual disease (MRD) in patients with NB,[10] and a significant impact when used as adjuvant therapy.[11] 131I has been a common isotope used both for imaging and therapy purposes. Although not widely available, pure -emitters such as $^{90}Y$,[12,13] alpha-emitting particles,[14,15] such as $^{211}At$, $^{212}Bi$ and $^{213}Ac$ have attractive properties with promising biological effectiveness.

Multiple radioisotopes of varying path lengths and half-lives may be needed to enhance radiocurability of both bulk and microscopic diseases. More recent developments in immunocytokines (e.g. IL-2, IL-12),[16] bispecific antibodies for pretargeting strategies (e.g. radioisotopes or drugs),[17,18] or T-bodies for retargeting immune cells [19-21] have further expanded the potentials of antibody-based immunotherapies.

Brain tumor antigens Examples of tumor antigens expressed on glial tumors include neuroectodermal- oncofetal antigens eg. neural cell adhesion molecules (NCAM),[22] gangliosides (GD2, GM2, 3'-6"-iso LD1)[23, 24] and neurohematopoeitic antigens (Thy-1, CD44 and splice variants).[25-27] All of these antigens are present to varying degrees on normal adult and fetal tissues, and for some hematopoeitic tissues as well. Notwithstanding the universal expression of NCAM by neuronal cells, anti-NCAM MoAb UJ13A was shown to accumulate in gliomas by virtue of disruption of blood brain barrier locally[28] and another MoAb ERIC-1 showed clinical benefit in resected glioma cavities.[29] Integrin-3, a 140 kDa protein expressed on gliomas and medulloblastomas and not in normal brain, is a potential target (MoAb ONS-M21)[30], but it is poorly expressed among other tumor types.[31] The extracellular matrix protein tenascin is expressed in 50-95% of gliomas as well as on mesenchymal tumors, carcinomas, normal human glial, liver and kidney cells.[32] Anti-tenascin monoclonal antibodies 81C6,[7] BC-2 and BC-4[33] administered directly into tumor-cavities have shown efficacy in patients with malignant gliomas. More recent investigations have focused on growth factor receptors. in particular type III mutant epidermal growth factor receptor (EGFRvIII) expressed on 52% of gliomas[34] as well as breast and lung carcinomas.[35] Given the relationship of these mutated receptors to their malignant potential, they may be ideal targets for MoAb. Although other glioma-specific antibodies with no cross reactivity with normal brain have been described (e.g. 6DS1, MabEp-C4),[36-38] they have limited reactivity with other neuroectodermal or mesenchymal tumors, and data regarding cross-reactivity with normal tissues are not available. To date, with the exception of EGFRvIII, the glial tumor antigens described are either found on normal brain and/or normal tissues, restricted to specific tumor types, or found in intracellular compartments/extracellular matrix which can limit their clinical utility for targeting to single cells or spheroids.

Sarcoma antigens Optimal tumor antigens, similarly, have not been defined for the large family of sarcomas. Although the MyoD family of oncofetal proteins are specific to rhabdomyosarcoma, they are localized to the nucleus and therefore do not offer targets for antibody-based therapy.[39] The ES family of tumors can be differentiated from other small blue round cell tumors of childhood by MoAbs recognizing glycoprotein p30/32 coded by the MIC2 oncogene. However, this protein is expressed on normal tissues (e.g. T-cells)[40] greatly limiting the utility of MoAb in marrow purging, radioimaging or radiotherapy.[41] Membrane targets on OS include GD2,[42] glycoprotein p72,[43] CD55[44] erB2/neu[45] and the antigen recognized by the MoAb TP-3.[46] CD55 is decay-accelerating factor, a ubiquitous protein on blood cells and most tissues to prevent complement activation. Clearly MoAb directed at CD55 would have significant limitations for in vivo targeting. The degree of tumor heterogeneity (e.g. erbB2 in OS) may also limit the efficacy of MoAb-targeted approach. The presence of GD2 on pain fibers causes significant pain side effects in clinical trials. Nevertheless, this side effect is self-limited and this cross-reactivity did not interfere with the biodistribution and clinical efficacy of specific MoAb (see preliminary results). Nevertheless, GD2 is generally low or absent in RMS, ES, PNET, and many soft-tissue sarcomas. In addition, the presence of GD2 in central neurons can limit its application in tumors arising or metastatic to the brain. Our laboratory has generated a novel MoAb 8H9 by hyperimmunizing female BALB/c mice with human NB.[47] 8H9 recognizes a unique surface antigen homogeneously expressed on cell membranes of a broad spectrum of tumors of neuroectodermal, mesenchymal and epithelial origin, with restricted distribution on normal tissues (see preliminary results).[48]

The availability of an antibody with broad specificity for pediatric tumors will facilitate several lines of clinical investigations. In vitro, such antibodies will be extremely useful for (1) detecting lymph node or marrow metastasis,[49] (2) enrichment/isolation of circulating tumor cells for RT-PCR detection strategies,[50] (3) purging of bone marrow before autologous bone marrow transplantation,[51] (4) purging of ex vivo activated T-cells prior to adoptive cell therapy. In vivo its utility can go beyond its diagnostic capability. When chimerized with a human-1Fc tail, it becomes tumoricidal through complement-mediated, and antibody-dependent cell-mediated cytotoxicities.[52] Through single-chain Fv constructs, new fusion proteins can now be delivered to tumor sites (e.g. IL-2, IL-12, toxins, or enzymes). Bivalent scFv and tetravalent scFv can be engineered to improve avidity.[53] Bispecific scFv can be constructed to engage cells and proteins in various targeting strategies (e.g. pretargeting).[17,18] ScFv can also be used in T-bodies to retarget T-cells, a powerful technique to increase clonal frequency and bypassing the HLA requirement of TCR functions.[19-21] Furthermore scFv-fusion proteins (e.g. CD28, zeta chain) transduced into T-cells can greatly enhance their survival following activation.[21] Even more importantly, the ability of such cells to proliferate in contact with tumor cells can further amplify the efficiency of T-cell cytotherapy.

Radioimmunoscintigraphy can test if an antibody-antigen system has targeting potential. Using radioiodines and technetium we have demonstrated the utility of the GD2 system for targeting in the last decade. This information has been translated into treatment strategies using both unlabeled and $^{131}I$ labeled antibody 3F8. Dosimetry calculations have allowed quantitative estimates of therapeutic index when cytotoxic agents are delivered through antibody-based methods. Uptake (peak dose and area under the curve AUC) in specific organs relative to tumor can be measured. These studies are resource intensive and to be done well, require laboratory, radiochemistry, nuclear medicine, medical physics and clinical resource support, as well as substantial personnel effort. In pediatric patients, issues of therapeutic index may be even more pressing given the potential of late effects of treatment. In addition, despite the potential life-years saved for pediatric cancer, orphan drugs are not economically attractive for most industrial sponsors. These circumstances have made the initial stages of clinical development even more stringent and relatively more difficult to accomplish.

Patient monitoring and correlative laboratory studies Pharmacokinetic studies are crucial in our understanding of antibody targeting, its toxicity and its efficacy. Radioimmunoscintigraphy uses the trace label principle and gamma imaging to define the distribution of a specific antibody in various human organs. It provides estimates of antibody (and radiation) dose delivered to blood, marrow and major organs. The continual development of improved software and hardware for calculating antibody deposits in tissues is critical in implementing these studies (see preliminary results). The quantitative relationship of free circulating antigens (if present) and biodistribution of MoAb needs to be defined. The formation of human-anti-mouse antibody (HAMA) response will clearly affect the in vivo properties of these antibodies. However, the induction of the idiotype network (see preliminary results) may have potential benefit in the long run. These parameters need to be monitored. These in vitro assays will provide important information in understanding and optimization of future use of 8H9 and other MoAb in the context of chemo-radiotherapy for a broad category of recalcitrant tumors in children, adolescents and young adults.

Memorial Sloan-Kettering Cancer Center (MSKCC) is devoted to the research and clinical care of cancer patients. The Center has an extensive patient referral base, particularly within the tri-state area. The center has an established commitment and past record in the use of monoclonal antibodies in the diagnosis and therapy of human cancers, including melanoma, colon cancer, and leukemias. Over the past 4 years we have an annual accrual of around 45 new NB, 27 OSs, 58 brain tumors, 23 Ewing's/PNET, 18 retinoblastoma, 12 rhabdomyosarcomas, 16 sarcomas and 7 DSRT at MSKCC. We are confident that we can accrue 60 patients within the next 2 years. In this past decade, we tested the utility of MoAb in the curative treatment of a lethal tumor (metastatic stage 4 NB in children). For this orphan disease, the lack of corporate/pharmaceutical sponsor has made our progress slow and difficult. Nevertheless, we made the following observations. (1) MoAb can extend the progression-free period in a cancer that was uniformly lethal two decades ago. (2) It is feasible to integrate MoAb into standard chemo-radiotherapy strategies, in order to derive maximal benefit from all available modalities. (3) Immune based therapies can be administered safely in the outpatient setting, thus reducing expensive in-patient costs and maximizing time in the home environment. (4) MoAb can induce idiotype network, a potential endpoint that underlies the biology in maintaining continual clinical remission. (5) GD2 is a useful marker of MRD, and specific MoAbs are highly efficacious in monitoring and purging of tumor cells. (6) Novel bioengineering strategies have been developed for the GD2-3F8 antigen-antibody system which are directly applicable to other MoAbs (single chain Fv,[54] and T-bodies[55]). During this period, >240 patients have been treated at Memorial Hospital with the antibody 3F8. A total of >3500 doses of unlabeled 3F8 have been given, 250 injections of $^{131}$I-3F8 for imaging, and 372 injections of $^{131}$I-3F8 for therapy. Although there were side effects, there were no lethal sequella during or immediately after antibody administration. 3F8 treatment is now routinely done in the outpatient clinic. Extending these findings to a second antigen-antibody system, especially one that will target to a broader spectrum of pediatric solid tumors is a priority. The murine IgG1 antibody 8H9 has obvious potential in monitoring and purging of MRD, radioimmunoscintigraphy, and radioimmunotherapy (both intravenous or compartmental). If our proposed study produces favorable results, i.e. selective tumor uptake at optimal AUC ratios (Tumor: tissues/organs), radioimmunotherapy can be explored for some of these solid tumors. More importantly, further development of the antibody would involve a major effort in humanizing and further genetic engineering to improve effector functions.

Preliminary Results:

$G_{D2}$-specific MoAb-based targeted therapy: a curative approach to a pediatric solid tumor: metastatic NB Improved understanding of the biology of NB has reshaped our clinical approach to this cancer. Non-infant stage 4 NB remains a therapeutic challenge despite four decades of combination chemotherapy. Similar to many cancers, MRD state can be achieved in patients with NB after intensive induction therapy.[56,57] Unfortunately, the transition from MRD to cure was a formidable hurdle.[56] Targeted immunotherapy besides being more specific and less toxic, may supplement what chemoradiotherapy has not accomplished.[58,59] Disialoganglioside $G_{D2}$ is a tumor antigen well suited for targeting therapy because (1) it is expressed at a high density in human NB, is restricted to neuroectodermal tissues and is genetically stable, unlike other tumor antigens such as immunoglobulin idiotypes;[60] (2) although it circulates in patients' serum, it does not interfere with the biodistribution of specific antibody (e.g. 3F8), allowing excellent tumor localization of NBs in patients;[10] (3) it is not modulated from cell surface upon binding to antibodies; (4) it is expressed homogeneously in human NB, with little heterogeneity within tumors and among patients. Several antibodies against $G_{D2}$ antigen has been described (3F8, 14.G2a, 14.18).[47,61] In vitro they can target lymphocytes,[62,63] granulocytes,[52,64,65] complement,[66,67] activated monocytes/macrophages,[68,69] IL2,[70] isotopes,[10,59,71,72] toxins,[73,74] and superantigen.[75] Phase I and phase II studies have shown only modest efficacy,[76-84] marrow disease more likely to respond than bulky tumors.[85] The major side effects included pain, allergic reactions and neuropathy.[78,85] With long followup, the role of these anti-$G_{D2}$ antibodies at the time of MRD appears promising.

Radiolabeled anti-$G_{D2}$ antibody 3F8 3F8 is a murine IgG$_3$ MoAb directed at the ganglioside $G_{D2}$ expressed on human NB cells. In preclinical studies $^{131}$I-3F8 targeted to human NB xenografts with exceptionally high % ID/gm. Intravenous $^{131}$I-labeled IgG$_3$ MoAb 3F8 produced a substantial dose dependent shrinkage of established NB in preclinical studies. Dose calculations suggested that tumors that received more than 4,200 rads were completely ablated. Marrow suppression was the dose limiting toxicity. In patient studies, it is not trapped nonspecifically by the reticuloendothelial system and penetrates NBs well (0.04 to 0.11% injected dose/gm).[10,86] Because of the intact blood brain barrier, $^{131}$I-3F8 does not normally localize to brain, spinal cord or penetrate the surrounding CSF.[10,59]

$^{131}$I-3F8 is more sensitive than conventional modalities, including metaiodobenzylguanidine (MIBG) in detecting NB in patients. The biodistribution of $^{131}$I-3F8 was studied in 42 patients (2 mCi per patient) with NB.[10] Comparison was made with $^{131}$I-MIBG, $^{99m}$Tc-MDP (technetium-labeled methylene diphosphonate) bone scan, as well as CT or MRI. $^{131}$I-3F8 detected more abnormal sites (283) than $^{131}$I-MIBG (138) or $^{99m}$Tc-MDP (69), especially in patients with extensive disease. In 20 patients with soft tissue tumors demonstrated by CT/MRI, $^{131}$I-3F8 detected the disease in 18 of them. Upon surgical resection, the two $^{131}$I-3F8-imaging-negative tumors revealed ganglioneuroma, one showing microscopic foci of NB. In contrast, $^{131}$I-3F8-imaging-positive tumors were all confirmed as NBs. In 26 patients with evidence of marrow disease by antibody scans, 14/26 had confirmation by iliac crest marrow aspirate/biopsy examinations. Agreement between the measured tissue radioactivity and the estimates based on planar scintigraphy validated the initial dosimetry calculations. The tumor uptake in patients with NB was 0.08%-0.1% ID/gm. The calculated radiation dose was 36 rads/mCi delivered to NB and 3-5 rad/mCi to blood.

$^{131}$I-3F8 differentiated Gliomas from normal brain tissues.[87,88] In 12 patients with brain tumors, 3F8 immunoscintigraphy was compared with $^{99m}$Tc-glucoheptonate/DTPA planar imaging, Thallium 201 single photon emission tomography (SPECT), and $^{18}$FDG positron emission tomography (PET). 10/11 malignant gliomas and 1/1 metastatic melanoma showed antibody localization. No nonspecific uptake in normal brain or CSF was detected. Average plasma and total body clearance were 20 h and 47 h, respectively. Antibody localization was measured on surgical specimens and time activity curves were calculated based on modified conjugate views or PET. Radioactivity uptake in high grade glioma peaked at 39 h, which then decayed with a half-life of 62 h. Tumor uptake at time of surgery averaged 3.5% ID/kg and highest activity by conjugate view method averaged 9.2% ID/kg (3.5 to 17.8).

Both primary and metastatic Small Cell Lung Cancer were detected by $^{131}$I-3F8[89] 10 Patients with SCLC were imaged with $^{131}$I-3F8. Five patients previously treated with chemo-radiotherapy were imaged with 2 mCi at the time of recurrence, while 5 patients were studied with 10 mCi/1.73 m$^2$ at the time of diagnosis. No significant toxicities were seen. All 10/10 tumors showed localization. Precision of localization was confirmed by comparing SPECT and CT in the 5 patients injected with the 10 mCi dose. Average half-lives for plasma and total body clearance were 15 h and 58 h, respectively. The tumor to non-tumor ratios appeared favorable based on the % ID/gm (see below).

FIG. 1), $^{131}$I-3F8 was used to consolidate >50 patients at the end of induction chemotherapy for their stage 4 NB diagnosed after 1 year of age. Except for hypothyroidism, there were no late effects of $^{131}$I-3F8 treatment.

$^{124}$I-3F8 PET imaging was first successfully applied to NB[92] Positron Emission Tomography (PET) can offer advantages over planar or single photon emission computed tomography (SPECT) imaging in the quantitation of spatial radioactivity distribution over time. $^{124}$I is a positron emitter with a 4-day half-life. We have studied the quantitative capability of PET imaging with $^{124}$I,[93] and have used it for scanning of $^{124}$I-labeled antibodies in animals and humans.[92,94,95] Using a brain PET scanner (PC4600, Cyclotron Corp.), with a relatively low resolution (FWHM=1.2 cm), we demonstrated that quantitation of $^{124}$I is possible (range examined was 0.4 to 4 uCi/ml). Studies using $^{124}$I in a rat tumor (4 gram) measured with this PET scanner were within 8% of the ex-vivo measurement. Subsequently, two patients were studied on this scanner using $^{124}$I-labeled 3F8 antibody.[88,92] A 3-compartment model was used to study the kinetics of the antibody to provide an estimate of the binding potential of 3F8 antibody for glioma. These quantitative studies have also allowed us to estimate the radiation dose to the tumor cell nucleus from low energy Auger electrons.[88] More accurate quantitation of $^{124}$I is now possible with the GE body PET scanner with even higher resolution.

$^{131}$I-3F8 therapy of leptomeningeal cancer[96] While overt meningeal disease is rapidly fatal, microscopic deposits in the cranio-spinal axis will spread even if the primary tumor is eradicated. The potentials of antibody-derived ligands for the diagnosis and therapy of LM cancer have not been fully explored. $G_{D2}$ is present on a broad spectrum of human tumors including medulloblastomas, high-grade astrocytomas, PNET, central NBs, small cell lung cancer, melanoma,

TABLE 3

% ID/kg after $^{131}$I-3F8 injection:

| Tumor | Day sampled | Heart | Small Bowel | Spleen | Liver | Spinal Cord | Large Bowel | Blood | Muscle | Kidney | Lung | Bone | Ovaries | Adrenal | Bladder | Stomach | Tumor | liver mets |
|---|---|---|---|---|---|---|---|---|---|---|---|---|---|---|---|---|---|---|
| NB | 4 | 1.7 | 1.7 | 1.7 | 2 | 2.2 | 2.4 | 3.1 | 3.1 | 3.1 | 3.6 | 4 | 4 | 5.7 | 6.7 | 6.7 | 40 | — |
| SCLC | 6 | 0.4 | 0.4 | 0.9 | 0.4 | — | — | — | 0.2 | 0.9 | 0.5 | — | — | 1.6 | 0.5 | — | 2 | 15 |

Myeloablative doses of $^{131}$I-3F8 are effective for NB with minimal extramedullary toxicities. Based on the tracer dose dosimetry, the absorbed doses to liver, spleen, red marrow, lung, total body and tumor were 537, 574, 445, 454, 499 and 4926 rads, respectively. The average rad/mCi were 2.3, 2.5, 2, 2, 1.9, and 13.7, respectively. The chemical toxicities of the antibody 3F8 have been studied in phase I[76,77] and phase II studies.[11,90] Acute toxicities included pain, urticaria, fever and hypotension which were self-limited. The radiological toxicities of $^{131}$I-3F8 were recently defined in a phase I dose escalation study. (6, 8, 12, 16, 20, 24, and 28 mCi/kg).[91] Among 10 patients (pts) with progressive disease evaluable for response, 2 cleared the marrow and 2 had partial responses of soft tissue tumors. Average tumor dose was 150 rad/mCi/kg. Acute toxicities of $^{131}$I-3F8 treatment included pain (20/24) during the infusion, fever (20/24) and mild diarrhea. All pts developed grade 4 myelosuppression. 22/24 pts were rescued with cryopreserved autologous bone marrow; one patient received GM-CSF; one died of progressive disease before marrow reinfusion. Hypothyroidism developed in despite thyroid blockade with oral SSKI plus synthroid or cytomel. In the subsequent phase II study (N7, IRB94-11, sarcomas, leukemia/lymphomas and peripheral NBs, many of which have LM spread. Clinical trials using intravenous injections of anti-$G_{D2}$ MoAb 3F8 have not encountered long-term neurotoxicity in patients followed for up to 13 years. Pharmacokinetic studies in rats showed that at least 50% of intraventricular $^{131}$I-3F8 was eliminated by bulk flow. When human melanoma leptomeningeal xenografts were present, CSF radioactivity was retained and AUC (area under curve) increased by 1.5 fold. AUC ratios of tumor to CSF, tumor to brain and tumor to blood were 14, 86, and 64, respectively. These ratios improved to 15, 209 and 97, respectively, if the rats were pretreated with diuretics. Direct intraventricular administration of 30 mCi of $^{131}$I-3F8 in cynomolgus monkeys did not induce clinical or histological toxicity. Since $G_{D2}$ tissue distribution (CNS and peripheral) in the cynomolgus monkey is identical to that of human, the high radiation dose of IT $^{131}$I-3F8 (up to 82 Gy) to CSF in contrast to blood (<2 Gy) may translate into a meaningful treatment approach. Moreover, serum antibody against the MoAb (AMA) was 14-22 fold higher than in the CSF, thereby accelerating blood clearance (reducing blood radiation dose) without affecting CSF pharmacokinetics.

Intra-CSF $^{131}$I-3F8 imaged $G_{D2}$-positive LM cancers successfully in patients. The pilot study included 5 patients who had a histologically confirmed diagnosis of a malignancy expressing $G_{D2}$ with LM disease refractory to conventional therapies or for which no conventional therapy exists. Ommaya catheter placement, patency and CSF flow was evaluated by $^{111}$In DTPA studies. Five patients (ages 1-61 years) with leptomeningeal or intraventricular melanoma, ependymoma, rhabdoid tumor (n=2) and retinoblastoma were evaluated. Active disease was identified by MR scans in 4 of 5 pts, and by positive CSF cytology in 2. Doses of 0.7-1.9 mCi of $^{131}$I-3F8 were injected by Ommaya catheter. Acute side effects included fever (n=2), and headache (n=2) both treated with tylenol, and one episode of vomiting (n=1). One pt had an elevated opening CSF pressure that remained increased for 36-48 hours post-injection. There was no appreciable change in WBC, platelet counts, liver or kidney functions tests or CSF cell counts in all 5 patients.

The CSF radioactivity biological half-life, distribution of radioactivity in the craniospinal axis, and dosimetry at plaques of disease and surrounding normal tissues were determined by $^{131}$I-3F8 Single Photon Emission Tomography (SPECT). Peak CSF values were achieved generally within the first hour of injection. The CSF biological half-life was 3-12.9 hours, and was in close agreement with the SPECT (7.2-13.1 hours). Estimated dose to the CSF was 14.9-56 cGy/mCi by CSF samples and 15-31 cGy/mCi by SPECT analysis. Focal areas of tumor uptake were 27-123 cGy/mCi by SPECT estimates. The radiation dose to the blood was 0.9-1.9 cGy/mCi based on blood radioactivity measurements. Post-injection $^{131}$I-3F8 SPECT scans showed distribution throughout the subarachnoid space along the spinal cord down to the level of the cauda equina by 4 hours, and progressively over the convexity by 24 hours in all patients. Focal $^{131}$I-3F8 uptake was demonstrated in the ventricles, spine and midbrain in 4 patients, corresponding to disease seen on MR. In the one patient who had no MR evidence of disease, $^{131}$I-3F8 clearance was most rapid (3 hours), with no focal accumulation observed on SPECT. Four patients with focal $^{131}$I-3F8 uptake received 10 mCi of $^{131}$I-3F8 through the Ommaya reservoir as part of a treatment protocol in a phase I toxicity study. Except for grade 2 toxicities (fever, headache, nausea and vomiting, increase in intracranial pressure) and a breakthrough seizure, there were no adverse side effects during their initial treatment. One patient had a radiographic and clinical response. On repeat treatment 2 months later, with the same dose, a rapid rise of intracranial pressure necessitated a shunt placement. Although all 4 treated patients progressed, 3 are still alive (2+, 3+ and 9+ months from treatment).

Adjuvant anti-$G_{D2}$ antibody 3F8 3F8 (without radioisotope) has also been tested in phase I and phase II studies.[58,76,77] Responses of metastatic NB in the bone marrow were seen. Another mouse antibody 14.G2a and its chimeric form 14.18 have also induced marrow remissions in patients with NB.[83] Acute self-limited toxicities of 3F8 treatment were pain, fever, urticaria, hypertension, anaphylactoid reactions, as well as decreases in blood counts and serum complement levels, and in rare patients self-limited neuropathy.[71,97-99]

Anti-GD2 antibody treatment of MRD in stage 4 NB diagnosed at more than one year of age.[11] Thirty-four patients (pts) were treated with 3F8 at the end of chemotherapy. Most had either bone marrow (31 pts) or distant bony metastases (29 pts). Thirteen pts were treated at second or subsequent remission (group I), and 12 pts in this group had a history of progressive/persistent disease after ABMT; 21 pts (all on N6 protocol) were treated in first remission following induction chemotherapy (group II). At the time of 3F8 treatment, all 34 patients had stable or minimal NB. Twenty-three patients were in CR, 8 in VGPR, 1 PR and 2 with histological evidence of marrow disease. Since microscopic occult NB could escape detection by conventional radiographic studies, three additional sensitive methods were used to document disease prior to 3F8 treatment. They were 131I-3F8 immunoscintigraphy, marrow immunocytology, and molecular detection of marrow GAGE by RT-PCR. Fourteen of 34 patients were 131I-3F8 scan-positive prior to 3F8 treatment. Nine had residual disease in their marrow by immunocytology and 12 had evidence of marrow disease by RT-PCR. A total of 25/34 patients were positive for disease by at least one of these three methods. Thirteen patients are progression-free (40 to 148+ months from the initiation of 3F8 treatment); one other patient is alive with disease 61+ months after 3F8 treatment. Both group I and group II patients achieved long-term progression-free probabilities of 38%. Among the 20 patients whose disease progressed after 3F8, 3 in group II had isolated relapse in the CNS, a sanctuary site where antibody 3F8 could not penetrate.86 Although the majority of patients were in CR/VGPR by conventional criteria right before 3F8 treatment, 74% had evidence of disease by the more sensitive methods (immunoscintigraphy with 131I-3F8, bone marrow immunocytology and RT-PCR). When these tests were repeated subsequent to 3F8 treatment, 6/9 patients with positive immunocytology reverted to undetectable. Among the 12 GAGE-positive patients, 7 became negative for GAGE expression. Six patients had post-3F8 treatment 131I-3F8 scans and all 6 showed resolution or improvement.

Human anti-mouse antibody response (HAMA) and patient outcome: Three patterns of HAMA response were identified. In pattern I, HAMA was not detectable during the 4-6 month followup period after first cycle of 3F8, 42% had no HAMA response even after receiving 2-4 cycles of 3F8 over a 4-25 month period. In pattern II, HAMA was detected but rapidly became negative during the 4-6 month followup period. In pattern III, HAMA titer was high (>5000 U/ml) and persistent during the 4-6 month followup period. When patients developed HAMA (>1000 U/ml) during a treatment cycle, pain side effects disappeared. In the absence of HAMA (pattern I) or when HAMA became negative (pattern II), patients received repeat 3F8 treatments. In the presence of HAMA, subsequent 3F8 treatments had to be delayed. Thus, patients in group III did not get repeat 3F8 treatment during the first 4-6 months, and had fewer total-cycles and fewer total-days of 3F8 treatment, while pattern I and II patients were comparable. Kaplan Meier analysis showed a survival advantage for those with pattern II HAMA response, i.e. a low self-limiting HAMA response (73% for pattern II versus 33% for pattern I, and 18% for pattern III). The probability of survival among patients with pattern II was significantly better than the pattern I and III patients combined (p<0.05). For patients progression-free for at least 12 months after the last cycle of chemotherapy, those receiving four 3F8 cycles had a PFS probability double those receiving less than 4 cycles (p=0.08). When patients with pattern II HAMA response and/or four cycles of 3F8 were considered as a group (FIG. 4), their survival was significantly better than the other 20 pts (p <0.001). We interpret these findings to mean a threshold (four 3F8 cycles, each 10-day cycles) plus a pattern II HAMA response may be necessary to maintain permanent tumor control.

Idiotype network is a possible mechanism for long term PFS. Since the HAMA response was primarily anti-idiotypic (Ab2), we postulate that the subsequent induction of an idiotype network which included anti-anti-idiotypic (Ab3) and anti-$G_{D2}$ (Ab3') responses may be responsible for tumor control in patients. Their serum HAMA, Ab3, and Ab3' titers prior to, at 6, and at 14 months after antibody treatment were measured by ELISA. Long term PFS and survival correlated significantly with Ab3' (anti-$G_{D2}$) response at 6 months, and with Ab3 response at 6 and 14 months. Non-idiotype antibody responses (anti-mouse-IgG3 or anti-tumor nuclear HUD antigen) had no apparent impact on PFS or survival. It appears that the successful induction of an idiotype network in patients maybe responsible for long term tumor control and prevention of late relapse among N6 and N7 patients (FIG. 5). Even among patients treated on N5 (with ABMT, FIG. 5), all of the survivors of bony and marrow metastases have had imaging studies with 3F8 and had detectable idiotype network by ELISA[100]; similarly no late relapses were seen. While N5 and N6 groups had no relapses after ~3 years from diagnosis or ~2 years from 3F8 therapy (including second remission group), among N7 patients, the relapse curve has leveled off even earlier, around 2 years from diagnosis.

Integration of 3F8 treatment into multi-modality therapy: N5, N6 and N7 for stage 4 NB>1 year of age: From 1987 to 1999, N5, N6 and N7 protocols were designed sequentially to test the clinical importance of dose intensity, 3F8, and [131]I-3F8 in consecutive patients with newly diagnosed stage 4 NB. Most of them had very high-risk clinical and biologic markers, almost all were diploid/tetraploid and of unfavorable histopathology. Except for [131]I-3F8 and autologous marrow transplant (ABMT), chemotherapy and 3F8 are routine outpatient procedures. Evaluations at sequential endpoints compared favorably with predictions: primary tumor resectability, overall response, and progression-free survival (PFS). There were no late relapses after 3.5 years from diagnosis. For N6 (all survivors past 5 years) 40% are progression-free; for N7, PFS is projected at 55% (p=0.02 when compared to N5). Causes of death included disease progression, secondary leukemia, and isolated CNS relapse. Although toxicities included hearing loss and hypothyroidism which required correction, a curative strategy for stage 4 NB appeared to be within reach.

Neuroblastoma, 3F8 and GD2 provided us with the proof of principle that MoAb may have potential in the permanent eradication of MRD in the curative treatment of solid tumors in the younger population. Both RIT and idiotype-netowrk induction are possible with murine MoAb. We therefore undertook an extensive screening of MoAbs to identify candidates with a broad reactivity with pediatric/adolescent solid tumors, that may have similar targeting potential as the antibody 3F8.

Novel antigen for MoAb targeting to solid tumors in children and young adults Female BALB/c mice were hyperimmunized with human neuroblastoma according to previously outlined methods.[47] Splenic lymphocytes were fused with SP2/0 mouse myeloma cells line. Clones were selected for specific binding to neuroblastoma on ELISA. The 8H9 hybridoma secreting an IgG1 monoclonal antibody was selected for further characterization after subcloning.

Normal and tumor tissue reactivity of 8H9 antibody Frozen sections from 315 tumors with histologically confirmed diagnoses of cancer were analyzed for immunoreactivity with MoAb 8H9. (Tables 5 and 6) 15 histologically normal human tissues and 8 normal monkey tissues were also analyzed ( ).

TABLE 5

| Neuroectodermal Tumors | No. | 8H9 positive | % |
|---|---|---|---|
| NB | 87 | 84 | 97 |
| Brain Tumors | | | |
| 1. Glial Tumors | | | |
| Glioblastomas multiforme | 17 | 15 | 88 |
| Mixed Glioma | 4 | 3 | — |
| Oligodendroglioma | 11 | 4 | 36 |
| Astrocytoma | 8 | 6 | 75 |
| Ependymoma | 3 | 2 | — |
| 2. Primitive PNET | | | |
| Medulloblastoma | 2 | 2 | — |
| 3. Mixed | | | |
| Neuronoglial tumor | 2 | 1 | — |
| 4. Other | | | |
| Schwannoma | 3 | 3 | — |
| Meningioma | 2 | 2 | — |
| Neurofibroma | 1 | 1 | — |
| Melanoma | 16 | 12 | 75 |
| Ewing's Family of tumors | 21 | 21 | 100 |
| TOTAL | 177 | 156 | 88 |

TABLE 6

| Mesenchymal Tumors | No. | 8H9 Reactive | % |
|---|---|---|---|
| Rhabdomyosarcoma | 26 | 25 | 96 |
| Osteosarcoma | 26 | 25 | 96 |
| Desmoplastic small round cell tumor | 34 | 32 | 94 |
| Malignant fibrous histiocytoma | 1 | 1 | — |
| Synovial sarcoma | 2 | 1 | — |
| Leiomyosarcoma | 4 | 4 | — |
| Undifferentiated sarcoma | 2 | 2 | — |
| TOTAL | 95 | 90 | 95 |

TABLE 7

| CARCINOMAS | No. | 8H9 Reactive | % |
|---|---|---|---|
| Breast | 12 | 4 | 33 |
| Bladder | 4 | 1 | — |
| Adrenal | 2 | 1 | — |
| Stomach | 1 | 1 | — |
| Prostate | 2 | 1 | — |
| Colon | 2 | 1 | — |
| Lung | 1 | 1 | — |
| Endometrium | 1 | 1 | — |
| Cervix | 1 | 0 | — |
| Renal | 1 | 1 | — |
| TOTAL | 27 | 12 | 44 |

TABLE 8

| Other Tumors | No. | 8H9 reactive | % |
|---|---|---|---|
| Hepatoblastoma | 4 | 3 | — |
| Wilm's tumor | 8 | 7 | — |
| Rhabdoid tumor | 3 | 3 | — |
| Paraganglioma | 1 | 1 | — |
| TOTAL | 16 | 14 | 88 |

Heterogenous, non-specific cytoplasmic staining was noticed in normal human pancreas, stomach, liver and adrenal cortex which was diminished when 8H9 F(ab')2 fragments were used instead of the whole antibody for immunostaining.

None of the other human tissues showed reactivity with 8H9. In particular normal human brain tissue sections including frontal lobe, spinal cord, pons and cerebellum were completely negative. Normal tissues from cynomolgus monkey also demonstrated similarly restricted reactivity with nonspecific staining observed in stomach and liver (Table 4). The majority of neuroectodermal and mesenchymal tumors tested showed positive reactivity with 8H9, epithelial tumors to a lesser extent. 8H9 immunoreactivity was seen in a characteristic, homogenous, cell membrane distribution in 272 of the 315 (86%) tumor samples examined. 88% of neuroectodermal tumors, 95% of mesenchymal tumors and 44% of epithelial tumors tested positive with 8H9 (Tables 4-8)

TABLE 4

| Tissues | Human | Cynomolgous |
|---|---|---|
| Frontal lobe | Negative | Negative |
| Pons | Negative | Negative |
| Spinal cord | Negative | — |
| Cerebellum | Negative | Negative |
| Lung | Negative | — |
| Heart | Negative | |
| Skeletal muscle | Negative | — |
| Thyroid | Negative | — |
| Testes | Negative | — |
| Pancreas | cytoplasmic staining | — |
| Adrenal cortex | cytoplasmic staining | cytoplasmic staining |
| Liver | cytoplasmic staining | cytoplasmic staining |
| Stomach | — | Negative |
| Sigmoid colon | Negative | — |
| Bone Marrow | Negative | — |
| Kidney | Negative | Negative |

Indirect immunofluorescence 8H9 immunoreactivity in 34 NB, melanoma, RMS, small cell lung cancer, OS, glioblastoma, leukemia, breast cancer and colon cancer cell lines was tested using indirect immunofluorescence. Moderate to strong cell membrane reactivity with 8H9 was detected in 16/16 NB, 2/2 melanoma, 2/2 RMS, 1/1 glioblastoma multiforme, 3/3 breast cancer, and 1/1 colon cancer, 2 of 3 Ewing's/PNET, and 2 of the 3 OS cell lines. The small cell lung cancer cell line HTB 119 tested negative with 8H9 as did Jurkat T-ALL cell line and EBV transformed lymphoblastoid cells. Normal human bone marrow mononuclear cells (n=80) and hepatocytes (n=2) had no reactivity with 8H9. Hepatocytes were isolated from human cadavers and stained with 8H9. In contrast to anti-cytokeratin 18 and anti-HLA-class-1 antibodies which reacted strongly with surface antigens, 8H9 staining was equivalent to control antibody.

Antigen modulation 8H9 binding to neuroblastoma line (NMB7), rhabdomysarcoma (HTB82) and OS (U2OS) (measured by indirect immunofluorescence) did not diminish significantly after 48 hr of incubation at 37° C. During the same period, binding to HLA (MoAb HB95) diminished by 85% and to GD2 (3F8) by 55%, respectively (FIG. 6). Electron microscopy using gold-labeled antibodies will be more definitive in tracking antibody internalization, a process clearly important for immunotoxins to be effective.

Enzyme-sensitivity There was a pronase dose-dependent reduction in reactivity with 8H9 with 75-85% loss of immunofluorescence at a final Pronase concentration of 0.3 mg/ml (FIG. 7). There was no appreciable loss of reactivity with 3F8 (specific for the ganglioside GD2) on NMB7 cells. Furthermore, the 8H9 antigen was not sensitive to neuraminidase or phosphatidyl-inositol specific phospholipase C (data not shown).

Biochemical Characterization of the novel antigen recognized by 8119 Using a nonradioactive cell surface labeling technique, the antigen was immunoprecipitated and analyzed on a SDS-PAGE.[101] In brief, NB NMB7 or OS U2OS cells were biotinylated using biotin-LC-NHS, lysed, precleared with protein-G sepharose, reacted with antibody 8H9 and then immunoprecipitated in fresh protein G sepharose. Antigen was then dissociated from the gel and separated by SDS-PAGE. Following transblotting onto nitrocellulose membrane, the protein bands were detected with HRP-strepavidin and visualized by ECL. A band of 90 kDa under non-denaturing conditions and 96 kDa in the presence of 2ME was found.

TABLE 9

| | % ID/gm | |
|---|---|---|
| | NB | RMS |
| | Time | |
| TISSUE | 24 h | 172 h |
| Tumor | 8.3 | 5.3 |
| Brain | 0.2 | 0.1 |
| Heart | 2.1 | 0.8 |
| Lung | 0.8 | 1.4 |
| Kidney | 2.3 | 0.7 |
| Liver | 7.5 | 0.6 |
| Spleen | 6.7 | 0.6 |
| Bladder | 1.0 | 1.1 |
| Stomach | 0.3 | 0.5 |
| Sm Intestine | 0.3 | 0.3 |
| Lg Intestine | 0.4 | 0.2 |
| Muscle | 0.2 | 0.2 |
| Femur | 0.7 | 0.3 |
| Adrenal | 1.0 | 0.3 |
| Skin | 0.2 | 0.4 |
| Spine | 1.7 | 0.4 |
| Blood | 3.8 | 3.3 |

Rat Anti-idiotypic MoAb specific for 8H9 By immunofluorescence the antigen was sensitive to low temperatures. In view of the lability of the antigen, we chose to synthesize anti-idiotypic antibodies as surrogate antigen-mimics, in order to allow in vitro monitoring of the antibody immunoreactivity e.g. after iodination of antibody 8H9. LOU/CN rats were immunized with protein-G purified 8H9 precipitated with goat-anti-mouse Ig, emulsified in CFA. Following in vitro hybridization to the myelomas SP2/0 or 8653, 3 IgG2a clones (2E9, 1E12, and 1F11) were selected for their high binding and specificity. When tested against a panel of 23 other myelomas or hybridoma antibodies, no cross-reactivity was found. The anti-idiotypic hybridomas were cloned and antibodies produced by high density miniPERM bioreactor from Unisyn Technologies (Hopkinton, Mass.). The anti-idiotypic antibodies are further purified by protein G (Pharmacia) affinity chromatography. To further prove that these anti-idiotypic antibodies are antigen-mimics, we immunoenrich phagemids and screen scFv on solid phase anti-idiotype, and successfully isolate a number of 8H9-scFv with similar binding specificity to tumors as the parent 8H9 (see below).

Tumor localization in xenografted SCID mice SCID mice with NB (NB) xenografts were injected iv with 100 ug $^{99m}$Tc labeled 8H9. Blood clearance was studied by blood cpm at various intervals after injection. Mice were sacrificed at 24 hours and tissue uptake expressed as percent injected dose per gram (Table 9). Significant uptake in the reticulo-endothelial system in liver and spleen was seen only with $^{99m}$Tc-8H9; none was evident when $^{131}$I-3F8 was used. There was no significant difference between $^{99m}$Tc-8H9 and $^{131}$I-8H9 biodistribution. When the specific activity of $^{131}$I-8H9 was increased from 5 to >20 mCi/mg, there was no degradation of tumor imaging or difference in biodistribution. In SCID mice xenografted with RMS (RMS) xenograft, following iv injection of 100 uCi of $^{125}$I-8H9, selective tumor uptake was evident at 4 to 172 hrs after injection, with a blood T½ of 0.8 h and T½ of 26 h. Mean tumor/tissue ratios were optimal at 172 h (for lung 4, kidney 7, liver 9, spleen 10, femur 16, muscle 21, brain 45). Average tumor/blood ratio were 0.7, 1.4 and 1.6, and tumor uptake was 9.5±3.4, 13.3±1.5, and 5.3±0.9% injected dose per gm at 24, 48 and 172 h, respectively. Control IgG1 MoAb antibody 2C9 remained in the blood pool without localization to sc RMS xenografts. Tumor to normal tissue ratio was favorable [range 5-55] for 8H9 (solid bar, FIG. 8) in contrast to control MoAb 2C9.

8H9-ScFv We have synthesized single chain antibody (scFv) from 8H9. Using polymerase chain reaction splicing by overlap extension, variable regions of the heavy ($V_H$) and light chains ($V_L$) of 8H9 were joined by a polylinker (L) (gly4Ser)$_3$ and selected by phagemid expression. scFv was characterized by DNA sequencing, western blots, in vitro ELISA, immunostaining/FACS, and idiotype analysis. Using this scFv as a targeting unit, we are in the process of synthesizing scFv-h 1-CH2-CH3 chimeric, scFv-m 3-CH2—CH3 chimeric, and T-bodies for retargeting T-cells.

Cell Populations Using 8H9-Magnetic Bead Immunoselection. ES is a small round blue cell tumor of childhood characterized by a t(11,22) in most patients. Because survival remains suboptimal with standard therapy, many patients receive autologous stem cell transplant and current trials investigating adoptive transfer of autologous T cells in the context of immune therapy are underway. However, approximately 50% of patients with advanced disease have PCR detectable ES in peripheral blood and/or bone marrow and the administration of autologous cell preparations contaminated with tumor may contribute to disease relapse. To date, there is no method reported for purging contaminated hematopoietic cell populations or bone marrow preparations of ES. Merino et al in the laboratory of Dr. Mackall at the Pediatric Oncology Branch, NCI, Bethesda, Md., successfully optimized 8H9 for immunomagnetic purging of ES. 8H9 bound to 9/9 of ES cell lines by flow cytometry. Binding to peripheral blood mononuclear T cell and B cell populations, as well as CD34+ cells from bone marrow was negative. Utilizing immunomagnetic selection, 8H9 was used to isolate ES cells from contaminated blood cell populations. Using real-time quantitative nested PCR with the Lightcycler instrument, purging efficiency was monitored by of t(11,22) RT-PCR. Contaminated specimens were reacted with 8H9 and then incubated with rat anti-mouse IgG1 magnetic beads. The sample was then run over a Miltenyi Variomax negative selection column Recovery was approximately 70% of the total PBMC. RNA was extracted from 10e7 cells from pre and post purge cell populations. Real time quantitative PCR was performed with a level of sensitivity to one tumor cell in 10e5 normal cells. A 2-log reduction of tumor cells was achieved at a contamination of one tumor cell in 10 normal PBMC and one tumor cell in 10e3 normal PBMC. Further studies evaluating efficacy in clinical samples are underway. These results demonstrate a potential new approach for purging contaminated patient samples to be used in the context of autologous bone marrow transplant and/or immunotherapy trials for ES.

8H9 purging of NB from marrow or blood cells In similar experiments using Dynal beads coated with human anti-mouse IgG (Dynal, Lake Success, N.Y.)$^{50}$ EGFP marked NMB7 cells could be quantitatively removed in a one-cycle (either 8H9 or 3F8) or 2-cycle (8H9 followed by 3F8) immunomagnetic strategies (Table 10).

Research Design and Methods:

We will test if intravenous injections of iodine-131 labeled murine MoAb 8H9 can detect primary and metastatic solid tumors. A total of 60 patients will be accrued over a period of 2 years.

1: To define the level of agreement between $^{131}$I-8H9 and conventional imaging modalities in the detection of primary and metastatic solid tumors in pediatrics.

1.1 Study Design

This is an open-label single arm study of $^{131}$I-8H9, injected intravenously at 10 mCi/1.73 m2 dose, after which patients will be imaged at approximately day 0 to 1, 2 d, 3 d and whenever possible 6 to 7 d for dosimetry calculations. Blood samples will also be obtained at least 12 times over the ensuing 7 days. Patients are eligible for the protocol prior to their surgical resection or biopsy of known or suspected tumor, or at the time of recurrent tumor. $^{131}$I-8H9 injection plus imaging can be repeated in each patient up to a total of 3 times, but only if he/she has no HAMA and no allergy to mouse proteins as evidenced by a negative skin test.

1.2 Pateint/Subject Inclusion Criteria

Gender and Minority Inclusion for Research Involving Human Subjects:

Memorial Sloan Kettering Cancer Center has filed form HHS 441 (Re: Civil Rights), form HHS 641 (Re: Handicapped individuals), and form 639-A (Re: sex discrimination). In selecting patients for study in the proposed project, due notice is taken of the NIH Policy concerning inclusion of women and minorities in clinical research populations. The study population will be fully representative of the whole range of patients seen at Memorial Hospital. No exclusions will be made on the basis of gender or ethnicity. However, because of the nature of these cancers which tend to present in children and young adults, most the human subjects would be of the younger age group.

Based on a December 1998-November 1999 analysis of the patient population accrued to therapeutic clinical protocols, the racial distribution of these patients were 16.6% black, Hispanic, or Asian, 78.2% white and 5.2% other or unknown. The gender was 55.9% male and 44.1% female. For the total patient population diagnosed and treated at MSKCC in 1996, 26% were black, Hispanic, Asian or Native American, 70% white and 6% unknown or not responding. Of these patients, 38% were male and 62% female.

Participation of children: Children, adolescents and young adults are the subjects of this clinical trial because of the nature of these cancers. There is no age limit.

1.3.0 Evaluation During Treatment/Intervention 1.3.1 After injection of radiolabeled antibody, 1-2 cc of blood in purple tops (EDTA) will be drawn at time 0, and around 15 min, 30 min, 1 h, 2 h, 4 h, 8 h, 18 h, 30 h, 42 h, 66 h, and once on day 6 or 7. Samples should be dated and timed. These samples are for pharmacokinetic and for dosimetry studies. Patients with delayed clearance will have one more imaging done between clay 9 to 11.

| Time | Procedure |
| --- | --- |
| day −10 | start daily oral SSKI, cytomel for thyroid blockade |
| day 0 | 5 mCi of iodine-131 on 0.25 to 0.75 mg of 8H9* blood samples at 0, and approximately 15 min, 30 min, 1 h, 2 h, 4 h, 8 h after injection |
| day 0 | Gamma camera scan plus whole body counts |
| day 1 | Gamma camera scan plus whole body counts |

-continued

| Time | Procedure |
|---|---|
| day 1 | blood samples at approximately 18 h and 30 h |
| day 2 | Gamma camera scan plus whole body counts |
| day 2, 3 | blood samples at approximately 42 h and 66 h |
| day 5(or 6 or 7) | Gamma camera scan plus whole body counts and blood sample day 9(or 10 or 11) if slow clearance |
| day 14 | Gamma camera scan plus whole body counts and blood sample Oral SSKI and cytomel discontinued |

*Premedication with acetaminophen and diphenhydramine.

1.3.2 Patients Will Undergo Gamma Imaging Days 0, 1, 2 and 5 or 6 or 7 After Injection.
1.3.3 Blood for HAMA q 1-2 Months
1.3.4 Tissue Biopsy is Recommended for Regions of Uptake by 8H9 Imaging and Negative by Conventional Radiographic Techniques.
1.4.0 Biostatistics To measure the level of agreement between conventional imaging modality (CT, MRI, and nuclear scans) and antibody 8H9 imaging in known and occult sites of disease. Index lesions will be confirmed either by surgery or by disease-specific imaging (e.g. MIBG for NB). For each individual, the proportion of sites found by 8H9 imaging will be scored. Given that there will be confirmation by surgery or by disease-specific imaging, sensitivity analysis of 8H9 for each disease can be conducted. The probability of agreement or positive predictive value will be calculated. The 95% confidence intervals can be calculated within +/−31% for each disease (NB, RMS, ES/PNET, DSRT, brain tumors and other sarcomas). The study will be performed on a total of 60 patients (10 with NB, 10 RMS, 10 osteosarcroma, 10 ES, 10 DSRT and 10 brain tumors plus other 8H9-positive tumors). Estimates on the level of agreement and the level of tumor uptake will be computed separately in each disease group. We are not using Kappa statistics for testing the association between $^{124}$I-3F8 imaging and other imaging modalities (CT, MRI) since only patients with measurable or evaluable tumors will be eligible for this protocol. In other words, patients with no evidence of disease by conventional studies will be not eligible. Therefore we cannot estimate the probability of negative 8H9 imaging when conventional imaging studies are negative, i.e. specificity analysis.
1.5.0 Preparation of $^{131}$I-8H9

8H9 is produced under GMP conditions and packaged in glass vials. $^{131}$I is purchased from Amersham Inc. 8H9 will be labeled with radioactive iodine using iodogen T method. The reaction mixture is filtered through an ion exchange (AG1X8) filter (Biorad) to remove free iodine. Protein incorporation is measured using TCA precipitation or thin layer chromatography Immunoreactivity is measured by 2 separate methods (1) a solid phase microtiter radioimmunoassay technique previously described,[102] and (2) anti-idiotype peak shift method, where anti-idiotypic antibody 2E9 is added at 50 to 1 molar ratio to $^{131}$I-8H9 for 30 minutes on ice with mixing. The percent cpm shifted on HPLC is a measure of immunoreactivity. Radioiodinated 8H9 has a mean trichloroacetic acid precipitability of >90%, and specific activity of $^{131}$I-8H9 averaging 10 mCi per mg protein. Administration of $^{131}$I-8H9 is undertaken within 1-2 hours of iodination to reduce the possibility of radiolysis. Antibody radiolabeling is carried out in the Central Isotope Laboratory under the supervision of Dr. Ronald Finn, according to FDA guidelines on radiolabeled biologics for human use.

1.6.0 Infusion of Radiolabeled Antibody Preparation and Monitoring of Patient Response in Immediate Post-Infusion Period, Including Radiation Safety Aftercare.

All radiolabeled MoAb preparations will be injected into patients by a trained research nurse or physician. Strict observance of appropriate radiation safety guidelines will be undertaken. The procedure will be explained to the patient thoroughly prior to the infusion by the physician, and appropriate pre-treatment (eg SSKI drops, perchloracap) checked. The radiolabeled antibody will be transported from the radiolabeling facility to the infusion area loaded into the infusion delivery system by the physician. The physician and nurse will be present throughout the infusion and in the post-infusion period.

The infusion procedure will consist of the radiolabeled antibody being administered intravenously either through a peripheral intravenous catheter or an indwelling central catheter over a 20 minute period. All patients will have vital signs monitored prior to and following the radiolabeled antibody infusion. Blood samples for pharmacokinetic calculation will be obtained immediately following the infusion, and at various time points thereafter as outlined above. The patient will be seen by a physician daily while hospitalized, and will be available for consultation (with appropriate radiation safety personnel) with an oncologist or nurse regarding issues relating to the radiolabeled antibody infusion or radiation safety. The patient will also be imaged in the Nuclear Medicine Department over the subsequent two week period, and all imaging procedures performed will be supervised by the physician to ensure that appropriate studies are obtained.
1.7.0 In Vitro Radioimmunoassay, ELISA, and Immunostaining Quantitative in vitro assays on biologic fluids collected during the course of clinical research studies in individual patients that employ radiolabeled antibodies will be carried out. The methods provided will include gamma counting of blood samples and HAMA assays. HAMA titer in blood and serum will be correlated with the clearance of $^{131}$I-8H9

1.7.1 General counting procedures Aliquots of whole blood/plasma/serum obtained from patients infused with radiolabeled antibodies will be counted in a gamma counter with standards of known activity for determination of sample activity. Tissue samples obtained by biopsy or surgery will also be counted in a gamma counter for determination of % injected dose/gram tissue. Appropriate quality control procedures will be observed for counting instruments and tissue specimens.

1.7.2 Quantitation of HAMA by ELISA The presence of HAMA can modify the biodistribution of $^{131}$I-8H9. Although in naive patients HAMA is typically undetectable, in patients with prior history of exposure to murine antibodies or to 8H9, the presence of HAMA before and soon after 8H9 injection will need to be monitored. In addition, the formation of HAMA was highly correlated with patient survival in the GD2-3F8 system, we plan to measure the serum antibody titer 6 months and 12 months after 8H9 exposure. The ELISA method has been described previously.[11] Using F(ab')2 fragments derived from the three anti-idiotypic antibodies (2E9, 1E12, and 1F11), serum Ab3 will also be monitored as previously demonstrated for the GD2-3F8 system.[103,104]

1.7.3 Quantitation of free circulating antigen Since the biodistribution of 8H9 will be greatly affected by any soluble antigen, patient sera before antibody injection will be analyzed for antigenemia using an ELISA inhibition assay using a modification of previously described method.[105] Microtiter wells are coated with anti-idiotype MoAb 2E9. Serial serum dilutions are used to inhibit the binding of biotinylated 8H9, which can be detected by peroxidase-streptavidin. Upon washing, color reaction is performed at room temperature using hydrogen peroxide as substrate and o-phenylenediamine (Sigma, St. Louis, Mo.) as chromogen. After stopping the reaction with 30 ul of 5N sulfuric acid, optical density of the wells are then read using MRX microplate reader (Dynex, Chantilly, Va.) and antibody titer calculated in units/ml.

1.7.4 Immunostaining of tumor tissues Tumor tissues will be tested for antigen expression using methods previously described.[74]

Anticipated results and potential pitfalls The injection of $^{131}$I-8H9 intravenously or intrathecally into cynomolgus monkeys were well tolerated. Although we do not anticipate any untoward side effects, patients will be closely monitored during the antibody infusion with oxygen, antihistamines, epinephrine, and hydrocortisone at the bed side. After the completion of antibody injection, patients will be observed for at least 1 hour before discharge from the clinic. Patients with unexpected grade 3-4 (other than urticaria, self-limited blood pressure/pulse/temperature changes) or any life-threatening toxicity will be reported immediately to the IRB and FDA. Given the lability of the antigen in the cold (whether free or cell-bound), immunoreactivity and soluble tumor antigen will be assayed using the anti-idiotype as the antigen-mimic The anti-idiotypic antibodies are rat IgG1 MoAb purified by acid elution from protein G affinity columns.

They have remained stable despite acid treatment, buffer changes and freezing and thawing. Soluble antigens can interfere with tumor targeting. In vitro, patient serum did not inhibit binding of 8H9 to its anti-idiotype. Indirect immunofluorescence of a spectrum of cell lines showed persistence of antigen and antibody on the cell surface at 37° C. over days. In xenograft biodistribution studies, there was no evidence of antigen shedding that interferes with tumor imaging. Although interference of 8H9 biodistribution by soluble antigen is unlikely, we will document the absence by the ELISA inhibtion assay. HAMA response within the first two weeks after MoAb injection is rarely observed among our patient population, partly because of the intensity of the chemotherapy they received. However, some are expected to mount a HAMA response when they are imaged a second time. Clearly their HAMA will be monitored before and after injection in order to interpret the biodistribution results. Because of this sensitization, these patients may not be eligible for subsequent MoAb therapies (as stated in the consent form). However, we hypothesize that this HAMA response will help induce the idiotype network, which may have benefit on patient survival, analogous to our success with the murine 3F8-GD2 system we described in preliminary results and progress report.

Interpretations and implications The ability of 8H9 to detect a broad class of primary and metastatic solid tumors will be the first step in defining the clinical utility of MoAb 8H9 in vivo. Besides being a useful diagnostic tool, its therapeutic potential will need to be explored. Clearly the amount of antibody deposited in various organs need to be taken into account if these antibodies are used to deliver radioisotopes, enzymes or drugs. Chimeric antibodies with improved Fc effector functions and reduced immunogenicity will also be explored Immunocytokines and T-bodies are also potential steps in future development of these agents.

2: To Estimate the radiation dose per mCi of $^{131}$I-8H9 delivered to tumors and to normal organs in patients.

To obtain data necessary for patient dosimetry, patients will be injected, intravenously, with $^{131}$I-8H9 according to their surface area, i.e. 10 mCi/1.73 m2. A total of three or four gamma camera images will be obtained within a 1 to 2 week period following injection. The following schedule is recommended but may be altered, if necessary: 1-4 h after injection (day 0) and then again on days 2, day 3, and day 6 or 7. If warranted, due to slow clearance kinetics, imaging on days 9, 10 or 11 may also be performed. Using this schedule weekend imaging may be avoided regardless of the weekday injected. Scan types and imaging parameters are listed below:

2.1 Data Collection:
  SPOT and SPECT images will be collected over pre-selected "index" tumor lesions, as identified from previously obtained CT or MR images.

2.1.1 Blood collection Blood samples will be collected as follows: prior to injection, and at 0, 15, 30 min, then 1 h, 2 h, 4 h, 8 h, 18 h or 30 h, 42 h, 66 h, day 6 or 7 following the injection. Plasma or serum will be collected and counted from each sample and the results will be expressed as per cent of the injected radioactivity per L serum or blood volume.

static spot view (SPOT)

HEHR collimation
10 to 20 min acquisition time
dual-window acquisition for scatter correction
128 × 128 × 16 matrix size

SPECT

HEHR collimation
6 degrees or 64 views in stop and shoot, elliptical orbit mode
1 to 4 min/view (0.5 to 2 h acquisition time on a dual-headed camera)
dual-window acquisition for scatter correction
64 × 64 × 16 matrix size whole-body sweep (SWEEP)

high-energy, high-resolution (HEHR) collimation,
8 to 12 cm/min sweep speed (20 to 25 min acquisition time)
dual-window acquisition for scatter correction
256 × 1024 × 16 matrix size Imaging schedule:

| Imaging day | SWEEP | SPOT | SPECT |
|---|---|---|---|
| 0 | X | X | |
| 1, 2 | X | X | X |
| 5, 6 or 7 | X | X | |
| 9, 10, or 11 | X | X | |

2.1.2 Pharmacokinetics Modeling Blood time-activity curves from serial blood samples and from ROI's around sequential SPECT images of the heart (when available). This data will be fitted, together with the whole-body clearance kinetics, to a pharmacokinetic model of antibody distribution. Previously developed models have been used for this type of analysis, further details regarding the approach have been published.[106]

2.1.3 Patient-specific dosimetry (3D-ID) The pharmacokinetic data obtained from SPECT and planar imaging and blood sampling will be combined with anatomical imaging information (MR or CT) to estimate the absorbed dose to tumor and selected normal organs that would be expected from a therapeutic injection of $^{131}$I-8H9. The methodology for this has been previously described.[107-115]

2.2 Tumor volume determinations Tumor volumes will be determined from CT or
  MRI when available. Patients with known disease at other sites are imaged in additional areas. All CT images will be transferred for display in 3D-ID; images collected at MSKCC will be transferred digitally, film from other institutions will be scanned using a Lumisys digital film scanner. Using 3D-ID, the consulting radiologist will review the images with the research technician. The research technician will then draw contours around the tumor regions; the contours will be reviewed by the consulting radiologist and adjusted, as needed. In some cases, disease may be represented by a collection of very small positive nodes; in those cases a contour around the group will be drawn and used in the volume assessment. Volume determination using 3D-ID is performed by summing the areas of regions that have been defined by the user on all slices making up the tumor. This general approach has been previously validated for CT. Although potentially labor-intensive, such a tumor outline-specific method is significantly more accurate than techniques based upon greater and minor diameters (i.e., ellipsoidal models)). The errors associated with CT-based volume estimation and the factors influencing these errors have been examined and will be considered in the volume determinations described above. A reliable total-body tumor burden will not be achievable for all patients, either because of the small volume of disease, or for cases in which lesions detected by SPECT are not visible by CT.

2.3 Red marrow dosimetry Bone marrow dosimetry will be performed according to the recommended guidelines, described in the AAPM recommendations,[116] i.e. blood time-activity curves will be multiplied by the appropriate factor (0.2-0.4) to derive marrow time-activity curves and absorbed dose to red marrow. S-Factors provided in MIRDOSE 3 will be used for the calculations. This data will be compared with direct measurement of the marrow activity from ROI's drawn over marrow cavities on SPECT images. The quantitative capability of SPECT will allow us to verify the accuracy of bone marrow dosimetry determined from activity levels, and the rate of antibody clearance from marrow, from the standard analysis of serial blood samples.

2.4 Three-dimensional dosimetry To perform 3D dosimetry, it is first necessary to register a set of nuclear medicine images (SPECT), depicting the radiolabeled antibody distribution to an anatomical imaging modality (CT or MRI). We have extensive experience with the clinical implementation of the Pelizzari and Chen method.[117] This technique requires that the user delineate the same surface on both sets of imaging modalities. When necessary, a SPECT transmission study is performed to obtain the appropriate surface. The program attempts to maximize the correlation of a set of several hundred points on the surface as identified on one scan (the "hat"), with a solid model of the same surface derived from the other scan (the "head"). A non-linear least-squares search is used to minimize the sum of the squares of distances from each "hat" point to the nearest point on the "head" surface. The coordinates of the "hat" are translated, rotated and scaled to provide the best fit. Users may control which parameters are varied during the search. The final set of transformations are then used to convert the coordinates of one image into those of the other. Phantom studies indicate that the Pelizzari and Chen technique for registration of SPECT to CT is accurate to within 3 mm The Nuclear Medicine Service at MSKCC has performed such registration for over 100 patient studies. The Pellizari and Chen package has also been used for thoracic and abdominal study registration by Chen and his collaborators at the University of Chicago (personal communication). Both the Chicago group and us have also included contours for liver and/or spleen along with the body contours. This further improves registration by providing more contours for the minimization algorithm. In some cases, a radioactive band has also been used as an aid to registration.[117] We are currently comparing this method with alternative algorithms for image registration for the whole images.[117-120]

Correlated serial SPECT images can be used to determine cumulative activity distributions by fitting and integrating an exponential uptake and/or clearance to the specific activity within an ROI over the tumor or organ. The variation in activity within individual voxels can be taken into account, through a weighted sum of the counts/activity within the corresponding voxel over time. Given such a distribution of the cumulated activity, a software package, 3D-ID, has been developed, to calculate the dose distribution. Target contours are drawn on side-by-side enlarged SPECT and CT/MR image slices that are selected from a scrollable image display. Contours drawn in one modality simultaneously appear in the other. The user may switch between modalities by positioning the cursor in the appropriate window. This provides for the simultaneous use of both imaging modalities to define tumor (e.g. using SPECT) and normal organ (using CT/MR) contours. The dose to all voxels within the target volume is obtained by convolving the activity distribution with a point kernel table of absorbed dose versus distance. Patient-specific S-factors may be calculated by defining source organ contours and assigning unit activity to all voxels within each source. The "dose" to a given target is thus the patient-specific S-factor. Dose histograms and patient-specific organ and tumor S-factors generated using 3D-ID in combination with SPECT will provide important information in understanding tumor response and organ toxicity in radioimmunotherapy.

Photon dose kernels for 14 radionuclides of interest in internal emitter therapy have been recently published.[112] Explicit expressions of radionuclide photon dose kernels, necessary for three-dimensional dosimetry, were not previously available. We recently described the overall structure and methodologies of a software package for three-dimensional internal dosimetry (3D-ID) calculations.[107,113] A series of software modules that address the logistical issues of performing patient-specific three-dimensional dosimetry were detailed. Software tools have been developed to combine images from different modalities, define regions-of-interest using available multi-modality data and identify source and target volumes for dosimetry. A point-kernel based dosimetry calculation has been implemented and several different approaches for displaying the spatial distribution of absorbed dose in a biologically pertinent manner were also described. The dose calculation, itself, was carried out in a separate module, so that different calculation schemes including Monte Carlo, may be used with 3D-ID.

2.5 Anticipated Results

The major sources of error in carrying out absorbed dose calculations are: 1. Inaccuracies in imaging-derived activity concentration estimates. 2. Mismatch between standard anatomy (used for dosimetry calculations) and individual patient anatomy. 3. Assumption of uniformity in the spatial distribution of radioactivity on both a micro (mm to mm) and macro (cm) scale. When applying conventional (MIRD Committee) approaches to estimating absorbed dose it is understood that the estimate is derived from a model which includes a certain number of assumptions. This approach has been sufficient in estimating doses for diagnostic applications wherein typical doses are already far below toxicity. An objective of radioimmunotherapy, however, is to treat to normal organ tolerance. In such a scenario, accurate, patient-specific dosimetry is critical. The dosimetry methodologies that will be used in this proposal address point 2 and a portion of point 3; dose calculations are performed for individual patient geometries and the spatial distribution of radioactivity in tumor or normal organs is accounted for on a macroscopic (cm) scale. In the past using planar imaging kinetics to project the kinetics of the spatial distribution had additional pitfalls. Although SPECT-based activity determinations are a step forward, we expect these inaccuracies in imaging derived activity to be further reduced when I-124-8H9 Postron emission tomography is used. This is an area of active development at Memorial Sloan Kettering in the last decade.[121]

Conventional dosimetry yields estimates of the absorbed dose, averaged over a normal organ or tumor volume. The methodology implemented in this proposal will yield the spatial distribution of absorbed dose as isodose contours, overlayed upon a 3-D CT image set. This makes it possible to evaluate the anatomical distribution of absorbed dose to tissues and from this, assess the potential impact in terms of toxicity. For example, the dose to surrounding tissue from activity that has concentrated in a tumor contained within a normal organ can be obtained by this means.

2.6 Interpretations and Implications

The average absorbed dose to a tumor may not reflect potential therapeutic efficacy and tumor shrinkage. That portion of a tumor volume receiving the lowest absorbed dose will lead to treatment failure regardless of the dose delivered to other regions of the tumor volume. The 3D-ID software package provides detailed information regarding the spatial distribution of absorbed dose within a target volume. This information is depicted as dose-volume histograms, wherein the fraction of tumor volume receiving a particular absorbed dose is plotted against absorbed dose. Using such information it will be possible to better assess the likelihood of tumor control. For example, if the average dose over a tumor volume is 2 to 3 Gy and a small region within this volume receives only 0.1 Gy, then treatment will be unsuccessful.

References

1. DiMaggio J J, Scheinberg D A, Houghton A N: Monoclonal antibody therapy of cancer. In: Pinedo H M, Chabner B A, Longo D L, (eds.): Cancer Chemotherapy and Biological Response Modifiers, Annual 11, Elsevier Science Publishers B. V., (Biomedical Division), 1990, pp 177-203
2. Schlom J: Monoclonal Antibodies in cancer therapy: Basic principles. In: DeVita V T, Hellman S, Rosenberg S A, (eds.): Biologic therapy of cancer, 2nd ed. Philadelphia, J. B. Lippincott Co, 1995, pp 507-520
3. Koehler G, Milstein C: Continuous culture of fused cells secreting antibody of pre-defined specificity. Nature 256: 495-496, 1975
4. Moffat R, Pinsky C M, Hammershaimb L, et al: Clinical utility of external immunoscintigraphy with the IMMU-4 technetium-99m Fab' antibody fragment in patients undergoing surgery for carcinoma of the colon and rectum:results of a pivotal, phase III trial. The Immunomedics Study Group. J Clin Oncol 14(8):2295-2305, 1996
5. Maloney D G, Grillo-Lopez A J, Bodkin D J, et al: IDEC-C2B8: Results of a phase I multiple-dose trial in patients with relapsed non-hodgkin's lymphoma. J Clin Oncol 15:3266-3274, 1997
6. Cobleigh M A, Vogel C L, Tripathy D, et al: Multinational study of the efficacy and safety of humanized anti-HER2 monoclonal antibody in women who have HER2-overexpressing metastatic breast cancer that has progressed after chemotherapy for metastatic disease. J Clin Oncol 17:2639-2648, 1999
7. Bigner D D, Brown M T, Friedman A H: Iodine-131-labeled antitenascin monoclonal antibody 81C6 treatment of patients with recurrent malignant gliomas:phase I trial results. Journal Clincal Oncology 16:2202-2212, 1998
8. Jurcic J G, Caron P C, Miller W H: Sequential targeted therapy for acute promyelocytic leukemia with all-trans retinoic acid and anti-CD33 monoclonal antibody M195. Leuk 9:244-248, 1995
9. Meredith R F, Khazaeli M B, Plott W E: Phase II study of dual 131I-labeled monoclonal antibody therapy with interferon in patients with metastatic colorectal cancer. Clin Can Res 2:1811-1818, 1996
10. Yeh S D, Larson S M, Burch L, et al: Radioimmunodetection of neuroblastoma with iodine-131-3F8: Correlation with biopsy, iodine-131-Metaiodobenzylguanidine (MIBG) and standard diagnostic modalities. J Nucl Med 32:769-776, 1991
11. Cheung N K V, Kushner B H, Cheung I Y, et al: Anti-GD2 antibody treatment of minimal residual stage 4 neuroblastoma diagnosed at more than 1 year of age. J Clin Oncol 16:3053-3060, 1998
12. Wheldon T E, O'Donoghue J A, Barrett A, Michalowski A S: The curability of tumors of differing size by targeted radiotherapy using 131-I or 90-Y. Radiother Oncol 21:91-99, 1991
13. Wilder R B, DeNardo G L, DeNardo S J: Radioimmunotherapy: recent results and future directions. J Clin Oncol 14:1383-1400, 1996
14. Zalutsky M R, McLendon R E, Garg P K, et al: Radioimmunotherapy of neoplastic meningitis in rats using an alpha-particle-emitting immunoconjugate. Cancer Res 54:4719-4725, 1994
15. McDevitt M R, Sgouros G, Finn R D, et al: Radioimmunotherapy with alpha-emitting nuclides. Eur J Nucl Med 25:1341-1351, 1998
16. Lode H N, Xiang R, Becker J C, et al: Immunocytokines: A promising approach to cancer immunotherapy. Pharmacology Therapeutics 80:277-292, 1998
17. DeNardo S J, DeNardo G L, DeNardo D G, et al: Antibody phage libraries for the next generation of tumor targeting radioimmunotherapeutics. Clin Can Res 5:3213s-3218s, 1999
18. DeNardo S J, DeNardo G L, Brush J, Carter P: Phage Library-derived human anti-TETA anti anti-DOTA ScFv for pretargeting RIT. Hybridoma 18:13-21, 1999
19. Eshhar Z, Waks T, Gross G, Schindler D G: Specific activation and targeting of cytotoxic lymphocytes through chimeric single chains consisting of antibody-binding domains and the or zeta subunits of the immunoglobulin and T-cell receptors. Proc Natl Acad Sci USA 90:720-24, 1993
20. Altenschmidt U, Kahl R, Moritz D, et al: Cytolysis of tumor cells expressing the Neu/erbB-2, erbB-3, and erbB-4 receptors by genetically targeted naive T lymphocytes. Clin Can Res 2:1001-1008, 1996
21. Krause A, Guo H F, Tan C, et al: Antigen-dependent CD-28 signaling enhances survival and proliferation in genetically modified activated human primary T lymphocytes. J Exp Med 188:619-626, 1998
22. Garin-Chesa P, Fellinger E J, Huvos A G: Immunohistochemical analysis of neural cell adhesion molecules. Am J Pathol 139:275-286, 1991
23. Ritter G, Livingston P O: Ganglioside antigens expressed by human cancer cells. Semin Cancer Biol 2:401-409, 1991
24. Wikstrand C J, Longee D C, McLendon R E, et al: Lactotetraose series ganglioside 3',6'-isoLD1 in tumors of central nervous and other systems in vitro and in vivo. Cancer Res 53:120-126, 1993
25. Seeger R C, Danon Y L, Rayner S A, Hoover F: Definition of a Thy-1 determinant on human neuroblastoma, glioma, sarcoma, and teratoma cells with a monoclonal antibody. J Immunol 128:983-989, 1982
26. Ylagan, Quinn L R: B: CD44 expression in astrocytic tumors. Modem Pathology 10:1239-1246, 1997

27. Kaaijp P, Troost D, Morsink F, et al: Expression of CD44 splice variants in human primary brain tumors. Journal of Neuro-Oncology 26:185-190, 1995
28. Richardson R B, Davies A G, Bourne S P, et al: Radioimmunolocalization of human brain tumors. Biodistribution of radiolabelled monoclonal antibody UJ13A. Eur J Nucl Med 12:313-320, 1986
29. Papanastassiou V, Pizer B L, Coakham H B, et al: Treatment of recurrent and cystic malignant gliomas by a single intracavitary injection of 131I-monoclonal antiobdy: Feasibility, pharmacokinetics and dosimetry. Br J Cancer 67:144-151, 1993
30. Kishima H, Shimizu K, Tamura K, et al: Monoclonal antibody ONS-21 recognizes integrin a3 in gliomas and gliomas and medulloblastomas. Br J Cancer 79:333-339, 1998
31. Moriuchi S, Shimuzu K, Miyao Y, Hayakawa T: Characterization of a new mouse monoclonal antibody (ONS-M21) reactive with both medulloblastomas and gliomas. Br J Cancer 68:831-837, 1993
32. Erikson H P, Lighter V A: Hexabrachion protein (tenascin, cytotactin, brachionectin) in connective tissues, embryonic tissues and tumors. Adv Cell Biol 2:55-90, 1988
33. Riva P, Frnceschi G, Frattarelli M, et al: 131I radioconjugated antibodies for the locoregional radioimmunotherapy of high-grade malignant glioma- phase I and II study. Acta Oncol 38:351-359, 1999
34. Kuan C T, Reist C J, Foulon C F, et al: 125I-labeled anti-epidermal growth factor receptor vIII single-chain Fv exhibits specific and high-level targeting of glioma xenografts. Clin Can Res 5:1539-1549, 1999
35. Wikstrand C J, Hale L P, Batra S K, et al: Monoclonal Antibodies against EGFRvIII are Tumor Specific and React with Breast and Lung Carcinomas and Malignant Gliomas. Cancer Res 55:3140-48, 1995
36. Kondo S, Miyatake S, Iwasaki K, et al: Human glioma-specific antigens detected by monoclonal antibodies. Neurosurgery 30:506-511, 1992
37. Dastidar S G, Sharma S K: Monoclonal antibody against human glioblastoma multiforme (U-87Mg) immunoprecipitates a protein of monoclonal mass 38 KDa and inhibits tumor growth in nude mice. J Neuroimmuno 56:91-98, 1995
38. Mihara Y, Matsukado Y, Goto S, et al: Monoclonal antibody against ependymoma-derived cell line. Journal of Neuro-Oncology 12:1-11, 1992
39. Wang N P, Marx J, McNutt M A: Expression of myogenic regulatory proteins(myogenin and MyoD1) in small blue round cell tumors of childhood. Am J Pathol 147:1799-1810, 1995
40. Weidner N, Tjoe J: Immunohistochemical profile of monoclonal antibody 013 that recognizes glycoprotein 930/32MIC2 and is useful in diagnosing ewing's sarcoma and peripheral neuroepithelioma. American Journal of Surgical Pathology 18:486494, 1994
41. Wedner N, Tjoe J: Immunohistochemical profile of monoclonal antibody 013 that recognizes glycoprotein 930/32MIC2 and is useful in diagnosing ewing's sarcoma and peripheral neuroepithelioma. Am J Pathol 18:486-494, 1994
42. Heiner J, Miraldi F D, Kallick S, et al: In vivo targeting of GD2 specific monoclonal antibody in human osteogenic sarcoma xenografts. Cancer Res 47:5377-5381, 1987
43. Price M R, Campbell D G, Robyn R A: Characteristics of the cell surface antigen p72, associated with a variety of human tumors and mitogen-stimulated T-lymnphoblasts. FEBS Letters 171:31-35, 1984
44. Spendlove I, James L L, Carmichael J, Durrant L G: Decay accelerating factor (CD55): a target for cancer vaccines? Cancer Res 59:2282-2286, 1999
45. Gorlick R, Huvos A G, Heller G, et al: Expression of HER2/erbB-2 correlates with survival in osteosarcoma. J Clin Oncol 17:2781-2788, 1999
46. Bruland O, Fodstad O, Funderud S, Pihl A: New monoclonal antibodies specific for human sarcomas. Int J Cancer 15:27-31, 1986
47. Cheung N K, Saarinen U M, Neely J E, et al: Monoclonal antibodies to a glycolipid antigen on human neuroblastoma cells. Cancer Res 45:2642-2649, 1985
48. Modak S, Gultekin S H, Kramer K, et al: Novel tumor-associated surface antigen: broad distribution among neuroectodermal, mesenchymal and epithelial tumors, with restricted distribution in normal tissues. Proceedings of ASCO 17:449a, 1998
49. Cheung N K, Heller G, Kushner B H, et al: Detection of metastatic neuroblastoma in bone marrow: when is routine marrow histology insensitive? J Clin Oncol 15:2807-2817, 1997
50. Ghossein R A, Osman I, Bhattacharya S, et al: Detection of circulating prostatic tumor cells using immunobead reverse transcriptase polymerase chain reaction for prostatic specific membrane antigen mRNA. Diag Mol Path 8:59-65, 1999
51. Leung W, Chen A R, Klann R C, et al: Frequent detection of tumor cells in hematopoietic grafts in neuroblastoma and ewing's sarcoma. Bone Marrow Transpl 22:971-979, 1998
52. Mueller B M, Romerdahl C A, Gillies S D, Reisfeld R A: Enhancement of antibody-dependent cytotoxicity with a chimeric anti-GD2 antibody. J Immunol 144:1382-1386, 1990
53. Santos A D, Kashmiri V S, Horan P H, et al: Generation and characterization of a single gene-encoded single-chain-tetravalent antitumor antibody. Clin Can Res 5:3118s-3123s, 1999
54. Guo H F, Rivlin K, Dubel S, Cheung N K V: Recombinant anti-ganglioside GD2 scFv-streptavidin fusion protein for tumor pretargeting. Proc Am Assoc Cancer Res 37:469, 1996 (abstract)
55. Fagnou C, Michon J, Peter M, et al: Presence of tumor cells in bone marrow but not in blood is associated with adverse prognosis in patients with ewing's tumor. J Clin Oncol 16:1707-1711, 1998
56. Cheung N K, Kushner B H, LaQuaglia M, Lindsley K: Treatment of advanced stage neuroblastoma. In: Reghavan D, Scher H I, Leibel S A, Lange P, (eds.): Principles and Practice of Genitourinary Oncology. Philadelphia, J.B. Lippincott Company, 1997, pp 1101-1111
57. Brodeur G M, Castleberry R P: Neuroblastoma. In: Pizzo P A, Poplack D G, (eds.): Principles and Practice of Pediatric Oncology, 3rd ed. Philadelphia, J. B. Lippincott Company, 1997, pp 761-797 chapter 29
58. Cheung N K V: Biological and molecular approaches to diagnosis and treatment. section I. Principles of Immunotherapy. In: Pizzo P A, Poplack D G, (eds.): Principles and Practice of Pediatric Oncology, 3rd ed. ed. Philadelphia, J. B. Lippincott Company, 1997, pp 323-342
59. Larson S M, Sgouros G, Cheung N K: Antibodies in cancer therapy: Radioisotope conjugates. In: DeVita V T, Hellman S, Rosenberg S A, (eds.): Biologic Therapy of Cancer, 2nd ed. Philadelphia, J. B. Lippincott Co., 1995, pp 534-552
60. Levy R, Miller R A: Antibodies in cancer therapy: B-cell lymphomas. In: DeVita V T, Hellman S, Rosenberg S A, (eds.): Biologic therapy of cancer, 1st ed. Philadelphia, J. B. Lippincott Co, 1991, pp 512-522
61. Reisfeld R A, Mueller B M, Handgretinger R: Potential of genetically engineered anti-ganglioside GD2 antibodies for cancer immunotherapy. In: Progress in Brain Search (Svennerhol, L, Asbury, A K, Reisfeld, R A, Sandhoff, K, Suzuki, K, Tettamani, G, Toffano, G, vol. 101. Cambridge, UK, Elsevier Trends Journals, 1994, pp 201-212
62. Munn D H, Cheung N K: Interleukin-2 enhancement of monoclonal antibody-mediated cellular cytotoxicity (ADCC) against human melanoma. Cancer Res 47:6600-6605, 1987
63. Hank J A, Robinson R R, Surfus J, et al: Augmentation of antibody dependent cell mediated cytotoxicity following in vivo therapy with recombinant interleukin-2. Cancer Res 50:5234-5239, 1990
64. Kushner B H, Cheung N K: GM-CSF enhances 3F8 monoclonal antibody-dependent cellular cytotoxicity against human melanoma and neuroblastoma. Blood 73:1936-1941, 1989
65. Kushner B H, Cheung N K V: Absolute requirement of CD11/CD18 adhesion molecules, FcRII and phosphatidylinositol-linked FcRIII for monoclonal antibody-mediated neutrophil anti-human tumor cytotoxicity. Blood 79:1484-1490, 1992
66. Cheung N K V, Walter E I, Smith-Mensah W H, et al: Decay-accelerating factor protects human tumor cells from complement-mediated cytotoxicity in vitro. J Clin Invest 81:1122-1128, 1988
67. Saarinen U M, Coccia P F, Gerson S L, et al: Eradication of neuroblastoma cells in vitro by monoclonal antibody and human complement: method for purging autologous bone marrow. Cancer Res 45:5969-5975, 1985
68. Munn D H, Cheung N K: Antibody-dependent antitumor cytotoxicity by human monocytes cultured with recombinant macrophage colony-stimulating factor. Induction of efficient antibody-mediated antitumor cytotoxicity not detected by isotope release assays. J Exp Med 170:511-526, 1989
69. Munn D H, Cheung N K: Phagocytosis of tumor cells by human monocytes cultured in recombinant macrophage colony-stimulating factor. J Exp Med 172:231-237, 1990
70. Sabzevari H, Gillies S D, Mueller B M, et al: A recombinant antibody-interleukin 2 fusion protein suppresses growth of hepatic human neuroblastoma metastases in severe combined immunodeficiency mice. Proceeds of the National Academy of Science USA 91:9626-9630, 1994
71. Murray J L, Cunningham J E, Brewer H M, et al: Phase I trial of murine anti-ganglioside (GD2) monoclonal antibody (Mab) 14G2A in cancer patients. J Biol Resp Modif 1991 (Soc. Biol. Therapy Meeting Abstract 1991.)
72. Ugur O, Kostakoglu L, Hui E T, et al: Comparison of the targeting characteristics of various radioimmunoconjugates for radioimmunotherapy of neuroblastoma: Dosimetry calculations incorporating cross-organ beta doses. Nucl Med Biol 23:1-8, 1996
73. Mujoo K, Reisfeld R A, Cheung L, Rosenblum M G: A potent and specific immunotoxin for tumor cells expressing disialoganglioside GD2. Cancer Immunol Immunother 34:198-204, 1991
74. Gottstein C, Schon G, Tawadros S, et al: Antidisialoganglioside Ricin A-chain immunotoxins show potent antitumor effects in vitro and in a disseminated human neuroblastoma severe combined immunodeficiency mouse model. Cancer Res 54:6186-6193, 1994
75. Holzer U, Bethge W, Krull F, et al: Superantigen-staphylococcal-enterotoxin-A-dependent and antibody-targeted lysis of GD2-positive neruoblastoma cells. Cancer Immunol Immunother 41:129-136, 1995
76. Cheung N K, Lazarus H, Miraldi F D, et al: Ganglioside GD2 specific monoclonal antibody 3F8- a phase I study in patients with neuroblastoma and malignant melanoma. J Clin Oncol 5:1430-1440, 1987
77. Cheung N K, Lazarus H, Miraldi F D, et al: Reassessment of patient response to monoclonal antibody 3F8. J Clin Oncol 10:671-672, 1992
78. Murray J L, Cunningham J E, Brewer H, et al: Phase I trial of murine monoclonal antibody 14G2a administered by prolonged intravenous infusion in patients with neuroectodermal tumors. J Clin Oncol 12:184-193, 1994
79. Saleh M N, Khazaeli M B, Wheeler R H, et al: Phase I trial of the chimeric anti-GD2 monoclonal antibody ch 14.18 in patients with malignant melanoma. Human Antibodies Hybridomas 3:19-24, 1992
80. Handgretinger R, Anderson K, Lang P, et al: A phase I study of human/mouse chimeric antiganglioside GD2 antibody ch 14.18 in patients with neuroblastoma. Eur J Cancer 31:261-267, 1995
81. Uttenreuther-Fischer M M, Huang C-S, Reisfeld R A, Yu A L: Pharmacokinetics of anti-ganglioside GD2 mAb 14G2a in phase 1 trial in pediatric cancer patients. Cancer Immunol Immunother 41:29-36, 1995
82. Cheung N K V, Kushner B H, Yeh S J, Larson S M: 3F8 monoclonal antibody treatment of patients with stage IV neuroblastoma: a phase II study. In: Evans A E, Guillio J D, Biedler J L, et al, (eds.): Advances in Neuroblastoma Research, vol. 4. New York, Wiley Liss, 1994, pp 319-329
83. Yu A L, Gillies S D, Reisfeld R A: Phase I clinical trial of ch14.18 in patients with refractory neuroblastoma. Proc Am Soc Clin Oncol 10:318, 1991
84. Handgretinger R, Baader P, Dopfer R, et al: A phase I study of neuroblastoma with the anti-ganglioside GD2 antibody 14.G2a. Cancer Immunol Immunother 35:199-204, 1992
85. Cheung N K: Biological and Molecular Approaches to Treatment. Immunotherapy. In: Pizzo P A, Poplack D G, (eds.): Principles and Practice of Pediatric Oncology, 2nd ed. Philadelphia, J. B. Lippincott Company, 1992, pp 357-370
86. Miraldi F D, Nelson A D, Kraly C, et al: Diagnostic imaging of human neuroblastoma with radiolabeled antibody. Radiology 161:413-418, 1986
87. Arbit E, Yeh S J, Cheung N K, Larson S M: Quantitative Immunoimaging of gliomas in humans with anti-ganglioside monoclonal antibodies. J Neurosurg 76:399a, 1991
88. Daghighian F, Pentlow K S, Larson S M, et al: Development of a method to measure kinetics of radiolabeled monoclonal antibody in human tumors with applications to microdosimetry: Positron emission tomography studies of iodine-124 labeled 3F8 monoclonal antibody in glioma. Eur J Nucl Med 20:402-409, 1993
89. Grant S C, Kostacoglu L, Kris M G, et al: Radioimmunodetection of small-cell lung cancer using the anti-GD2 ganglioside monoclonal antibody 3F8: a pilot trial. Eur J Nucl Med 23:145-149, 1996
90. Cheung N K V, Kushner B H, Yeh S J, Larson S M: 3F8 monoclonal antibody treatment of patients with stage IV neuroblastoma: A phase II Study. Int J Oncol 12:1299-1306, 1998
91. Cheung N K, Yeh S D, Kushner B H, et al: Phase I study of radioimmunotherapy of neuroblastoma using iodine 131 labeled 3F8. In: Prog. Clin. Biol. Res: Advances in Neuroblastoma Research 4. New York, Wiley Liss, 1994, pp 329

92. Larson S M, Pentlow K S, Volkow N D, et al: PET scanning of iodine-124-3F8 as an approach to tumor dosimetry during treatment planning for radioimmunotherapy in a child with neuroblastoma. J Nucl Med 33:2020-2023, 1992
93. Pentlow K S, Graham M C, Lambrecht R M, et al: Quantitative imaging of 1-124 using positron emission tomography with applications to radioimmunodiagnosis and radioimmunotherapy. Medical Physics 18:357-366, 1991
94. Pentlow K S, Graham M C, Lambrecht R M: Quantitative imaging of iodine-124 with PET. J Nucl Med 37:1557-1562, 1996
95. Lewellen T K, Kohlmyer S G, Miyaoka R S, Kaplan M S: Investigation of the performance of the general electric advance positron emission tomograph in 3D mode. Transplantation Nuclear Science 1996
96. Kramer K, Cheung N K V, DiResta G, et al: Pharmacokinetics and acute toxicology of intraventricular I-monoclonal antibody targeting disialoganglioside in non-human primates. J Neuro Oncol 1996
97. Dropcho E J, Saleh M N, Grizzle W E, Oh S J: Peripheral neuropathy following treatment of melanoma with a murine anti-GD2 monoclonal antibody (MoAb). Neurology 1992 (abstract in press)
98. Saleh M N, Khazaeli M B, Wheeler R H, et al: A phase I trial of the murine monoclonal anti-GD2 antibody 14.G2a in metastatic melanoma. Cancer Res 52:4342-4347, 1992
99. Saleh M N, Wheeler R H, Khazaeli M B, et al: A phase I trial of chimeric anti-GD2 monoclonal antibody C14.18 in patients with metastatic melanoma. International Conference on Monoclonal Antibody Immunoconjugates for cancer 1991 (abstract)
100. Cheung N K, Cheung I Y, Canete A, et al: Antibody response to murine anti-GD2 monoclonal antibodies: Correlation with patient survival. Cancer Res 54:2228-2233, 1994
101. Drengler R L, Kuhn J G, Schaaf L J, et al: Phase I and pharmacokinetic trial of oral irinotecan administered daily for 5 days every 3 weeks in patients with solid tumors. J Clin Oncol 17:685-696, 1999
102. Cheung N K, Landmeier B, Neely J, et al: Complete tumor ablation with iodine 131-radiolabeled disialoganglioside GD2 specific monoclonal antibody against human neuroblastoma xenografted in nude mice. J Natl Cancer Inst 77:739-745, 1986
103. Cheung I Y, Cheung N K V, Kushner B H: Induction of Ab3' following anti-GD2 monoclonal antibody 3F8 therapy predicts survival among patients (pts) with advanced neuroblastoma. Proc Am Assoc Cancer Res 40:574, 1999
104. Chen S, Caragine T, Cheung N K, Tomlinson S: Surface antigen expression and complement susceptibility of differentiated neuroblastoma clones. Am J Pathol In press:, 1999
105. Cheung N K, Canete A, Cheung I Y, et al: Disialoganglioside GD2 anti-idiotypic monoclonal antibodies. Int J Cancer 54:499-505, 1993
106. Loh A, Sgouros G, O'Donoghue J A, et al: A pharmacokinetic model of 131I-G250 antibody in patients with renal cell carcinoma. J Nucl Med 3:484-489, 1998
107. Kolbert K S, Sgouros G, Scott A M, et al: Implementation and evaluation of patient-specific three dimensional internal dosimetry. J Nucl Med 38:301-308, 1997
108. Sgouros G, Jureidini I M, Scott A M, et al: Bone marrow dosimetry: Regional variability of marrow-localizing antibody. J Nucl Med 37:695-698, 1996
109. Sgouros G, Divgi C R, Scott A M, et al: Hematologic toxicity in radioimmunotherapy: An evaluation of different predictive measures. J Nucl Med 37:43P-44P, 1996
110. Sgouros G, Deland D, Loh A C, et al: Marrow and whole-body absorbed dose vs marrow toxicity following 131I-G250 antibody therapy in patients with renal-cell carcinoma. J Nucl Med 38:252P, 1997
111. Sgouros G: Treatment planning for internal emitter therapy: methods, applications and clinical implications. 1996
112. Furhang E E, Sgouros G, Chui C S: Radionuclide photon dose kernels for internal emitter dosimetry. Medical Physics 23:759-764, 1996
113. Furhang E E, Chui C S, Sgouros G: A monte carlo approach to patient-specific dosimetry. Medical Physics 23:1523-1529, 1996
114. Furhang E E, Chui C S, Kolbert K S, et al: Implementation of a monte carlo dosimetry method for patient-specific internal emitter therapy. Medical Physics 24:1163-1172, 1997
115. Sgouros G: Yttrium-90 biodisribution by yttrium-87 imaging: a feasibility analysis. Medical Physics 2000
116. Siegel J A, Wessels B W, Watson E E, et al: Bone marrow dosimetry and toxicity in radioimmunotheray. Antibody Immunoconjugates Radiopharmaceuticals 3:213-233, 1990
117. Scott A M, Macapinlac H, Zhang J, et al: Image registration of SPECT and CT images using an external fiduciary band and three-dimensional surface fitting in metastatic thyroid cancer. J Nucl Med 36:100-103, 1995
118. Woods R P, Mazziotta J C, Cherry S R: Quantification of brain function. Tracer kinetics and image analysis in brain PET. 1993 (ED. Uemura K, Elseiver Science Publishers)
119. Talairach J, Tournouz P: Co-planar stereotactic atlas of the human brain. Georg Thieme Verlag 1988
120. Meyer C R, Boes J L, Kim B, et al: Demonstration of accuracy and clinical versatility of mutual information for automatic multimodality image fusion using affine and thin-plate spline warped geometric deformations. Medical Image Analysis 1:195-206, 1997
121. Sgouros G, Chiu S, Pentlow K S, et al: Three-dimensional dosimetry for radioimmunotherapy treatment planning J Nucl Med 34:1595-1601, 1993

Third Series of Experiments

Immunomagnetic Purging of Ewing's Sarcoma from Blood: Quantitaion by Real-Time PCR Ewing's sarcoma is a childhood tumor characterized by a t(11,22) in most patients. Because survival remains suboptimal with standard therapy, many patients receive autologous stem cell transplant and trials investigating adoptive transfer of autologous T cells in the context of immune therapy are underway. However, approximately 50% of patients with advanced disease have PCR detectable disease in peripheral blood and/or bone marrow and administration of contaminated auologous cell preparations may contribute to disease relapse. To date, there is no reported method for purging contaminated hematopoietic cell populations of Ewing's Sarcoma. 8H9 is a mouse monoclonal IgG1 antibody previously reported to react with 21/21 Ewing's sarcoma/PNET tumors (Proc ASCO 17:44a, 1998). Peripheral blood T cell and B cell populations and CD34+ cells from bone marrow analyzed by flow cytometry for binding of 8H9 were negative. We sought to use magnetic bead immunoselection of 8H9 labeled cells to purge peripheral blood cell populations contaminated with Ewing's sarcoma. Using real-time quantitative nested PCR with Lightcycler, we monitored purging efficiency by evaluation of t(11,22) by RT-PCR. Contaminated specimens were labeled with 8H9 and incubated with rat anti-mouse IgGI magnetic beads. The sample was then run over a Miltenyi Variomax negative slection column. Recovery was approximately 70%. RNA was extracted from 10e7 cells from pre and post purge cell populations. Real-time quantitative PCR was performed with a level of sensitivity to one tumor cell in 10e5 normal cells. We demonstrated at least a two-log reduction of tumor in preparations contaminated at a ratio of 1:10 normal PBMC and 1:10e3 normal PBMC. Further studies evaluating efficacy in clinical samples are underway. These results demonstrate a potential new approach for purging contaminated patient samples to be used in the context of autologous bone marrow transplant and/or immunotherapy trials for Ewing's sarcoma.

Immunomagnetic Purging of Ewing's Sarcoma from Blood and Bone Marrow: Quantitation by Real-Time PCR The propensity for hematogenous spread of Ewing's sarcoma and the resulting contamination of autologous cell preparations complicates the use of cellular therapies in this disease. To date, there has been no reported method for purging marrow and other cellular products of Ewing's sarcoma. In this paper, we introduce monoclonal antibody 8H9, which showed binding by flow cytometry to 9/9 Ewing's sarcoma cell lines studied. Binding to lymphocytes and bone marrow progenitor cells was negative. In order to test whether 8H9 could be used for immunomagnetic based purging, normal PBMCs or bone marrow cells were artificially contaminated with varying amounts of Ewing's sarcoma. Quantitative PCR or t(11;22) was shown to accurately measure the level of contamination with a sensitivity of $1:10^6$. Samples were then purged using the Miltneyi Variomax negative selection system selecting for monoclonal antibody 8H9 bound cells. A 2 to 3-log reduction in tumor burden was consistently observed following immunomagnetic selection. In clinical non-mobilized apheresis studied, Ewing's contamination ranged between $1:10^5$-$1:10^6$. Therefore 8H9 based purging of clinical samples is predicted to result in a contamination level which is below the limit of detection by sensitive quantitative PCR. These results demonstrate a potential new approach for purging contaminated patient samples to be used in the context of autologous bone marrow transplant and/or immunotherapy trials for Ewing's sarcoma.

Current concepts hold that Ewing's sarcoma is a systemic disease from the time of onset as demonstrated by the observation that over 90% of patients with clinically localized disease will recur distantly if treated with local measures alone[Jaffe, 1976 #49]. Indeed, the generally accepted factor responsible for the recent improvement in survival observed in patients with clinically localized disease is control of hematogenously disseminated micrometastasis via neoadjuvant multi-agent chemotherapy[1]. Recently, the use of sensitive molecular monitoring to detect circulating Ewing's sarcoma cells has confirmed hematogenous dissemination in a substantial number of patients with Ewing's sarcoma. West et al[2] found a 25% incidence of translocation (11;22) positivity in the peripheral blood or bone marrow in patients with clinically localized disease, and higher rates have been observed in other series[3] and in patients with overt metastatic disease.[3, 4] Interestingly, in the reports by de Alava and Toretsky, evidence for positivity in peripheral blood persisted following initiation of chemotherapy suggesting that ongoing dissemination may occur intermittently throughout treatment protocols.

In an attempt to improve survival in high-risk patients with Ewing's sarcoma, several groups have studied the use of high dose chemotherapy followed by bone marrow or peripheral stem cell transplantation.[5-17]. Up to a 40% survival in poor risk patients has been reported after high dose therapy followed by autologous stem cells in contrast to historical survival rates of 0-20% with chemotherapy/radiation therapy alone[5, 6]. One factor complicating the use of autologous stem cell products in therapy of Ewing's sarcoma is the propensity for hematogenous dissemination with resultant contamination of stem cell products. In one report, despite CD34 based positive selection for progenitor cells, autologous peripheral blood progenitor preparations were shown to contain EWS/FLI1 translocation positive cells in 54% of samples evaluated[4]. While the true clinical impact of contaminating tumor cells in autologous products remains unclear, genetically marked tumor cells residing in autologous bone marrow have been shown to be present at disease relapse in patients with neuroblastoma and AML[18, 19]. Similar concern regarding the potential for autologous cell preparations to contribute to disease recurrence arise in the context of immune based therapy trials which are currently being undertaken and involve the transfer of autologous T cells harvested prior to the initiation of therapy[20].

To date there has been no method reported for purging autologous hematopoietic cells of Ewing's sarcoma. In this report, we introduce a monoclonal antibody based purging technique which allows us to reduce the tumor burden in contaminated bone marrow or peripheral blood specimens by two to three logs which is predicted to be below the limit of detection of PCR positivity in the vast majority of clinically contaminated specimens.

Materials and Methods

Monoclonal Antibody Production (Memorial Sloan-Kettering Cancer Center)

Cell Preparations

Peripheral Blood Mononuclear Cells: PBMCs used in tumor spiking experiments were obtained by ficoll-based density gradient separation of the fresh buffy coat fraction of normal healthy donor blood units obtained at the Department of Transfusion Medicine, Clinical Center, NCI according to approved protocols. For analysis of T cell reactivity to anti-CD3 monoclonal antibody following purging, PBMCs were T cell enriched using a negative selection column (R & D Biosystems, Minneapolis) which results in a purity of approximately 80%. Patient apheresis samples analyzed for contamination were obtained as part of NCI POB 97-0052 following informed consent. Leukapheresis procedures were done using the CS3000 Plus (Fenwal Division, Baxter, Deerfield, Ill.) which processed 5-15 liters of blood volume. Countercurrent centrifugal elutriation of the apheresis product was performed using a Beckman J-6M centrifuge equipped with a JE 5.0 rotor (Beckman Instruments, Palo Alto, Calif.) in HBSS without magnesium, calcium and phenol red (BioWhittaker, Walkersville, Md.) at a centrifuge speed of 3000 rpm (1725×g)[21]. Cell fractions (450-550 ml each) were collected at flow rates of 120, 140, and 190 ml/min during centrifugation and at 190 ml/min with the rotor off (RO). The first two fractions are typically enriched for lymphocytes while the last two fractions are enriched for monocytes. All fractions were cryopreserved in 10% DMSO (Cryoserv, Research Industries, Salt Lake City, Utah), RPMI with penicillin, streptomycin and L-glutamine and 25% fetal calf serum.

Progenitor Cells: CD34+ cells used for purging experiments were selected using the Miltenyi Variomax® direct isolation system (Miltenyi, Auburn, Calif.) from cryopreserved peripheral stem cells from a Ewing's sarcoma patient obtained for therapeutic use at Children's National Medical Center, Washington, D.C. according to approved protocols and following informed consent. Stem cells were used for research purposes after the patient's death. These cells were not positive by RT-PCR for Ewing's sarcoma and were therefore artificially contaminated for the purging experiments. Non-CD34 selected bone marrow used for purging experiments and enriched CD34+ populations used in the CFU assay were obtained from fresh human marrow harvested from normal volunteers according to approved protocols and following informed consent (Poietics Laboratories, Gaithersburg, Md.). The mononuclear fraction was obtained by ficoll-based density gradient separation, and subsequently enriched for CD 34+ cells by the Miltenyi Variomax® (Miltenyi, Auburn, Calif.) direct CD34 selection system.

Tumor Cell Lines: Ewing's sarcoma cell lines used for screening included TC71, 5838, RD-ES, CHP100, A4573 which have been previously reported[22] and JR and SB which are cell lines derived from patients treated at the National Cancer Institute which have also been previously reported[22]. LG was a cell line derived from a patient with isolated intrarenal recurrence of Ewing's sarcoma treated with resection at the University of Maryland.

Flow Cytometry Analysis

Flow cytometric analysis was performed using the Becton-Dickinson FacsCalibur machine. Briefly, fluorescence data were collected using a 3-decade log amplification on 10,000 viable gated cells as determined by forward and side light scatter intensity. Monoclonal antibodies used for immunofluorescence were: MoAb 8H9, murine IgG1 isotype, goat anti-mouse IgG1-FITC, CD3-PE (S4.1), CD34-PE (581) Caltag (Burlingame, Calif.), CD99-FITC (TU12) (Pharmingen, San Diego, Calif.). For immunofluorescence analysis, cells were incubated with antibody at a concentration of 1 ug/$10^6$ cells for 20 minutes at 4°, followed by washing with PBS with 0.2% human serum albumin and 0.1% Sodium Azide. For 8H9 and isotype staining, this was followed by incubation with goat anti-mouse FITC for 10 minutes at 4° C. followed by washing prior to analysis.

Immunomagnetic Purging

All cell products were spiked with tumor cells from the Ewing's sarcoma cell line TC71 at the levels of contamination indicated for individual experiments. For purging of CD34+ peripheral stem cells, a total of 10×$10^6$ were spiked. 1×$10^6$ cells were analyzed for pre-purged and post-purged PCR. For PBMC and non-CD34 selected bone marrow specimens, 30-80×$10^6$ cells were spiked with TC71 with 10×$10^6$ cells analyzed for pre-purged and post-purged PCR. For purging, cells were incubated at 4° C. with monoclonal antibody 8H9 at a concentration of 1 ug/$10^6$ total cells for 20 minutes and washed with buffer (PBS, 0.5% BSA, 2mM EDTA). Cells were then incubated with rat anti-mouse IgG1 magnetic beads (Miltneyi, Auburn, Calif.) at a ratio of 1:1 for 20 minutes at 4° C. Purging was accomplished using the Miltenyi Variomax® system wherein the sample is run over the Miltenyi (Auburn, Calif.) AS depletion column with a flower resistor of 24G. Cells from the depleted fraction were then washed with 3 cc buffer. The positively selected fractions of cells was removed by releasing the column from the magnet and washing with 3 cc buffer, and analyzed by PCR where indicated. In cases where clonogenicity of the positive fraction was evaluated, the positive fraction was pelleted and resuspended in RPMI with 10% FCS, L-glutamine (4 uM), penicillin (100 u/ml), and streptomycin (100 ug/ml), and placed in an incubator at 37° C. with 5% $CO_2$ for 5 days.

Conventional PCR

For analysis of contamination of patient apheresis fractions, RNA was extracted from 20-50×$10^6$ cells using TRIzol Reagent (Life Technologies, Rockville, Md.) or guanidinium isothiocynate/CsCl method[23]. After cDNA was generated from 250 ng RNA using a random hexamer, PCR was performed with Perkin Elmer GeneAmp PCR system 2400 using ESPB1 and ESBP2 primers and the following conditions: 40 cycles 95° C. 30 s, 60° C. 30 s, 72° C. 30 s followed by 72° C. for 7 minutes. To assess the integrity and quantity RNA, a PCR reaction with GAPDH primers was performed for each patient sample. 10 ul of each PCR product were run on 1.3% TBE agarose gel and transferred to a nylon membrane. A [$^{32}$P]γ-ATP 20-mer oligonucleatide probe was generated using T4 polynucleotide kinase. The membrane was hybridized using ExpressHyb Hybridization Solution (Clontech, Palo Alto, Calif.) according to the manufacturer's instructions. The membrane was then exposed to Kodak Xomat film (Kodak, Rochester, N.Y.) for 24-144 hours.

Real-Time Quantitative PCR

Real-time quantitative PCR was performed using the Lightcycler® Instrument (Roche Molecular Biochemicals, Indianapolis, Ind.). RNA was extracted from 10×$10^6$ cells from all samples except for the CD34+ population in which 1×$10^6$ cells were used. The Trizol® phenol/chloroform extraction or RNA-easy columns (Qiagen, Valencia, Calif.) were used. The $1^{st}$ Strand Synthesis kit (Roche, Indianapolis, Ind.) was used to generate cDNA from 1 ug of RNA from each sample. PCR was then run on 5 ul of cDNA on the Lightcycler® instrument with primers ESBP1 and ESBP2 for 40 cycles. In cases where nested PCR was performed, an initial 20 cycles of PCR were carried out with the primer pair ESBPI-ESBP2 followed by 40 additional cycles using 2 ul of the product of the first reaction using the primer pair EWS 696- Fl1 1041 By conventional PCR, primer pair ESBP1-ESBP2, and EWS 696-FLI 1041 generate fragments of 310 bp and 205 bp respectively. Both sets of primers are outside the breakpoint of the EWS/FLI 1 translocation. In the initial evaluation of the quantitative PCR, both nested and non-nested Lightcycler® PCR products were confirmed by size using 1% TAE agarose gel with ethidium bromide (data not shown). Hybridization probes spanning the EWS/FLI 1 breakpoint were used to detect target template in the Lightcyler reaction. To provide a positive control and to quantitate total amplified RNA, G6PD was amplified from 5 ul of cDNA and analyzed using sequence specific hybridization probes G6PDHP1 and G6PDHP2. On all hybridization probes, the 5' probe (HP1) was labeled at the 3'end with Fluorescein, the 3' probe (HP2) was labeled at the 5' end with Lightcycler Red 640 and phosphorylated at the 3' end. Cycle crossing number was ascertained at the point in which all samples had entered the log linear phase. Cycle crossing number was used to determine log cell concentration according to a standard curve. The standard curve was generated by amplifying 5 ul of cDNA derived from lug of RNA from 10×$10^6$ normal PBMCs spiked with TC71 tumor cells at decreasing concentrations from 1:10 to 1:$10^7$.

```
Sequences
[32P]γ Probe   5'TACTCTCAGCAGAACACCTATG
ESBP1          5' CGA CTA GTT ATG ATC AGA GCA 3'

ESBP2          5' CCG TTG CTC TGT ATT CTT ACT GA 3'
```

```
EWS 696           5' AGC AGC TAT GGA CAG CAG 3'

FLI 1 1041        5' TTG AGG CCA GAA TTC ATG TT 3'

G6PD1             5' CCG GAT CGA CCA CTA CCT GGG CAA G 3'

G6PD 2            5' GTT CCC CAC GTA CTG GCC CAG GAC CA 3'

Lightcycler Hybridization Probes
EWSHP1            5' TAT AGC CAA CAG AGC AGC AGC TAC - F 3'

EWSHP2            5' LC RED 640 - GGC AGC AGA ACC CTT CTT - P 3'

G6PDHP1           5' GTT CCA GAT GGG GCC GAA GAT CCT GTT G - F 3'

G6PDHP2           5' LC RED 640 - CAA ATC TCA GCA CCA TGA GGT TCT GCA C - P 3'
```

Primers
OKT3 Mediated Proliferation of Purged T Cell Specimens $1 \times 10^8$ CD3 enriched cells were contaminated with Ewing's sarcoma at a level of $1:10^3$. Cells from pre-purged and post-purged samples were added in triplicate to a 96 well plate at a concentration of $2 \times 10^5$ cells/well containing decreasing concentrations of plate bound anti-CD3 antibody OKT3 (Ortho Biotech Inc., Raritan, N.J.) from 100 ug/ml to 3 ug/ml. Cells were incubated with 200 ul of RPMI with 10% FCS, L-glutamine, penicillin, and streptomycin for a 48 hours and then pulsed with 1 uCi of [$^3$H] thymidine per well. Cells were harvested after 18 hours of pulsing and $^3$H incorporation was enumerated using the TopCount NXT (Packard, Meriden Conn.). Subtracting background activity with media alone generated net counts.

CFU Assay

CD34+ cells were enriched from pre- and post-purged samples from fresh human bone marrow using the Miltenyi® direct CD34+ progenitor isolation kit. $35 \times 10^6$ bone marrow mononuclear cells from each sample were run over a positive selection (MS) column yielding a CD34+ enriched population with estimated purities of >70% [24]. 1000 cells were plated in triplicate in methylcellulose media supplemented with recombinant cytokines (MethoCultGF+H4435, Stem cell Technologies, Vancouver, BC). CFUs were counted after 14 days of culture.

Results

Monoclonal Antibody 8119 Binds all Ewing's Sarcoma Cell Lines Tested but not Normal Lymphocytes or Hematopoietic Progenitors.

In order to identify a potential reagent that could be used to target contaminating Ewing's sarcoma cells, monoclonal antibodies induced via immunization with neuroblastoma were screened for cross reactivity with Ewing's sarcoma. Monoclonal antibody 8H9 was observed to bind to 9/9 Ewing's sarcoma cell lines evaluated (FIG. 9). The level of reactivity was variable with some lines showing diminished levels of reactivity compared to CD99 whereas two lines (SB and RD-ES), showed increased reactivity compared to CD99 Importantly, lymphoid and hematopoietic populations showed no reactivity with 8H9 as shown in FIG. 10a (CD3 gated PBMC), and FIG. 10b (CD34 gated bone marrow cells), whereas CD99 showed significant binding to T cell populations.

Quantification of Ewing's Sarcoma Contamination using real-time PCR of artificially contaminated specimens accurately quantitates tumor contamination with sensitivity to $1:10^6$.

Figure 11C:
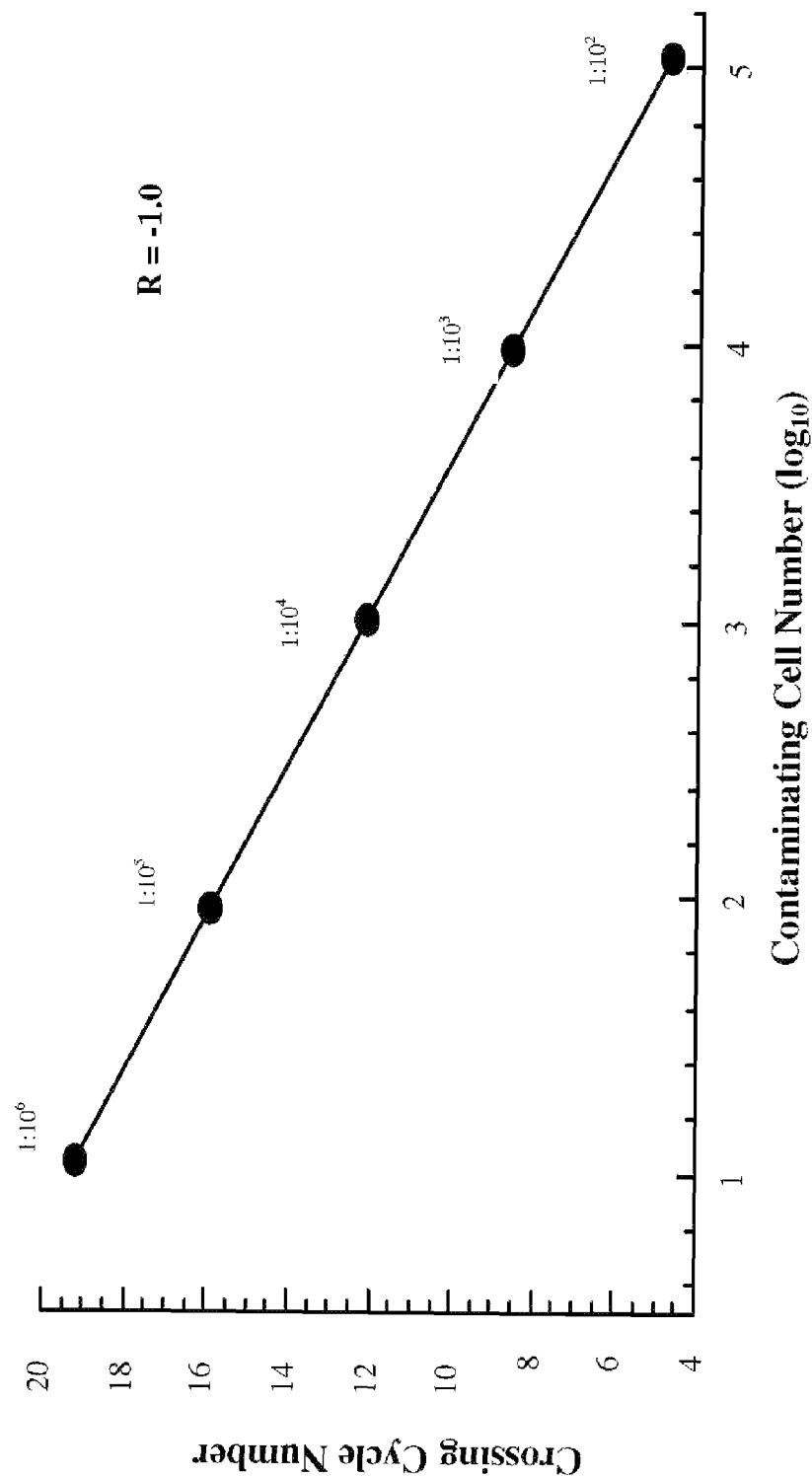

To study whether immunomagnetic purging of marrow and peripheral blood populations contaminated with Ewing's sarcoma could be quantitatively monitored, we sought to devise an approach wherein variable levels of contamination could be quantified using RT-PCR. We began by artificially contaminating PBMC populations with a log based titration of Ewing's contamination (e.g. $1:10$-$1:10^7$). The degree of contamination was evaluated using real-time PCR. Using a non-nested PCR, we observed linear relationships across four log levels of contamination, (FIG. 11a). However, the limit of detection for a non-nested PCR was 1 tumor cell in $10^4$ background cells. In an effort to increase the sensitivity, we also evaluated nested PCR, using an initial 20 cycles of amplification followed by 40 cycles amplification with internal primers. With this approach, quantitative accuracy was lost for only the highest level of contamination, which likely began to plateau with the initial 20 cycles (11b). However, quantitative accuracy was observed for levels of contamination between $1:100$ to $1:10^6$ was observed (FIG. 11c). Because $10 \times 10^6$ starting cells were used in these experiments, we can estimate that using the nested approach, amplification was accomplished from 10 contaminating cells. This confirmed the utility of quantitative PCR to provide an accurate quantitative assessment of tumor contamination with a level of sensitivity of one tumor in $10^6$ background cells, thus allowing measurements of the efficacy of 8H9 based approaches for purging of Ewing's sarcoma cells.

MoAb 8H9 Based Immunomagnetic Purging Yields a 2 to 3-Log Reduction in Artificially Contaminated Peripheral Blood and Bone Marrow Populations.

Figure 12A:
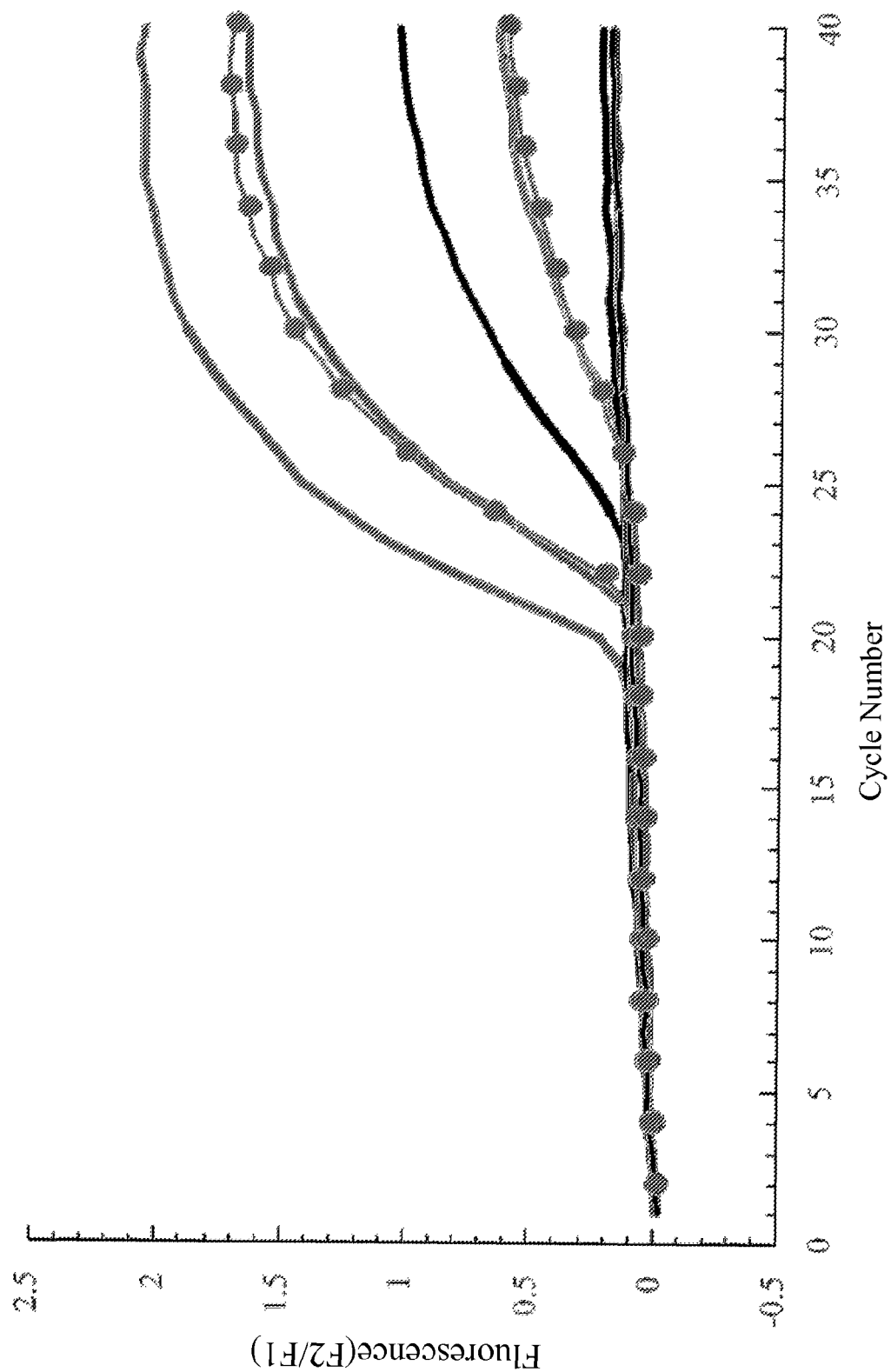
Figure 12B:
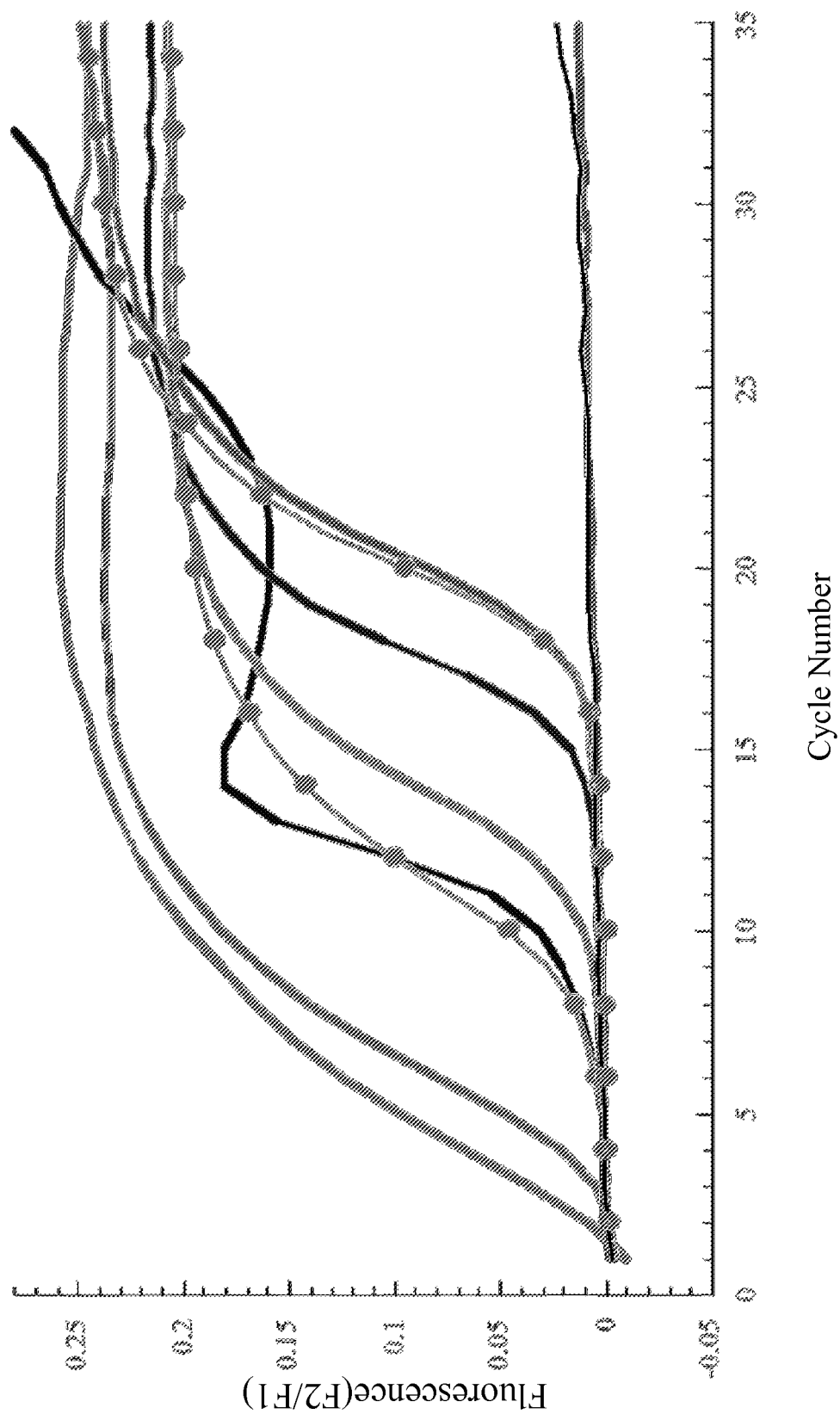

In order to purge hematopoietic progenitor populations of Ewing's sarcoma, variably contaminated 8H9 incubated bone marrow or peripheral blood stem cell populations were run over a Variomax® negative selection column as described in methods. Non-nested PCR evaluation of non-CD34 selected bone marrow from a healthy donor spiked with Ewing's sarcoma cells at a level of 1:100 is shown in FIG. 12a. These results demonstrate a 2-log reduction in tumor following 8H9 based purging. To evaluate the efficiency of 8H9 based purging with progenitor contamination at lower levels and to assess the ability to purge CD34+ selected cells, CD34+ selected cells from G-CSF mobilized peripheral blood were spiked at a level of $1:10^3$ and purged as shown in FIG. 12b. Using the quantitative PCR, we observed a 3-log reduction in the level of contamination following one run over the column.

Figure 12C:
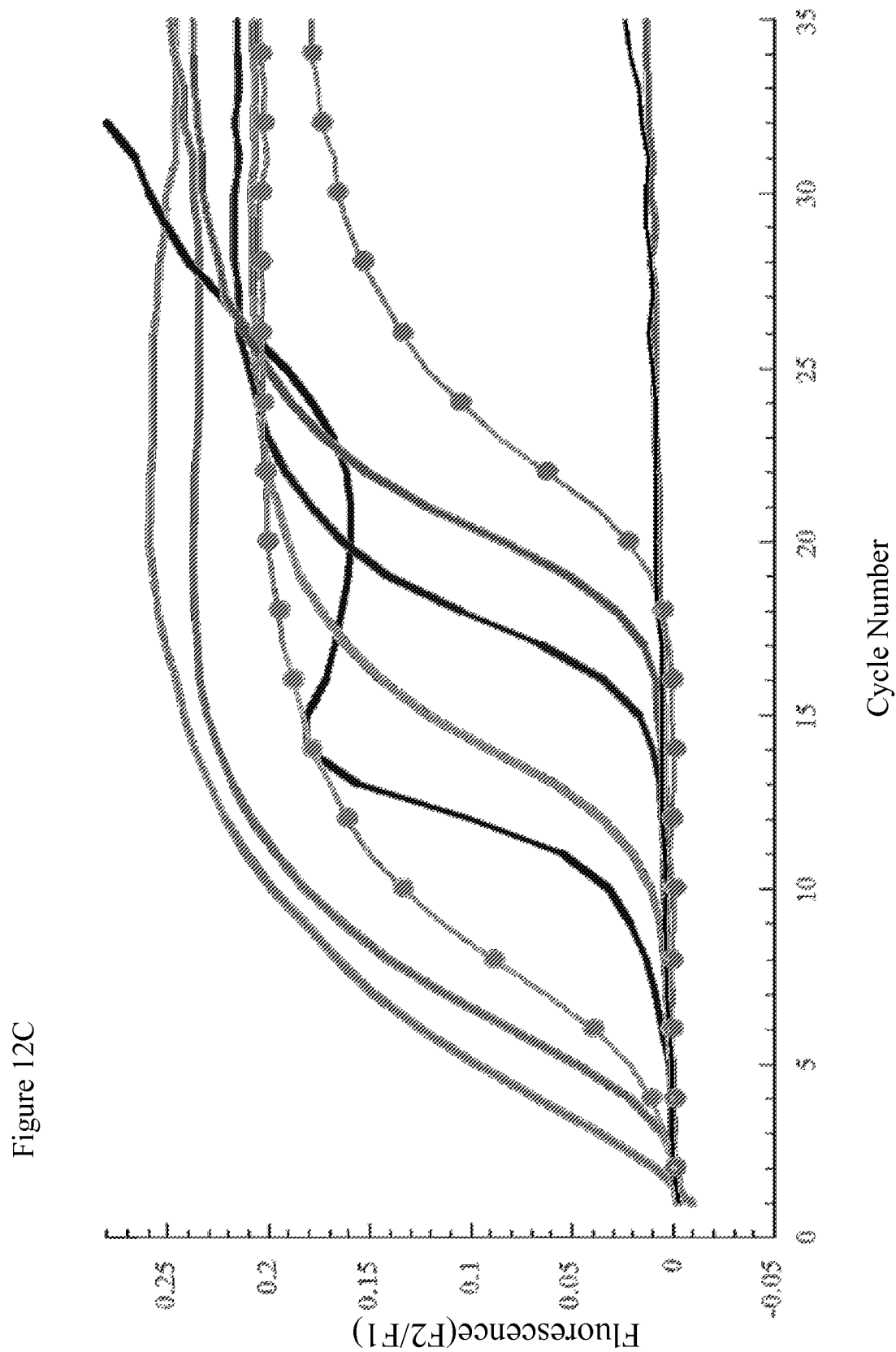
Figure 12D:
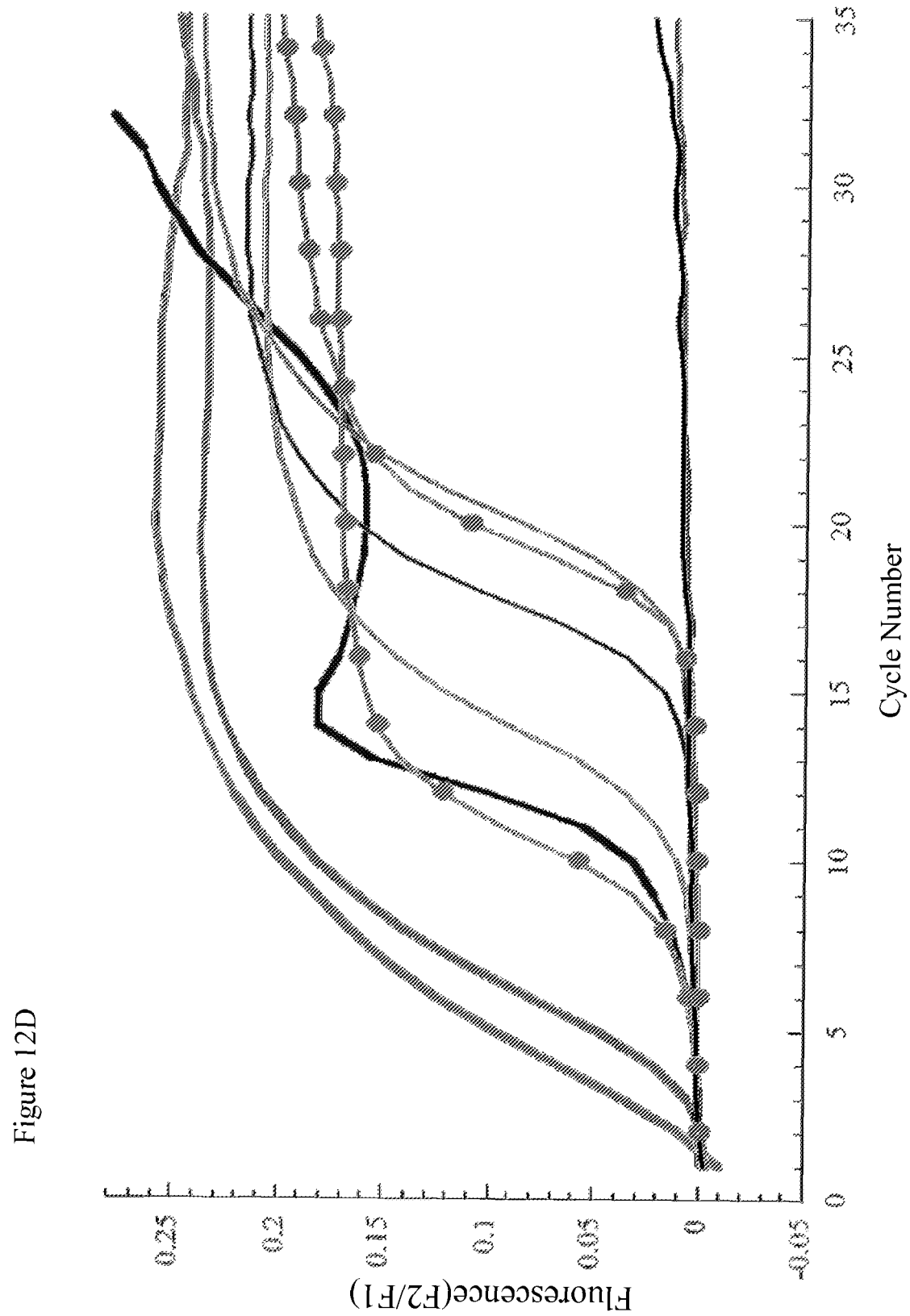

In the next experiments, evaluation of the ability to purge contaminated PBMC populations was undertaken. Similar to the results observed with CD34+ enriched peripheral blood stem cells, at least a 3-log reduction in contamination following 8H9 based purging of PBMCs contaminated at 1:100 was attained as shown in FIG. 12c. Evaluation of purging of PBMCs contaminated at a lower level ($1:10^3$) is shown in FIG. 12d where a 3-log reduction is again observed. In each of these experiments analysis of the positive fraction demonstrated PCR positivity confirming selection of contaminating Ewing's cells (data not shown). To account for any variation from the expected uniform amounts of starting RNA or cDNA, G6PD amplification was performed from each sample in a quantitative fashion. We observed a variation in crossing time (reflective of starting template) of less than 2% in all of the samples indicating a low degree of variation in starting template between samples and confirming viable RNA and cDNA in the negative samples (data not shown). These results suggested that monoclonal antibody 8H9 may be a suitable candidate for immunomagnetic based purging of contaminated blood, bone marrow, and CD 34+ enriched progenitor populations specimens with the likelihood for purging to PCR negativity being high if the level of contamination present in clinical samples is less than $1:10^4$.

Contamination of Non-Mobilized Patient Apheresis Fractions with Ewing's Sarcoma is Between $1:10^5$-$1:10^6$.

In order to evaluate the degree of contamination typically observed in clinical specimens, we studied non-mobilized peripheral blood apheresis specimens derived from patients treated on immunotherapy trials for Ewing's sarcoma at our institution. We observed a 66% (8/12) incidence of t(11,22) PCR positivity in non-mobilized apheresis specimens acquired for use in immunotherapy protocols as analyzed by conventional PCR (Table 1). As shown in Table 1, all elutriated apheresis fractions were observed to contain tumor with variability across individual patients. When elutriated apheresis specimens from several patients at presentation of metastatic Ewing's sarcoma were analyzed using quantitative PCR, this level of contamination was estimated to be between $1:10^5$ and $1:10^6$ with similar levels of contamination sometimes observed in multiple apheresis fractions. (FIG. 13). Patient A (top panel) showed positivity of all fractions at levels of approximately $1:10^6$. Patient B (middle panel) showed a level of contamination of approximately $1:10^6$ in the 120 ml/min (lymphocyte) fraction with no evidence for positivity in the 190 ml/min or rotor off (monocyte) fractions. Patient C (bottom panel) showed a level of contamination between $1:10^5$ and $1:10^6$ in multiple fractions. In no instance have we observed levels of contamination greater than $1:10^4$. Therefore, because clinical specimens contaminated with Ewing's sarcoma appears to be in the range of $1:10^5$-$1:10^6$, it is anticipated that reduction in contamination to at least $1:10^7$ following 8H9 based purging will be achievable in the vast majority of patients.

TABLE 1

Contamination of non-mobilized apheresis fractions with Ewing's sarcoma as analyzed by conventional PCR.

| Patient Number | Lymphocyte Fractions | | Monocyte Fractions | |
|---|---|---|---|---|
| | 120 ml/min | 140 ml/min | 190 ml/min | Rotor Off |
| 1 | N/A | Positive | Negative | Positive |
| 2 | Positive | Positive | Positive | Positive |
| 3 | Positive | Negative | Positive | N/A |
| 4 | Negative | Negative | N/A | Positive |
| 5 | Negative | Negative | Negative | Negative |
| 6 | N/A | Negative | Negative | Positive |
| 7 | Negative | Negative | Negative | Negative |
| 8 | Negative | Negative | Negative | Negative |
| 9 | Negative | Positive | Positive | Negative |
| 10 | Positive | Positive | N/A | Positive |
| 11 | Negative | Negative | Negative | Negative |
| 12 | Negative | Negative | Negative | Positive |

Positive indicates band hybridized with the EWS/FLI radiolabeled probe.
Negative indicated no band was noted.
N/A indicated that no RNA was obtained for that fraction.

8H9 Based Purging does not Adversely Affect Stem Cell or T Cell Function.

To further evaluate the clinical feasibility of this technique for purging of bone marrow or PBSC autografts, we sought to confirm retained proliferative and differentiating capacity in 8H9 purged bone marrow populations. We studied CFU formation following purging as an assay of CD34 function. We compared CFU formation before and after purging in CD34 selected bone marrow cells cultured in methycellulose media with recombinant cytokines before and after purging (FIG. 14). We observed normal colony numbers and morphology in both samples with no significant difference between samples indicating that CD34+ progenitors remain functional following 8H9 based purging.

T Cell Proliferation is Unchanged Before and After Purging.

Because T cells can contribute to post chemotherapy immune reconstitution[25], we are currently utilizing autologous T cell infusions harvested prior to initiation of chemotherapy in order to study effects on immune reconstitution. In order to study T cell function following 8H9 based purging, we evaluated T cell proliferation following anti-CD3 cross linking as a measure of T cell function. We compared T cell proliferation unmanipulated T cells and 8H9 based purged T cells. As shown in FIG. 15, there was no difference in T cell proliferation elicited by plate bound OKT3 antibody at concentrations ranging from 100 ug/ml to 3 ug/nl as measured by [$^3$H] thymidine uptake indicating that T cell proliferative capacity is retained following 8H9 based purging (FIG. 15).

Discussion

The contribution of contaminated autologous preparations to disease relapse following autologous SCT in solid tumor patients is not fully known. Rill and Brenner et al. have shown than in certain solid tumors, tumors contaminating autologous grafts are tumorigenic and present at relapse[18, 19]. In a disease such as Ewing's sarcoma, which has been shown to have a high degree of hematogenous spread, this becomes an important issue in the context of therapies which utilize autologous cells. In high-risk patients, survival after high dose chemotherapy followed by stem cell rescue continues to be suboptimal with the most common cause of death due to disease relapse. Contamination of autografts with subsequent survival and clonogenic growth of tumor post-infusion cannot be excluded as contributing to this poor prognosis. In addition to the medical consequences of the administration of contaminated products to patients, psychologically there is reluctance on the part of patients and their families to receive contaminated products. It follows, therefore, that if a purging method was available, its evaluation for use in patients receiving autologous products is warranted.

An ideal purging method should target only tumor cells and show no binding to normal cell populations. The identification of such a tumor specific antigen has historically posed a challenge in Ewing's sarcoma. While CD99 typically shows high expression on Ewing's sarcoma cells, it is also expressed on T cells (FIG. 10a) and CD 34 stem cells 26, making it unsuitable for purging hematologic products. Monoclonal antibody 8H9 was initially developed due to its reactivity with neuroblastoma and was subsequently reported to react with 19/19 fresh Ewing's sarcoma/PNET tumor confirming that 8H9 reactivity is not limited to established cell lines.[27]. Our results (FIG. 9) confirmed this reactivity in all Ewing's cell lines evaluated. Since this antibody showed no reactivity with T cells and CD34+ cells, it was ideally suited for purging. Indeed, we demonstrated a 2-3 log reduction in all experiments following one run over the negative selection column In the clinical setting of autologous stem cell transplant, the combination of positive selection for CD34+ cells, which results in an approximate 2-log passive depletion of tumor[28, 29], followed by 8H9 purging of tumor cells would be expected to result in up to 5 logs of depletion, which is predicted to be well below the limit of detection using currently available techniques. Further, even in the setting of autologous T cell transplantation, as potentially used in the context of immune reconstitutive therapies[20], the use of 8H9 based purging with its 2-3 log reduction will substantially diminish the tumor burden contained in autologous cellular products.

This is the first published report of 8H9 as a Ewing's reactive monoclonal antibody. Interestingly, 8H9 also shows reactivity with several rhabdomyosarcoma and osteosarcoma cell lines (data not shown). This introduces the exciting possibility of a sarcoma specific antibody with potential applications in immune directed therapy. In addition, identification and characterization of the tumor specific epitope which binds to 8H9 could offer important insight into the biology of these tumors. These studies are currently underway. Further, during the course of the studies reported here, we sought to evaluate in a general sense, the function of sarcoma cells selected with 8H9. We observed that Ewing's sarcoma cells positively selected using 8H9 retain their clonogenic properties and are able to be maintained in cell culture. This property has the potential aid in the generation and study of tumor cell lines derived from patients with pediatric sarcomas, which is currently difficult in these tumors due to limitations of tumor size and surgical accessibility of primary tumors. We are currently investigating whether Ewing's sarcoma cells derived from apheresis or bone marrow samples in patients with metastatic disease which are positively selected and grown in culture could provide a ready source of tumor samples for further biologic study.

RT-PCR is a powerfully sensitive tool for use in monitoring minimal residual disease MRD[30]. It remains unclear, however, whether evidence of small amounts of residual tumor by molecular analysis is predictive for relapse in solid tumors and data in the literature is conflicting. de Alava et al. evaluated MRD in Ewing's sarcoma patients and showed a correlation between PCR positivity and disease relapse. In this report however, some patients remained PCR positive without disease relapse[3]. Using real-time PCR, it is now possible to quantitate starting template and compare starting template amount between samples obtained at different timepoints. Real-time quantitative PCR has been used as a tool to monitor MRD in leukemia patients[31, 32] and may be useful in evaluation of disease response[33] and in predicting relapse in patients by the detection of increasing levels of tumor specific transcript.

This is the first report of the use of real-time quantitative PCR used to detect and quantify Ewing's sarcoma transcript. It is possible that quantitative PCR could allow for further identification of patients with a high risk of relapse by detection of increasing amounts of Ewing's transcripts over time. However, because contamination of peripheral blood by solid tumors is likely to be relatively low (in the range of $1:10^5$-$1:10^6$ in this series), the sensitivity of this analysis must be very high in order to allow for the detection of very low levels of circulating tumor in patients with solid tumors. The level of sensitivity of our technique reached 1 Ewing's sarcoma cell in $10^6$ normal cells with nested PCR from $10\times10^6$ cells. It is possible that the level of sensitivity would be even higher if higher cell numbers were evaluated since this method appears capable in our hands of amplifying product from 10 contaminating cells. Tumor enrichment using positive selection is another method to increase sensitivity of tumor detection. The positive immunomagnetic selection procedure described in this paper for purging could also provide a suitable approach for tumor enrichment in for monitoring MRD or even in contributing to making the correct diagnosis at the time of initial presentation with metastatic disease. Indeed, cells eluted from the column were positive by PCR analysis, demonstrating the feasibility of this technique for tumor enrichment which would be predicted to increase the sensitivity of PCR detection of contaminating Ewing's sarcoma in patient samples. One caveat which should be noted is that the quantitative technique, relies on the assumption that the level of expression of t (11;22) is consistent among cell lines and patient samples.

This, may not be the case, however, and may lead to under or over estimation of the absolute level of tumor burden when comparing patient samples to a standard curve. Such limitations would not preclude evaluation of changes in the level of PCR positivity of an individual patient over time, wherein substantial changes in the level of expression of t(11;22) may be less likely.

In this report we have demonstrated a purging technique that reduces tumor burden in artificially contaminated products by at least 2-3 logs. This approach is predicted to substantially reduce the tumor burden contained in autologous cellular products which are administered in the context of innovative therapies for Ewing's sarcoma. The demonstration that CFU assays on progenitor cells as well as CD3 induced T cell proliferation are normal after purging demonstrates no detrimental effects on normal progenitor cell and T cell function, making this a potentially feasible addition to autologous protocols. We conclude that immunomagnetic purging via negative selection using MoAb 8H9 warrants evaluation in clinical trials for Ewing's sarcoma involving the use of autologous products.

References

1. Arndt C A, Crist W M. Common musculoskeletal tumors of childhood and adolescence. N Engl J Med. 1999; 341:342-52.
2. West D C, Grier H E, Swallow M M, Demetri G D, Granowetter L, Sklar J. Detection of circulating tumor cells in patients with Ewing's sarcoma and peripheral primitive neuroectodermal tumor. J Clin Oncol. 1997; 15:583-8.
3. de Alava E, Lozano M D, Patino A, Sierrasesumaga L, Pardo-Mindan F J. Ewing family tumors: potential prognostic value of reverse- transcriptase polymerase chain reaction detection of minimal residual disease in peripheral blood samples. Diagn Mol Pathol. 1998; 7:152-7.
4. Toretsky JA, Neckers L, Wexler L H. Detection of (11;22) (q24;q12) translocation-bearing cells in peripheral blood progenitor cells of patients with Ewing's sarcoma family of tumors. J Natl Cancer Inst. 1995; 87:385-6.

5. Burdach S, Jurgens H, Peters C, et al. Myeloablative radio-chemotherapy and hematopoietic stem-cell rescue in poor-prognosis Ewing's sarcoma. J Clin Oncol. 1993; 11:1482-8.
6. Burdach S, Nurnberger W, Laws H J, et al. Myeloablative therapy, stem cell rescue and gene transfer in advanced Ewing tumors. Bone Marrow Transplant. 1996; 18 Suppl 1:S67-8.
7. Chan K W, Petropoulos D, Choroszy M, et al. High-dose sequential chemotherapy and autologous stem cell reinfusion in advanced pediatric solid tumors. Bone Marrow Transplant. 1997; 20:1039-43.
8. Fischmeister G, Zoubek A, Jugovic D, et al. Low incidence of molecular evidence for tumour in PBPC harvests from patients with high risk Ewing tumours. Bone Marrow Transplant. 1999; 24:405-9.
9. Frohlich B, Ahrens S, Burdach S, et al. [High-dosage chemotherapy in primary metastasized and relapsed Ewing's sarcoma. (EI)CESS]. Klin Padiatr. 1999; 211: 284-90.
10. Horowitz M E, Kinsella T J, Wexler L H, et al. Total-body irradiation and autologous bone marrow transplant in the treatment of high-risk Ewing's sarcoma and rhabdomyosarcoma. J Clin Oncol. 1993; 11:1911-8.
11. Ladenstein R, Lasset C, Pinkerton R, et al Impact of megatherapy in children with high-risk Ewing's tumours in complete remission: a report from the EBMT Solid Tumour Registry [published erratum appears in Bone Marrow Transplant 1996 September; 18(3):675]. Bone Marrow Transplant. 1995; 15:697-705.
12. Ladenstein R, Philip T, Gardner H. Autologous stem cell transplantation for solid tumors in children. Curr Opin Pediatr. 1997; 9:55-69.
13. Laws H J, Burdach S, van Kaick B, et al. Multimodality diagnostics and megatherapy in poor prognosis Ewing's tumor patients. A single-center report. Strahlenther Onkol. 1999; 175:488-94.
14. Pape H, Laws H J, Burdach S, et al. Radiotherapy and high-dose chemotherapy in advanced Ewing's tumors. Strahlenther Onkol. 1999; 175:484-7.
15. Perentesis J, Katsanis E, DeFor T, Neglia J, Ramsay N. Autologous stem cell transplantation for high-risk pediatric solid tumors. Bone Marrow Transplant. 1999; 24:609-15.
16. Pession A, Prete A, Locatelli F, et al. Phase I study of high-dose thiotepa with busulfan, etoposide, and autologous stem cell support in children with disseminated solid tumors. Med Pediatr Oncol. 1999; 33:450-4.
17. Stewart D A, Gyonyor E, Paterson A H, et al. High-dose melphalan +/− total body irradiation and autologous hematopoietic stem cell rescue for adult patients with Ewing's sarcoma or peripheral neuroectodermal tumor. Bone Marrow Transplant. 1996; 18:315-8.
18. Rill D R, Santana V M, Roberts W M, et al. Direct demonstration that autologous bone marrow transplantation for solid tumors can return a multiplicity of tumorigenic cells. Blood. 1994; 84:380-3.
19. Brenner M K, Rill D R, Moen R C, et al. Gene-marking to trace origin of relapse after autologous bone-marrow transplantation. Lancet. 1993; 341:85-6.
20. Mackall C, Long L, Dagher R, et al. Combined Immune Reconstitution/Tumor Vaccination to induce anti-tumor immune responses in the setting of minimal residual neoplastic disease [abstract]. Blood. 1999; 94:133a.
21. Quinones R R, Gutierrez R H, Dinndorf P A, et al. Extended-cycle elutriation to adjust T-cell content in HLA-disparate bone marrow transplantation. Blood. 1993; 82:307-17.
22. Kontny H U, Lehmbecher T M, Chanock S J, Mackall C L. Simultaneous expression of Fas and nonfunctional Fas ligand in Ewing's sarcoma. Cancer Res. 1998; 58:5842-9.
23. Chirgwin J M, Przybyla A E, MacDonald R J, Rutter W J. Isolation of biologically active ribonucleic acid from sources enriched in ribonuclease. Biochemistry. 1979; 18:5294-9.
24. de Wynter E A, Coutinho L H, Pei X, et al. Comparison of purity and enrichment of CD34+ cells from bone marrow, umbilical cord and peripheral blood (primed for apheresis) using five separation systems. Stem Cells. 1995; 13:524-32.
25. Mackall C L, Gress R E. Pathways of T-cell regeneration in mice and humans: implications for bone marrow transplantation and immunotherapy. Immunol Rev. 1997; 157: 61-72.
26. Dworzak M N, Fritsch G, Buchinger P, et al. Flow cytometric assessment of human MIC2 expression in bone marrow, thymus, and peripheral blood. Blood. 1994; 83:415-25.
27. Modak S, Gultekin S, Kramer K, et al. Novel Tumor-Associated Antigen: Broad distrubution among neuroectodermal, mesenchymal and epiethelial tumors, with restricted distribution in normal tissues. Abstract: Proceedings at ASCO. 1998.
28. Vogel W, Scheding S, Kanz L, Brugger W. Clinical applications of CD34(+) peripheral blood progenitor cells (PBPC). Stem Cells. 2000; 18:87-92.
29. Dyson P G, Horvath N, Joshua D, et al. CD34+ selection of autologous peripheral blood stem cells for transplantation following sequential cycles of high-dose therapy and mobilisation in multiple myeloma [In Process Citation]. Bone Marrow Transplant. 2000; 25:1175-84.
30. Emig M, Saussele S, Wittor H, et al. Accurate and rapid analysis of residual disease in patients with CML using specific fluorescent hybridization probes for real time quantitative RT-PCR. Leukemia. 1999; 13:1825-32.
31. Mensink E, van de Locht A, Schattenberg A, et al. Quantitation of minimal residual disease in Philadelphia chromosome positive chronic myeloid leukaemia patients using real-time quantitative RT-PCR. Br J Haematol. 1998; 102:768-74.
32. Pongers-Willemse M J, Verhagen O J, Tibbe G J, et al. Real-time quantitative PCR for the detection of minimal residual disease in acute lymphoblastic leukemia using junctional region specific TaqMan probes. Leukemia. 1998; 12:2006-14.
33. Branford S, Hughes T P, Rudzki Z. Monitoring chronic myeloid leukaemia therapy by real-time quantitative PCR in blood is a reliable alternative to bone marrow cytogenetics. Br J Haematol. 1999; 107:587-99.

Fourth Series of Experiments

Disialoganglioside GD2 and Novel Tumor-Restricted Antigen 8H9: Potential Targets for Antibody-Based Immunotherapy Against Desmoplastic Small Round Cell Tumor.

Desmoplastic small round cell tumor (DSRCT) is an aggressive, often misdiagnosed neoplasm of children and young adults. It is chemotherapy-sensitive, yet patients often relapse off therapy because of residual microscopic disease at distant sites: peritoneum, liver, lymph node and lung. Strategies directed at minimal residual disease (MRD) may be necessary for cure. Monoclonal antibodies selective for cell surface tumor-associated antigens may have utility for diagnosis and therapy of MRD, as recently demonstrated in advanced-stage neuroblastoma (JCO 16: 3053, 1998). Using immunohistochemistry, we studied the expression of two antigens: (1) $G_{D2}$ using antibody 3F8 and (2) a novel antigen using antibody 8H9, in a panel of 36 freshly frozen DSRCT. $G_{D2}$ is a disialoganglioside which is widely expressed among neuroectodermal tumors as well as adult sarcomas. 8H9 recognizes a surface 58kD antigen expressed among neuroectodermal, mesenchymal and epithelial tumors with restricted expression on normal tissues. 27 of 37 tumors (73%) were reactive with 3F8, and 35 of 37 (95%) with 8H9. Both $G_{D2}$ and the 58kD antigen were found on tumor cell membrane and in stroma. In general, immunoreactivity was stronger and more homogeneous with 8H9 than with 3F8. These antigens are potential targets for immunodiagnosis and antibody-based therapy of DSRCT.

Desmoplastic small round cell tumor (DSRCT) is an aggressive, ill-understood tumor affecting children and young adults. It is characterized clinically by widespread abdominal serosal involvement, metastasizes to peritoneum, liver, lungs and lymph nodes, and is associated with a poor prognosis (Gerald et al., 1991). Histologically, it consists of small, undifferentiated round cells surrounded by an abundant desmoplastic stroma. Immunohistochemically, the coexpression of epithelial, neural and muscle markers is typical (Ordonez et al., 1993). DSRCT is associated with a specific chromosomal translocation, t(11;22)(p13;q12). The fused gene product aligns the NH2 terminal domain of the EWS gene to the zinc finger DNA-binding domain of the WT1 gene and is diagnostic of DSRCT (Ladanyi et al., 1994). This fusion results in the induction of endogenous platelet derived growth factor-A which stimulates fibroblast growth and may contribute to the unique fibrosis observed with this tumor (Lee et al, 1997). Further evidence of upregulation of growth factors includes the reported expression of IGF-II, PDGF-α receptor and IL-11 in DSRCT (Froberg et al., 1999).

Although dramatic response to aggressive multimodality therapy has been demonstrated in the patients with DSRCT (Kushner et al., 1996), many patients relapse with recurrent local disease or distant metastases. Strategies aimed at eradication of MRD are, therefore, warranted in the management of patients with DSRCT. Monoclonal antibodies selective for cell surface tumor-associated antigens are potential candidates as recently demonstrated in neuroblastoma where immune targeting of the diasialoganglioside $G_{D2}$ has significantly improved long-term survival in patients with stage 4 disease (Cheung et al., 1998). Few such tumor-associated targets have been defined for DSRCT. We describe here two possible targets for such immunotherapy: $G_{D2}$ targeted by the monoclonal antibody 3F8 and a novel tumor antigen recognized by the monoclonal antibody 8H9.

Materials and Methods
Tumor and Normal Tissue Samples

Frozen tumors from 37 patients with DSRCT were analyzed. Diagnosis was confirmed by hematoxylin and eosin assessment of paraffin-fixed specimens.

Monoclonal Antibodies

The murine $IgG_3$ monoclonal antibody 3F8 was purified from ascites as previously described (Cheung et al., 1985). Using a similar technique, female BALB/c mice were hyperimmunized with human neuroblastoma. Lymphocytes derived from these mice were fused with SP2/0 mouse myeloma cells line. Clones were selected for specific binding on ELISA. The 8H9 hybridoma secreting an $IgG_1$ monoclonal antibody was selected. 8H9 was produced in vitro and purified by protein G (Pharmacia, Piscataway, N.J.) affinity chromatography.

Immunohistochemical Studies

Eight μm cryostat frozen tumor sections were fixed in acetone and washed in PBS. Immunohistochemical studies were performed as previously described (Kramer et al. 1996) Endogenous peroxidases were blocked in 0.3% $H_2O_2$ in PBS. Sections were incubated in 10% horse serum (Gibco BRL Gaithersburg, MD) after blocking with avidin and biotin. Incubation with purified 8H9 diluted in PBS to 2 μg/ml was carried out at room temperature for 1 hour. An IgG1 myeloma was used as a control (Sigma Chemical, St Louis Mo.). Sections were incubated with a secondary horse anti-mouse biotinylated antibody (Vector Laboratories, Burlingame, Calif.) followed by incubation with ABC complex (Vector Laboratories, Burlingame, Calif.) and stained with Vector VIP peroxidase substrate (Vector Laboratories, Burlingame, Calif.) or DAB peroxidase substrate kit (Vector Laboratories, Burlingame, Calif.). A 10% hematoxylin counterstain for 2 minutes was used.

Staining was graded as positive or negative and homogenous or heterogenous reactivity noted.

Results
Clinical Profile

Of the 37 patients studied, 32 were male and five female. Age at diagnosis ranged from 13 to 46 years (median 18 years). All received treatment with an aggressive multimodality regimen including dose-intensive chemotherapy.

Immunoreactivity

Tumor sections from 37 patients were tested for the expression of $G_{D2}$ and the antigen recognized by 8H9 by immunohistochemistry. 27 of 37 (73%) tested positive for $G_{D2}$. (Table 1). Most tumors had strong immunoreactivity (>1+) Immunoreactivity was seen homogeneously in most tumors and was localized to the cell membrane (FIG. 16). Intense stromal staining was marked in all tumors studied.

TABLE 1

Immunoreactivity of 3F8 and 8H9 with DSRCT

| Marker | No. tested | Reactivity | | | | No. pos. (%) | Homo-geneous | Hetero-geneous |
|---|---|---|---|---|---|---|---|---|
| | | 0 | 1+ | 2+ | 3+ | | | |
| $G_{D2}$ | 36 | 10 | 10 | 12 | 4 | 26 (72) | 19 | 7 |
| Antigen 8H9 | 36 | 2 | 9 | 17 | 8 | 34 (94) | 32 | 2 |

35 of 37 (95%) tumors tested positive for 8H9 Immunoreactivity had a characteristic cell membrane localization and was homogeneous in almost all tumors (FIG. 17). Immunoreactivity was more strongly marked than that with 3F8. Equally strong stromal staining was seen.

Clinicopathologic Correlation

In this group of highly aggressive disseminated tumors, there was no correlation between outcome and the expression of either $G_{D2}$ or the 8H9 antigen (Table 2)

TABLE 2

$G_{D2}$ and Antigen 8H9: Correlation with outcome

| | $G_{D2}$ positive | 8H9 positive |
|---|---|---|
| Expired* | 10/17 | 16/17 |
| Survivors <18 mo since diagnosis | 11/14 | 13/14 |
| Survivors >18 mo since diagnosis | 5/5 | 5/5 |

*1 patient died of treatment-related toxicity

Discussion The clinicopathological spectrum of DSRCT continues to be further defined since the initial series was reported in 1991 (Gerald et al., 1991). Chemosensitivity to doxorubicin and alkylator-based chemotherapy has been reported (Gonzalez-Crussi et al., 1990). Prolonged survival in response to an aggressive multimodality regimen including high-dose chemotherapy, radiation and surgery has also been reported (Kushner et al., 1996). However, most patients succumb to recurrent local disease or metastases to peritoneum, liver, lymph nodes, or lung. Relapses can be largely attributed to the failure of eradication of MRD. Alternative therapeutic strategies to target MRD are therefore warranted. One such strategy could be directed at the upregulated growth factors particularly PDGFA and related factors expressed on DSRCT (Froberg et al., 1999). Targeted immunotherapy utilizing monoclonal antibodies, which does not add to the toxicity of chemotherapy, is another approach.

DSRCT is characterized by the coexpression of epithelial, mesenchymal and neuroectodermal markers. Recent publications have defined the immunohistochemical and molecular make-up of DSRCT (Ordonez, 1998; Gerald, 1999). However, most of the markers identified cannot be used as targets for antibody mediated immunotherapy either due to crossreactivity with normal tissues or inaccessibility to monoclonal antibodies due to localization in the nucleus or cytoplasm. (Table 3). The most commonly expressed markers on DSRCT including desmin, cytokeratin, vimentin, epithelial membrane antigen and neuron-specific enolase are also widely expressed on normal tissues. The MIC2 antigen has been reported to be expressed on 20-35% of DSRCT. However, unlike Ewing's sarcoma family of tumors, which have membrane localization, immunoreactivity in DSRCT is primarily cytoplasmic (Gerald et al, 1998). MOC31, a monoclonal antibody that recognizes epithelial glycoprotein 2 (EGP-2) has been shown to be reactive with most DSRCT tested (Ordonez, 1998). EGP-2 is overexpressed on epithelial tumors, but is also present on normal epithelial cells (de Leij et al, 1994). Antibodies directed against the WT1 protein have strong, specific, nuclear immunoreactivity with almost all DSRCT tested (Gerald et al, 1998)

TABLE 3

Previously reported antigens on DSRCT

| Antigen | Localization | Crossreactivity |
|---|---|---|
| Intermediate filaments | | |
| Desmin | cytoplasm | skeletal, cardiac & smooth muscle |
| Vimentin | cytoplasm | mesenchymal tissues |
| Keratin | cytoplasm | epithelial cells |
| Epithelial antigens | | |
| Epithelial membrane antigen | cytoplasm | epithelial cells |
| Epithelial glycoprotein-2 | cytoplasm | epithelial cells |
| Ber-Ep4 antigen | cytoplasm | epithelial cells |
| Neural antigens | | |
| CD57 | cytoplasm | neural tissues |
| Neuron-specific enolase | cytoplasm | neural tissues |
| MIC-2 | cytoplasm & cell membrane | lymph nodes, epithelial cells |
| WT1 protein | Nucleus | None |
| PDGFA | Cell membrane | Endothelial cells, hematopoeitic cells |
| PDGF-α receptor | Cell membrane | Endothelial cells, hematopoeitic cells |

The reported expression of neuroectodermal antigens on DSRCT led us to study these tumors for the expression of $G_{D2}$: a disialoganglioside which is expressed on other small blue round cell tumors such as neuroblastoma, small cell lung cancer, melanoma and osteosarcoma (Heiner et al., 1987) as well as on adult soft tissue sarcomas (Chang et al., 1992). $G_{D2}$ is a safe target for immunotherapy based on clinical trials of the anti-$G_{D2}$ antibody 3F8 in patients with neuroblastoma. tissues of the nervous system (Cheung et al., 1998). Serum $G_{D2}$ does not interfere with the biodistribution of specific antibodies and the antigen is not modulated from the cell surface upon binding by antibodies. Successful targeting of the monoclonal antibody 3F8 to $G_{D2}$ was previously demonstrated in neuroblastoma (Yeh et al., 1991) and small cell lung cancer (Grant et al., 1996). 3F8 has also shown efficacy in clinical trials in patients with neuroblastoma (Cheung et al., 1998b) and melanoma (Cheung et al., 1987). Furthermore, 3F8 appeared to induce long-term remissions in patients with Stage 4 neuroblastoma. Reported side effects are short-lived and manageable (Cheung et al., 1998). In our study 72% of DSRCT tested were immunoreactive with the anti-GD2 antibody 3F8. Most tumors showed strong, homogeneous reactivity localized to the cell membrane. (Table 1) (FIG. 16) DSRCT may be a putative tumor for in vivo antibody targeting with 3F8. Alternatively, an anti-idiotypic vaccine approach can be utilized as has been suggested for neuroblastoma. (Cheung et al, 1994)

The monoclonal antibody 8H9 is a murine IgG$_1$ derived from mice immunized with neuroblastoma. It has been shown to have a broad expression on neuroectodermal, mesenchymal and epithelial tumors with limited expression on normal tissues. (data not shown). Its immunoreactive profile led us to use it for testing DSRCT. 95% of tumors tested positive with DSRCT Immunoreactivity with DSRCT was localized to the stroma and cell membrane (FIG. 17) and for most tumors was intense and homogeneous, and in general, stronger than that observed for GD2 (Table 2).

The target antigen for 8H9 appears to be a novel 58 kD glycoprotein with a unique distribution on cell membranes of tumors of varying lineage, but restricted expression in normal tissues. This tissue distribution makes it likely to be a unique antigen not previously described on DSRCT. The cell membrane localization of 8H9 allows it to be targeted by monoclonal antibodies. 8H9 conjugated with $I^{131}$ has been shown to radioimmunolocalize neuroblastoma and rhabdomyosarcoma xenografts in mice without significant crossreactivity with other organs. (data not shown).

In the therapy of DSRCT, strategies to eliminate minimal residual disease are necessary to produce cures. Monoclonal antibody based therapy may augment aggressive multimodality therapy by targeting minimal residual disease without adding to toxicity. Our study has identified $G_{D2}$ and antigen 8H9 as two hitherto undescribed markers for DSRCT, which can potentially be targets for differential diagnosis and immunotherapy.

References

Chang H. R., Cordon-Cardo C., Houghton A. N., Cheung N. K., and Brennan M. F., Expression of disialogangliosides $G_{D2}$ and $G_{D3}$ on human soft tissue sarcomas. Cancer 70: 633-8, (1992)

Cheung N. K., Saarinen, U., Neely, J., Landmeier, B., Donovan D., and Coccia, P. Monoclonal antibodies to a glycolipid antigen on human neuroblastoma cells. Cancer Res., 45: 2642-2649, (1985)

Cheung N. K., Lazarus, H., Miraldi F. D., Abramowsky, C. R., Kallick S., Saarinen, U. M., Spitzer, T., Strandjord, S. E., Coccia, P. F., and Berger, N. A. Ganglioside $G_{D2}$ specific monoclonal antibody 3F8: a phase I study in patients with neuroblastoma and malignant melanoma. J. Clin.Oncol. 5: 1430-40, (1987)

Cheung, N. K., Cheung, I. Y., Canete, A., Yeh, S. J., Kushner, B., Bonilla, M. A., Heller, G., and Larson, S. M. Antibody response to murine anti $G_{D2}$ monoclonal antibodies: correlation with patient survival. Cancer Res. 54: 2228-33 (1994)

Cheung N K., Kushner B. H., Yeh S. D. J., and Larson S. M., 3F8 monoclonal antibody treatment of patients with stage 4 neuroblastoma: a phase II study. Int. J. Oncol 12: 1299-306, (1998b)

Cheung, N. K., Kushner, B. H., Cheung, I. Y., Kramer, K., Canete, A., Gerald, W., Bonilla, M. A., Finn, R., Yeh, S., and Larson, S. M., Anti $G_{D2}$ antibody treatment of minimal residual stage 4 neuroblastoma diagnosed at more than 1 year of age. J. Clin. Oncol., 16: 3053-60, (1998)

De Leij, L., Helrich, W., Stein, R., and Mattes M. J. SCLC-cluster-2 antibodies detect the pancarcinoma/epithelial glycoprotein E GP-2 (supplement) Int. J. Cancer 8: 60-3, 1994

Froberg, K., Brown, R. E., Gaylord, H., Manivel, C., Intra-abdominal desmoplastic small round cell tumor: immunohistochemical evidence for up-regulation of autocrine and paracrine growth factors. Ann Clin Lab Sci 29: 78-85, 1999

Gonzalez-Crussi, F., Crawford, S. E., and Sun, C. J. Intraabdominal desmoplastic small-cell tumors with divergent differentiation. Observation on three cases of childhood. Am. J. Surg. Pathol. 15: 499-513, (1991)

Grant, S. C., Kostakoglu, L., Kris, M. G., Yeh, S. D., Larson, S. M., Finn, R. D., Oettgen, H. F., and Cheung, N. K. targeting of small-cell lung cancer using the anti-$G_{D2}$ ganglioside monoclonal antibody 3F8: a pilot trial. Eur. J. Nucl. Med. 23: 145-9 (1996)

Heiner, J. P., Miraldi, F., Kallick, S., Makley J., Neely, J., Smith-Mensah, W. H., and Cheung N. K. Localization of $G_{D2}$-specific monoclonal antibody 3F8 in human osteosarcoma. Cancer Res. 47: 5377-81 (1987)

Kramer, K., Gerald, W., Le Sauteur, L., UriSaragovi, H., and Cheung, N. K. Prognostic Value of TrkA Protein Detection by Monoclonal Antibody 5C3 in Neuroblastoma. Clin. Cancer Res. 2: 1361-1367, 1996

Kushner, B. H., LaQuaglia M. P., Wollner, N., Meyers, P. A., Lindsley, K. L., Ghavimi, F., Merchant, T. E., Boulad, F., Cheung, N. K., Bonilla, M. A., Crouch, G., Kelleher, J. F., Steinherz, P. G., and Gerald, W. L., Desmoplastic small round-cell tumor: prolonged progression-free survival with aggressive multimodality therapy. J. Clin. Oncol. 14: 1526-31, (1996)

Ladanyi, M., and Gerald, W., Fusion of the EWS and WT1 genes in the desmoplastic small round cell tumor. Cancer Res. 54: 2837-40, (1994)

Lee, S. B., Kolquist, K. A., Nichols, K., Englert, C., Maheshwaran, S., Ladanyi, M., et al., The EWS-WT1 translocation product induces PDGFA in desmoplastic small round-cell tumour. Nat Genet 17, 309-13, 1997

Gerald, W. L., Miller, H. K., Battifora, H., Miettenen, M., Silva, E. G., and Rosai, J., Intrabdominal desmoplastic small round cell tumor. Report of 19 cases of a distinctive type of high-grade polyphenotypic malignancy affecting young individuals. Am. L. Surg. Pathol. 15, 499-513, (1991)

Gerald, W. L., Ladanyi, M. L., De Alava, E., Cuatrecasas, M., Kushner, B. H., LaQuaglia, M. P., and Rosai, J. Clinical pathologic, and molecular spectrum of tumors associated with t(11;22)(p13;q12): desmoplastic small round-cell tumor and its variants. J. Clin. Oncol., 16: 3028-36, (1998)

Ordonez, N. G., El-Naggar, A. K., Ro, J. Y., Silva, E. G., Mackay B., Intra-abdominal desmoplastic small cell tumor: a light microscopic, immunocytochemical, ultrastructural, and flow cytometric study. Hum. Pathol. 24, 850-65, (1993)

Ordonez, N. G. Desmoplastic small round cell tumor: II: an ultrastructural and immunohistochemical study with emphasis on new immunohistochemical markers. Am. J. Surg. Pathol. 22: 1314-27, (1998)

Yeh S. D., Larson, S. M., Burch, L., Kushner, B. H., LaQuaglia, M, Finn, R., and Cheung, N. K. Radioimmunodetection of neuroblastoma with iodine-131-3F8: correlation with biopsy, iodine-131-metaiodobenzylguanidine and standard diagnostic modalities. J. Nucl. Med. 32: 769-76 (1991)

Fifth Series of Experiments

Anti-Idiotypic Antibody as the Surrogate Antigen for Cloning ScFv and its Fusion Proteins ScFv provides a versatile homing unit for novel antibody-fusion constructs. However, a reliable screening and binding assay is often the limiting step for antigens that are difficult to clone or purify. We demonstrate that anti-idiotypic antibodies can be used as surrogate antigens for cloning scFv and their fusion proteins. 8H9 is a murine IgG1 monoclonal antibody specific for a novel antigen expressed on the cell surface of a wide spectrum of human solid tumors but not in normal tissues (Cancer Res 61:4048,2001) Rat anti-8H9-idiotypic hybridomas (clones 2E9, 1E12 and 1F11) were produced by somatic cell fusion between rat lymphocytes and mouse SP2/0 myeloma. In direct binding assays (ELISA) they were specific for the 8H9 idiotope. Using 2E9 as the surrogate antigen, 8H9-scFv was cloned from hybridoma cDNA by phage display. 8H9scFv was then fused to human-1-CH2-CH3 cDNA for transduction into CHO and NSO cells. High expressors of mouse scFv-human Fc chimeric antibody were selected. The secreted homodimer reacted specifically with antigen-positive tumor cells by ELISA and by flow cytometry, inhibitable by the anti-idiotypic antibody. The reduced size resulted in a shorter half-life in vivo, while achieving comparable tumor to nontumor ratio as the native antibody 8H9. However, it could not mediate antibody-dependent cell-mediated or complement-mediated cytotoxicities in vitro.

1. Introduction

The ability to condense the binding site by genetic fusion of variable region immunoglobulin genes to form scFv has greatly expanded the potential and development of antibody-based targeted therapies (Bird et al., 1988; Huston et al., 1988; Winter and Milstein, 1991; George et al., 1994). Using phage display libraries, scFv can now be cloned from cDNA libraries derived from rodents, immunized volunteers, or patients (Burton and Barbas III, 1994; Winter et al., 1994; Cai and Garen, 1995; Raag and Whitlow, 1995). The availability of hIg-transgenic and transchromosomal mice will allow immunization schema or pathogens not feasible or safe in humans. Construction of the scFv is the critical first step in the synthesis of various fusion proteins, including scFv-cytokine (Shu et al., 1993), scFv-streptavidin (Kipriyanov et al., 1995), scFv-enzyme (Michael et al., 1996), scFv-toxins (Wikstrand et al., 1995), bispecific scFv (diabodies) (Alt et al., 1999), bispecific chelating scFv (DeNardo et al., 1999), scFv-Ig (Shu et al., 1993), tetravalent scFv (Alt et al., 1999; Santos et al., 1999) and scFv-retargeted T-cells (Eshhar et al., 1993). ScFv-Ig constructs mimic natural IgG molecules in their homodimerization through the Fc region, as well as their ability to activate complement (CMC) and mediate antibody dependent cell-mediated cytotoxicites (ADCC).

The construction of scFv requires a reliable antigen preparation both for panning phages and for binding assays. They often become a rate-limiting step (Lu and Sloan, 1999), particularly for antigens that are difficult to clone or purify. Cell-based phage display (Watters et al., 1997), and enzyme linked immunosorbent assays (ELISA) when optimized, have been successfully applied as alternatives. However, subtle differences in the panning step can determine the success or failure of phage display (Tur et al., 2001). For example, a reduction in wash pH is needed for scFv directed at ganglioside GD2 in order to reduce nonspecific adherence of phage particles (Tur et al., 2001). Moreover, phage binding assay may require membrane preparations to withstand the vigorous washing procedure.

Anti-idiotypic antibodies are frequently used as antigen mimics of infectious agents and tumor antigens (Thanavala et al., 1986; Wagner et al., 1997). When made as MoAb, they are ideal surrogates when the target antigen is not readily available. The physico-chemical behavior of immunoglobulins as antigens in panning and binding assays is generally known and can be easily standardized. We recently described a novel tumor antigen reactive with a murine MoAb 8H9 (Modak et al., 2001). Given its lability and glycosylation, this antigen is difficult to purify. Here we describe the use of an anti-idiotypic antibody as a surrogate antigen for cloning a scFv derived from the 8H9 hybridoma cDNA library, and for the selection of chimeric mouse scFv-human Fc fusion constructs.

2. Materials and Methods 2.1 Animals

BALB/c mice were purchased from Jackson Laboratories, Bar Harbor, Me. Lou/CN rats were obtained from the National Cancer Institute-Frederick Cancer Center (Bethesda, Md.) and maintained in ventilated cages. Experiments were carried out under a protocol approved by the Institutional Animal Care and Use Committee, and guidelines for the proper and humane use of animals in research were followed.

2.2 Cell Lines

Human neuroblastoma cell lines LAN-1 was provided by Dr. Robert Seeger (Children's Hospital of Los Angeles, Los Angeles, Calif.), and NMB7 by Dr. Shuen-Kuei Liao (McMaster University, Ontario, Canada). Cell lines were cultured in 10% defined calf serum (Hyclone, Logan, Utah) in RPMI with 2 mM L-glutamine, 100 U/ml of penicillin (Sigma-Aldrich, St. Louis, Mo.), 100 ug/ml of streptomycin (Sigma-Aldrich), 5% $CO_2$ in a 37° C. humidified incubator. Normal human mononuclear cells were prepared from heparinized bone marrow samples by centrifugation across a Ficoll-Hypaque density separation gradient. Human AB serum (Gemini Bioproducts, Woodland, Calif.) was used as the source of human complement.

2.3 Monoclonal Antibodies

Cells were cultured in RPMI 1640 with 10% newborn calf serum (Hyclone, Logan, Utah) supplemented with 2 mM glutamine, 100 U/ml of penicillin and 100 ug/ml of streptomycin (Sigma-Aldrich). 3F8, an IgG3 MoAb raised in a Balb/c mouse against human neuroblastoma, specifically recognizes the ganglioside GD2. The BALB/c myeloma proteins MOPC-104E, TEPC-183, MOPC-351, TEPC-15, MOPC-21, UPC-10, MOPC-141, FLOPC-21, and Y5606 were purchased from Sigma-Aldrich. MoAb R24 (anti-GD3), V1-R24, and K9 (anti-GD3) were gifts from Dr. A. Houghton, OKB7 and M195 (anti-CD33) from Dr. D. Scheinberg, and 10-11 (anti-GM2) from Dr. P. Livingston of Memorial Sloan Kettering Cancer Center, New York; and 528 (EGF-R) from Dr. J. Mendelsohn of MD Anderson, Houston, Tex. 2E6 (rat anti-mouse IgG3) was obtained from hybridomas purchased from American Type Culture Collection [ATCC] (Rockville, Md.). NR-Co-04 was provided by Genetics Institute (Cambridge, Mass.). In our laboratory, 5F9, 8H9, 3A5, 3E7, 1D7, 1A7 were produced against human neuroblastoma; 2C9, 2E10 and 3E6 against human breast carcinoma, and 4B6 against glioblastoma multiforme. They were all purified by protein A or protein G (Pharmacia, Piscataway, N.J.) affinity chromatography.

2.4 Anti-8H9 Anti-Idiotypic Antibodies

LOU/CN rats were immunized intraperitoneally (ip) with 8H9 (400 ug per rat) complexed with rabbit anti-rat serum (in 0.15 ml), and emulsified with an equal volume (0.15 ml) of Complete Freund's Adjuvant (CFA) (Gibco-BRL, Gaithersburg, Md.). The 8H9-rabbit-IgG complex was prepared by mixing 2 ml (8 mg) of purified 8H9 with 4 ml of a high titer rabbit anti-rat precipitating serum (Jackson Immunoresearch Laboratories, West Grove, Pa.). After incubation at 4° C. for 3 hours, the precipitate was isolated by centrifugation at 2500 rpm for 10 minutes, and resuspended in PBS. Three months after primary immunization, the rats were boosted ip with the same antigen in CFA. One month later, a 400 ug boost of 8H9-rabbit-anti-mouse complex was injected intravenously. Three days afterwards, the rat spleen was removed aseptically, and purified lymphocytes were hybridized with SP2/0-Ag14 (ATCC). Clones selection was based on specific binding to 8H9 and not to control antibody 5F9, a murine IgG1. Repeated subcloning using limiting dilution was done. Isotypes of the rat monoclonal antibodies were determined by Monoclonal Typing Kit (Sigma-Aldrich). Rat anti-idiotypic antibody clones (2E9, 1E12, 1F11) were chosen and produced by high density miniPERM bioreactor (Unisyn technologies, Hopkinton, Mass.), and purified by protein G affinity chromatography (Hitrap G, Pharmacia). The IgG fraction was eluted with pH 2.7 glycine-HCl buffer and neutralized with 1 M Tris buffer pH 9. After dialysis in PBS at 4° C. for 18 hours, the purified antibody was filtered through a 0.2 um millipore filter (Millipore, Bedford, Mass.), and stored frozen at −70° C. Purity was determined by SDS-PAGE electrophoresis using 7.5% acrylamide gel.

The "standard" ELISA to detect rat anti-idiotypic antibodies (Ab2) was as follows: Purified 8H9, or irrelevant IgG1 myeloma, were diluted to 5 ug/ml in PBS and 50 ul per well was added to 96-well flat-bottomed polyvinylchloride (PVC) microtiter plates and incubated for 1 hour at 37° C. Rows with no antigen were used for background subtraction. Filler protein was 0.5% BSA in PBS and was added at 100 ul per well, and incubated for 30 minutes at 4° C. After washing, 50 ul duplicates of hybridoma supernatant was added to the antigen-coated wells and incubated for 3 hours at 37° C. The plates were washed and a peroxidase-conjugated mouse anti-rat IgG+IgM (Jackson Immunoresearch Laboratory) at 100 ul per well was allowed to react for 1 hour at 4° C. The plate was developed using the substrate o-phenylenediamine (Sigma-Aldrich) (0.5 mg/ml) and hydrogen peroxide (0.03%) in 0.1 M citrate phosphate buffer at pH 5. After 30 minutes in the dark, the reaction was quenched with 30 ul of 5 N sulfuric acid and read using an ELISA plate reader.

2.5 Specificity by Direct Binding Assay

Fifty ul per well of purified mouse monoclonal antibodies or myelomas were coated onto 96-well PVC microtiter plates at 5 ug/ml for 60 minutes at 37° C., aspirated and then blocked with 100 ul of 0.5% BSA filler protein per well. After washing and air-drying, the wells were allowed to react with anti-idiotypic antibodies. The rest of the procedure was identical to that described in the "standard" assay.

2.6 Specificity by Inhibition Assay

To further examine the specificity of these anti-idiotypic antibodies, inhibition of 8H9 immunofluorescent staining of tumor cells by anti-idiotypic antibodies was tested. Purified 8H9 and anti-GD2 MoAb 3F8, (all 10 ug/ml in 0.5% BSA) were preincubated with various concentrations of anti-idiotypic antibodies for 30 minutes on ice before reacting with $10^6$ cells of either GD2-positive/8H9 positive LAN-1 (neuroblastoma) or GD2-negative/8H9-positive HTB-82 (rhabdomyosarcoma). The cells were then washed twice in PBS with 0.1% sodium azide and reacted with FITC-conjugated rat anti-mouse IgG (Biosource, Burlingame, Calif.) on ice for 30 minutes in the dark. The cells were washed in PBS with azide, fixed in 1% paraformaldehyde and analyzed by FACScan (Becton-Dickinson, Calif.). The mean fluorescence was calculated and the inhibition curve computed.

2.7 Construction of scFv Gene mRNA was isolated from 8H9 hybridoma cells using a commercially available kit (Quick Prep Micro mRNA Purification, Pharmacia Biotech) following the procedures outlined by the manufacturer. $5\times10^6$ hybridoma cells cultured in RPMI-1640 medium supplemented 10% calf serum, L-glutamine (2mmol/L), penicillin (100 u/L) and streptomycin sulphate (100 ug/ml) were pelleted by centrifugation at 800×g and washed once in RNase-free phosphate buffered saline (pH 7.4). The recentrifuged cells were lysed directly in the extraction buffer. Poly(A)-RNA was purified by a single fractionation over oligo (dT)-cellulose and eluted from oligo (dT) cellulose in the elution buffer. The mRNA sample was precipitated for 1 hour with 100 ug glycogen, 40 ul of 2M potassium acetate solution and 1 ml of absolute ethanol at −20° C. The nucleic acid was recovered by centrifugation at 10,000 ×g for 30 min. The sample was evaporated until dry, and dissolved in 20 ul RNase-free water.

ScFv gene was constructed by recombinant phage display. 5 ul of mRNA was reversely transcribed in a total volume of 11 ul reaction mixture and 1 ul dithiothreitol (DTT) solution for 1 hour at 37° C. For the PCR amplification of 8H9 immunoglobulin variable regions, light chain primer mix and the heavy chain primer set (Pharmacia) were added respectively to generate suitable quantities of the heavy (340 bp) and light (325 bp) chain. Following an initial 10 min dwell at 95° C., 5U AmpliTaq Gold DNA polymerase (Applied Biosystems, Foster City, Calif.) was added. The PCR cycle consisted of a 1 min denaturation step at 94° C., a 2 min annealing step at 55° C. and a 2 min extension step at 72° C. After 30 cycles of amplification, PCR derived fragment was purified by the glassmilk beads (Bio101, Vista, Calif.) and then separated by 1.5% agarose gel electrophoresis in TAE buffer and detected by ethidium bromide staining.

For the assembly and fill-in reaction, both purified heavy chain and light chain fragments were added to an appropriate PCR mixture containing a 15 amino acid linker-primer for 8H9, dNTPs, PCR buffer and Ampli Taq Gold DNA polymerase. PCR reactions were performed at 94° C. for 1 min, followed by a 4 min annealing reaction at 63° C. The heavy and light chain DNA of 8H9 were joined by the linker $(GGGS)_3$ (Pharmacia) into scFv in a VH-VL orientation after 7 thermocycles.

Using an assembled scFv DNA of 8H9 as template, a secondary PCR amplification (30 standard PCR cycles) was carried out using primers containing either Sfi I or Not I restriction sites. Thus, the Sfi I and Not I restriction sites were introduced to the 5' end of heavy chain and the 3' end of light chain, respectively. Amplified ScFv DNAs were purified by glassmilk beads and digested with Sfi I and Not I restriction endonucleases. The purified ScFv of 8H9 was inserted into the pHEN1 vector (kindly provided by Dr. G. Winter, Medical Research Council Centre, Cambridge, UK) containing Sfi I/Nco I and Not I restriction sites. Competent *E. coli* XL 1-Blue cells (Stratagene, La Jolla, Calif.) were transformed with the pHEN1 phagemid. Helper phage M13 KO7 (Pharmacia) was added to rescue the recombinant phagemid.

2.8 Enrichment of Recombinant Phagemid by Panning 50 ul of anti-8H9 idiotypic antibody 2E9 (50 ug/ml) in PBS was coated on the 96-well PVC microtiter plates and incubated at 37° C. for 1 hour. 100 ul of the supernatant from phage library was added to each well and incubated for 2 hours. The plate was washed 10 times with PBS containing 0.05% BSA. Antigen-positive recombinant phage captured by the anti-idiotype MoAb 2E9 was eluted with 0.1M glycine-HCl (pH 2.2 containing 0.1% BSA) and neutralized with 2 M Tris solution. This panning procedure was repeated three times. The phagemid 8HpHM9F7-1 was chosen for the rest of the experiments.

2.9 ELISA

The selected phage was used to reinfect *E. coli* XL 1-Blue cells. Colonies were grown in 2×YT medium containing ampicillin (100 ug/ml) and 1% glucose at 30° C. until the optical density of 0.5 unit at 600 nm was obtained. Expression of scFv antibody was induced by changing to the medium containing 100 uM IPTG (Sigma-Aldrich) and incubating at 30° C. overnight. The supernatant obtained from the medium by centrifugation was directly added to the plate coated with anti-idiotype 2E9. The pellet was resuspended in the PBS containing 1 mM EDTA and incubated on ice for 10 min. The periplasmic soluble antibody was collected by centrifugation again and added to the plate. After a 2-hour incubation at 37° C., plates were washed and anti-MycTag antibody (clone 9E10 from ATCC) was added for 1 hour at 37° C. After washing, affinity purified goat anti-mouse antibody (Jackson Immunoresearch) was allowed to react for 1 hour at 37° C. and the plates were developed with the substrate o-phenylenediamine (Sigma-Aldrich) as previously described.

2.10 Construction of ScFv-Human-1-CH2—CH3 Mouse Human-Chimeric Gene

A single gene encoding scFv8H9 was generated by PCR method using phagemid 8HpHM9F7-1 as the template. Secondary PCR amplification (30 PCR cycles) was carried out to insert the human IgG1 leader sequence at the 5'end of the scFv8H9 DNA plus the restriction sites at the two opposite ends, i.e. Hind III and Not I, at the 5' end of human IgG1 leader and at the 3' end of scFv8H9, respectively. Amplified human IgG1 leader—scFv8H9 DNA was purified by glassmilk beads and digested with Hind III and Not I restriction endonucleases according to manufacturer's instructions. The Hind III—Not I fragment of human IgG1 leader-scFv8H9 cDNA was purified on agarose gel and ligated into pLNCS23 vector carrying the human-(1-CH2—CH3 gene (kindly provided by Dr. J. Schlom, National Cancer Institute, NIH, Bethesda, Md.) (Shu et al., 1993). Competent *E. coli* XL 1-Blue cells were transformed with pLNCS23 containing the scFv phagemid. The scFv-CH2—CH3 DNA was primed with appropriate primers and sequenced using the Automated Nucleotide Sequencing System Model 373 (Applied Biosystems). The sequences agreed with the cDNA sequences of the light and heavy chains of 8H9 as well as the human- 1-CH2—CH3 available from GenBank, including the ASN 297 of the CH2 domain. In this construct, Cys220 of the genetic hinge was replaced by a proline residue, while Cys226 and Cys229 were retained in the functional hinge (Shu et al., 1993)

2.11 Cell Culture and Transfection

CHO cell or NSO myelomas cells (Lonza Biologics PLC, Bershire, UK) were cultured in RPMI 1640 (Gibco-BRL) supplemented with glutamine, penicillin, streptomycin (Gibco-BRL) and 10% fetal bovine serum (Gibco-BRL). Using effectene transfection reagent (Qiagen, Valencia, Calif.), recombinant ScFv8H9-human-1-CH2—CH3 was introduced via the pLNCS23 into CHO cell or NSO myelomas cells. Cells were fed every 3 days, and G418 (1 mg/ml; Gibco-BRL) resistant clones were selected. After subcloning by limiting dilution, chimeric antibodies were produced by high density miniPERM bioreactor from Unisyn Technologies using 0.5% ULG-FBS in Hydridoma-SFM (Invitrogen Corporation, Carlsbad, Calif.). The chimeric antibodies were purified by protein G (Pharmacia) affinity chromatography.

2.12 SDS-PAGE and Western Blot Analysis

The supernatant, the periplasmic extract and cell extract from the positive clones were separated by reducing and nonreducing SDS-PAGE. 10% SDS-polyacrylamide slab gel and buffers were prepared according to Laemmli (Laemmli, 1970). Electrophoresis was performed at 100V for 45 min. After completion of the run, western blot was carried out as described by Towbin (Towbin et al., 1979). The nitrocellulose membrane was blocked by 5% nonfat milk in TBS solution for 1 hour and incubated with anti-idiotype 2E9 antibody overnight at 4° C. After incubating with HRP-conjugated goat anti-rat Ig (Fisher Scientific Co., Pittsburgh, Pa.), the signal was detected by ECL system (Amersham-Pharmacia Biotech).

2.13 Cytotoxicity Assay

Target NMB7 or LAN-1 tumor cells were labeled with $Na_2^{51}CrO_4$ (Amersham Pharmacia) at 100 uCi/$10^6$ cells at 37° C. for 1 hour. After the cells were washed, loosely bound $^{51}Cr$ was leaked for 1 hour at 37° C. After further washing, 5000 target cells/well were admixed with lymphocytes to a final volume of 200 µl/well. Antibody dependent cell-mediated cytotoxicity (ADCC) was assayed in the presence of increasing concentrations of chimeric antibody. In complement mediated cytotoxicity (CMC), human complement (at 1:5, 1:15 and 1:45 final dilution) was used instead of lymphocytes. The plates were incubated at 37° C. for 4 hours. Supernatant was harvested using harvesting frames (Skatron, Lier, Norway). The released $^{51}Cr$ in the supernatant was counted in a universal gamma-counter (Packard Bioscience, Meriden, Conn.). Percentage of specific release was calculated using the formula 100%×(experimental cpm−background cpm)/(10% SDS releasable cpm−background cpm), where cpm were counts per minute of $^{51}Cr$ released. Total release was assessed by lysis with 10% SDS (Sigma-Aldrich), and background release was measured in the absence of cells. The background was usually <30% of total for either NMB7 or LAN-1 cells. Antibody 3F8 was used as the positive control (Cheung et al., 1985).

2.14 Iodination

MoAb was reacted for 5 min with $^{125}I$ (NEN Life Sciences, Boston, Mass.) and chloramine T (1 mg/ml in 0.3M Phosphate buffer, pH 7.2) at room temperature. The reaction was terminated by adding sodium metabisulfite (1 mg/ml in 0.3M Phosphate buffer, pH 7.2) for 2 min. Free iodine was removed with A1GX8 resin (BioRad, Richmond, Calif.) saturated with 1% HSA (New York Blood Center Inc., New York, N.Y.) in PBS, pH 7.4. Radioactive peak was collected and radioactivity (mCi/ml) was measured using a radioisotope calibrator (Squibb, Princeton, N.J.). Iodine incorporation and specific activities were calculated. Trichloroacetic acid (TCA) (Fisher Scientific) precipitable activity was generally >90%.

2.15 In Vitro Immunoreactivity of Iodinated Antibody.

Immunoreactivity of radioiodine labeled antibody was assayed using purified anti-idiotype antibody 2E9 as the antigen. Appropriate dilutions of $^{125}I$ labeled antibodies were added to plates in duplicates, and then transferred to freshly prepared antigen plates after 1 h of binding at 4° C., respectively. The final binding step was allowed to proceed overnight at 4° C. The total percent radioactivity bound was a summation of 3 time points for each antibody dilution. For native 8H9, maximum immunoreactivity averaged ~65%, while 8H9 scFv-Fc chimeric antibody was ~48%.

2.16 Animal Studies

Athymic nude mice (nu/nu) were purchased from NCI, Frederick Md. They were xenografted subcutaneously with LAN-1 neuroblastoma cell line ($2\times10^6$ cells/mouse) suspended in 100 ul of Matrigel (Beckton-Dickinson Bio-Sciences, Bedford, Mass.) on the flank. After 3 weeks, mice bearing tumors of 1-1.5 cm in longest dimension were selected. Animals were injected intravenously (retrorbital plexus) with 20 µCi of $^{125}I$ labeled antibody. They were anesthesized with ketamine (Fort Dodge Animal Health, Fort Dodge, Pa.) intraperitoneally and imaged at various time intervals with a gamma camera (ADAC, Milpitas, Calif.) equipped with grid collimators. Serial blood samples were collected at 5 min, 1, 2, 4, 8, 18, 24, 48, 72, 120 h from mice injected with 10-11 uCi $^{125}I$ labeled antibody. Groups of mice were sacrificed at 24 h, 48 h, and 120 h and samples of blood (cardiac sampling), heart, lung, liver, kidney, spleen, stomach, adrenal, small bowel, large bowel, spine, femur, muscle, skin, brain and tumor were weighed and radioactivity measured by a gamma counter. Results were expressed as percent injected dose per gram. Animal experiments were carried out under an IACUC approved protocol, and institutional guidelines for the proper and humane use of animals in research were followed.

3. Results 3.1 Anti-8H9-Idiotypic Antibodies

Figure 18C:
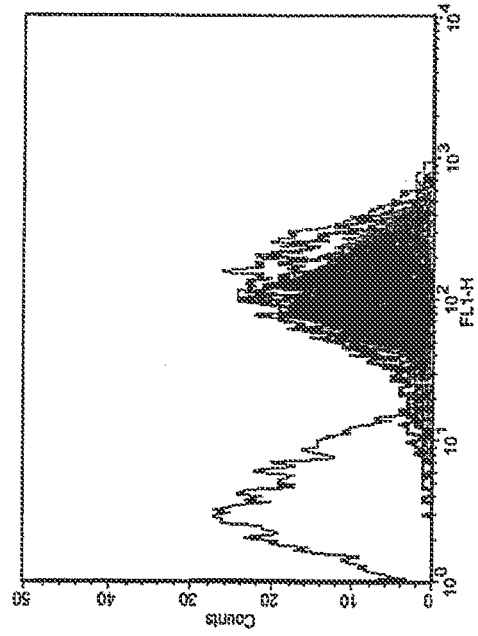

Rat hybridomas specific for 8H9 and nonreactive with control murine IgG1 were selected. After subcloning by limiting dilution, rat antibodies were produced by bulk culture in roller bottles and purified by protein G affinity column By ELISA, 2E9, 1E12, and 1F11, all of rat subclass IgG2a, were specific for 8H9, while nonreactive with a large panel of purified monoclonal antibodies (Table I). In contrast, the antibodies 3C2, 4C2 5C7, 7D6 and 8E12 from the same fusions were not specific for 8H9. The rest of the experiments in this study was carried out using antibody 2E9. 2E9 specifically inhibited the binding of 8H9 to LAN-1 neuroblastoma (FIG. 18A) and HTB82 rhabdomyosarcoma (FIG. 18B) while control rat IgG1 (A1G4) had no effect (FIG. 18C).

TABLE I

Anti-8H9-idiotypic antibodies: Specificity by ELISA

| MoAb | Class | 1E12 λ2a | 1F11 λ2a | 3C2 λ2b | 4C2 µ | 5C7 µ | 7D6 λ1 | 8E12 µ | 2E9 λ2a |
|---|---|---|---|---|---|---|---|---|---|
| MOPC 315 | a | − | − | +++ | − | − | − | − | − |
| 20.4 | λ1 | − | − | +++ | +++ | ++ | +++ | − | − |
| 2C9 | λ1 | − | − | +++ | +++ | +++ | +++ | ++ | − |
| 2E10 | λ1 | − | − | +++ | − | − | + | − | − |
| 3E6 | λ1 | − | − | +++ | +++ | +++ | +++ | +++ | − |
| 3E7 | λ1 | − | − | +++ | — | — | + | − | − |
| 4B6 | λ1 | − | − | +++ | ++ | ++ | +++ | − | − |
| 5F9 | λ1 | − | − | +++ | +++ | +++ | +++ | + | − |
| 8H9 | λ1 | +++ | ++ | +++ | +++ | ++ | +++ | − | ++ |
| MOPC 21 | λ1 | − | − | +++ | +++ | +++ | +++ | − | − |
| UJ 13A | λ1 | − | − | +++ | ++ | + | − | − | − |
| 3A5 | λ2a | − | − | +++ | − | − | − | − | − |
| HOPC-1 | λ2a | − | − | +++ | + | − | − | − | − |
| 3F8 | λ3 | − | − | +++ | − | − | − | − | − |
| FCOPC21 | λ3 | − | − | +++ | ++ | − | ++ | − | − |
| NRCO-04 | λ3 | − | − | +++ | − | − | − | − | − |
| R24 | λ3 | − | − | +++ | − | − | − | − | − |
| TIB114 | λ3 | − | − | +++ | + | − | ++ | − | − |
| Y5606 | λ3 | − | − | +++ | − | − | − | − | − |
| 3A7 | µ | − | − | + | − | − | − | − | − |

TABLE I-continued

Anti-8H9-idiotypic antibodies: Specificity by ELISA

| MoAb | Class | 1E12 λ2a | 1F11 λ2a | 3C2 λ2b | 4C2 μ | 5C7 μ | 7D6 λ1 | 8E12 μ | 2E9 λ2a |
|---|---|---|---|---|---|---|---|---|---|
| 3G6 | μ | − | − | +++ | − | − | − | − | − |
| 5F11 | μ | − | − | + | − | − | − | − | − |
| K9 | μ | − | − | +++ | − | − | − | − | − |
| MOPC 104E | μ | − | − | +++ | − | − | − | − | − |

Note:
OD <0.5 = −, 0.5 ~ 1 = +, 1 ~ 2 = ++, >2 = +++

3.2 Construction and Expression of 8H9 ScFv

After three rounds of panning on 2E9, the eluted phage was used to infect *E. coli* HB2151 cells and scFv expression was induced by IPTG. ScFv from periplasmic soluble protein fraction was tested for binding to 2E9 on ELISA. Three 8H9 scFv clones when compared with the MoAb 8H9 showed similar titers. The clone 8HpHM9F7-1 was selected for subcloning. The DNA sequence of 8HpHM9F7-1 agreed with those of the 8H9VH and 8H9VL as well as the CH2—CH3 region of human gamma chain. The supernatant, periplasmic soluble and cells pellet lysates of 8HpHM9F7-1 were separated by nonreducing SDS-PAGE, and analysed by western blotting. A protein band with molecular weight of 31KD was found in the supernatant, the periplasmic and cell pellet extracts using anti-MycTag antibody which recognized the sequence GAPVPDPLEPR. No such band was detected in control cells or 8HpHM9F7-1 cells without IPTG treatment.

3.3 Construction of Chimeric Mouse scFv-Human Fc

Chimeric clones from CHO and NSO were screened by ELISA binding on 2E9. Clone 1C5 from NSO and clone 1G1 from CHO were chosen for scale-up production. By SDS-PAGE and by western blot analysis, a single chain of 54 kD under reducing conditions, and a homodimer of 102 kD under nonreducing conditions were found (FIG. 19). Antigen specificity was demonstrated by its binding to tumor cells (FIG. 20A, dose titration), and its inhibition by anti-idiotypic antibody 2E9 (FIG. 20B) on FACS analysis.

3.4 In Vitro and In Vivo Properties of scFv-Human Fc

The scFv-Fc chimeric antibody was inefficient in mediating ADCC in the presence of human lymphocytes or human neutrophils (17% maximum cytotoxicity at 50:1 E:T ratio compared to >50% by the murine IgG3 MoAb 3F8). It was also ineffective in CMC (data not shown). In biodistribution studies, it localized well to HTB82 and LAN-1 xenografts (FIG. 21). Blood clearance studies showed that chimeric 8H9 (102 kD MW) had T-½ of 5.3 h, and T-½ of 43 h when compared to averages of 4.5 h and 71 h, respectively, for native 8H9 (160 kD MW), a result of the smaller molecular size of the construct (FIG. 22). Similarly, although the percent injected dose per gram of the chimeric construct was lower for all tissues (average of 44% at 48 h, and 75% at 120 h), the tumor-non tumor ratios were similar to those of native 8H9 (98% at 48 h and 85% at 120 h) (Table II).

TABLE II

Percent Injected Dose per gram and Tumor-non-tumor ratios

| | chimeric | | | native | |
|---|---|---|---|---|---|
| Organs | 24 | 48 | 120 | 48 | 120 |
| | Percent Injected dose/gm over time (h) | | | | |
| Skin | 1.4 | 0.7 | 0.2 | 1.8 | 0.7 |
| Heart | 1.3 | 0.9 | 0.4 | 2.6 | 0.7 |
| Lung | 2.9 | 1.9 | 0.5 | 4.0 | 1.1 |
| Liver | 1.2 | 0.8 | 0.2 | 1.4 | 0.5 |
| Spleen | 0.9 | 0.5 | 0.2 | 1.4 | 0.4 |
| Kidney | 1.5 | 0.9 | 0.5 | 1.9 | 0.5 |
| Adrenal | 0.9 | 0.5 | 0.5 | 1.8 | 0.3 |
| Stomach | 1.3 | 0.6 | 0.3 | 1.3 | 0.5 |
| Small intestine | 0.6 | 0.3 | 0.2 | 0.7 | 0.2 |
| Large intestine | 0.6 | 0.3 | 0.2 | 0.6 | 0.2 |
| Bladder | 1.2 | 0.6 | 0.4 | 1.0 | 0.6 |
| Muscle | 0.5 | 0.3 | 0.2 | 0.5 | 0.2 |
| Femur | 0.6 | 0.3 | 0.2 | 0.8 | 0.2 |
| Spine | 0.6 | 0.4 | 0.2 | 0.8 | 0.3 |
| Tumor | 4.0 | 3.6 | 2.1 | 9.4 | 4.0 |
| Brain | 0.2 | 0.1 | 0.1 | 0.2 | 0.1 |
| Blood | 5.3 | 3.1 | 1.2 | 8.3 | 2.3 |
| | Tumor:Nontumor ratios over time (h) | | | | |
| Skin | 3.0 | 6.0 | 10.7 | 5.2 | 7.2 |
| Heart | 3.3 | 4.0 | 5.6 | 3.6 | 7.7 |
| Lung | 1.6 | 2.2 | 4.5 | 2.3 | 5.0 |
| Liver | 3.5 | 5.2 | 8.7 | 6.5 | 10.1 |
| Spleen | 5.1 | 8.1 | 12.8 | 6.7 | 15.1 |
| Kidney | 2.8 | 4.3 | 5.9 | 5.1 | 8.9 |
| Adrenal | 4.8 | 8.7 | 10.0 | 5.8 | 11.6 |
| Stomach | 3.6 | 6.7 | 13.8 | 7.5 | 14.5 |
| Small intestine | 6.6 | 11.8 | 16.0 | 13.3 | 21.7 |
| Large intestine | 7.1 | 12.7 | 25.9 | 15.7 | 28.5 |
| Bladder | 3.5 | 14.3 | 10.2 | 12.4 | 12.3 |
| Muscle | 7.9 | 13.6 | 21.3 | 18.2 | 26.8 |
| Femur | 6.7 | 11.8 | 20.5 | 11.8 | 27.9 |
| Spine | 6.7 | 6.8 | 14.2 | 11.1 | 19.6 |
| Tumor | 1.0 | 1.0 | 1.0 | 1.0 | 1.0 |
| Brain | 22.7 | 40.9 | 38.7 | 44.6 | 68.2 |
| Blood | 0.8 | 1.2 | 1.8 | 1.1 | 2.3 |

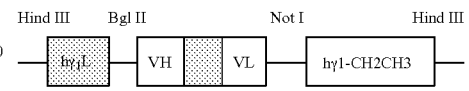

Hind III    Bgl II         Not I                Hind III
[hγ1]—[VH]—[VL]—[hγ1-CH2CH3]

4. Discussion

We demonstrated that by using rat anti-idiotypic antibody as antigen surrogate, scFv and scFv-fusion proteins can be conveniently produced. As proof of principle we utilized the anti-idiotypic antibody to clone scFv from the murine hybridoma cDNA library. The anti-idiotypic antibody was then used to select for scFv-Fc chimeric antibodies. Both the scFv and scFv-Fc fusion protein derived by our method were specific for the natural antigen, comparable to the native antibody 8H9. However, the scFv-Fc fusion protein could only mediate ADCC poorly and not CMC at all.

While scFv provides the building block for scFv-fusion proteins, it is not the ideal targeting agent by itself. Being a small protein, its clearance is rapid. Moreover, it is often retained by the kidney, delivering undesirable side effects if the scFv construct is cytotoxic. Since avidity is a key parameter in tumor targeting in vivo, its biggest limitation is its uni-valency and often suboptimal affinity for the antigen. By using VH-VL linkers of decreasing length, spontaneous dimeric, trimeric and polymeric scFv have been produced. However, these oligomers are not bonded by covalent linkage, and may dissociate in vivo. An alternative approach is to take advantage of the human Fc, which has the natural ability to homodimerize through disulfide-bonds, thereby allowing the juxtaposition of two binding domains. Fc functions such as CMC and ADCC could also be achieved achieved (Shu et al., 1993; Kato et al., 1995; Brocks et al., 1997; Wang et al., 1999; Powers et al., 2001). Unlike standard 2-chain chimeric antibodies, only one polypeptide is needed for the scFv-Fc chimeric; unbalanced synthesis of heavy and light chains is not an issue. Larger dimeric fragments are also likely to have increased serum-half life compared to scFv and thus improved tumor targeting (Adams et al., 1993; Wu et al., 1996). Homodimerization of tumor cell-surface antigens by soluble antibody may also trigger apoptosis of tumor cells (Ghetie et al., 1997). No less important is the availability of validated purification techniques using protein A or protein G through their binding to the Fc portion (Powers et al., 2001). Tetravalent scFv (monospecific or bispecific) are natural extensions of the diabody approach to scFv-Fc fusion strategy (Alt et al., 1999; Santos et al., 1999), where a significant increase in avidity can be achieved. More recently, scFv-streptavidin fusion protein has been produced for pretargeted lymphoma therapy (Schultz et al., 2000). Here scFv-streptavidin forms natural tetramers, to which biotinyated ligands can bind with high affinity.

Anti-idiotypic antibodies have greatly facilitated clone selection in the construction of soluble scFv-fusion proteins or cell bound surface scFv. We have successfully applied similar technology to anti-GD2 monoclonal antibodies (Cheung et al., 1993). Being immunoglobulins, their structure, stability, biochemistry, are generally known. Unlike natural antigens where each individual system has its unique and difficult to predict properties. As surrogate antigens, anti-idiotypic antibodies are ideal for standardization and quality control, especially for initial clinical investigations where the nature of the antigen is not fully understood. Potential limitations exist for the anti-idiotype approach. Only those anti-ids (Ab2) that recognize the antigen-binding site of the immunizing MoAb can mimic the original antigen. A reliable test for Ab2 is its ability to induce an antigen-specific immune response. Alternatively, antigen specificity of the scFv selected by the anti-idiotype must be validated by binding to cells or membrane preparations. Once validated, the anti-idiotype can be used as antigen surrogate for cloning and assay of other scFv-fusion proteins.

Our scFv-Fc fusion protein lacks CMC and ADCC activity. This finding differs from previous scFv-Fc fusion proteins (Shu et al., 1993; Wang et al., 1999; Powers et al., 2001). This is unlikely to be due to the p58 antigen recognized by this scFv, since anti-GD2 scFv-Fc made with the same cassette were also deficient in CMC and ADCC activity (data not shown). One possible explanation might be due to the oligosaccharide structures in the Fc region (Wright and Morrison, 1997). In normal IgG, these oligosaccharides are generally of complex biantennary type, with low levels of terminal sialic acid and bisecting N-acetylglucosamine (GlcNAc), the latter being critical for ADCC. ADCC function is often inefficient among chimeric antibodies expressed in cell lines which lack the enzyme (1,4)-N-acetylglucosaminyltransferase III (GnIII) (Umana et al., 1999), that catalyzes the formation of bissecting oligosaccharides. This enzyme can be transfected into producer lines to increase the level of bisecting GlcNAc and to increase the ADCC function of secreted chimeric antibodies (Umana et al., 1999). Since our chimeric antibodies from both CHO and NSO expression systems were inefficient in CMC and ADCC, both cell lines may be lacking in the GnIII enzyme. It is also possible that the absence of the CH1 domain in the Fc may modify the accessability of the ASN297 residue to glycosyltransferases in some scFv-Fc constructs such as ours (Wright and Morrison, 1997). On the other hand, an scFv-Fc that lacks binding to Fc receptor may have less nonspecific binding to white cells, thereby decreasing blood pooling in targeted therapy. These findings may have implications in scFv-Fc strategies to improve effector functions.

References

Adams, G. P., McGartney, J. E., Tai, M.-S., Oppermann, H., Huston, J. S., Stafford, W. F., Bookman, M. A., Fand, I., Houston, L. L. and Weiner, L. W. (1993) Highly specific in vivo tumor targeting by monovalent and divalent forms of 741F8 anti-c-erbB-2 single-chain Fv. Cancer Research 53, 4026-4034.

Alt, M., Muller, R. and Kontermann, R. E. (1999) Novel tetravalent and bispecific IgG-like antibody molecules combining single-chain diabodies with the immunoglobulin γ1 Fc or CH3 region. FEBS Letters 454, 90-94.

Bird, R. E., Hardman, K. D., Jacobson, J. W., Johnson, S., Kaufman, B. M., Lee, S. M., Lee, T., Pope, S. H., Riordan, G. S. and Whitlow, M. (1988) Single-chain antigen-binding proteins. Science 242, 423-426.

Brocks, B., Rode, H. J., Klein, M., Gerlach, E., Dubel, S., Little, M., Pfizenmaier, K. and Moosmayer, D. (1997) A TNF receptor antagonistic scFv, which is not secreted in mammalian cells, is expressed as a soluble mono- and bivalent scFv derivative in insect cells. Immunotechnology 3, 173-84.

Burton, D. R. and Barbas III, C. G. (1994) Human antibodies from combinatorial libraries. Advances in Immunology 57, 191-280.

Cai, X. and Garen, A. (1995) Anti-melanoma antibodies from melanoma patients immunized with genetically modified autologous tumor cells: selection of specific antibodies from single-chain Fv fusion phage libraries. Proceedings of the National Academy of Sciences of the United States of America 92, 6537-41.

Cheung, N. K., Canete, A., Cheung, I. Y., Ye, J. N. and Liu, C. (1993) Disialoganglioside GD2 anti-idiotypic monoclonal antibodies. International Journal of Cancer 54, 499-505.

Cheung, N. K., Saarinen, U., Neely, J., Landmeier, B., Donovan, D. and Coccia, P. (1985) Monoclonal antibodies to a glycolipid antigen on human neuroblastoma cells. Cancer Research 45, 2642-2649.

DeNardo, S. J., DeNardo, G. L., DeNardo, D. G., Xiong, C. Y., Shi, X. B., Winthrop, M. D., Kroger, L. A. and Carter, P. (1999) Antibody phage libraries for the next generation of tumor targeting radioimmunotherapeutics. Clinical Cancer Research 5, 3213s-3218s.

Eshhar, Z., Waks, T., Gross, G. and Schindler, D. G. (1993) Specific activation and targeting of cytotoxic lymphocytes through chimeric single chains consisting of antibody-binding domains and the gamma or zeta subunits of the immunoglobulin and T-cell receptors. Proceedings of the National Academy of Sciences of the United States of America 90, 720-4.

George, A. J. T., Spooner, R. A. and Epenetos, A. A. (1994) Applications of Monoclonal Antibodies in Clinical Oncology. Immunology Today 15, 559-561.

Ghetie, M. A., Podar, E. M., Ilgen, A., Gordon, B. E., Uhr, J. W. and Vitetta, E. S. (1997) Homodimerization of tumor-reactive monoclonal antibodies markedly increases their ability to induce growth arrest or apoptosis of tumor cells. Proceedings of the National Academy of Sciences of the United States of America 94, 7509-14.

Huston, J. S., Levinson, D., Mudgett-Hunter, M., Tai, M. S., Novotny, J., Margolies, M. N., Ridge, R. J., Bruccoleri, R. E., Haber, E. and Crea, R. (1988) Protein engineering of antibody binding sites: recovery of specific activity in an anti-digoxin single-chain Fv analogue produced in Escherichia coli. Proceedings of the National Academy of Sciences of the United States of America 85, 5879-83.

Kato, T., Sato, K., Suzuki, S., Sasakawa, H., Kurokawa, M., Nishioka, K. and Yamamoto, K. (1995) Mammalian expression of single chain variable region fragments dimerized by Fc regions. Molecular Biology Reports 21, 141-146.

Kipriyanov, S. M., Bretling, F., Little, M. and Dubel, S. (1995) Single-chain antibody streptavidin fusions: tetrameric bifunctional scFv-complexes with biotin binding activity and enhanced affinity to antigen. Human Antibodies Hybridomas 6, 93-101.

Laemmli, U. K. (1970) Cleavage of structural proteins during the assembly of the head of bacteriophage T4. Nature 227, 680-85.

Lu, J. and Sloan, S. R. (1999) An alternating selection strategy for cloning phage display antibodies. Journal of Immunological Methods 228, 109-119.

Michael, N. P., Chester, K. A., Melton, R. G., Robson, L., Nicholas, W., Boden, J. A., Pedley, R. B., Begent, R. H., Sherwood, R. F. and Minton, N. P. (1996) In vitro and in vivo characterisation of a recombinant carboxypeptidase G2::anti-CEA scFv fusion protein. Immunotechnology 2, 47-57.

Modak, S., Kramer, K., Humayun, G., Guo, H. F. and Cheung, N. K. V. (2001) Monoclonal antibody 8H9 targets a novel cell surface antigen expressed by a wide spectrum of human solid tumors. Cancer Research 61, 4048-4054.

Powers, D. B., Amersdorfer, P., Poul, M. A., Nielsen, U. B., Shalaby, R., Adams, G. P., Weiner, L. M. and Marks, J. D. (2001) Expression of single-chain Fv-Fc fusions in pinchia pastoris. Journal of Immunological Methods 251, 123-135.

Raag, R. and Whitlow, M. (1995) Single-chain Fvs. FASEB Journal 9, 73-80. Santos, A. D., Kashmiri, S. V., Hand, P. H., Schlom, J. and Padlan, E. A. (1999) Generation and characterization of a single gene-encoded single-chain-tetravalent antitumor antibody. Clinical Cancer Research 5, 3118s-3123s.

Schultz, J., Lin, Y., Sanderson, J., Zuo, Y., Stone, D., Mallett, R., Wilbert, S. and Axworthy, D. (2000) A tetravalent single-chain antibody-streptavidin fusion protein for pretargeted lymphoma therapy. Cancer Research 60, 6663-6669.

Shu, L., Qi, C. F., Schlom, J. and Kashmiri, S. V. (1993) Secretion of a single-gene-encoded immunoglobulin from myeloma cells. Proceedings of the National Academy of Sciences of the United States of America 90, 7995-9.

Thanavala, Y. M., Brown, S. E., Howard, C. R., Roitt, I. M. and Steward, M. W. (1986) A surrogate hepatitis B virus antigenic epitope represented by a synthetic peptide and an internal image antiidiotype antibody. Journal of Experimental Medicine 164, 227-236.

Towbin, H., Staehelin, T. and Gordon, J. (1979) Electrophoretic transfer of proteins from polyacrylamide gels to nitrocellulose sheets: procedure and some applications. Proceedings of the National Academy of Sciences of the United States of America 76, 4350-4.

Tur, M. K., Huhn, M., Sasse, S., Engert, A. and Barth, S. (2001) Selection of scFv phages on intact cells under low pH conditions leads to a significant loss of insert-free phages. Biotechniques 30, 404-413.

Umana, P., Jean-Mairet, J., Moudry, R., Amstutz, H. and Bailey, J. E. (1999) Engineered glycoforms of an antineuroblastoma IgG1 with optimized antibody-dependent cellular cytotoxic activity. Nature Biotechnology 17, 176-180.

Wagner, U., Schlebusch, H., Kohler, S., Schmolling, J., Grunn, U. and Krebs, D. (1997) Immunological responses to the tumor-associated antigen CA125 in patients with advanced ovarian cancer induced by the murine monoclonal anti-idiotype vaccine ACA125. Hybridoma 16, 33-40.

Wang, B., Chen, Y. B., Ayalon, O., Bender, J. and Garen, A. (1999) Human single-chain Fv immunoconjugates targeted to a melanoma-associated chondroitin sulfate proteoglycan mediate specific lysis of human melanoma cells by natural killer cells and complement. Proceedings of the National Academy of Sciences of the United States of America 96, 1627-32.

Watters, J. M., Telleman, P. and Junghans, R. P. (1997) An optimized method for cell-based phage display panning. Immunotechnology 3, 21-9.

Wikstrand, C. J., Hale, L. P., Batra, S. K., Hill, M. L., Humphrey, P. A., Kurpad, S. N., McLendon, R. E., Moscatello, D., Pegram, C. N. and Reist, C. J. (1995) Monoclonal antibodies against EGFRvIII are tumor specific and react with breast and lung carcinomas and malignant gliomas. Cancer Research 55, 3140-8.

Winter, G., Griffiths, A. D., Hawkins, R. E. and Hoogenboom, H. R. (1994) Making antibodies by phage display technology. Annual Review of Immunology 12, 433-55.

Winter, G. and Milstein, C. (1991) Man-made antibodies. Nature 349, 293-299.

Wright, A. and Morrison, S. L. (1997) Effect of glycosylation on antibody function: implications for genetic engineering. Trends in Biotechnology 15, 26-31.

Wu, A. M., Chen, W., Raubitschek, A., Williams, L. E., Neumaier, M., Fischer, R., Hu, S. Z., Odom-Maryon, T., Wong, J. Y. and Shively, J. E. (1996) Tumor localization of anti-CEA single-chain Fvs: improved targeting by non-covalent dimers Immunotechnology 2, 21-36.

Sixth Series of Experiments

Using Anti-Idiotypic Antibody to Enhance scFv Chimeric Immune Receptor Gene Transduction and Clonal Expansion of Human Lymphocytes Background: Chimeric immune receptors (CIR) transduced into lymphocytes link target recognition by single chain antibody Fv (scFv) to activation through CD28/TCR. signaling. The murine monoclonal antibody (MoAb) 8H9 reacts with a novel antigen widely expressed on solid tumors (Cancer Research 61:4048, 2001). We want to test if its anti-idiotypic MoAb 2E9 can optimize the CIR technology.

Methods: Rat anti-idiotypic MoAb 2E9 (IgG2a) was used as an antigen surrogate for initial cloning of 8H9scFv from the hybridoma cDNA library. A CIR consisting of human CD8-leader sequence, 8H9scFv, CD28 (transmembrane and cytoplasmic domains), and TCR-zeta chain was constructed, ligated into the pMSCVneo vector, and used to transfect the packaging line GP+envAM12 bearing an amphotropic envelope.

Results: Three sequential affinity enrichments with MoAb 2E9 significantly improved the percentage of producer clones positive for surface 8H9-scFv and the efficiency of their supernatant in transducing the indicator cell line K562. By three weeks of in vitro culture, >95% of transduced primary human lymphocytes were CIR-positive. With periodic stimulation with soluble 2E9, these lymphocytes underwent "monoclonal" expansion, reaching 50-100 fold increase by 2 months. They mediated antigen-specific non-MHC restricted cytotoxicity efficiently. When injected intravenously, they inhibited tumor growth in SCID mice xenografted with rhabdomyosarcoma.

Conclusion: Anti-idiotypic antibody may provide a useful tool, especially for carbohydrate or unstable antigens, in facilitating the cloning of scFv and their CIR fusion constructs, as well as their transduction into human lymphocytes.

Introduction

Adoptive cell therapy using ex vivo expanded tumor-selective T-cells can effect dramatic remissions of virally induced malignancies, a process critically dependent on clonal frequency, where rapid exponential expansion of specific cytolytic T-lymphocytes (CTL) is required. T-cells proliferate when activated (e.g. anti-CD3) but apoptose unless a costimulatory signal (e.g. anti-CD28) is provided (1). However, human tumor targets often lack costimulatory molecules (e.g. CD80), or overstimulate inhibitory receptors (e.g. CTL4) such that the CD28 pathway is derailed. In addition, many tumors downregulate major histocompatibility complex (MHC) molecules to escape engagement by the T-cell receptor (TCR). Through genetic engineering, chimeric immune receptors (CIR) linking tumor-selective scFv to T-cell signal transduction molecules (e.g. TCR-zeta chain and CD28) will activate lymphocytes following tumor recognition, triggering the production of cytokines and tumor lysis (2-7). T-cell can also be genetically engineered to secrete cytotoxic cytokines (8), toxins (9) or to metabolize prodrugs (10, 11). However, significant technologic gaps remain: (1) Gene transduction into human lymphocytes is inefficient, (2) antigen specific T-cells cannot be easily enriched and expanded, and (3) optimal T-cell activation may require multiple signals. Furthermore, although CIR redirected T-cells can recycle their lytic activity (12), a costimulatory signal, either through CD28 or 4-1BB engagement, may help reduce activation-induced apoptotic death. CIR with multidomains was recently described, where the intracellular domain of CD28 was ligated to the 5' end of TCR zeta chain and introduced into Jurkat cells, with the expected "two birds with one stone effect" when scFv binds to tumor cells (13). IL-2 production was 20 times more than CIR with zeta chain only. Whether this same effect can be achieved with primary human T-cells is not known.

To monitor scFv gene expression, anti-linker antibody may be useful, although its efficiency depends on the accessibility of the scFv-linker portion. Although purified antigens can also be used to monitor scFv expression, certain classes (complex carbohydrates or unstable antigens) can be difficult to prepare and their chemistry highly variable. Without a standardized reagent for affinity purification or enrichment of virus producer cells, monitoring and sorting of transduced lymphocytes, CIR technology remains inefficient. Recently Eshhar et al described a dicistronic construct consisting of scFv-CD28-(and green fluorescent protein (GFP), where the latter was used to monitor gene transduction and to enrich producer lines (7). Although GFP can validate the gene transfer process, its added immunogenicity and its safety in clinical applications remain uncertain.

Anti-idiotypic antibodies are frequently used as antigen-mimics for infectious diseases and cancer (14, 15). Internal image rat anti-idiotypic antibodies can be conveniently produced against mouse MoAb. Since large scale production of clinical grade MoAb is now routine, anti-idiotypic antibodies may be ideal surrogates especially if the antigen is not easily available. In addition, the biochemistry of immunoglobulins in positive selection (panning, affinity chromatography, sorting) and binding assays is well-known and is easy to standardize. We recently described a novel tumor antigen reactive with a murine MoAb 8H9 (16). The antigen was difficult to purify given its lability and glycosylation.

Here we demonstrate that anti-idiotypic MoAb can be used as surrogate antigens for cloning CIR into lymphocytes, i.e. a CIR of 8H9scFv, human CD28 and human TCR-zeta chain. Anti-idiotypic MoAb allows rapid affinity enrichment of producer cell line, monitoring of scFv expression on cells, and in vitro clonal expansion of transduced lymphocytes. Highly cytotoxic lymphocytes, both in vitro and in vivo, can be produced in bulk. Besides providing an antigen surrogate, anti-idiotypic MoAb appears to have utility for the optimization and quality control of scFv-based gene therapies.

Materials and Methods

Materials. Cells were cultured in RPMI 1640 with 10% newborn calf serum (Hyclone, Logan, Utah) supplemented with 2 mM glutamine, 100 U/ml of penicillin and 100 ug/ml of streptomycin. The BALB/c myeloma proteins, MOPC-104E, TEPC-183, MOPC-351, TEPC-15, MOPC-21, UPC-10, MOPC-141, FLOPC-21, Y5606, were purchased from Sigma-Aldrich Co., St. Louis, Mo. MoAb R24, V1-R24, and K9 were gifts from Dr. A. Houghton, OKB7 and M195 from Dr. D. Scheinberg, and 10-11 (anti-GM2) from Dr. P. Livingston of Memorial Sloan-Kettering Cancer Center, New York; 528 from Dr. J. Mendelsohn (MD Anderson Cancer Center, Houston, Tex.). 2E6 (rat anti-mouse IgG3) was obtained from hybridomas purchased from ATCC (Rockville, Md.). NR-Co-04 was provided by Genetics Institute (Cambridge, Mass.). LS2D173 (anti-GM2) was provided by Dr. L. Grauer (Hybritech, Calif.). From our laboratory, 3F8 was an IgG3 MoAb specific for ganglioside GD2 (17); 5F9, 8H9, 3A5, 3E7, 1D7, 1A7 were produced against human neuroblastoma, 2C9, 2E10 and 3E6 against human breast carcinoma: 4B6 against glioblastoma multiforme. They were all purified by protein A or protein G (Pharmacia, Piscataway, N.J.) affinity chromatography.

Anti-8119-idiotypic MoAb. Anti-idiotypic antibodies were produced from LOU/CN rats as previously described (18). Clones were selected based on selective binding to 5F11 antibody and not to other myelomas. Repeated subcloning was done using limiting dilution until the cell lines became stable. Among the three specific rat IgG2a clones (2E9, 1E12, 1F11), 2E9 was chosen for scaled up production using high density miniPERM bioreactor (Unisyn technologies, Hopkinton, Mass.), and purified by protein G affinity chromatography (Hitrap G, Amersham-Pharmacia, Piscataway, N.J.). The IgG fraction was eluted with pH 2.7 glycine-HCl buffer and neutralized with 1 M Tris buffer pH 9. After dialysis in PBS at 4° C. for 18 hours, the purified antibody was filtered through a 0.2 um Millipore filter (Millipore Inc. Bedford Mass.), and stored frozen at −70° C. Purity was determined by SDS-PAGE electrophoresis using 7.5% acrylamide gel. ELISA was used to detect rat anti-idiotypic antibodies (Ab2) as previously described (18). Rat IgG1 anti-5F11 anti-idiotypic MoAb was similarly produced.

Construction of ScFv Gene scFv was constructed from 8H9 hybridoma cDNA by recombinant phage display using a scFv construction kit according to manufacturer's instructions with modifications (Amersham-Pharmacia). Amplified ScFv DNA was purified by glassmilk beads and digested with Sfi I and Not I restriction endonucleases. The purified scFv of 8H9 was inserted into the pHEN1 vector (kindly provided by Dr. G. Winter, Medical Research Council Centre, Carmbridge, UK) containing SfiI/NcoI and Not I restriction sites. Competent El Coli XL 10Blue cells (Stratagene, La Jolla, Calif.) were transformed with the pHEN1 phagemid. Helper phage M13 KO7 (Pharmacia) was added to rescue the recombinant phagemid. The phagemid 8HpHM9F7-1 was chosen for the rest of the experiments. The supernatant, the periplasmic extract and cell extract from the positive clones separated by nonreducing SDS-PAGE and western blotting (19) using anti-Myc Tag antibody demonstrated a 31 kD band.

Enrichment of Recombinant Phagemid by Panning 50 ul of anti-8H9 idiotype antibody 2E9 (50 ug/ml) in PBS were coated on the 96-well polyvinyl microtiter plates and incubated at 37° C. for 1 hour. 100 ul of the supernatant from phage library were added to each well and incubated for 2 hours. The plate was washed 10 times with PBS containing 0.05% BSA. Antigen-positive recombinant phage captured by the idiotype 2E9 was eluted with 0.1M HCl (pH 2.2 with solid glycine and 0.1% BSA) and neutralized with 2M Tris solution. This panning procedure was repeated three times.

ELISA The selected phage was used to reinfect *E. coli* XL 1-Blue cells. Colonies were grown in 2×YT medium containing ampicillin (100 ug/ml) and 1% glucose at 30° C. until the optical density at 600 nm of 0.5 was obtained. Expression of scFv antibody was induced by change of the medium containing 100 uM IPTG (Sigma-Aldrich) and incubating at 30° C. overnight. The supernatant obtained from the medium by centrifugation was directly added to the plate coated with idiotype 2E9. The pellet was resuspended in the PBS containing 1 mM EDTA and incubated on ice for 10 min. The periplasmic soluble antibody was collected by centrifugation again and added to the plate. After incubating 2 hours at 37° C., plates were washed and anti-MycTag antibody (clone 9E10 from ATCC) was added to react for 1 hour at 37° C. After washing, affinity purified goat anti-mouse antibody (Jackson Immunoresearch, West Grove, Pa.) was allowed to react for 1 hour at 37° C. and the plates were developed with the substrate o-phenylenediamine (Sigma-Aldrich).

Construction of sc8H9-hCD28$_{TM}$-hCD28$_{cyto}$-hTCRzeta-pMSCVneo Using the assembled gene sequences, secondary PCR amplifications using synthetic oligodeoxynucleotide primers (see below) were performed. Briefly, a 50 µl reaction mixture containing 200 µM of each deoxynucleotide triphosphate, 0.2 µM of each primer, 2 units of AmpliTag Gold DNA polymerase (Appled Biosystems, Foster City, Calif.), and 50 ng of template DNA was subjected to a 10 min denaturation and activation step at 95° C., followed by 30 cycles of denaturation (1 min at 95° C.), annealing (2 min at 55° C.), and extension (2 min at 72° C.). This was followed by a final extension for 8 min at 72° C. Each of the amplified products was purified with Geneclean Kit (Bio 101, Vista, Calif.).

Synthetic Oligodeoxynucleotide Primers for DNA Amplification

Templates for DNA Amplification and Construction The single gene encoding hCD8a-leader-sc3G6-CD28 was previously described (20). Its cDNA was generated by PCR using the Hpa I, Xho I fragment of hCD8a-leader-scFv-CD28 cDNA, and ligated into pMSCVneo vector (Clontech, Palo Alto, Calif.). ScFv-8H9 was amplified from the 8HpHM9F7-1 phagemid. Excised 8H9 scFv gene was then swapped into the hCD8a-leader-scFv3G6-CD28 cassette of pMSCVneo using the Cla I-Not I restriction enzymes. Human TCR-zeta-chain was amplified from the plasmid pcDNA3.1/VJABLZH (kindly provided by Dr. Ira Bergman, University of Pittsburgh, Pa.), and ligated downstream of CD28 gene, using Xho I and Bgl II restriction sites. Using the method supplied by manufacturer (Stratagene), competent *E. coli* XL 1-Blue cells were transformed with the vector pMSCVneo containing the insert. All gene constructs were checked by DNA sequencing.

Cell Culture and Transfection The amphotropic packaging cell line GP+envAM12 and all retroviral producer lines were maintained in Dulbecco's modified Eagle's medium (Gibco-BRL, Gaithersburg, Md.) supplemented with glutamine, penicillin, streptomycin (Gibco-BRL), and 10% fetal bovine serum (Gibco-BRL). Using effectene transfection Reagent (Qiagen, Valencia, Calif.), recombinant retrovirus was produced by the transfection of vector DNA into GP+envAM12 packaging cells (kindly provided by Genetix Pharmaceuticals, Cambridge, Mass.). Cells were fed every 3 days with G418 (400 ug/ml; Gibco-BRL). Resistant clones were selected after a 10-day period.

Enrichment and Cloning of Packing Lines by Affinity Column The retroviral producer lines were affinity enriched using MACS goat anti-rat IgG MicroBeads on the Mini-MACS system (Miltenyi, Auburn, Calif.). In brief, the transduced packing lines were reacted with purified rat anti-idiotypic antibodies (10 ug per $10^6$ packing cells) on ice for 30 minutes, washed and then applied to the anti-rat column. Cell were eluted according to manufacturer's instructions and recultured at 37° C. for 24 hours. Following staining with anti-idiotypic antibody 2E9 or 1E12, immunofluorescence was detected with FITC conjugated mouse anti-rat IgG antibody and analyzed by a FACSCalibur flow cytometer (Becton Dickinson Immunocytometry systems, San Jose, Calif.). A series of three affinity purifications is performed on the retroviral producer line before subcloning by limiting dilution. Virus-containing supernatant from each clone was used to

```
hCD8a leader - scFv - CD28:
355 S Sense Primer (Hpa I - Human CD8a Leader)
5'- TTA TTA CGA GTT/AAC ATG GCC TTA CCA GTG ACC -3';

355 A Antisense Primer (Xho I - Human CD28)
5'- CTT GGT C/TCGAG TGT CAG GAG CGA TAG GCT GC -3';

scFv8H9:
365 S Sense Primer (Cla I - 8H9 heavy chain)
5'- TTA TTA CGA AT/CGAT T GCC CAG GTC AAA CTG -3';

365 A Antisense Primer (Not I- 8H9 light chain)
5'- CTT GGT G/CGGCCGC CTG TTT CAG CTC CAG -3';

hTCR-zeta chain
379S Sense primer (Bst U I- CD28 end - Xho I - hTCR zeta
[cytoplasmic domain])
5'- CG/C GAC TTA GCA GCC TAT CGC TCC TGg CAC/TCG AGa AGA GTG AAG

TTC -3';

379A Antisense Primer (BglII - hTCR z)
5'-CTT GGT A/GA TCT TCA GCG AGG GGG CAG GGC -3'.
``` infect K562 cells, and gene transduction was measured by surface expression of scFv on K562 using FACS. One of the scFv-transduced K562 cell lines was further enriched by MACS system before cloning by limiting dilution.

Peripheral Blood Mononuclear cells (PBMCs) PBMCs were isolated by centrifugation on Ficoll (density, 1.077 g/ml) for 30 min at 25° C. and washed twice with PBS. They were activated with soluble anti-CD3 (1 μg/ml; clone OKT3; PharMingen, San Diego, Calif.) and anti-CD28 (1 ug/ml; clone CD28.2; PharMingen) MoAbs for 3 days at 37° C. In some experiments, immobilized anti-CD3 and anti-CD28 MoAbs were used, where 12-well non-tissue culture-treated plates were incubated with the antibody (1 μg/ml in PBS) at 1 ml/well for 4 hours at 37° C. The coated plates were blocked with 1% HSA in PBS for 30 min at room temperature, washed once with PBS, and then used for PBMC activation. PBMCs ($10^6$/ml) were cultured in RPMI 1640 supplemented with 10% human AB serum (Gemini Bio-Products, Woodland, Calif.), 50 μM 2-mercaptoethanol, 2 μM L-glutamine, and 1% penicillin-streptomycin (Gibco-BRL), for a total of 3 days before retroviral transfection.

Retroviral Transduction Protocol The target cells (e.g. K562 or cultured PBMCs) were resuspended at a concentration of $1-5 \times 10^5$ cells/ml of freshly harvested supernatant from retroviral producer cells, containing 8-10 ug/ml hexadimethrine bromide (polybrene, Sigma), centrifuged at 1000×g at room temperature for 60 minutes, and then cultured in 12-well tissue culture plates overnight. The viral supernatant was then aspirated and fresh IMDM (Gibco) medium containing 100 U/ml of IL2 and changed approximately every 5 days to maintain a cell count between $1-2 \times 10^6$ cells/ml (21). After 2 weeks in culture, soluble anti-idiotypic antibody 2E9 was added at 3-10 ug/ml to the transfected lymphocytes for 3 days out of every 2-week culture period, to ensure clonal expansion of the scFv-positive transfected lymphocytes.

Cytotoxicity Assay Neuroblastoma targets NMB-7 and LAN-1 or rhabdomyosarcoma HTB-82 tumor cells were labeled with $Na_2^{51}CrO_4$ (Amersham Pharmacia Biotechnology Inc., Piscataway, N.J.) at 100 uCi/$10^6$ cells at 37° C. for 1 hour. After the cells were washed, loosely bound $^{51}Cr$ was removed by washing. 5000 target cells/well were admixed with lymphocytes to a final volume of 200 μl/well. Following a 3 minute centrifugation at 200×g, the plates were incubated at 37° C. for 4 hours. Supernatant was harvested using harvesting frames (Skatron, Lier, Norway). The released $^{51}Cr$ in the supernatant was counted in a universal gamma-counter (Packard Bioscience, Meriden, Conn.). Percentage of specific release was calculated using the formula 100%×(experimental cpm−background cpm)/(10% SDS releasable cpm−background cpm), where cpm are counts per minute of $^{51}Cr$ released. Total release was assessed by lysis with 10% SDS (Sigma-Aldrich), and background release was measured in the absence of cells. The background was usually <30% of total for these cell lines.

Mice and Treatment CB-17 SCID-Beige mice were purchased from Taconic (Germantown, N.Y.). Tumor cells were planted ($2 \times 10^6$ cells) in 100 ul of Matrigel (BD BioSciences, Bedford, Mass.) subcutaneously. Following implantation, tumor sizes (maximal orthogonal diameters) were measured. Tumor volume was calculated as $4Br^3/3$ where r is the mean tumor radius. Treatment studies started in groups of 5 mice per cage when tumor diameter reached 0.8 cm, usually by one week of tumor implantation. Mice received 5 weekly intravenous lymphocyte injections by retroorbital route, $2 \times 10^6$ per injection together with 500 U of IL-2 ip. 50 ug of anti-idiotypic antibody was administered ip 3 days after each lymphocyte injection. Tumor sizes were measured twice a week. Experiments were carried out under an IACUC approved protocol and institutional guidelines for the proper, and humane use of animals in research were followed.

Statistical Analysis Tumor growth was calculated by fitting a regression slope for each individual mouse to log transformed values of tumor size. Mean slope scores were back-transformed to give an estimate of the percent increase in tumor size per day. Slopes were compared between groups.

Results

Anti-8H9-idiotypic antibodies Rat hybridomas specific for 8H9 and nonreactive with control murine MoAb (IgM, IgG1 and other subclasses) were selected. By ELISA, 2E9, 1E12, and 1F11 were all of rat subclass IgG2a. The antibody 2E9 was chosen for the rest of the experiments.

Construction and expression of 8H9 scFv After secondary PCR amplification, the PCR product of scFv fitted with Sfi I and Not I restriction sites were inserted into pHEN1 vectors. Three rounds of panning were conducted to enrich for 2E9-binding recombinant phages. The phages eluted from the third round panning were used to infect *E. coli* HB2151 cells and induced by IPTG for expression. ScFv periplasmic soluble protein was allowed to react in plates coated with 2.5 ug 2E9/well and assayed by ELISA as described in Material and Methods. The clone 8HpHM9F7-1 was selected for subcloning. The scFv DNA sequence of 8HpHM9F7-1 agreed with those of the VH and VL regions of the MoAb 8H9. The supernatant, periplasmic soluble and cells pellet lysates of 8HpHM9F7-1 were separated by nonreducing SDS-PAGE, and analyzed by western blotting. A protein band with the apparent molecular weight of 31 KD was found in the supernatant, the periplasmic and cell pellet extracts using anti-MycTag antibody which recognized the sequence GAPVPDPLEPR. No such band was detected in control cells or 8HpHM9F7-1 cells without IPTG treatment.

Construction of sc8H9-CD28-hTCRzeta-pMSCVneo Using the assembled gene sequences, secondary PCR amplifications using synthetic oligodeoxynucleotide primers were performed using synthetic oligodeoxynucleotide primers 355S, 355A for the hCD8a leader-scFv-CD28, 365S, 365A for scFv8H9, and 379S, 379A for hTCR-zeta chain. The final gene construction hCD8_leader-8H9scFv-hCD28$_{TM}$-hCD28$_{cyto}$-TCR. was transfected into the amphotropic packaging line GP+envAM12, and selected in G418.

Enrichment and cloning of packing lines by affinity column The retroviral producer lines were affinity-enriched using MACS goat anti-rat IgG MicroBeads on the Mini-MACS system. Following each enrichment, viral supernatant from the producer line was used to infect the erythroleukemia line K562. Surface 8H9-scFv expression on both the producer lines and the transfected K562 (3-5 days after infection) were measured by immunofluorescence using anti-idiotypic antibody 2E9. With each successive affinity enrichment (FIGS. 23A and 23C) of producer line and subsequent successive subcloning (FIGS. 1B and 1D), the surface expression (mean fluorescence) of 8H9-scFv increased and became more homogeneous for the producer clones (FIGS. 23A and 23B) and for the indicator line K562 (FIGS. 23C and 23D).

Retroviral transduction of primary human peripheral blood mononuclear cells Following activation in vitro with soluble anti-CD3 and anti-CD28, primary human peripheral blood mononuclear cells were infected with the virus from producer line supernatant by centrifugation at 1000×g for 60 minutes at room temperature. By 21 days of in vitro culture, close to 100% of cells were scFv-positive by FACS (FIG. 24). This clonal evolution to homogeneity was found in CD4+, CD8+ and the small CD56+ populations. Soluble anti-idiotypic MoAb 2E9 was added at 3-10 ug/ml to the transfected lymphocytes for 3 days out of every 2 weeks, to stimulate clonal expansion of the scFv-positive transfected lymphocytes (FIG. 25). ScFv expression was constant throughout until at least day 62 (FIG. 24), while the cells underwent active clonal expansion of 100-fold. The proportion of CD8+cells increased steadily from an initial 20-60% to 90% by day 40 of culture.

Transduced lymphocytes carried out efficient non MHC-restricted cytotoxicity in vitro against neuroblastoma and rhabdomyosarcoma In vitro cytotoxicity against NMB-7 (FIG. 26A) and LAN-1 (FIG. 26B) neuroblastoma, or rhabdomyosarcoma HTB-82 (FIG. 26C) were efficient, all inhibitable by 8H9 antibody demonstrating antigen specificity. Daudi cell line (FIG. 26D) was not killed because it was antigen-negative. This cytotoxicity was independent of target HLA expression or HLA types. Unmodified lymphocytes from the same donor, cultured under the same conditions (100 U/ml of IL2), did not show antigen-specific killing (LAK, FIG. 26).

Inhibition of rhabdomyosarcoma tumor xenografted in SCID mice. Human rhabdomyosarcoma was strongly reactive with 8H9, but not with 5F11 (anti-GD2) antibodies. To study the in vivo effects of 8H9scFv-CIR gene-modified lymphocytes, we used 5F11scFv-CIR as control. 5F11scFv-CIR modified lymphocytes could kill tumors in vitro, but only if they were GD2-positive (data not shown). When subcutaneous tumor implants grew to 0.8 cm diameter, mice were treated with $2 \times 10^6$ gene-modified human lymphocytes intravenously plus 500 U of IL2 intraperitoneally once a week for a total of 5 weeks. 50 ug of anti-idiotypic antibody 2E9 was given ip 3 days after each lymphocyte infusion. All groups received IL2. Control groups received either no cells+2E9, cultured unmodified lymphocytes+2E9 (LAK), or 5F11scFv-CIR modified lymphocytes+anti-idiotype 1G8 (specific for 5F11 idiotype). Suppression of tumor growth was most significant with lymphocytes transduced with the 8H9scFv-CIR gene (p=0.066, FIG. 27). Although 5F11scFv-CIR modified lymphocytes also delayed tumor growth, they were not different from unmodified lymphocytes.

Discussion

The use of retroviral vectors to transduce chimeric immune receptors into primary human lymphocytes has been limited by the low gene transfer efficiency when viral supernatant infections were carried out. Transfer rates into primary human T cells using amphotropic virus ranged from 1 to 12% (22). Several strategies were explored to increase the transduction rates to 20-50%. These include: (1) using gibbon ape leukemia virus (GaLV strain SEATO) pseudotyped virions (20, 23, 24), (2) coculturing producer and target cells (25) where the clinical safety was of some concern, (3) using phosphate depletion followed by centrifugation and incubation at 32° C. (22), (4) adding fibronectin CH296 to enhance virus/lymphocyte interactions (26). More recently, Eshhar et al described a dicistronic construct consisting of scFv-CD28- (and green fluorescent protein (GFP), where the latter was used to monitor gene transduction and to enrich producer line (7). In our study, we used anti-idiotypic antibody to select for high surface scFv-expressing producer lines with improved efficiency of gene transduction. More importantly, lymphocytes transduced by CD-28- chimeric fusion receptors proliferated in the presence of the anti-idiotypic MoAb to become "monoclonal" with respect to scFv expression, in both the CD4+and CD8+populations. These lymphocytes possessed antigen-specific tumorcidal activity both in vitro and in vivo that was non-MHC restricted. Whether CD56-positive cells (presumably NK cells) acquire similar abilities will need further studies, although activation of NK cells through CD28 signaling has been reported previously (27).

We have shown that anti-idiotypic antibodies can facilitate clone selection in the construction of soluble scFv-fusion proteins or cell bound surface scFv. We have successfully applied similar technology to the GD2 antigen system (unpublished data). Being immunoglobulins, their structure, stability, biochemistry are generally known. This is in contrast to natural antigens where each individual system has its unique and often difficult-to-predict properties. As surrogate antigens, anti-idiotypic MoAb are ideal for standardization and quality control, especially for initial clinical investigations of carbohydrate antigens or when the nature of the antigen is not fully understood.

The advantage of using anti-idiotypic antibody for affinity purification and for clonal expansion of gene-modified lymphocytes are many fold. To prepare polyclonal CTLs specific for a tumor target, lymphocytes have to be pulsed periodically in vitro with the tumor cells (21). Clearly this can create safety (tumor contamination) and quality control issues. In contrast, anti-idiotypic MoAb can be manufactured under standard good manufacturing practice (GMP) conditions, with ease of manipulation both in vitro or in vivo. Another advantage of anti-idiotypic MoAb is its ability to mark the clonal population of target-specific lymphocytes. Although tetramers can mark TCR and T-cell clones, identity of the peptide antigen is required and this technology is not easily available. Furthermore, anti-idiotypic MoAb can mark T-cell clones in vivo when radiolabeled, an option not yet possible with tetramers. Finally, the potential of anti-idiotypic MoAb to activate the transduced lymphocytes in vivo is appealing, especially when tumor cells are poorly immunogenic, or when they are scarcely distributed. Although we used anti-idiotypic MoAb in our SCID mice experiments, this strategy clearly requires further optimization after a better understanding of in vivo biology of these transduced cells become available.

Despite these encouraging results, other structural issues of CIR technology will have to be considered for future optimization. The choice of the appropriate spacer (between scFv and signaling molecule), transmembrane domain and the signaling molecules may be important (28). That 8H9scFv-modified T-cells proliferate with anti-idiotype and kill antigen-positive tumor cells argue strongly that the CD28 trans-membrane domain in this CIR design does not require a CD8 hinge, permitting effective interaction with soluble as well as cell-bound antigens. This interaction effects positive lymphocyte signaling, for both survival and activation, as previously reported for similar chimeric fusion protein containing both CD28 and TCR-.chains (13). It is possible that the level of activation could be improved by the addition of a hinge or the adoption of other trans-membrane domains, as previously suggested (29). Previous reports have suggested that a human IgG hinge-CH2-Ch3 spacer can optimize T-cell activity, surface expression, and target affinity (28, 30). Moreover, using domains or molecules further downstream in the T-cell activation pathway could potentially overcome the T-cell defects commonly found in cancer patients (31). Another variable in T-cell activation is the affinity of interaction between TCR and MHC peptide complex (32). Whether a chimeric receptor of low affinity scFv may better mimic naive TCR interaction needs to be further tested. An optimal density of CIR for T-cell activation is probably important (33), since excessive TCR signaling may trigger premature death. In addition, since most target antigens are not tumor-specific, it may be useful to standardize the level of expression of CIR such that an engineered T-cell is optimally activated only by a narrow threshold of antigen.

The choice of tumor system and antigen target will likely determine the clinical success of CIR strategy. Primary lymphoid tumors e.g. B-cell lymphomas have distinct attributes. Because of their innate tropism, T-cells home to these lymphomas. In addition, these tumors have unique tumor antigens with homogeneous expression that do not modulate from the cell surface (e.g. CD20). Furthermore, these B-cell tumors express costimulatory molecules (30). Most solid tumors lack these attributes. However, metastatic cancers in lymph nodes, blood and bone marrow are unique compartments where CIR technology may be applicable. Depending on the compartment, targeting of T-cells may require different chemokine receptors or adhesion molecules. For example, while L-selectin is required for homing to lymphoid organs, its role for trafficking to other metastatic organs such as marrow is less well defined.

In adoptive cell therapies, the precise evaluation of the quantity and persistence of these cells in vivo, as well as their distribution and function within tissues is critical (34). In studies of T-cell therapy, this is of particular importance since many infused cells will undergo activation-induced death in vivo (35), or immune elimination of gene-modified cells may occur, especially following repeated injections (36). The development of sensitive, accurate and reproducible methods to quantify gene-marked cells in peripheral blood and tissues are essential for defining the long-term fate of adoptively-transferred cells. While PCR and quantitative RT-PCR methods are ideal for studying tissues extracts, anti-idiotypic MoAb will provide useful tools to enumerate individual scFv-positive cells in blood, marrow and tumor. In addition, non-invasive imaging methods using radiolabeled anti-idiotypic MoAb may also be possible. Similar to the marker gene HSV-tk that allows cells to be tracked and quantified by the substrate $^{131}$I-FIAU or $^{124}$I-FIAU, anti-idiotypic MoAb labeled with either $^{131}$I or $^{124}$I can also take advantage of instrumentation and software developed for SPECT and PET/micro-PET imaging, respectively. These tools can provide unprecedented precision and dynamic information on cell traffic in patient trials.

References

1. Daniel, P. T., Kroidl, A., Cayeux, S., Bargou, R., Blankenstein, T., and Dorken, B. Costimulatory signals through B7.1/CD28 prevent T cell apoptosis during target cell lysis. J Immunol, 159: 3808-3815, 1997.
2. Eshhar, Z., Waks, T., Gross, G., and Schindler, D. G. Specific activation and targeting of cytotoxic lymphocytes through chimeric single chains consisting of antibody-binding domains and the gamma or zeta subunits of the immunoglobulin and T-cell receptors. Proceedings of the National Academy of Sciences of the United States of America, 90: 720-724, 1993.
3. Stancovski, I., Schindler, D. G., Waks, T., Yarden, Y., Sela, M., and Eshhar, Z. Targeting of T lymphocytes to Neu/HERe-expressing cells using chimeric single chain Fv receptors. J Immunol, 151: 6577-6582, 1993.
4. Moritz, D., Wels, W., Mattern, J., and Groner, B. Cytotoxic T lymphocytes with a grafted recognition specificity for ERBB2-expressing tumor cells. Proc. Natl Acad Sci, USA, 91: 4318-4322, 1994.
5. Wels, W., Moritz, D., Schmidt, M., Jeschke, M., Hynes, N. E., and Groner, B. Biotechnological and gene therapeutic strategies in cancer treatment. Gene, 159: 73-80, 1995.
6. Hwu, P., Shafer, G. E., Treisman, J., Schindler, D. G., Gross, G., Cowherd, R., Rosenberg, S. A., and Eshhar, Z. Lysis of ovarian cancer cells by human lymphocytes redirected with a chimeric gene comosed of an antibody variable region and the Fc-receptor gamma-chain. J. Exp. Med., 178: 361-369, 1993.
7. Eshhar, Z., Waks, T., Bendavid, A., and Schindler, D. G. Functional expression of chimeric receptor genes in human T cells. J Immunol Methods, 248: 67-76, 2001.
8. Rosenberg, S. A. Cell transfer therapy: clinical applications. In: V. T. J. DeVita, S. Hellman, and S. A. Rosenberg (eds.), Biologic therapy of cancer, second edition, pp. 487-506. Philadelphia: J. B. Lippincott Company, 1995.
9. Yang, A.-G. and Chen, S.-Y. A new class of antigen-specific killer cells. Nat Biotechnol, 15: 46-51, 1997.
10. Culver, K. W., Ram, Z., Wallbridge, S., Ishii, H., Oldfield, E. H., and Blaese, R. M. In vivo gene transfer with retroviral vector-producer cells for treatment of experimental brain tumors. Science, 256: 1550, 1992.
11. Wei, M. X., Tamiya, T., and Chase, M. Experimental tumor therapy in mice using the cyclophosphamide-activating cytochrome P450 2B1 gene. Hum Gene Ther, 5: 969, 1994.
12. Weijtens, M. E., Willemsen, R. A., Valerio, D., Stam, K., and Bolhuis, R. L. Single chain Ig/gamma gene-redirected human T lymphocytes produce cytokines, specifically lyse tumor cells, and recycle lytic capacity. J Immunol, 157: 836-843, 1996.
13. Finney, H. M., Lawson, A. D. G., Bebbington, C. R., and Weir, N. C. Chimeric receptors providing both primary and costimulatory signaling in T cells from a single gene product. J Immunol, 161: 2791-2797, 1998.
14. Thanavala, Y. M., Brown, S. E., Howard, C. R., Roitt, I. M., and Steward, M. W. A surrogate hepatitis B virus antigenic epitope represented by a synthetic peptide and an internal image antiidiotype antibody. Journal of Experimental Medicine, 164: 227-236, 1986.
15. Wagner, U., Schlebusch, H., Kohler, S., Schmolling, J., Grunn, U., and Krebs, D. Immunological responses to the tumor-associated antigen CA125 in patients with advanced ovarian cancer induced by the murine monoclonal anti-idiotype vaccine ACA125. Hybridoma, 16: 33-40, 1997.
16. Modak, S., Kramer, K., Humayun, G., Guo, H. F., and Cheung, N. K. V. Monoclonal antibody 8H9 targets a novel cell surface antigen expressed by a wide spectrum of human solid tumors. Cancer Research, 61: 4048-4054, 2001.
17. Cheung, N. K., Saarinen, U., Neely, J., Landmeier, B., Donovan, D., and Coccia, P. Monoclonal antibodies to a glycolipid antigen on human neuroblastoma cells. Cancer Research, 45: 2642-2649, 1985.
18. Cheung, N. K., Canete, A., Cheung, I. Y., Ye, J. N., and Liu, C. Disialoganglioside GD2 anti-idiotypic monoclonal antibodies. International Journal of Cancer, 54: 499-505, 1993.
19. Towbin, H., Staehelin, T., and Gordon, J. Electrophoretic transfer of proteins from polyacrylamide gels to nitrocellulose sheets: procedure and some applications. Proceedings of the National Academy of Sciences of the United States of America, 76: 4350-4354, 1979.
20. Krause, A., Guo, H. F., Tan, C., Cheung, N. K. V., and Sadelain, M. Antigen-dependent CD-28 signaling enhances survival and proliferation in genetically modified activated human primary T lymphocytes. J. Exp. Med., 188: 619-626, 1998.
21. Koehne, G., Gallardo, H. F., Sadelain, M., and O'Reilly, R. J. Rapid selection of antigen-specific T lymphocytes by retroviral transduction. Blood, 96: 109-117, 2000.
22. Bunnell, B. A., Muul, L. M., Donahue, R. E., Blaese, R. M., and Morgan, R. A. High-efficiency retroviral-mediated 23. Miller, A. D., Garcia, J. V., von Suhr, N., Lynch, C. M., Wilson, C., and Eiden, M. V. Construction and properties of retrovirus packaging cells based on gibbon ape leukemia virus. J Virol, 1991: 2220-2224, 1991.
24. Lam, J. S., Reeves, M. E., Cowherd, R., Rosenberg, S. A., and Hwu, P. Improved gene transfer into human lymphocytes using retroviruses with gibbon ape leukemia virus envelope. Hum Gene Ther, 7: 1415-1422, 1996.
25. Bonini, C., Ferrari, G., Verzeletti, S., Servida, P., Zappone, E., Ruggieri, L., Ponzoni, M., Rossini, S., Mavilio, F., Traversari, C., and Bordignon, C. HSV-TK gene transfer into donor lymphocytes for control of allogeneic graft-versus-leukemia. Science, 276: 1719-1723, 1997.
26. Pollok, K. E., Hanenberg, H., Noblitt, T. W., Schroeder, W. L., Kato, I., Emanuel, D., and Williams, D. A. High-efficiency gene transfer into narmal and adenosine deaminase-deficient T lymphocytes is mediated by transduction on recombinant fibronectin fragments. J Virol, 72: 4882-4892, 1998.
27. Galea-Lauri, J., Darling, D., Gan, S.-U., Krivochtchapov, L., Kuiper, M., Gaken, J., Souberbielle, B., and Farzaneh, F. Expression of a variant of CD28 on a subpopulation of human NK cells: implications for B7-mediated stimulation of NK cells. J Immunol, 163: 62-70, 1999.
28. Patel, S. D., Moskalenko, M., Smith, D., Maske, B., Finer, M. H., and McArther, J. G. Impact of chimeric immune receptor extracellular protein domains on T cell function. Gene Therapy, 6: 412-419, 1999.
29. Fitzer-Attas, C. J., Schindler, D. G., Waks, T., and Eshhar, Z. Harnessing Syk familytyrosine kinases as signaling domains for chimeric single chain of the variable domain receptors: optional design for T cell activation. J Immunol, 160: 145-154, 1998.
30. Jensen, M., Tan, G., Forman, S., Wu, A. M., and Raubitschek, A. CD20 is a molecular target for scFvFc: receptor redirected T cells: implications for cellular immunotherapy of CD20+ malignancy. Biol Blood Marrow Transplant, 4: 75-83, 1998.
31. Eshhar, Z. and Fitzer-Attas, C. J. Tyrosine kinase chimeras for antigen-selective T-body therapy. Adv Drug Deliv Rev, 31: 171-182, 1998.
32. Valitutti, S. and Lanzavecchia, A. Serial triggering of TCRs: a basis for the sensitivity and specificity of antigen recognition. Immunology Today, 18: 299-304, 1997.
33. Varez-Vallina, L. and Russell, S. J. Efficient discrimination between different densities of target antigen by tetracycline-regulatable T bodies. Hum Gene Ther, 10: 559-563, 1999.
34. Yee, C., Riddell, S. R., and Greenberg, P. D. In vivo tracking of tumor-specific T cells. Curr Opin Immunol, 13: 141-146, 2001.
35. Xiaoning, R. T., Ogg, G. S., Hansasuta, P., Dong, T., Rostron, T., Luzzi, G., Conlon, C. P., Screaton, G. R., McMichael, A. J., and Rowland-Jones, S. Rapid death of adoptively transferred T cells in acquired immunodeficiency syndrome. Blood, 93: 1506-1510, 1999.
36. Riddell, S. R., Elliott, M., Lewinsohn, D. A., Gilbert, M. J., Wilson, L., Manley, S. A., Lupton, S. D., Overell, R. W., Reynolds, T. C., Corey, L., and Greenberg, P. D. T-cell mediated rejection of gene-modified HIV-specific cytotoxic T lymphocytes in HIV-infected patients. Nat Med, 2: 216-223, 1996.

Seventh Series of Experiments
Radioimmunotargeting to Human Rhabdomysarcoma (RMS) using Monoclonal Antibody (MoAb) 8H9

Metastatic rhabdomyosarcoma is a chemotherapy-responsive tumor. However, cure is elusive because of the failure to eradicate minimal residual disease (MRD). MoAb may have potential for selective targeting of therapy to MRD. Few MoAb of clinical utility have been described for RMS. We previously reported the broad tumor reactivity of a murine MoAb 8H9 with low/no staining of normal human tissues. The target antigen was typically expressed in a homogeneous fashion among neuroectodermal (neuroblastoma, Ewing's sarcoma, PNET, brain tumors), mesenchymal (RMS, osteosarcoma, DSRT, STS) and select epithelial tumors. Of 25 RMS tumors, 24 stained positive. Radioimmunolocalization of subcutaneous RMS xenografts in SCID mice was studied using radiolabeled 8H9. Following iv injection of 120 uCi of $^{125}$I-8H9, selective tumor uptake was evident at 4 to 172 hrs after injection, with a blood T½ of 0.8 h and T½ of 26 h. Mean tumor/tissue ratios were optimal at 172 h (for lung 4, kidney 7, liver 9, spleen 10, femur 16, muscle 21, brain 45). Average tumor/blood ratio were 0.7, 1.4 and 1.6, and tumor uptake was 9.5±3.4, 13.3±1.5, and 5.3±0.9% injected dose per gm at 24, 48 and 172 h, respectively. The selective targeting of 8H9 to RMS xenografts suggests its potential for radioimmunodetection and MoAb-based targeted therapy of MRD in RMS.

Radioimmunotargeting of Human Rhabdomyosarcoma using Monoclonal Antibody 8H9

Abstract

Purpose: Although metastatic rhabdomyosarcoma (RMS) is chemotherapy and radiotherapy-responsive, few patients are cured. 8H9, a murine IgG$_1$ monoclonal antibody (MoAb), recognizes a unique cell surface antigen that has restricted expression on normal tissues but is broadly distributed on neuroectodermal, epithelial and mesenchymal tumors including RMS. In this report we test its immunotargeting potential in mice with subcutaneous human RMS.

Experimental design: Athymic nude mice with established RMS xenografts were injected intravenously with $^{125}$I-8H9 or $^{125}$I-control MoAb. $^{125}$I-8H9 immunoreactivity was tested on solid-phase anti-8H9-idiotypic rat MoAb 2E9. Mice were imaged using a gamma camera and biodistribution of radiolabeled antibodies determined. The anti-tumor effect was studied following intravenous (IV) administration of 18.5 MBq $^{131}$I-8H9.

Results: Following IV injection of 4.44 MBq of $^{125}$I-8H9, selective tumor uptake was evident 4 to 172 h after injection. Average tumor uptake was 11.5±3.9, 15.1±3.7, and 5.4±1.2% injected dose per gm at 24, 48 and 172 h, respectively. Mean tumor/tissue ratios were optimal at 172 h (for lung, 4, kidney 6, liver 7, spleen 11, femur 14, muscle 18, brain 48). Tumor/tissue ratios were improved when a lower dose (0.74 MBq) of $^{125}$I-8H9 was injected. No hematological or histological abnormalities were observed. Mice injected with $^{125}$I- negative control did not demonstrate specific tumor uptake. In contrast to $^{131}$I-control treated mice, which showed unabated tumor progression, mice treated with 18.5 MBq of $^{131}$I-8H9 showed tumor suppression of >50%.

Conclusions: Radiolabeled 8H9 effectively targeted RMS xenografts and may have a potential clinical role in immunodetection and immunotherapy.

Introduction

Metastatic rhabdomyosarcoma (RMS) is associated with a dismal prognosis with reported cure rates of no greater than 25% despite demonstrated chemosensitivity and radiosensitivity (1,2,3). Myeloablative chemotherapy with autologous stem cell rescue has failed to impact survival (4,5). The failure to eradicate minimal residual disease (MRD) leads to local and distant relapses for both alveolar and embryonal RMS. Alternative strategies to target MRD are therefore warranted. Monoclonal antibodies (MoAbs) have recently been reported to be of clinical benefit in the treatment of solid tumors. In children with high-risk neuroblastoma (NB), the addition of the anti-ganglioside $G_{D2}$ antibody 3F8 to a multimodality approach has significantly improved prognosis (6) without increasing long-term toxicity (7). Radiolabeled antibodies can selectively deliver radiation to human tumors. Demonstration of specific binding to NB xenografts by $^{131}$I-3F8 was initially demonstrated in xenograft models (8). Indeed, $^{131}$I-3F8 completely ablated NB xenografts in athymic nude mice with reversible toxicity (9). Based on the pharmacokinetics and dosimetry calculations to tumors and normal tissues radioimmunodetection and radioimmunotherapy, clinical protocols utilizing $^{131}$I-3F8 were initiated in patients with NB. Subsequently, effective and specific targeting of NB in humans was demonstrated (10,11), and later utilized both for detection and therapy.

The adoption of a similar strategy to RMS has been limited by the paucity of antigens that can be targeted by MoAbs. Most antigens expressed on RMS either have a nuclear or cytoplasmic localization which makes them inaccessible to MoAbs, or are coexpressed on normal tissues thus limiting their clinical utility (Table 1). The PAX-FKHR fusion transcript is specific for alveolar RMS. It has been used in the detection of micrometastases in alveolar RMS by RT-PCR (12, 13) and as a tumor antigen for the generation of cytotoxic T-cells (14). However, its nuclear localization shields the intact protein from antibody-based targeting approaches. Furthermore, for the more frequent embryonal variant, such specific markers are not yet available. We recently described a novel tumor antigen with an apparent molecular weight of 58 kD (15) recognized by the MoAb 8H9. This glycoprotein is expressed on cell surface of a broad spectrum of solid tumors in childhood and adults, including both alveolar and embryonal RMS and has restricted distribution on normal tissues. We now report the in vivo targeting of $^{125}$I and $^{131}$I labeled 8H9 in human RMS xenografts.

TABLE 1

Previously reported antigens on rhabdomyosarcoma

| Antigen | Localization | Crossreactivity |
|---|---|---|
| Desmin (22) | cytoplasm | Skeletal, Cardiac and Smooth Muscle |
| Cytokeratin (23) | cytoplasm | Epithelial cells |
| EMA (23) | cytoplasm | Epithelial cells |
| Vimentin (23) | cytoplasm | All mesenchymal tissues |
| NSE (23) | cytoplasm | Brain and neural tissue |
| MYOD1 (17) | nucleus | Restricted to RMS |
| Ag BW575 (18) | cell membrane | Neural cells |
| Myosin (19) | cell membrane | Muscle cells |
| 5.1 H11 (25) | cytoplasm | Neural cells |
| IGFI receptor (21) | cell membrane | Normal cells |
| Fetal acetylcholine receptor (20) | cell membrane | Extraocular muscles, thymus, denervated skeletal muscle |

TABLE 2

% injected dose/gram of $^{125}$I-8H9 distributed in HTB82 xenografts and normal tissues 24, 48 and 172 hours after injection

| | 24 h (n = 9 mice) Mean ± SD | 48 h (n = 9 mice) Mean ± SD | 172 h (n = 8 mice) Mean ± SD |
|---|---|---|---|
| Adrenal | 1.4 ± 1.6 | 1.4 ± 0.5 | 0.4 ± 0.3 |
| Bladder | 2.6 ± 1.2 | 2.9 ± 0.8 | 0.9 ± 0.6 |
| Blood | 14.1 ± 3.0 | 10.7 ± 2.1 | 3.2 ± 0.9 |
| Brain | 0.3 ± 0.1 | 0.3 ± 0.1 | 0.1 ± 0.0 |
| Femur | 1.4 ± 0.5 | 1.1 ± 0.5 | 0.4 ± 0.1 |
| Heart | 4.3 ± 1.9 | 2.9 ± 0.5 | 0.9 ± 0.2 |
| Kidney | 3.9 ± 1.6 | 3.0 ± 0.7 | 0.8 ± 0.3 |
| Large Intestine | 1.7 ± 0.6 | 1.2 ± 0.3 | 0.2 ± 0.1 |
| Liver | 4.0 ± 1.7 | 2.2 ± 0.3 | 0.7 ± 0.3 |
| Lung | 5.7 ± 3.5 | 5.3 ± 1.1 | 1.4 ± 0.5 |
| Muscle | 1.2 ± 0.6 | 1.1 ± 0.4 | 0.3 ± 0.1 |
| Skin | 2.3 ± 1.6 | 2.5 ± 1.5 | 0.6 ± 0.4 |
| Small Intestine | 1.5 ± 0.4 | 1.1 ± 0.2 | 0.3 ± 0.1 |
| Spine | 2.1 ± 0.8 | 1.7 ± 0.7 | 0.5 ± 0.2 |
| Spleen | 5.8 ± 2.4 | 3.3 ± 0.8 | 0.5 ± 0.2 |
| Stomach | 2.4 ± 2.1 | 1.6 ± 0.7 | 0.5 ± 0.4 |
| Tumor | 11.5 ± 3.9 | 15.1 ± 3.7 | 5.4 ± 1.2 |

TABLE 3

Tumor:non-tumor ratios in mice injected with 0.74 MBq compared to 4.44 MBq of $^{125}$I-8H9 172 h post injection (5 mice per group)

| | 0.74 MBq Mean ± SD | 4.44 MBq Mean ± SD |
|---|---|---|
| Adrenal | 26.3 ± 20.4 | 12.5 ± 3.6 |
| Bladder | 35.0 ± 31.4 | 7.9 ± 1.5 |
| Blood | 2.6 ± 1.7 | 1.7 ± 0.3 |
| Brain | 150.9 ± 36.1 | 51.9 ± 20.1 |
| Femur | 26.7 ± 20.6 | 13.7 ± 2.0 |
| Heart | 11.5 ± 8.5 | 5.7 ± 1.0 |
| Kidney | 8.4 ± 3.5 | 6.5 ± 1.4 |
| Large Intestine | 32.3 ± 18.6 | 23.0 ± 5.0 |
| Liver | 13.0 ± 6.7 | 7.0 ± 0.9 |
| Lung | 7.7 ± 6.0 | 4.1 ± 0.6 |
| Muscle | 33.0 ± 22.3 | 18.9 ± 4.4 |
| Skin | 13.0 ± 8.9 | 7.2 ± 3.1 |
| Small Intestine | 29.4 ± 17.0 | 20.8 ± 6.4 |
| Spine | 20.4 ± 11.1 | 10.3 ± 3.7 |
| Spleen | 16.4 ± 11.3 | 11.9 ± 2.0 |
| Stomach | 23.4 ± 15.9 | 14.5 ± 4.3 |
| Tumor | 1.0 ± 0 | 1.0 ± 0 |

TABLE 4

$^{125}$I-8H9 and $^{125}$I-HTB82 xenografts (values represent dose/gram). Biodistribution of 2C9 in mice with 120 h after injection % injected

| | $^{125}$I-8H9 Mean ± SD | $^{125}$I-2C9 Mean ± SD |
|---|---|---|
| Adrenal | 0.5 ± 0.2 | 0.7 ± 0.4 |
| Bladder | 1.5 ± 0.8 | 1.5 ± 0.4 |
| Blood | 4.6 ± 0.7 | 8.4 ± 1.4 |
| Brain | 0.1 ± 0.1 | 0.2 ± 0.1 |
| Femur | 0.6 ± 0.1 | 0.9 ± 0.2 |
| Heart | 1.0 ± 0.2 | 1.7 ± 0.4 |
| Kidney | 1.2 ± 0.3 | 1.4 ± 0.4 |
| Large intestine | 0.4 ± 0.3 | 0.5 ± 0.1 |
| Liver | 0.9 ± 0.1 | 1.4 ± 0.1 |
| Lung | 2.9 ± 0.7 | 5.3 ± 1.5 |
| Muscle | 0.4 ± 0.1 | 0.5 ± 0.1 |
| Skin | 0.8 ± 0.1 | 1.0 ± 0.3 |
| Skin | 0.8 ± 0.1 | 1.0 ± 0.3 |
| Small intestine | 0.4 ± 0.1 | 0.6 ± 0.1 |
| Spine | 0.6 ± 0.1 | 1.3 ± 0.5 |
| Spleen | 1.3 ± 0.6 | 2.2 ± 0.5 |

TABLE 4-continued $^{125}$I-8H9 and $^{125}$I-HTB82 xenografts (values represent dose/gram).
Biodistribution of 2C9 in mice with 120 h after injection % injected

|  | $^{125}$I-8H9 Mean ± SD | $^{125}$I-2C9 Mean ± SD |
|---|---|---|
| Stomach | 0.5 ± 0.2 | 1.1 ± 0.2 |
| Stomach contents | 0.3 ± 0.1 | 0.3 ± 0.2 |
| Tumor | 7.2 ± 0.9 | 2.5 ± 0.9 |

TABLE 5

Mean hematological and liver function parameters
in mice (5 per group) injected with $^{131}$I-8H9

|  | Day 15 | Day 30 | Reported normal values |
|---|---|---|---|
| CBC |  |  |  |
| Hb (g/dl) | 11.2 ± 0.3 | 13.1 ± 3.2 | 11.0-14.0 |
| WBC (10$^3$) | 4.43 ± 0.7 | 6.2 ± 2.7 | 2.8-9.2 |
| Platelets (10$^3$) | 1309 ± 371 | 1300 ± 798 | 1523 ± 218 |
| Segmented (%) | 46.8 ± 9.9 | 42.5 ± 11.4 | 42-45.5 |
| Lymphocytes (%) | 49.6 ± 11.6 | 51.2 ± 16.2 | 54.5-58 |
| Liver function tests (pooled serum) |  |  |  |
| Alk. Phosphatase (IU/L) | 96 | 174 | 66-258 |
| ALT (IU/L) | 36 | 33 | 62-121 |
| AST (IU/L) | 169 | 93 | 87-318 |
| GGT (IU/L) | 0 | 0 |  |
| Albumin (g/dl) | 3.1 | 4.8 | 2.5-4.8 |
| Total protein (g/dl) | 5.5 | 5.1 | 3.5-7.2 |
| Total bilirubin (mg/dl) | 0.1 | 0.3 | 0.1-0.9 |

Materials and Methods
Monoclonal Antibodies

MoAb 8H9 The murine MoAb 8H9 was produced by hyperimmunizing BALB/c mice with human neuroblastoma as previously described. (15).

MoAb 2C9 Using similar methods, mice were immunized with human breast cancer and the hybridoma demonstrating specificity against cytokeratin 8 was isolated.

Anti-idiotypic MoAbs Rat anti-8H9-idiotype MoAbs were produced by immunizing LOU/CN rats with purified 8H9. Following in vitro hybridization with the myelomas SP2/0 or 8653, three IgG$_{2a}$ clones (2E9, 1E12 and 1F11) were selected for their high binding and specificity by ELISA. When tested against a panel of 23 other myelomas, no crossreactivity was found. The anti-idiotypic hybridomas were cloned and the antibody 2E9 chosen for scaled up production using high-density MiniPERM bioreactor (Unisyn technologies, Hopkinton, Mass.). Anti-idiotypic antibodies were further purified by protein G affinity (Hitrap G, Pharmacia, Piscataway, N.J.) chromatography and filtered through a 0.2 µm Millipore filter (Millipore Inc., Bedford, Mass.).

Cell Lines

RMS cell line HTB82 and small cell lung cancer cell line HTB119 (8H9 negative control) were purchased from American Type Culture Collection, Bethesda, Md. Cell lines were grown in RPMI (Gibco BRL, Gaithersburg, Md.) supplemented with 10% newborn calf serum (Hyclone, Logan, Pa.), 2 mM glutamine, 100 U/ml penicillin and 100 ug/ml streptomycin (Gibco-BRL, Gaithersburg, Md.). Cells were cultured in a 37° C. incubator and harvested using 2 mM EDTA.

Iodination

MoAb 8H9 was allowed to react for 5 min with $^{125}$I or $^{131}$I (NEN Life Sciences, Boston, Mass.) and chloramine T (1 mg/ml in 0.3 M Phosphate buffer, pH 7.2) at room temperature. The reaction was stopped by adding sodium metabisulfite (1 mg/ml in 0.3M Phosphate buffer, pH 7.2) for 2 min. Radiolabeled MoAb was separated from free iodine using A1GX8 resin column (BioRad, Richmond, Calif.) saturated with 1% HSA (New York Blood Center Inc., Melville Biologics Division, New York, N.Y.) in PBS, pH 7.4. Peak radioactive fractions were pooled and the radioactivity (MBq/ml) was measured using a radioisotope calibrator (Squibb, Princeton, N.J.). Iodine incorporation and specific activities were calculated. Trichloroacetic acid (TCA) (Fisher Scientific, Pittsburgh, Pa.) precipitation was used to assess the percentage of protein bound $^{125}$I or $^{131}$I. Thin layer chromatography was performed by running 1 µl of $^{125}$I-8H9 on a silica gel on glass TLC plate (Sigma Chemical, St. Louis, Mo.) and scanning it with System 200 Imaging Scanner (Bioscan, Washington, D.C.).

In Vitro Immunoreactivity of Iodinated 8H9

Immunoreactivity of labeled antibody was determined by a specific microtiter solid phase radioimmunoassay developed using the anti-8H9-idiotypic antibody 2E9 as the antigen. Briefly, microtiter plates were precoated with diminishing concentrations of 2E9. Appropriate dilutions of $^{125}$I-8H9 were added in duplicate. Binding was maximized by serial incubations at 4° C. in 3 separate antigen plates for periods of 1 h, 4 h and overnight respectively. The percent of bound activity was summed for each dilution to obtain the maximum percent binding. Similar assay was carried out to assess immunoreactivity of $^{131}$I-8H9.

Immunoreactivity was also measured by specific binding to cell pellets. HTB82 cells were suspended in Eppendorff tubes at concentrations of $10^8$, $10^7$ and $10^6$/ml in 100 µl medium. 100 µl of appropriate dilution of $^{125}$I-8H9 was added and allowed to react at 37° C. for 60 mins. Tubes were subsequently centrifuged at 1400 rpm×10 mins Radioactivity in 100 µl of supernatant was counted using Minaxi gamma counter (Packard BioScience, Downer's Grove, Ill.) and compared with total counts in a control sample consisting of medium without cells. Percent binding was calculated as (Experimental cpm/control cpm)×100%. The 8H9-negative cell line HTB 119 was used as control.

Animal Studies
Biodistribution and Pharmacokinetics

All animal experiments were carried out under an IACUC approved protocol and institutional guidelines for the proper and humane use of animals in research were followed. Athymic nude mice (Ncr nu/nu) were purchased from NCI, Frederick Md. They were xenografted subcutaneously with HTB82 cell line (2×10$^6$ cells/mouse) suspended in 100 ul of Matrigel (Beckton-Dickinson BioSciences, Bedford, Mass.) on the right flank. After 3-4 weeks, mice bearing tumors of 1 to 1.5 cm in longest dimension were selected. Mice were injected intravenously (retrorbital plexus) with 0.74 MBq or 4.44 MBq of $^{125}$I-8H9, or with 4.44 MBq $^{125}$I-2C9. They were anesthesized with ketamine (Fort Dodge Animal Health, Fort Dodge, Iowa) intraperitoneally and imaged at various time intervals with a gamma camera (ADAC, Milpitas, Calif.) equipped with a high-resolution general-purpose collimator for $^{131}$I and thyroid X-ray grids for $^{125}$I. Serial blood samples were collected at 5 min, 1, 2, 4,8,18,24,48,72, 120, 144 and 172 h to determine blood clearance of $^{125}$I-8H9. Groups of mice injected with $^{125}$I-8H9 were sacrificed at 24 h, 48 h, 120 h or 172 h immediately after imaging. Mice injected with $^{125}$I-2C9 were imaged either at 120 h (and then sacrificed) or at 172 h. Samples of blood (cardiac sampling), heart, lung, liver, kidney, spleen, stomach, adrenal, small bowel, large bowel, spine, femur, muscle, skin, brain and tumor were weighed and radioactivity measured with a Minaxi-gamma counter. Results were expressed as percent injected dose per gram and biodistribution determined.

Toxicity

Athymic nude mice without xenografts were each injected with 4.44 MBq of $^{131}$I-8H9. Groups of mice were euthanized at 15 and 30 days. Complete blood counts were carried out in each mouse via terminal bleed and liver function tests were performed on pooled sera. Complete necropsies including gross and histological examinations were carried out to evaluate possible toxicity of $^{131}$I-8H9.

Evaluation of Anti-Tumor Activity

RMS xenografts were established as described above. Their maximal perpendicular axes were measured using calipers in control and tumor groups. After 3 weeks, mice bearing tumors of approximately 0.7 cm$^3$ (tumor volume was calculated using the formula V=4πr$^3$/3 where r=mean radius) were selected and injected with 18.5 MBq of $^{131}$I-8H9 or $^{131}$I-3F8 (3F8 was used as a negative control antibody). Average serial tumor volumes and body weights were monitored in the two groups and compared over time. Mice were euthanized as per guidelines published in NIH Publication No. 85-23 ('Principles of Laboratory Animal Care'). Data are expressed as % increase or decrease in tumor volume when compared to initial measurement on day 0 of treatment.

Results

Immunoreactivity

Protein bound $^{125}$I and $^{131}$I as assessed by TCA precipitation averaged 96±4.2% and 98±2.2%, respectively for 8H9, and >95% for control antibodies 2C9 and 3F8. TLC demonstrated free iodine peak of 1%, 99% being protein bound. Average maximum immunoreactivity as measured by solid-phase RIA using the anti-8H9-idiotype 2E9 as antigen was 67±26% for 8H9 and 11% for 2C9. Maximum immunoreactivity measured by cell pellet binding assay was 83% for 8H9, maximum binding to the negative control cell line HTB119 being 9%. 2C9 demonstrated maximum binding of 6% on the HTB82 cell pellet.

Imaging

Animals tolerated intravenous injection without apparent ill effects. Tumor localization could be detected in animals imaged with $^{125}$I-8H9 as early as 4 hours after injection. At 24 h, tumor localization was obvious along with some blood pool, liver and spleen uptake. At 48 h, blood pooling had significantly diminished and almost disappeared at 172 h. In contrast, mice injected with the control IgG1 $^{125}$I-2C9 demonstrated no specific uptake in RMS xenografts (FIG. 28).

Blood Kinetics

Average blood clearance in groups of 5 mice with and without RMS xenografts injected with $^{125}$I-8H9 is depicted in FIG. 29. Blood activity of $^{125}$I-8H9 at 24 h was14.3% and 17.3% injected dose per gm (%ID/g) respectively and dropped off to 3.3% and 5.3% ID/g, respectively at 172 h. 13 half-life of $^{125}$I-8H9 was 70.9 h.

Biodistribution

Table 2 lists the biodistribution of 4.44 MBq $^{125}$I-8H9 in three groups of mice with RMS xenografts studied at 24, 48 and 172 h, respectively. Blood-pooling effect was observed at 24 h, which had diminished at 48 h and had almost completely subsided at 172 h after injection. There was no significant activity in normal organs apart from blood at 172 h. Average tumor uptake was 11.5±3.9, 15.1±3.7, and 5.4±1.2% injected dose per gm at 24, 48 and 172 h, respectively. Blood to tumor ratio was 1.24, 0.71 and 0.59 at 24, 48 and 172 h respectively. Mean tumor/tissue ratios (FIG. 30) increased from 24 to 48 h and were optimal at 172 h (for lung, 4, kidney 7, liver 8, spleen 11, femur 15, muscle 20, brain 47).

In mice injected with 0.74 MBq $^{125}$I-8H9, there was a further increase in tumor:tissue ratios particularly marked at 172 h post injection (for lung, 6, kidney 8, liver 12, spleen 14, femur 21, muscle 28, brain 56) (Table 3). Table 4 summarizes the biodistribution of $^{125}$I-8H9 compared to $^{125}$I-2C9 at 120 h post injection. Average tumor uptake was 7.3±0.9% injected dose per gram for $^{125}$I-8H9 as compared to 2.5+0.9% for $^{125}$I-2C9. Tumor to tissue ratios (FIG. 31) were <1 for almost all tissues for $^{125}$I-2C9, as compared to 2.6-56.0 for $^{125}$I-8H9.

Anti-Tumor Activity

Mice injected with 18.5 MBq $^{131}$I-8H9 showed a significant suppression in tumor volume (FIG. 32). Average tumor volume had diminished to <50% of initial volume 21 days after injection. None of the tumors showed any evidence of regrowth. In contrast, in the control group, mice injected with 18.5 MBq of $^{131}$I-3F8, an anti-GD2 MoAb that does not react with HTB82, there was progressive and rapid tumor growth.

Toxicity

No significant weight loss was noted in mice injected with 4.44 MBq of $^{131}$I-8H9, 15 and 30 days post injection (data not shown). Complete blood count and liver function studies did not reveal any abnormalities (Table 5). Complete necropsy evaluations did not reveal any gross or histological lesions (data not shown). In the groups of mice treated with $^{131}$I labeled MoAbs, there was no significant weight loss 21 days after the initial dose for both the 3F8 and 8H9 groups (+11.7±8.8% for the 3F8 group and −2±1.8% for the 8H9 group). The increase in weight in the control group could be attributed to increasing tumor mass.

Discussion

Few tumor specific antigens that can be targeted by MoAbs have been described for RMS. (Table 1) Myogenin, a myogenic regulatory protein specific for rhabdomyoblasts is nuclear in localization (16) and therefore not amenable for targeting by MoAbs. Similarly, the MyoD family of oncofetal proteins is expressed in nuclei (17). Conversely, the cell membrane-expressed antigens, BW475 (18) and myosin (19), are also expressed on normal neural and muscle tissue respectively. The fetal form of the acetylcholine receptor, α2βγδ, a possible target for antibody-based immunotherapy, although not present on most normal muscles tissue, is expressed in extraocular muscles, thymic myoid cells and in denervated skeletal muscle. (20.) Blockade of the insulin-like growth factor I (IGFI) receptor, which has been implicated in an autocrine pathway in the growth of RMS by murine monoclonals has been demonstrated to inhibit the growth of established RMS xenografts in nude mice (21). However, IGF receptors are ubiquitously expressed in normal tissues.

MoAb 8H9 recognizes a unique cell membrane antigen which is expressed on a wide range of pediatric and adult solid tumors (15). Furthermore, this novel antigen has restricted expression on normal tissues. In particular skeletal muscle and hematopoietic tissues are negative. Indeed 8H9 has been utilized to purge Ewing's sarcoma from blood and bone marrow (26). In RMS, the 8H9 antigen is expressed on both alveolar and embryonal variants. 96% (29/30) RMS studied expressed the 8H9 antigen. Expression in most cases was strong and homogeneous. RMS cell lines including the HTB82 cell line have been shown to express this antigen on cell membranes. It therefore has the potential to be utilized as a tumor target in RMS.

RMS is a chemosensitive and radiosensitive tumor, yet in patients with metastatic disease, MRD often leads to relapse and prevents cure Immunotherapy using radiolabeled and unlabeled 8H9 may provide a valuable adjunct in the eradication of MRD. A similar approach has led to successful cures being achieved in high-risk neuroblastoma (6). In this study we evaluated the in vivo targeting of RMS by radiolabeled 8H9. We have demonstrated that radiolabeled 8H9 can be effectively used in the radioimmunodetection and radioimmunotherapy of RMS xenografts in mice. Our results showed that $^{125}$I or $^{131}$I labeled 8H9 retained immunoreactivity after radiolabeling. A relatively high specific activity of >370 MBq/mg of $^{125}$I was obtained without loss of immunoreactivity. Hence, 8H9 has the potential to be labeled with relatively large doses of iodine radioisotopes for radioimmunotherapy approaches.

Our imaging results show that 8H9 can specifically and selectively bind to human RMS xenografted in nude mice. Uptake in xenografts could be detected as early as 4 h after injection. Excellent selectivity for tumor over normal tissue was demonstrated. There was no focal uptake in any normal organs including reticuloendothelial tissues. This is in keeping with the specific distribution of the antigen recognized by 8H9 as demonstrated by immunohistochemistry in human tissues and tumors (15). Specificity of 8H9 binding was demonstrated by comparing the binding of $^{125}$I-8H9 to that of $^{125}$I-2C9. 2C9, an IgG1 MoAb specific for cytokeratin8, an antigen not expressed by the RMS cell line HTB82, was used as a negative control. As expected, radiolabeled 2C9 remained in the bloodstream and did not show any specific binding for RMS xenografts with tumor: tissue ratios of 0.1-1. In comparison, radiation dose to tumor relative to normal tissues for 125I-8H9 ranged from 2.6 to 25.3 fold. Specificity of $^{125}$I-8H9 was also demonstrated in vitro by studying the binding of $^{125}$I-8H9 to the 8H9 negative cell line HTB 119 in comparison to the 8H9 positive line HTB82. Maximum binding of $^{125}$I-8H9 was 83% in comparison to 9% for HTB119 indicating that $^{125}$I-8H9 binding was antigen specific.

Biodistribution studies provided us with preclinical data in consideration of a possible use for 8H9 in human trials. β half-life of a single dose of 4.4 MBq of $^{125}$I-8H9 was 70.9 h. There was, in general, an excellent radiation dose differential between RMS and normal tissues. Optimum tumor to non-tumor ratios were reached at 172 h after intravenous 8H9 injection. Blood:tumor ratios were relatively high at 24 h indicative of blood pooling. Blood pooling diminished 48 h after injection and was further greatly reduced by 172 h. Probable uptake by cells of the reticuloendothelial system resulted in relatively high levels for liver and spleen in the first 24 h. There was increased uptake in the tumors at 48 h compared to 24 h suggesting further selective targeting of 8H9 between 24 to 48 h. Persistence of $^{125}$I-8H9 in the blood during the first 48 h of administration implies that there is no appreciable neutralization of antibody by circulating 8H9 antigen. When lower doses of $^{125}$I-8H9 for imaging (0.74 MBq compared to 4.44 MBq), tumor: non-tumor ratios were improved, consistent with reduced blood pooling (Table 4). The persistence of binding of $^{125}$I-8H9 to tumor implies that the 8H9 antigen is not immunomodulated off the cell after antibody binding. Similar findings were demonstrated in vitro, where the antigen-antibody binding on cell surface as detected by immunofluorescence persisted >60 h (15). This persistence should permit a steady delivery of radiation to tumor cells by radiolabeled 8H9. At doses of 6.66 MBq/m$^2$, there were no clinical (body weights), chemical (CBC and LFTs) or gross or histologic organ toxicities at necropsies.

In an effort to develop systems to study antigen-antibody reactions pending the definitive identification of the glycosylated 58kDa protein antigen recognized by 8H9, we used anti-8H9-idiotypic MoAbs to serve as surrogate antigens. These have enabled us to study the binding of radiolabeled (radioimmunoassay) and unlabeled (ELISA) 8H9 in vitro. Our data indicate that there was good correlation between the binding of $^{125}$I-8H9 to anti-8H9 anti-idiotypes and to native antigen on cell pellets.

The observed radioimmunotherapeutic effect of $^{131}$I-8H9 was remarkable, with >50% reduction in tumor volume of well-established RMS xenografts being achieved with a dose of 18.5 MBq of $^{131}$I-8H9 without any adverse effects. The antigen specific nature of this response was confirmed when RMS xenografts treated with equivalent doses of nonspecific antibody demonstrated unabated tumor growth. Radiolabeled 8H9 therefore, may have a possible clinical role in the therapy of RMS.

Given the broad reactivity of MoAb 8H9 with human solid tumors including sarcomas, neuroblastoma and brain tumors, these studies provide the proof of principle for exploring antibody-based targeting strategies directed at this antigen.

References

Crist W, Gehan E A, Ragab A H, Dickman P S, Donaldson S S, Fryer C, Hammond D, Hays D M, Herrmann J and Heyn R. The Third Intergroup Rhabdomyosarcoma Study J Clin Oncol 13:610-30, 1995

Maurer H M, Gehan E A, Beltangady M, Crist W, Dickman P S, Donaldson S S, Fryer C, Hammond D, Hays D M and Herrmann J. The Intergroup Rhabdomyosarcoma Study-II. Cancer 71:1904-22, 1993

Okamura J, Sutow W W, and Moon T E. Prognosis in children with metastatic rhabdomyosarcoma. Med Pediatr Oncol 3:243-51, 1977

Weigel B J, Breitfeld P P, Hawkins D, Crist W M, and Baker K S. Role of high-dose chemotherapy with hematopoietic stem cell rescue in the treatment of metastatic or recurrent rhabdomyosarcoma. J Pediatr Hematol Oncol 23:272-276, 2001

Ruymann F B and Grovas A C. Progress in the diagnosis and treatment of rhabdomyosarcoma and related soft tissue sarcomas. Cancer Invest 18:223-241, 2000

Cheung N K, Kushner B H, Cheung I Y, Kramer K, Canete A, Gerald W, Bonilla M A, Finn R, Yeh S J, and Larson S M. Anti $G_{D2}$ antibody treatment of minimal residual stage 4 neuroblastoma diagnosed at more than 1 year of age. J. Clin. Oncol., 16: 3053-60, 1998

Cheung N K, Kushner B H, Yeh S D J, and Larson S M. 3F8 monoclonal antibody treatment of patients with stage 4 neuroblastoma: a phase II study. Int. J. Oncol 12: 1299-306, 1998

Cheung N K, Neely J E, Landmeier B, Nelson D and Miraldi F. Targeting of ganglioside GD2 monoclonal antibody to neuroblastoma J Nuc Med 28:1577-83, 1987

Cheung N K, Landmeier B, Neely J, Nelson A D, Abramowsky C, Ellery S, Adams R B and Miraldi F. Complete tumor ablation with iodine 131-radiolabeled disialoganglioside GD2-specific monoclonal antibody against human neuroblastoma xenografted in nude mice. J Natl Cancer Inst . 77:739-745, 1986

Yeh S D, Larson S M, Burch L, Kushner B H, LaQuaglia M, Finn R and Cheung N K. Radioimmunodetection of neuroblastoma with iodine-131-3F8: correlation with biopsy, iodine-131-metaiodobenzylguanidine and standard diagnostic modalities. J. Nucl. Med. 32: 769-76, 1991

Kramer K, Cheung N K, Humm J L, Dantis E, Finn R, Yeh S J, Antunes N L, Dunkel I J, Souwedaine M and Larson S M. Targeted radioimmunotherapy for leptomeningeal cancer using (131)I-3F8. Med Pediatr Oncol 35:716-8, 2000

Thomson B, Hawkins D, Felgenhauer J, and Radich J. RT-PCR evaluation of peripheral blood, bone marrow and peripheral blood stem cells in children and adolescents undergoing VACIME chemotherapy for Ewing's sarcoma and alveolar rhabdomyosarcoma. Bone Marrow Transplant 24:527-33, 1999

Athale U H, Shurtleff S A, Jenkins J J, Poquette C A, Tan M, Downing J R and Pappo A S. Use of Reverse Transcriptase Polymerase Chain Reaction for Diagnosis and Staging of Alveolar Rhabdomyosarcoma, Ewing Sarcoma Family of Tumors, and Desmoplastic Small Round Cell Tumor. Am J Pediatr Hematol Oncol 23(2):99-104, 2001

Mackall C, Berzofsky J and Heiman L J. Targeting tumor specific translocations in sarcomas in pediatric patients for immunotherapy. Clin Orthop. 373:25-31, 2000

Modak S, Kramer K, Gultekin S H, Guo H F and Cheung N K. Monoclonal antibody 8H9 targets a novel cell surface antigen expressed by a wide spectrum of human solid tumors. Cancer Res. 61:4048-54, 2001.

Kumar S, Perlaman, E, Harris C A, Raffeld M and Tsokos M. Myogenin is a specific marker for rhabdomyosarcoma: an immunohistochemical study in paraffin embedded tissues. Mod Pathol 13: 988-93, 2000

Wang N. P., Marx J., McNutt M. A., Rutledge J. C., and Gown A. M., Expression of myogenic regulatory proteins (myogenin and MyoD1) in small blue round cell tumors of childhood. Am J Pathol 147: 1799-1810, 1995

Fujisawa T, Xu Z. J., Reynolds C. P Schultz G., Bosslet I. V., and. Seeger R. C., A monoclonal antibody with selective immunoreactivity for neuroblastoma and rhabdomyosarcoma. (abs) Proc. AACR 30: 345, 1989

Gruchala A, Niezabitowski A, Wasilewska A, Sikora K, Rys J, Szklarski W, Jaszcz A, Lackowska B and Herman K. Rhabdomyosarcoma. Morphologic, immunohistochemical, and DNA study. Gen Diagn Pathol 1142:175-84, 1997.

Gattenloehner S, Vincent A, Leuschner I, Tzartos S, Muller-Hermelink H K, Kirchner T and Marx A. The fetal form of the acetylcholine receptor distinguishes rhabdomyosarcomas from other childhood tumors. Am J Pathol. 152:437-44, 1998

Kalebic T, Tsokos M, Heiman L J. In vivo treatment with antibody against IGF-1 receptor suppresses growth of human rhabdomyosarcoma and down-regulates p34cdc2. Cancer Res 54:5531-4, 1994

Truong L D, Rangdaeng S, Cagle P, Ro J Y, Hawkins H, Font R L. The diagnostic utility of desmin A study of 584 cases and review of the literature Am J Clin Pathol 93:305-14, 1990

Qualman S J, Coffin C M, Newton W A, Hojo H, Triche T J, Parham D M, and Crist W M. Intergroup Rhabdomyosarcoma Study: update for pathologists Pediatr Dev Pathol 1:550-61, 1998

Garin-Chesa P., Fellinger E. J., Huvos A. G., Beresford H. R., Melamed M. R., Triche T. J., and Rettig W. J., Immunohistochemical analysis of neural cell adhesion molecules. Differential expression in small round cell tumors of childhood and adolescence. Am. J. Pathol. 139: 275-286, 1991

Strother D R, Parham D M and Houghton P J. Expression of the 5.1 H11 antigen, a fetal muscle surface antigen, in normal and neoplastic tissue. Arch Pathol Lab Med 114: 593-596, 1990

Merino M E, Navid F, Christensen B L, Toretsky J A, Heiman L J, Cheung N K and Mackall C L. Immunomagnetic purging of ewing's sarcoma from blood and bone marrow: quantitation by real-time polymerase chain reaction. J Clin Oncol 19:3649-3659, 2001

What is claimed is:

1. An isolated antibody that binds the same antigen as that of monoclonal antibody 8H9, wherein the isolated antibody comprises SEQ ID NOs:29-34, and the isolated antibody comprises sequences of human origin.

2. The antibody of claim 1, wherein the antibody is a scFv.

3. The antibody of claim 1, wherein the antibody is labelled.

4. The antibody of claim 1, wherein the antibody is directly or indirectly coupled to a cytotoxic agent.

5. A composition comprising the antibody of claim 1 and a pharmaceutically acceptable carrier.

6. An isolated polypeptide that binds the same antigen as that of monoclonal antibody 8H9, wherein the isolated polypeptide comprises SEQ ID NOs:29-34 and sequences of human origin.

7. The polypeptide of claim 6, wherein the polypeptide is a scFv.

8. The polypeptide of claim 6, wherein the polypeptide is labelled.

9. The polypeptide of claim 6, wherein the polypeptide is directly or indirectly coupled to a cytotoxic agent.

10. A composition comprising the polypeptide of claim 6 and a pharmaceutically acceptable carrier.

* * * * *

SEQUENCE LISTING

<160> NUMBER OF SEQ ID NOS: 40

<210> SEQ ID NO 1
<211> LENGTH: 731
<212> TYPE: DNA
<213> ORGANISM: Mus musculus

<400> SEQUENCE: 1

```
caggtcaaac tgcagcagtc tggggctgaa ctggtaaagc ctggggcttc agtgaaattg      60
tcctgcaagg cttctggcta caccttcaca aactatgata taaactgggt gaggcagagg     120
cctgaacagg gacttgagtg gattggatgg atttttcctg gagatggtag tactcaatac     180
aatgagaagt tcaagggcaa ggccacactg actacagaca catcctccag cacagcctac     240
atgcagctca gcaggctgac atctgaggac tctgctgtct atttctgtgc aagacagact     300
acggctacct ggtttgctta ctggggccaa gggaccacgg tcaccgtctc ctcagatgga     360
ggcggttcag gcggaggtgg ctctggcggt ggcggatcgg acatcgagct cactcagtct     420
ccaaccaccc tgtctgtgac tccaggagat agagtctctc tttcctgcag ggccagccag     480
agtattagcg actacttaca ctggtaccaa caaaaatcac atgagtctcc aaggcttctc     540
atcaaatatg cttcccaatc catctctggg atcccctcca ggttcagtgg cagtggatca     600
gggtcagatt tcactctcag tatcaacagt gtggaacctg aagatgttgg agtgtattac     660
tgtcaaaatg gtcacagctt tccgctcacg ttcggtgctg gaccaagct ggagctgaaa      720 caggcggccg c                                                          731
```

<210> SEQ ID NO 2

<211> LENGTH: 243
<212> TYPE: PRT
<213> ORGANISM: Mus musculus

<400> SEQUENCE: 2

Gln Val Lys Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gln Thr Thr Ala Thr Trp Phe Ala Tyr Trp Gly Gln Gly Thr
            100                 105                 110

Thr Val Thr Val Ser Ser Asp Gly Gly Gly Ser Gly Gly Gly Gly Ser
        115                 120                 125

Gly Gly Gly Gly Ser Asp Ile Glu Leu Thr Gln Ser Pro Thr Thr Leu
    130                 135                 140

Ser Val Thr Pro Gly Asp Arg Val Ser Leu Ser Cys Arg Ala Ser Gln
145                 150                 155                 160

Ser Ile Ser Asp Tyr Leu His Trp Tyr Gln Gln Lys Ser His Glu Ser
                165                 170                 175

Pro Arg Leu Leu Ile Lys Tyr Ala Ser Gln Ser Ile Ser Gly Ile Pro
            180                 185                 190

Ser Arg Phe Ser Gly Ser Gly Ser Gly Ser Asp Phe Thr Leu Ser Ile
        195                 200                 205

Asn Ser Val Glu Pro Glu Asp Val Gly Val Tyr Tyr Cys Gln Asn Gly
    210                 215                 220

His Ser Phe Pro Leu Thr Phe Gly Ala Gly Thr Lys Leu Glu Leu Lys
225                 230                 235                 240

Gln Ala Ala

<210> SEQ ID NO 3
<211> LENGTH: 243
<212> TYPE: PRT
<213> ORGANISM: Artificial Sequence
<220> FEATURE:
<223> OTHER INFORMATION: Mutated 8H9 scFv with decreased normal
      tissue adherence

<400> SEQUENCE: 3

Gln Val Lys Leu Gln Gln Ser Gly Ala Glu Leu Val Glu Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Lys Ala Thr Leu Thr Thr Asp Thr Ser Ser Ser Thr Ala Tyr
65                  70                  75                  80

```
Met Gln Leu Ser Arg Leu Thr Ser Glu Asp Ser Ala Val Tyr Phe Cys
                85                  90                  95
Ala Arg Gln Thr Thr Ala Thr Trp Phe Ala Tyr Trp Gly Gln Gly Thr
            100                 105                 110
Thr Val Thr Val Ser Ser Asp Gly Gly Ser Gly Gly Gly Ser
        115                 120                 125
Gly Gly Gly Gly Ser Asp Ile Glu Leu Thr Gln Ser Pro Thr Thr Leu
    130                 135                 140
Ser Val Thr Pro Gly Asp Gln Val Ser Leu Ser Cys Arg Ala Ser Gln
145                 150                 155                 160
Ser Ile Ser Asp Tyr Leu His Trp Tyr Gln Gln Lys Ser His Glu Ser
                165                 170                 175
Pro Gln Leu Leu Ile Lys Tyr Ala Ser Gln Ser Ile Ser Gly Ile Pro
            180                 185                 190
Ser Arg Phe Ser Gly Ser Gly Ser Gly Ser Asp Phe Thr Leu Ser Ile
        195                 200                 205
Asn Ser Val Glu Pro Glu Asp Val Gly Val Tyr Tyr Cys Gln Asn Gly
    210                 215                 220
His Ser Phe Pro Leu Thr Phe Gly Ala Gly Thr Glu Leu Glu Leu Glu
225                 230                 235                 240
Gln Ala Ala

<210> SEQ ID NO 4
<211> LENGTH: 22
<212> TYPE: DNA
<213> ORGANISM: Artificial Sequence
<220> FEATURE:
<223> OTHER INFORMATION: [32P]r Probe

<400> SEQUENCE: 4
tactctcagc agaacaccta tg                                            22

<210> SEQ ID NO 5
<211> LENGTH: 21
<212> TYPE: DNA
<213> ORGANISM: Artificial Sequence
<220> FEATURE:
<223> OTHER INFORMATION: Primer: ESBP1

<400> SEQUENCE: 5
cgactagtta tgatcagagc a                                             21

<210> SEQ ID NO 6
<211> LENGTH: 23
<212> TYPE: DNA
<213> ORGANISM: Artificial Sequence
<220> FEATURE:
<223> OTHER INFORMATION: Primer: ESBP2

<400> SEQUENCE: 6
ccgttgctct gtattcttac tga                                           23

<210> SEQ ID NO 7
<211> LENGTH: 18
<212> TYPE: DNA
<213> ORGANISM: Artificial Sequence
<220> FEATURE:
<223> OTHER INFORMATION: Primer: EWS 696

<400> SEQUENCE: 7
agcagctatg gacagcag                                                 18
```

<210> SEQ ID NO 8
<211> LENGTH: 20
<212> TYPE: DNA
<213> ORGANISM: Artificial Sequence
<220> FEATURE:
<223> OTHER INFORMATION: Primer: FLI 1 1041

<400> SEQUENCE: 8
ttgaggccag aattcatgtt                                              20

<210> SEQ ID NO 9
<211> LENGTH: 25
<212> TYPE: DNA
<213> ORGANISM: Artificial Sequence
<220> FEATURE:
<223> OTHER INFORMATION: Primer: G6PD1

<400> SEQUENCE: 9
ccggatcgac cactacctgg gcaag                                        25

<210> SEQ ID NO 10
<211> LENGTH: 26
<212> TYPE: DNA
<213> ORGANISM: Artificial Sequence
<220> FEATURE:
<223> OTHER INFORMATION: Primer: G6PD2

<400> SEQUENCE: 10
gttccccacg tactgggcca ggacca                                       26

<210> SEQ ID NO 11
<211> LENGTH: 24
<212> TYPE: DNA
<213> ORGANISM: Artificial Sequence
<220> FEATURE:
<223> OTHER INFORMATION: Lightcycler Hybridization Probe: EWSHP1

<400> SEQUENCE: 11
tatagccaac agagcagcag ctac                                         24

<210> SEQ ID NO 12
<211> LENGTH: 18
<212> TYPE: DNA
<213> ORGANISM: Artificial Sequence
<220> FEATURE:
<223> OTHER INFORMATION: Lightcycler Hybridization Probe: EWSHP2

<400> SEQUENCE: 12
ggcagcagaa cccttctt                                                18

<210> SEQ ID NO 13
<211> LENGTH: 28
<212> TYPE: DNA
<213> ORGANISM: Artificial Sequence
<220> FEATURE:
<223> OTHER INFORMATION: Lightcycler Hybridization Probe: G6PDHP1

<400> SEQUENCE: 13
gttccagatg gggccgaaga tcctgttg                                     28

<210> SEQ ID NO 14
<211> LENGTH: 28
<212> TYPE: DNA
<213> ORGANISM: Artificial Sequence
<220> FEATURE:

-continued

<223> OTHER INFORMATION: Lightcycler Hybridization Probe: G6PDHP2

<400> SEQUENCE: 14
caaatctcag caccatgagg ttctgcac                                              28

<210> SEQ ID NO 15
<211> LENGTH: 32
<212> TYPE: DNA
<213> ORGANISM: Artificial Sequence
<220> FEATURE:
<223> OTHER INFORMATION: Synthetic sequence

<400> SEQUENCE: 15
ttattacgag ttacatggcc ttaccagtga cc                                         32

<210> SEQ ID NO 16
<211> LENGTH: 32
<212> TYPE: DNA
<213> ORGANISM: Artificial Sequence
<220> FEATURE:
<223> OTHER INFORMATION: Synthetic sequence

<400> SEQUENCE: 16
ttattacgag taacatggcc ttaccagtga cc                                         32

<210> SEQ ID NO 17
<211> LENGTH: 31
<212> TYPE: DNA
<213> ORGANISM: Artificial Sequence
<220> FEATURE:
<223> OTHER INFORMATION: Synthetic sequence

<400> SEQUENCE: 17
cttggtccga gtgtcaggag cgataggctg c                                          31

<210> SEQ ID NO 18
<211> LENGTH: 31
<212> TYPE: DNA
<213> ORGANISM: Artificial Sequence
<220> FEATURE:
<223> OTHER INFORMATION: Synthetic

<400> SEQUENCE: 18
cttggttcga gtgtcaggag cgataggctg c                                          31

<210> SEQ ID NO 19
<211> LENGTH: 30
<212> TYPE: DNA
<213> ORGANISM: Artificial Sequence
<220> FEATURE:
<223> OTHER INFORMATION: Synthetic sequence

<400> SEQUENCE: 19
ttattacgaa tgattgccca ggtcaaactg                                            30

<210> SEQ ID NO 20
<211> LENGTH: 30
<212> TYPE: DNA
<213> ORGANISM: Artificial Sequence
<220> FEATURE:
<223> OTHER INFORMATION: Synthetic sequence

<400> SEQUENCE: 20
ttattacgaa cgattgccca ggtcaaactg                                            30

<210> SEQ ID NO 21
<211> LENGTH: 28
<212> TYPE: DNA
<213> ORGANISM: Artificial Sequence
<220> FEATURE:
<223> OTHER INFORMATION: Synthetic sequence

<400> SEQUENCE: 21
cttggtgggc cgcctgtttc agctccag                                          28

<210> SEQ ID NO 22
<211> LENGTH: 28
<212> TYPE: DNA
<213> ORGANISM: Artificial Sequence
<220> FEATURE:
<223> OTHER INFORMATION: Synthetic sequence

<400> SEQUENCE: 22
cttggtcggc cgcctgtttc agctccag                                          28

<210> SEQ ID NO 23
<211> LENGTH: 46
<212> TYPE: DNA
<213> ORGANISM: Artificial Sequence
<220> FEATURE:
<223> OTHER INFORMATION: Synthetic sequence

<400> SEQUENCE: 23
cggacttagc agcctatcgc tcctggcacc gagaagagtg aagttc              46

<210> SEQ ID NO 24
<211> LENGTH: 46
<212> TYPE: DNA
<213> ORGANISM: Artificial Sequence
<220> FEATURE:
<223> OTHER INFORMATION: Synthetic sequence

<400> SEQUENCE: 24
cggacttagc agcctatcgc tcctggcatc gagaagagtg aagttc              46

<210> SEQ ID NO 25
<211> LENGTH: 46
<212> TYPE: DNA
<213> ORGANISM: Artificial Sequence
<220> FEATURE:
<223> OTHER INFORMATION: Synthetic sequence

<400> SEQUENCE: 25
ccgacttagc agcctatcgc tcctggcacc gagaagagtg aagttc              46

<210> SEQ ID NO 26
<211> LENGTH: 46
<212> TYPE: DNA
<213> ORGANISM: Artificial Sequence
<220> FEATURE:
<223> OTHER INFORMATION: Synthetic sequence

<400> SEQUENCE: 26
ccgacttagc agcctatcgc tcctggcatc gagaagagtg aagttc              46

<210> SEQ ID NO 27
<211> LENGTH: 29
<212> TYPE: DNA
<213> ORGANISM: Artificial Sequence
<220> FEATURE:
<223> OTHER INFORMATION: Synthetic sequence

```
<400> SEQUENCE: 27
cttggtaatc ttcagcgagg gggcagggc                                              29

<210> SEQ ID NO 28
<211> LENGTH: 29
<212> TYPE: DNA
<213> ORGANISM: Artificial Sequence
<220> FEATURE:
<223> OTHER INFORMATION: Synthetic sequence

<400> SEQUENCE: 28
cttggtgatc ttcagcgagg gggcagggc                                              29

<210> SEQ ID NO 29
<211> LENGTH: 5
<212> TYPE: PRT
<213> ORGANISM: Mus musculus

<400> SEQUENCE: 29

Asn Tyr Asp Ile Asn
1               5

<210> SEQ ID NO 30
<211> LENGTH: 11
<212> TYPE: PRT
<213> ORGANISM: Mus musculus

<400> SEQUENCE: 30

Trp Ile Phe Pro Gly Asp Gly Ser Thr Gln Tyr
1               5                   10

<210> SEQ ID NO 31
<211> LENGTH: 9
<212> TYPE: PRT
<213> ORGANISM: Mus musculus

<400> SEQUENCE: 31

Gln Thr Thr Ala Thr Trp Phe Ala Tyr
1               5

<210> SEQ ID NO 32
<211> LENGTH: 11
<212> TYPE: PRT
<213> ORGANISM: Mus musculus

<400> SEQUENCE: 32

Arg Ala Ser Gln Ser Ile Ser Asp Tyr Leu His
1               5                   10

<210> SEQ ID NO 33
<211> LENGTH: 7
<212> TYPE: PRT
<213> ORGANISM: Mus musculus

<400> SEQUENCE: 33

Tyr Ala Ser Gln Ser Ile Ser
1               5

<210> SEQ ID NO 34
<211> LENGTH: 9
<212> TYPE: PRT
<213> ORGANISM: Mus musculus

<400> SEQUENCE: 34
```

Gln Asn Gly His Ser Phe Pro Leu Thr
1               5

<210> SEQ ID NO 35
<211> LENGTH: 243
<212> TYPE: PRT
<213> ORGANISM: Mus musculus

<400> SEQUENCE: 35

Gln Val Lys Leu Gln Gln Ser Gly Ala Glu Leu Val Lys Pro Gly
                 5                  10                  15

Ala Ser Val Lys Leu Ser Cys Lys Ala Ser Gly Tyr Thr Phe Thr
                 20                  25                  30

Asn Tyr Asp Ile Asn Trp Val Arg Gln Arg Pro Glu Gln Gly Leu
                 35                  40                  45

Glu Trp Ile Gly Trp Ile Phe Pro Gly Asp Gly Ser Thr Gln Tyr
                 50                  55                  60

Asn Glu Lys Phe Lys Gly Lys Ala Thr Leu Thr Thr Asp Thr Ser
                 65                  70                  75

Ser Ser Thr Ala Tyr Met Gln Leu Ser Arg Leu Thr Ser Glu Asp
                 80                  85                  90

Ser Ala Val Tyr Phe Cys Ala Arg Gln Thr Thr Ala Thr Trp Phe
                 95                  100                 105

Ala Tyr Trp Gly Gln Gly Thr Thr Val Thr Val Ser Ser Gly Gly
                 110                 115                 120

Gly Gly Ser Gly Gly Gly Ser Gly Gly Gly Ser Asp Ile
                 125                 130                 135

Glu Leu Thr Gln Ser Pro Thr Thr Leu Ser Val Thr Pro Gly Asp
                 140                 145                 150

Arg Val Ser Leu Ser Cys Arg Ala Ser Gln Ser Ile Ser Asp Tyr
                 155                 160                 165

Leu His Trp Tyr Gln Gln Lys Ser His Glu Ser Pro Arg Leu Leu
                 170                 175                 180

Ile Lys Tyr Ala Ser Gln Ser Ile Ser Gly Ile Pro Ser Arg Phe
                 185                 190                 195

Ser Gly Ser Gly Ser Gly Ser Asp Phe Thr Leu Ser Ile Asn Ser
                 200                 205                 210

Val Glu Pro Glu Asp Val Gly Val Tyr Tyr Cys Gln Asn Gly His
                 215                 220                 225

Ser Phe Pro Leu Thr Phe Gly Ala Gly Thr Lys Leu Glu Leu Lys
                 230                 235                 240

Gln Ala Ala
243

<210> SEQ ID NO 36
<211> LENGTH: 731
<212> TYPE: DNA
<213> ORGANISM: Mus musculus

<400> SEQUENCE: 36
caggtcaaac tgcagcagtc tggggctgaa ctggtaaagc ctggggcttc agtgaaattg      60
tcctgcaagg cttctggcta caccttcaca aactatgata taaactgggt gaggcagagg     120
cctgaacagg gacttgagtg gattggatgg atttttcctg gagatggtag tactcaatac     180
aatgagaagt tcaagggcaa ggccacactg actacagaca catcctccag cacagcctac     240
atgcagctca gcaggctgac atctgaggac tctgctgtct atttctgtgc aagacagact     300

| | |
|---|---|
| acggctacct ggtttgctta ctggggccaa gggaccacgg tcaccgtctc ctcaggtgga | 360 |
| ggcggttcag gcggaggtgg ctctggcggt ggcggatcgg acatcgagct cactcagtct | 420 |
| ccaaccaccc tgtctgtgac tccaggagat agagtctctc tttcctgcag ggccagccag | 480 |
| agtattagcg actacttaca ctggtaccaa caaaaatcac atgagtctcc aaggcttctc | 540 |
| atcaaatatg cttcccaatc catctctggg atccctcca ggttcagtgg cagtggatca | 600 |
| gggtcagatt tcactctcag tatcaacagt gtggaacctg aagatgttgg agtgtattac | 660 |
| tgtcaaaatg gtcacagctt tccgctcacg ttcggtgctg ggaccaagct ggagctgaaa | 720 |
| caggcggccg c | 731 |

<210> SEQ ID NO 37
<211> LENGTH: 731
<212> TYPE: DNA
<213> ORGANISM: Mus musculus

<400> SEQUENCE: 37

| | |
|---|---|
| gtccagtttg acgtcgtcag accccgactt gaccatttcg daccccgaag tcactttaac | 60 |
| aggacgttcc gaagaccgat gtggaagtgt ttgatactat atttgaccca ctccgtctcc | 120 |
| ggacttgtcc ctgaactcac ctaacctacc taaaaaggac ctctaccatc atgagttatg | 180 |
| ttactcttca agttcccgtt ccggtgtgac tgatgtctgt gtaggaggtc gtgtcggatg | 240 |
| tacgtcgagt cgtccgactg tagactcctg agacgacaga taaagacacg ttctgtctga | 300 |
| tgccgatgga ccaaacgaat gaccccggtt cctggtgcc agtggcagag gagtccacct | 360 |
| ccgccaagtc cgcctccacc gagaccgcca ccgcctagcc tgtagctcga gtgagtcaga | 420 |
| ggttggtggg acagacactg aggtcctcta tctcagagag aaaggacgtc ccggtcggtc | 480 |
| tcataatcgc tgatgaatgt gaccatggtt gttttagtg tactcagagg ttccgaagag | 540 |
| tagtttatac gaagggttag gtagagaccc taggggaggt ccaagtcacc gtcacctagt | 600 |
| cccagtctaa agtgagagtc atagttgtca caccttggac ttctacaacc tcacataatg | 660 |
| acagttttac cagtgtcgaa aggcgagtgc aagccacgac cctggttcga cctcgacttt | 720 |
| gtccgccggc g | 731 |

<210> SEQ ID NO 38
<211> LENGTH: 731
<212> TYPE: DNA
<213> ORGANISM: Mus musculus

<400> SEQUENCE: 38

| | |
|---|---|
| caggtcaaac tgcagcagtc tggggctgaa ctggtaaagc ctggggcttc agtgaaattg | 60 |
| tcctgcaagg cttctggcta caccttcaca aactatgata taaactgggt gaggcagagg | 120 |
| cctgaacagg gacttgagtg gattggatgg attttttcctg gagatggtag tactcaatac | 180 |
| aatgagaagt tcaagggcaa ggccacactg actacagaca catcctccag cacagcctac | 240 |
| atgcagctca gcaggctgac atctgaggac tctgctgtct atttctgtgc aagacagact | 300 |
| acggctacct ggtttgctta ctggggccaa gggaccacgg tcaccgtctc ctcagatgga | 360 |
| ggcggttcag gcggaggtgg ctctggcggt ggcggatcgg acatcgagct cactcagtct | 420 |
| ccaaccaccc tgtctgtgac tccaggagat agagtctctc tttcctgcag ggccagccag | 480 |
| agtattagcg actacttaca ctggtaccaa caaaaatcac atgagtctcc aaggcttctc | 540 |
| atcaaatatg cttcccaatc catctctggg atccctcca ggttcagtgg cagtggatca | 600 |

```
gggtcagatt tcactctcag tatcaacagt gtggaacctg aagatgttgg agtgtattac    660
tgtcaaaatg gtcacagctt tccgctcacg ttcggtgctg ggaccaagct ggagctgaaa    720
caggcggccg c                                                         731
```

```
<210> SEQ ID NO 39
<211> LENGTH: 243
<212> TYPE: PRT
<213> ORGANISM: Mus musculus

<400> SEQUENCE: 39

Gln Val Lys Leu Gln Gln Ser Gly Ala Glu Leu Val Lys Pro Gly
                 5                  10                  15

Ala Ser Val Lys Leu Ser Cys Lys Ala Ser Gly Tyr Thr Phe Thr
            20                  25                  30

Asn Tyr Asp Ile Asn Trp Val Arg Gln Arg Pro Glu Gln Gly Leu
        35                  40                  45

Glu Trp Ile Gly Trp Ile Phe Pro Gly Asp Gly Ser Thr Gln Tyr
    50                  55                  60

Asn Glu Lys Phe Lys Gly Lys Ala Thr Leu Thr Thr Asp Thr Ser
65                  70                  75

Ser Ser Thr Ala Tyr Met Gln Leu Ser Arg Leu Thr Ser Glu Asp
            80                  85                  90

Ser Ala Val Tyr Phe Cys Ala Arg Gln Thr Thr Ala Thr Trp Phe
        95                 100                 105

Ala Tyr Trp Gly Gln Gly Thr Thr Val Thr Val Ser Ser Asp Gly
    110                 115                 120

Gly Gly Ser Gly Gly Gly Ser Gly Gly Gly Ser Asp Ile
    125                 130                 135

Glu Leu Thr Gln Ser Pro Thr Thr Leu Ser Val Thr Pro Gly Asp
            140                 145                 150

Arg Val Ser Leu Ser Cys Arg Ala Ser Gln Ser Ile Ser Asp Tyr
        155                 160                 165

Leu His Trp Tyr Gln Gln Lys Ser His Glu Ser Pro Arg Leu Leu
    170                 175                 180

Ile Lys Tyr Ala Ser Gln Ser Ile Ser Gly Ile Pro Ser Arg Phe
            185                 190                 195

Ser Gly Ser Gly Ser Gly Ser Asp Phe Thr Leu Ser Ile Asn Ser
        200                 205                 210

Val Glu Pro Glu Asp Val Gly Val Tyr Tyr Cys Gln Asn Gly His
    215                 220                 225

Ser Phe Pro Leu Thr Phe Gly Ala Gly Thr Lys Leu Glu Leu Lys
            230                 235                 240

Gln Ala Ala
243

<210> SEQ ID NO 40
<211> LENGTH: 243
<212> TYPE: PRT
<213> ORGANISM: Artificial Sequence
<220> FEATURE:
<223> OTHER INFORMATION: Mutated 8H9 scFv with decreased normal tissue
      adherence

<400> SEQUENCE: 40

Gln Val Lys Leu Gln Gln Ser Gly Ala Glu Leu Val Glu Pro Gly
                 5                  10                  15
```

-continued

```
Ala Ser Val Lys Leu Ser Cys Lys Ala Ser Gly Tyr Thr Phe Thr
             20                  25                  30

Asn Tyr Asp Ile Asn Trp Val Arg Gln Arg Pro Glu Gln Gly Leu
             35                  40                  45

Glu Trp Ile Gly Trp Ile Phe Pro Gly Asp Gly Ser Thr Gln Tyr
             50                  55                  60

Asn Glu Lys Phe Lys Gly Lys Ala Thr Leu Thr Thr Asp Thr Ser
             65                  70                  75

Ser Ser Thr Ala Tyr Met Gln Leu Ser Arg Leu Thr Ser Glu Asp
             80                  85                  90

Ser Ala Val Tyr Phe Cys Ala Arg Gln Thr Thr Ala Thr Trp Phe
             95                 100                 105

Ala Tyr Trp Gly Gln Gly Thr Thr Val Thr Val Ser Ser Asp Gly
            110                 115                 120

Gly Gly Ser Gly Gly Gly Gly Ser Gly Gly Gly Ser Asp Ile
            125                 130                 135

Glu Leu Thr Gln Ser Pro Thr Thr Leu Ser Val Thr Pro Gly Asp
            140                 145                 150

Gln Val Ser Leu Ser Cys Arg Ala Ser Gln Ser Ile Ser Asp Tyr
            155                 160                 165

Leu His Trp Tyr Gln Gln Lys Ser His Glu Ser Pro Gln Leu Leu
            170                 175                 180

Ile Lys Tyr Ala Ser Gln Ser Ile Ser Gly Ile Pro Ser Arg Phe
            185                 190                 195

Ser Gly Ser Gly Ser Gly Ser Asp Phe Thr Leu Ser Ile Asn Ser
            200                 205                 210

Val Glu Pro Glu Asp Val Gly Val Tyr Tyr Cys Gln Asn Gly His
            215                 220                 225

Ser Phe Pro Leu Thr Phe Gly Ala Gly Thr Glu Leu Glu Leu Glu
            230                 235                 240

Gln Ala Ala
243
```